US012753181B2

(12) United States Patent
Nam et al.

(10) Patent No.: US 12,753,181 B2
(45) **Date of Patent: *Oct. 6, 2026**

(54) COMPOUNDS FOR DEGRADATION OF CYCLIN-DEPENDENT KINASE 7(CDK7)

(71) Applicant: QURIENT CO., LTD., Gyeonggi-Do (KR)

(72) Inventors: Kiyean Nam, Gyeonggi-Do (KR); Jaeseung Kim, Seoul (KR); Dongsik Park, Gyeonggi-Do (KR); Mooyoung Seo, Gyeonggi-Do (KR); Yeejin Jeon, Gyeonggi-Do (KR); Donghoon Yu, Gyeonggi-Do (KR)

(73) Assignee: QURIENT CO., LTD., Gyeonggi-Do (KR)

( * ) Notice: Subject to any disclaimer, the term of this patent is extended or adjusted under 35 U.S.C. 154(b) by 361 days.

This patent is subject to a terminal disclaimer.

(21) Appl. No.: 18/562,676

(22) PCT Filed: May 27, 2022

(86) PCT No.: PCT/EP2022/064443

§ 371 (c)(1),
(2) Date: Nov. 20, 2023

(87) PCT Pub. No.: WO2022/248682

PCT Pub. Date: Dec. 1, 2022

(65) Prior Publication Data

US 2024/0343732 A1 Oct. 17, 2024

Related U.S. Application Data

(60) Provisional application No. 63/194,277, filed on May 28, 2021.

(51) Int. Cl.
*C07D 487/04* (2006.01)
*A61K 31/53* (2006.01)

(52) U.S. Cl.
CPC ............ *C07D 487/04* (2013.01); *A61K 31/53* (2013.01)

(58) Field of Classification Search
CPC .................................................... C07D 487/04
USPC .......................................................... 514/246
See application file for complete search history.

(56) References Cited

U.S. PATENT DOCUMENTS

2025/0205242 A1* 6/2025 Nam .................... A61K 31/519
2025/0263413 A1* 8/2025 Nam ......................... A61P 9/00

FOREIGN PATENT DOCUMENTS

WO 2019/197546 A1 10/2019
WO 2020/035049 A1 2/2020
WO 2021/026109 A1 2/2021

OTHER PUBLICATIONS

Diab, Sarah et al. "CDK7 Inhibitors in Cancer Therapy: The Sweet Smell of Success?" Journal of Medicinal Chemistry, 63(14):7458-7474, Mar. 9, 2020.

Liu, Yi et al. "Transcriptional cyclin-dependent kinases: Potential drug targets in cancer therapy." European Journal of Medicinal Chemistry 229, pp. 1-22, (Year: 2022).

* cited by examiner

*Primary Examiner* — Niloofar Rahmani
(74) *Attorney, Agent, or Firm* — SALIWANCHIK, LLOYD & EISENSCHENK

(57) ABSTRACT

The present invention relates to compounds for degradation of cyclin-dependent kinase 7 (CDK7). The present invention also relates to pharmaceutical compositions comprising such compound(s). Furthermore, the present invention also relates to uses of such compound(s) or of such pharmaceutical compositions in a method of prevention and/or treatment of a disease associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7). Moreover, the present invention relates to methods of preventing and/or treating a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7).

16 Claims, 3 Drawing Sheets

COMPOUNDS FOR DEGRADATION OF CYCLIN-DEPENDENT KINASE 7(CDK7)

CROSS REFERENCE TO RELATED APPLICATIONS

Figure 1:
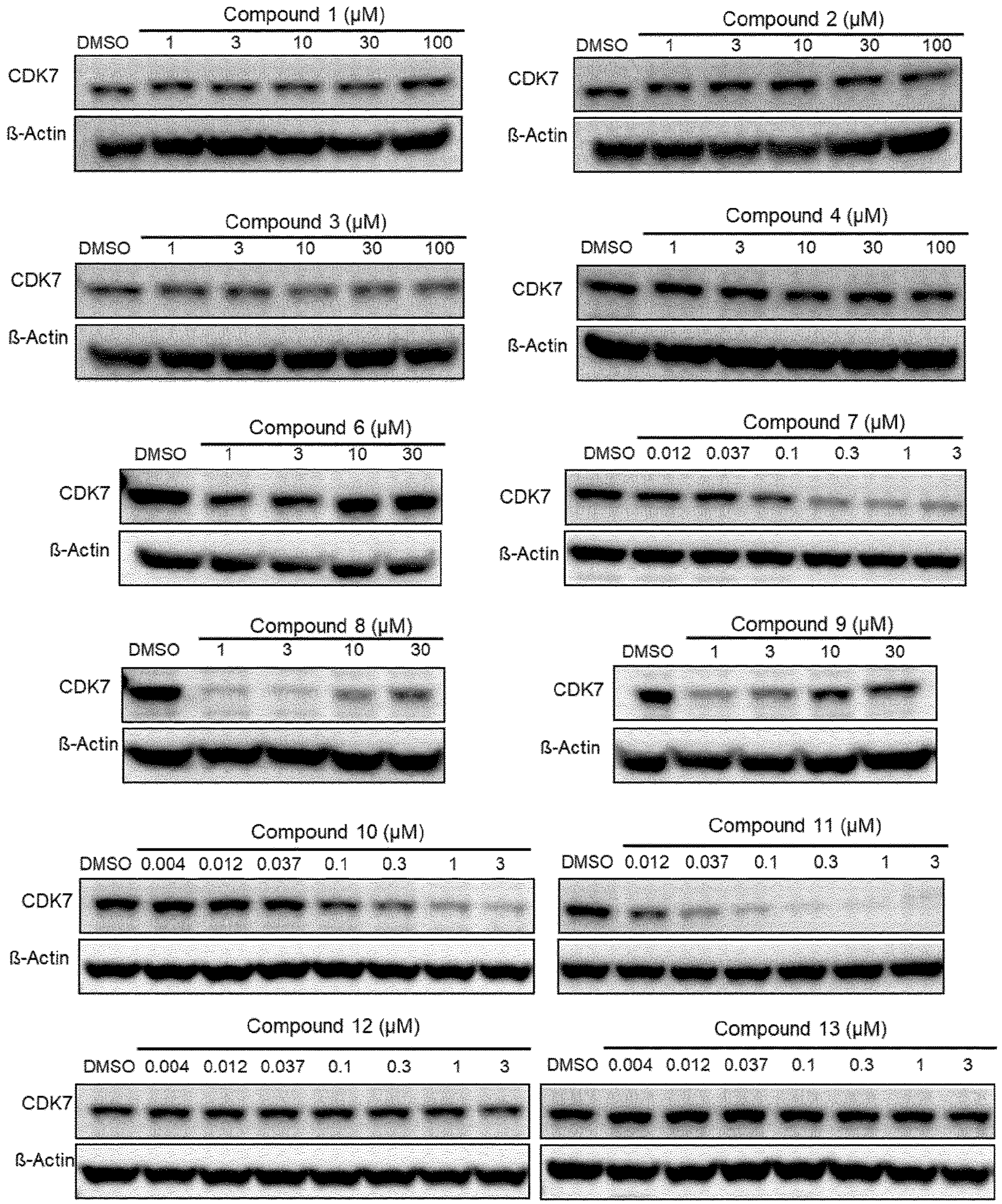
Figure 1:
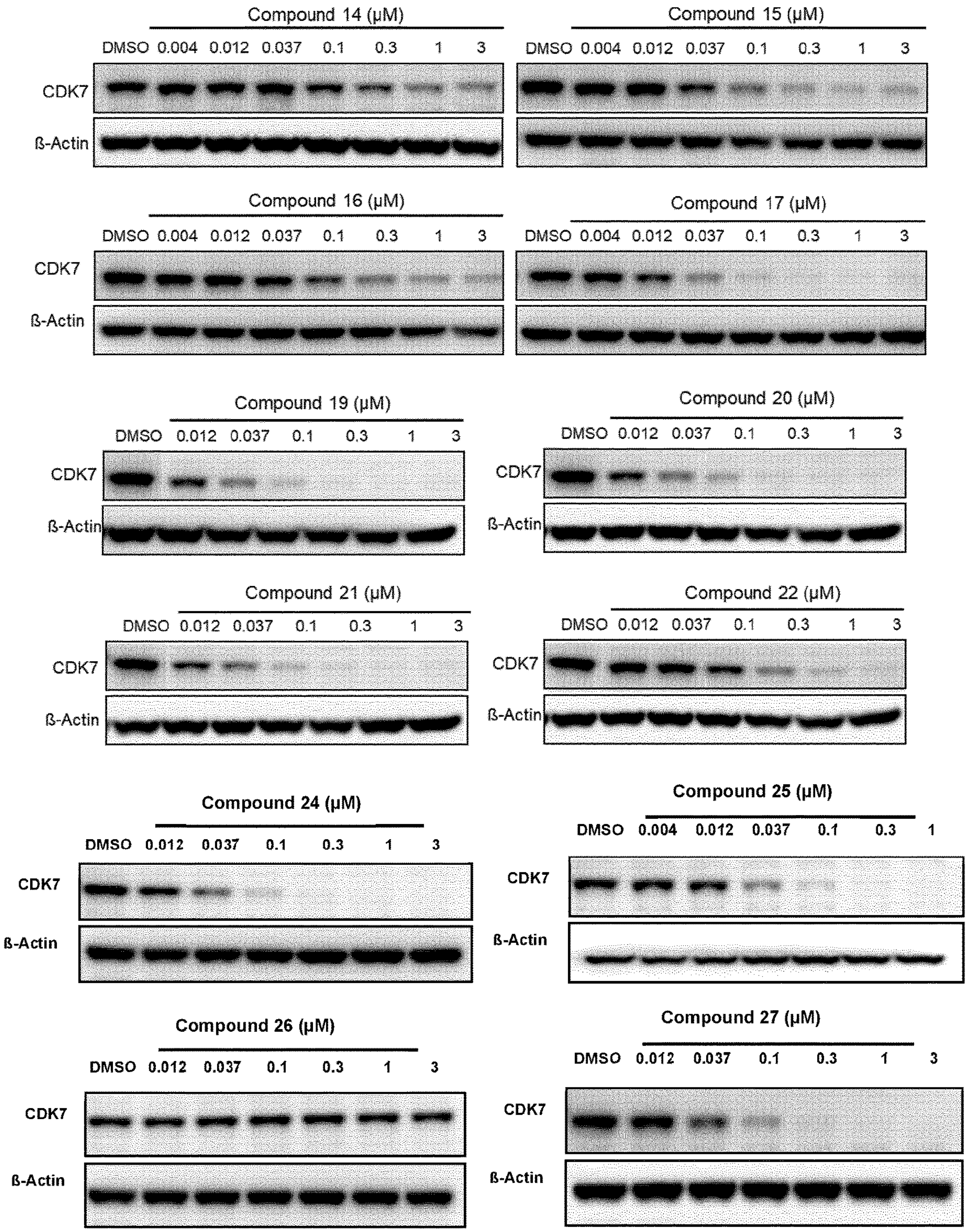
Figure 1:
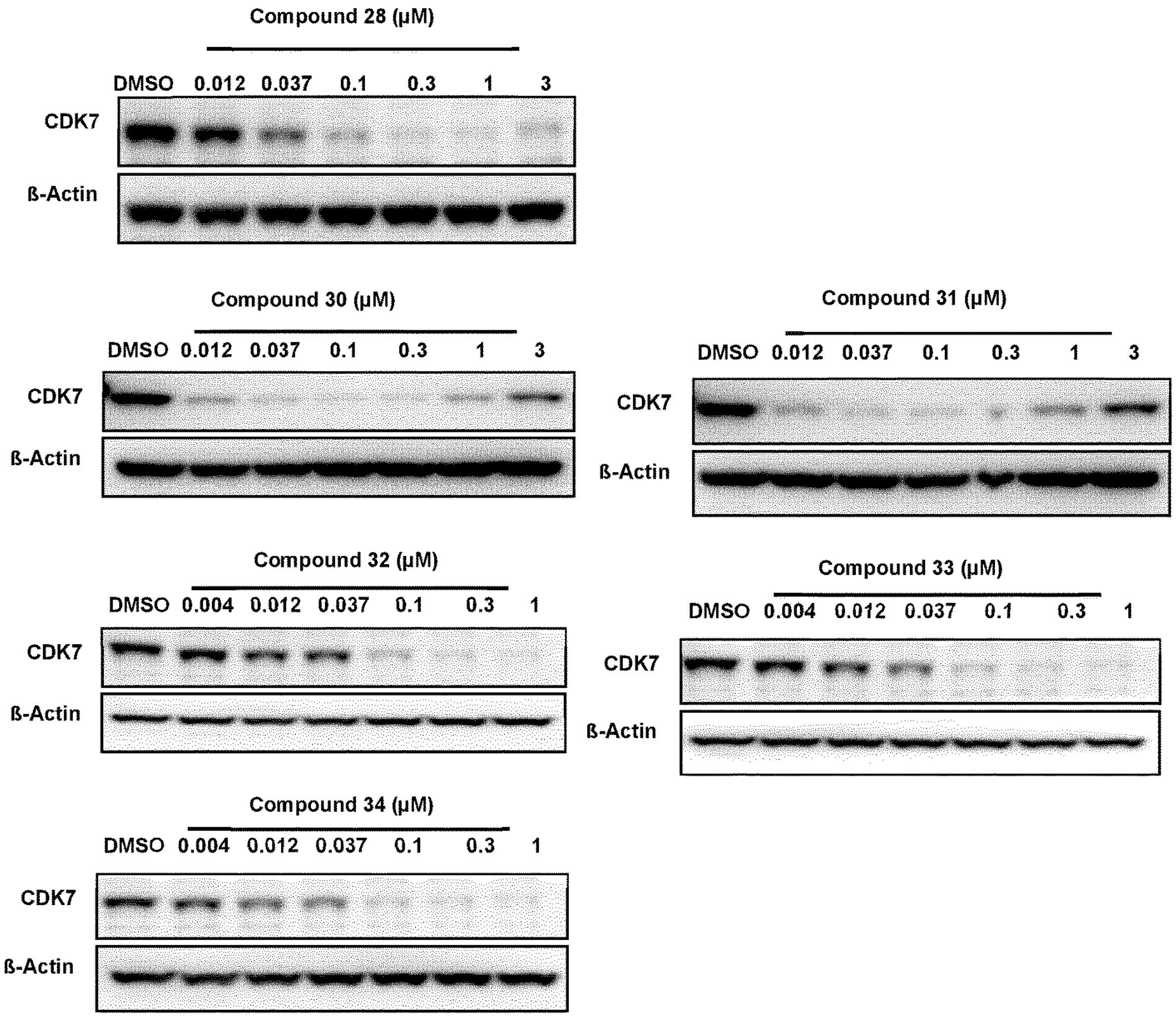

This application is a National Stage Application of International Application Number PCT/EP2022/064443, filed May 27, 2022; which claims priority to U.S. Provisional Application Ser. No. 63/194,277, filed May 28, 2021, both of which are incorporated herein by reference in their entirety.

FIELD OF THE INVENTION

The present invention relates to compounds for degradation of cyclin-dependent kinase 7 (CDK7). The present invention also relates to pharmaceutical compositions comprising such compound(s). Furthermore, the present invention also relates to uses of such compound(s) or of such pharmaceutical compositions in a method of prevention and/or treatment of a disease associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7). Moreover, the present invention relates to methods of preventing and/or treating a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7).

BACKGROUND OF THE INVENTION

Cyclin-dependent kinases have been implicated in various processes such as cell cycle control and progression through the cell cycle as well as gene-transcription and RNA processing. However, the precise role of cyclin-dependent kinases is far from being fully understood. Various inhibitors of cyclin-dependent kinases have been described. For example, Palbociclib has been reported to provide encouraging results in a clinical trial of patients having (HR)-positive, HER2-negative breast cancer. Cyclin-dependent kinase 7 is a component of transcription factor TFIIH and is also believed to be involved in cell cycle progression. Mevociclib is an inhibitor of cyclin-dependent kinase 7 and has been reported to inhibit cell growth of various cancer types as nanomolar concentrations in-vitro. However, initial clinical trials of this compound did not support an optimal profile for patients in terms of toxicity of the compound.

Many inhibitors of cyclin-dependent kinases are small molecule inhibitors. In many instances, such small molecule inhibitors run the risk of having limited use. For example, sustainably high systemic drug levels are needed to maintain adequate intracellular concentrations of such inhibitors for therapeutic efficacy. This often causes off-target effects and side effects due to the competitive nature of small molecule inhibitors. Moreover, in some instances small molecule inhibitors typically only disrupt the activity of a single domain of multi domain proteins such that functional activities of other domains within the multi domain proteins and their interactions with other proteins, and possible signalling cascades associated therewith, are preserved. In cancer cells, the inhibition of multi domain kinases may even lead to compensatory feedback activation of downstream signalling cascades via other alternative kinases.

Accordingly, there remains a need to provide alternative inhibitors of cyclin-dependent kinases that not only inhibit one or several cyclin-dependent kinases as such, but also block or reduce downstream signalling of such cyclin-dependent kinases, which downstream signalling might otherwise still occur in spite of the respective CDK been inhibited. Furthermore, there is a need to provide alternative inhibitors of cyclin-dependent kinases, in particular of cyclin-dependent kinase 7 which are highly selective for CDK7 versus other cyclin-dependent kinases.

SUMMARY OF THE INVENTION

In a first aspect, the present invention relates to a compound having the general formula I Formula I

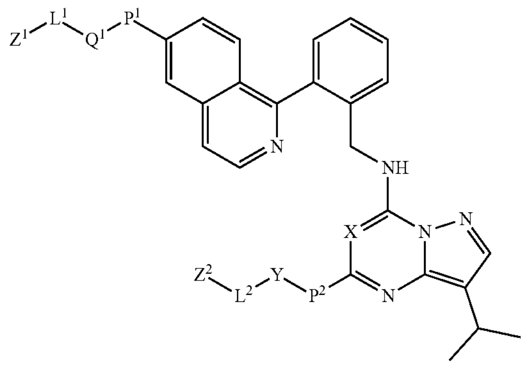

wherein

X is, at each occurrence, independently selected from CH and N;

$P^1$ is either absent or independently, at each occurrence, selected from the group consisting of —$NR^1$—, —O—, $k^a$-$CH_2O$-$k^b$, $k^a$-$OCH_2$-$k^b$, $k^a$-C(═O)O-$k^b$ and $k^a$-O(O═)C-$k^b$;

$k^a$ indicates the point of attachment to an aromatic ring, e. g. isoquinoline, and $k^b$ indicates the point of attachment to $Q^1$;

$Q^1$ is either absent or is independently selected from hydrogen, —C(═O)—, any structure of (a-1) to (a-5) and any structure of (a-6) to (a-18) of Group A:

Group A (a-1)

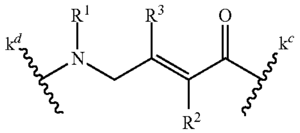

(a-2)

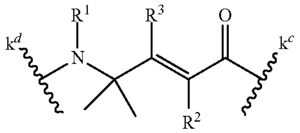

(a-3)

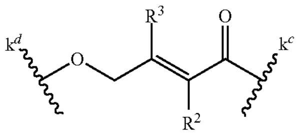

-continued (a-4)

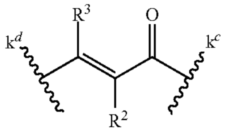

(a-5)

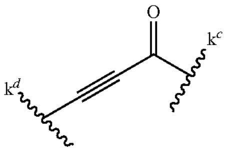

(a-6)

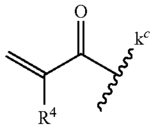

(a-7)

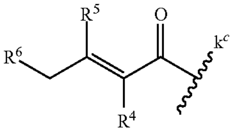

(a-8)

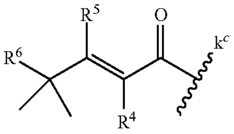

(a-9)

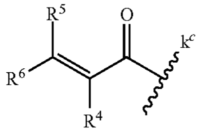

(a-10)

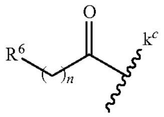

(a-11)

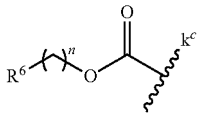

(a-12)

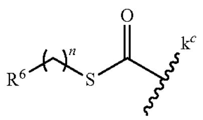

(a-13)

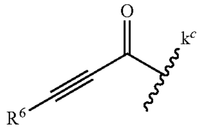

(a-14)

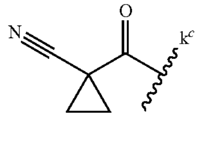

-continued (a-15)

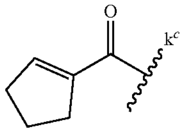

(a-16)

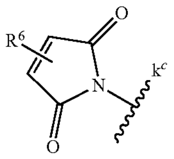

(a-17)

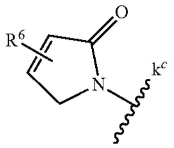

(a-18)

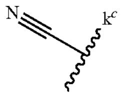

wherein n is 1, 2 or 3; $k^e$ indicates the point of attachment to $P^1$ and $k^d$ indicates the point of attachment to $L^1$ or $Z^1$;

$R^1$ is, independently at each occurrence, selected from hydrogen, C1-C3 alkyl and C3-C6 cycloalkyl;

$R^2$ and $R^3$ are, at each occurrence, independently selected from the group consisting of hydrogen, halogen, C1-C6 alkyl, C1-C3 haloalkyl, heterocyclyl and —CN;

$R^4$ and $R^5$ are, at each occurrence, independently selected from the group consisting of hydrogen, halogen, C1-C6 alkyl, C1-C3 haloalkyl, heterocyclyl and —CN;

$R^6$ is selected from the group consisting of hydrogen, halogen, C1-C6 alkyl, C3-C10 cycloalkyl, —$NR^7R^8$, —$OR^7$, —CN and heterocyclyl;

$R^7$ and $R^8$ are, at each occurrence, independently selected from hydrogen, C1-C3 alkyl and C3-C6 cycloalkyl;

wherein, if $Q^1$ is selected from hydrogen and any structure of (a-6) to (a-18), then $L^1$ and $Z^1$ are absent;

$L^1$ is either absent or is a linker;

$Z^1$ is either absent or is an E3 ubiquitin ligase binding group;

$P^2$ is either absent or is independently, at each occurrence, selected from the group consisting of —$NR^1$—, $k^e$-$NR^1CH_2$-$k^f$, —O— and $k^e$-$OCH_2$-$k^f$;

$R^1$ being as defined above;

$k^e$ indicates the point of attachment to an aromatic ring, e. g. a heteroaryl ring, such as pyrazolo[1,5-a]pyrimidine or pyrazolo[1,5-a]triazine, and $k^f$ indicates the point of attachment to Y;

Y is at each occurrence, independently, selected from the group consisting of halogen, C1-C6 alkyl, C1-C6 alkylene, C1-C3 haloalkyl, C1-C3 haloalkylene, C3-C8 cycloalkyl, C3-C8 cycloalkylene, aryl, arylene, heteroaryl, heteroarylene, heterocyclyl, heterocyclylene, heterocyclyl substituted with one or two of $R^9$, and heterocyclylene substituted with one or two of $R^9$;

$R^9$ is, at each occurrence independently, selected from the group consisting of halogen, —$NR^7R^8$, —$OR^7$, C1-C3 alkyl and C1-C3 haloalkyl;

$R^7$ and $R^8$ being as defined above;

$L^2$ is either absent or is a linker;

$Z^2$ is either absent or is an E3 ubiquitin ligase binding group;

wherein, if $Q^1$ is absent, L is absent and $Z^1$ is absent, then $L^2$ is a linker and $Z^2$ is an E3 ubiquitin ligase binding group;

wherein, if $Q^1$ is any structure of (a-6) to (a-18) or H, L is absent and $Z^1$ is absent, then $L^2$ is a linker and $Z^2$ is an E3 ubiquitin ligase binding group;

wherein, if $L^2$ is absent and $Z^2$ is absent, then $Q^1$ is either absent or any structure of (a-1) to (a-5), and $L^1$ is a linker, and $Z^1$ is an E3 ubiquitin ligase binding group It should be noted that the term "compound" as used herein, is also meant to refer and include enantiomers, stereoisomeric forms, mixtures of enantiomers, diastereomers, mixtures of diastereomer, racemates of such compound or pharmaceutically acceptable salts of the compounds, as defined herein.

In one preferred embodiment, $P^1$ is either absent or is —NH—.

In one further or also or alternatively preferred embodiment, X is N.

In one further or also or alternatively preferred embodiment, Y is selected from piperidinyl, piperidinyl substituted with one or two of —$R^9$, piperidinylene, piperidinylene substituted with one or two of —$R^9$, piperazinyl, piperazinyl substituted with one or two of —$R^9$, piperazinylene, and piperazinylene substituted with one or two of —$R^9$;

wherein $R^9$ is selected from the group consisting of halogen, —$NR^7R^8$, —$OR^7$, C1-C3 alkyl and C1-C3 haloalkyl;

wherein $R^7$ and $R^8$ are as defined further above.

In one further or also or alternatively preferred embodiment, $R^1$ is, independently at each occurrence, selected from hydrogen and C1-C3 alkyl, wherein, preferably, $R^1$ is hydrogen.

In one further or also or alternatively embodiment, $R^7$ and $R^8$ are, at each occurrence, independently selected from hydrogen and C1-C3 alkyl, wherein, preferably, $R^7$ and $R^8$ are hydrogen.

In one further or also or alternatively preferred embodiment, $R^9$ is, independently at each occurrence, selected from the group consisting of —$NH_2$, —OH and C1-C3 alkyl.

In one embodiment, Q, is absent, L is a linker, $Z'$ is an E3 ubiquitin ligase binding group, $L^2$ is absent, and $Z^2$ is absent.

In one embodiment, $Q^1$ is selected from any structure of (a-1) to (a-5), as defined above, L, is a linker, $Z^1$ is an E3 ubiquitin ligase binding group, $L^2$ is absent, and $Z^2$ is absent; or $Q'$ is selected from any structure of (a-6) to (a-18), as defined above, L and $Z^1$ are absent, $L^2$ is a linker and $Z^2$ is an E3 ubiquitin ligase binding group.

In one embodiment, $L^2$ is a linker, $Z^2$ is an E3 ubiquitin ligase binding group, $Q^1$ is absent or hydrogen, $L^1$ is absent and $Z^1$ is absent.

In one preferred embodiment, L or $L^2$ is an unsubstituted or substituted C1-C20 hydrocarbon chain, optionally wherein one or more carbon chain atoms of the hydrocarbon chain are independently replaced with —C(=O)—, —O—, —$NR^{10}$—, —S— and/or a heterocyclic group; wherein $R^{10}$ is selected from hydrogen and C1-C3 alkyl; and wherein preferably said heterocyclic group is selected from piperidinyl, piperidinylene, piperazinyl, and piperazinylene.

In one further or also or alternatively preferred embodiment, L or $L^2$ is independently selected from any structure of (b-1) to (b-44) of Group B, as defined herein:

Group B (b-1)

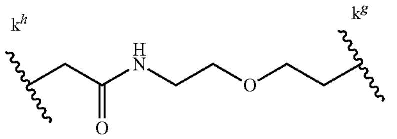

(b-2)

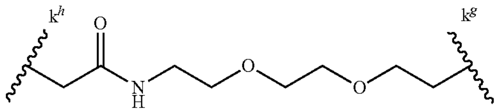

(b-3)

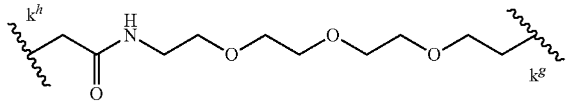

(b-4)

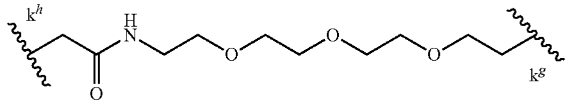

(b-5)

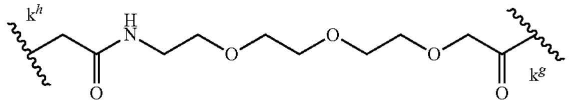

(b-6)

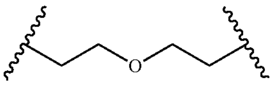

(b-7)

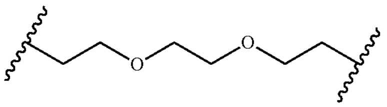

(b-8)

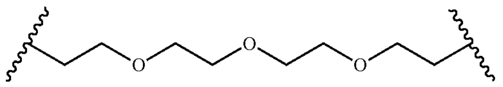

(b-9)

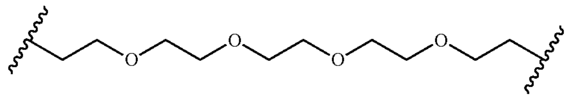

(b-10)

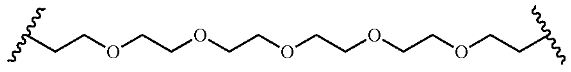

(b-11)

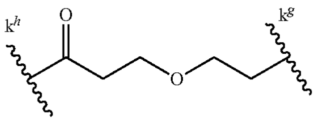

(b-12)

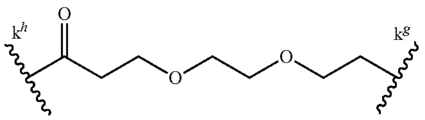

-continued
(b-13)
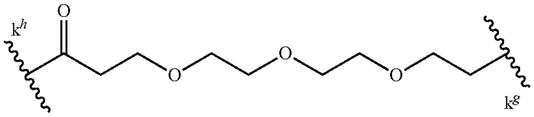
(b-14)
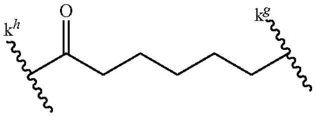
(b-15)
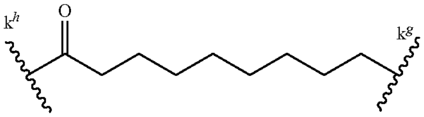
(b-16)
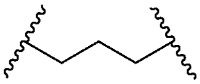
(b-17)
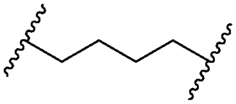
(b-18)
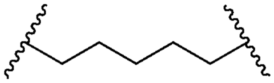
(b-19)
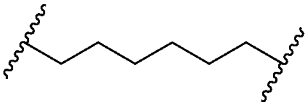
(b-20)
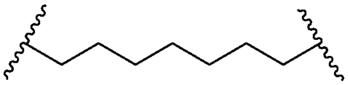
(b-21)
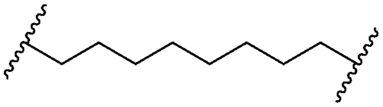
(b-22)
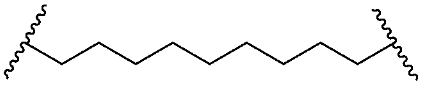
(b-23)
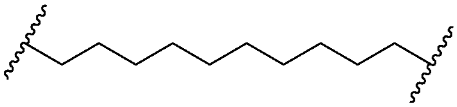
(b-24)
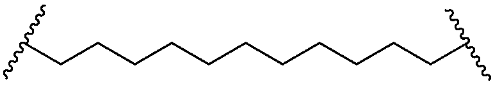
(b-25)
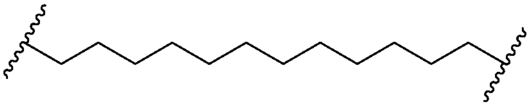
-continued
(b-26)
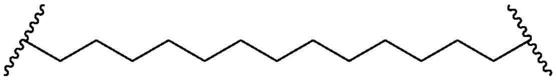
(b-27)
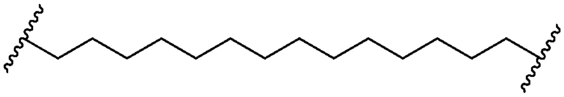
(b-28)
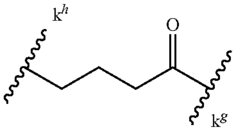
(b-29)
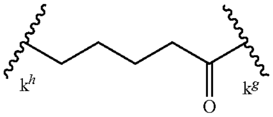
(b-30)
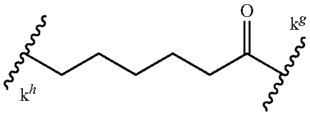
(b-31)
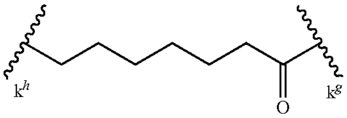
(b-32)
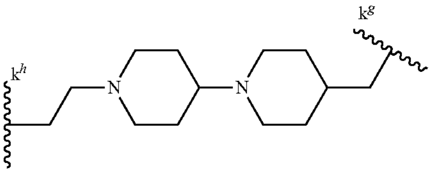
(b-33)
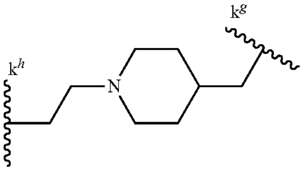
(b-34)
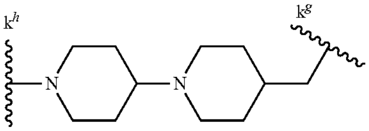
(b-35)
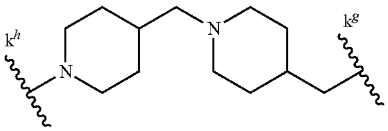
(b-36)
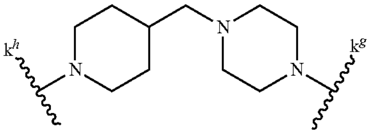

-continued (b-37)

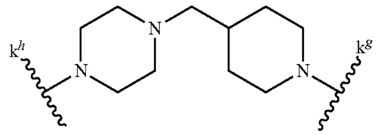

(b-38)

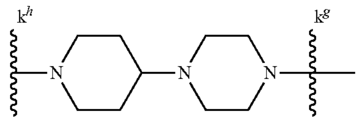

(b-39)

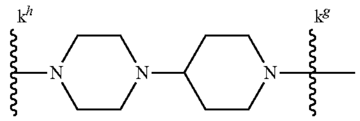

(b-40)

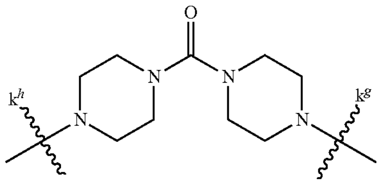

(b-41)

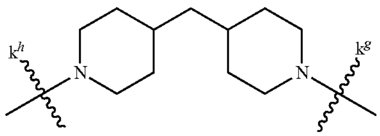

(b-42)

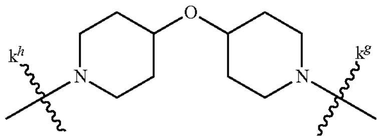

(b-43)

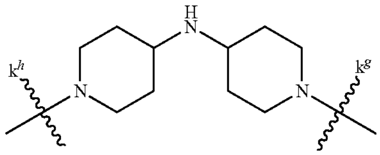

(b-44)

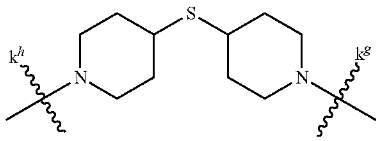

wherein kg indicates the point of attachment to Q, or Y; If $Q^1$ is absent, then kg indicates the point of attachment to $P^1$ or Y; and wherein if $Q^1$ and $P^1$ is absent, then k indicates the point of attachment to an aromatic ring, e.g. isoquinoline, or Y;

wherein $k^h$ indicates the point of attachment to $Z^1$ or $Z^2$.

In one preferred embodiment, $Z^1$ or $Z^2$ is an E3 ubiquitin ligase binding group which binds to von Hippel-Landau tumor suppressor protein (VHL).

In one particularly preferred embodiment, $Z^1$ or $Z^2$ is selected from any structure of (c-1) to (c-6) of Group C;

Group C (c-1)

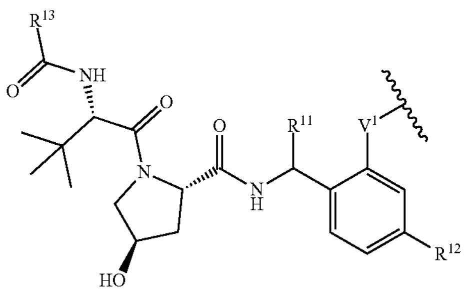

(c-2)

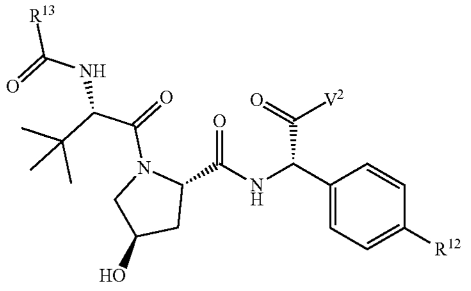

(c-3)

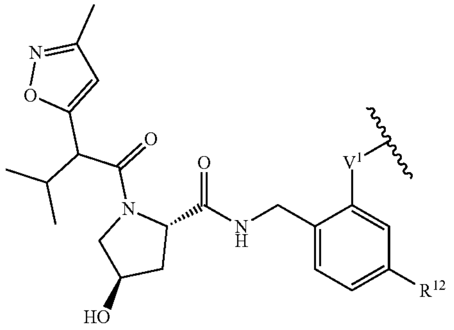

(c-4)

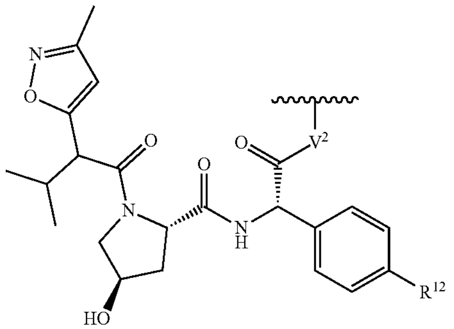

(c-5)

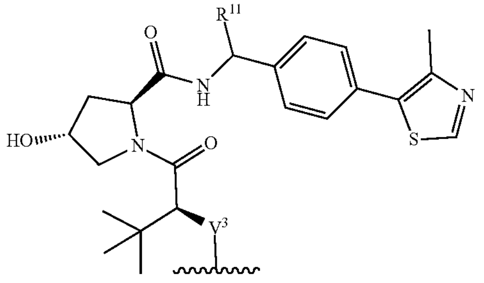

-continued (c-6)

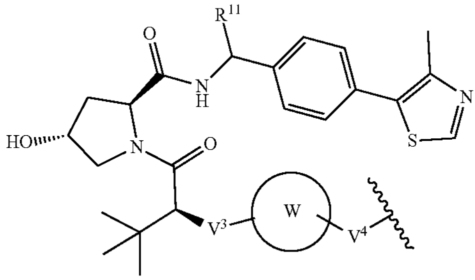

wherein $R^{11}$ is hydrogen or C1-C3 alkyl;

$R^{12}$ is selected from hydrogen, halogen, —C≡CH, —CN, heteroaryl and heteroaryl substituted with C1-C3 alkyl;

$R^{13}$ is selected from hydrogen, C1-C3 alkyl, C1-C3 haloalkyl, C3-C6 cycloalkyl and C3-C6 cycloalkyl substituted with halogen, C1-C3 alkyl, —C(═O)$CH_3$ and —NHC(═O)$CH_3$;

$V^1$ is absent or selected from —NH—, —$CH_2$NH—, —O—, —$CH_2$O—, —C(═O)O—, —O(C═O)—, —C(═O)NH— and —NH(C═O)—;

$V^2$ is absent or selected from —NH— and —O—;

W is selected from C3-C6 cycloalkyl, aryl, heteroaryl and heterocyclyl;

$V^3$ and $V^4$ are, at each occurrence, either absent or independently selected from —NH—, —$CH_2$NH—, —NH$CH_2$—, —O—, —$CH_2$O—, —O$CH_2$—, —C(═O)O—, —O(C═O)—, —C(═O)NH— and —NH(C═O)—.

In one preferred embodiment, $Z^1$ or $Z^2$ is an E3 ubiquitin ligase binding group which binds to cereblon (CRBN).

In one particularly preferred embodiment, $Z^1$ or $Z^2$ is selected from any structure of Group D;

Group D (d-1)

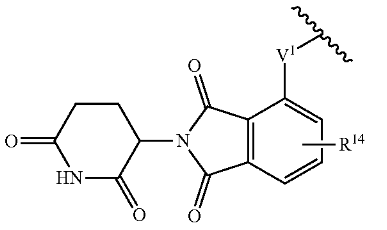

(d-2)

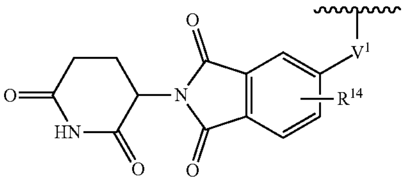

(d-3)

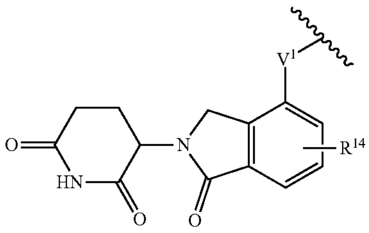

-continued (d-4)

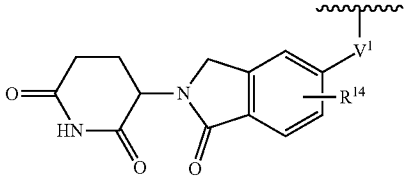

wherein $V^1$ is absent or selected from —NH—, —$CH_2$NH—, —O—, —$CH_2$O—, —C(═O)O—, —O(C═O)—, —C(═O)NH— and —NH(C═O)—.

$R^{14}$ is selected from hydrogen, halogen, and C1-C3 alkyl, wherein, preferably, $R^{14}$ is hydrogen or fluorine;

In one preferred embodiment, $Z^1$ or $Z^2$ is an E3 ubiquitin ligase binding group which binds to an inhibitor of apoptosis protein (IAP).

In one particularly preferred embodiment, $Z^1$ or $Z^2$ is any structure of Group E;

Group E (e-1)

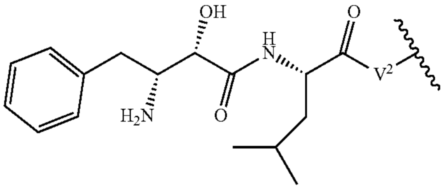

(e-2)

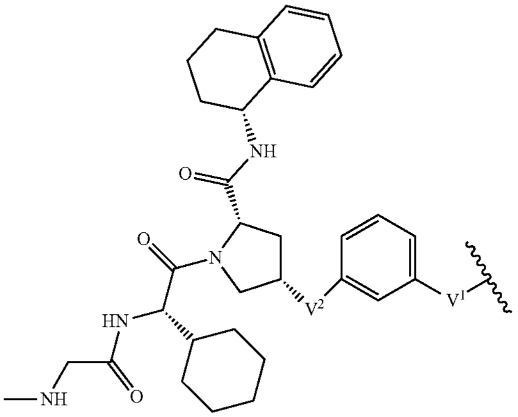

(e-3)

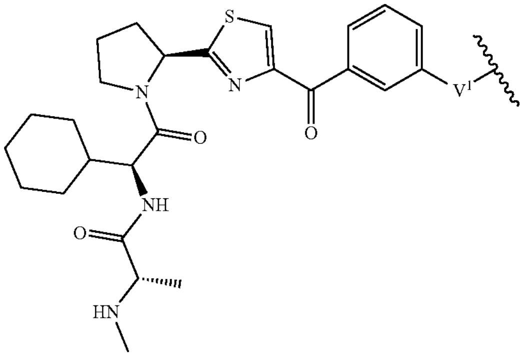

-continued
(e-4)
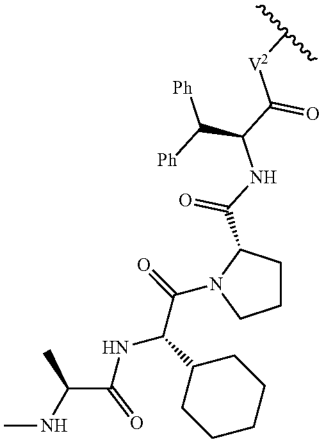
wherein $V^1$ is absent or selected from —NH—, —$CH_2$NH—, —O—, —$CH_2$O—, —C(═O)O—, —O(C═O)—, —C(═O)NH— and —NH(C═O)—; and wherein $V^2$ is absent or selected from —NH— and —O—.
In one embodiment, the compound has one of the structures 1-36, as defined in the following table:
| Cpd. No. | Structure |
|---|---|
| 1 | 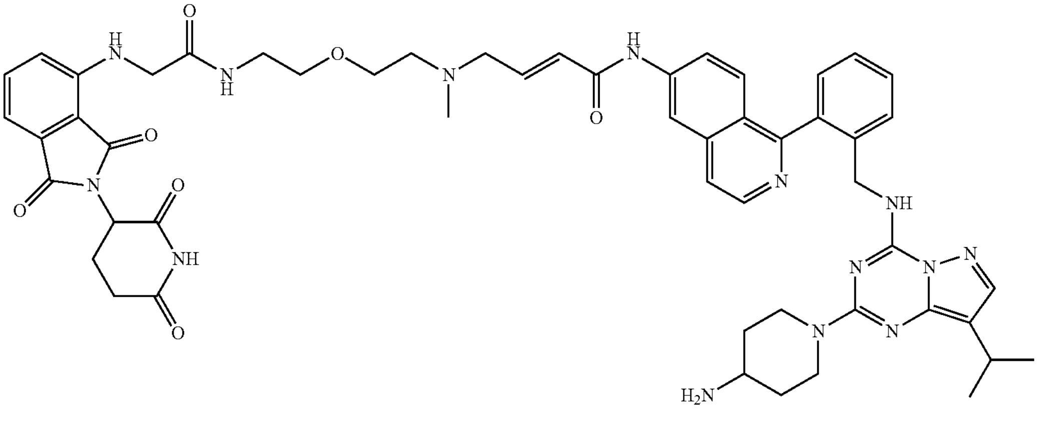 [SMILES: CC(C)c1cnn2c(NCc3ccccc3-c3nccc4cc(NC(=O)/C=C/CN(C)CCOCCNC(=O)CNc5cccc6c5C(=O)N(C5CCC(=O)NC5=O)C6=O)ccc34)nc(N3CCC(N)CC3)nc12] |
| 2 | 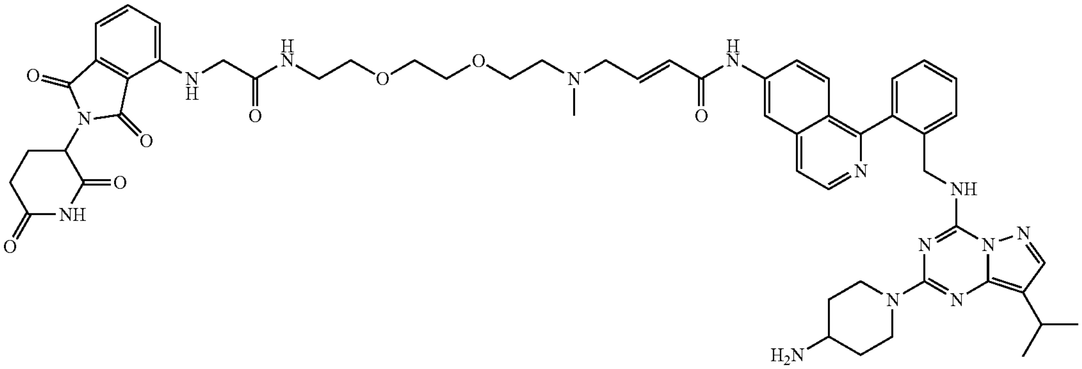 [SMILES: CC(C)c1cnn2c(NCc3ccccc3-c3nccc4cc(NC(=O)/C=C/CN(C)CCOCCOCCNC(=O)CNc5cccc6c5C(=O)N(C5CCC(=O)NC5=O)C6=O)ccc34)nc(N3CCC(N)CC3)nc12] |

-continued
| Cpd. No. | Structure |
|---|---|
| 3 | 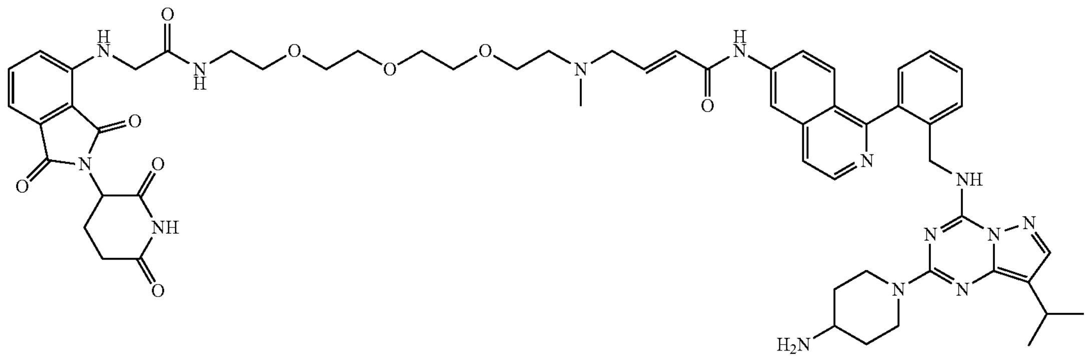 [SMILES: CC(C)c1cnn2c(NCc3ccccc3-c3nccc4cc(NC(=O)/C=C/CN(C)CCOCCOCCOCCNC(=O)CNc5cccc6c5C(=O)N(C5CCC(=O)NC5=O)C6=O)ccc34)nc(N3CCC(N)CC3)nc12] |
| 4 | 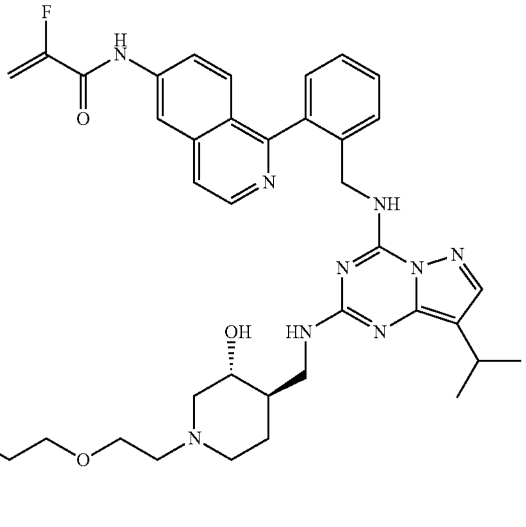 |
| 5 | 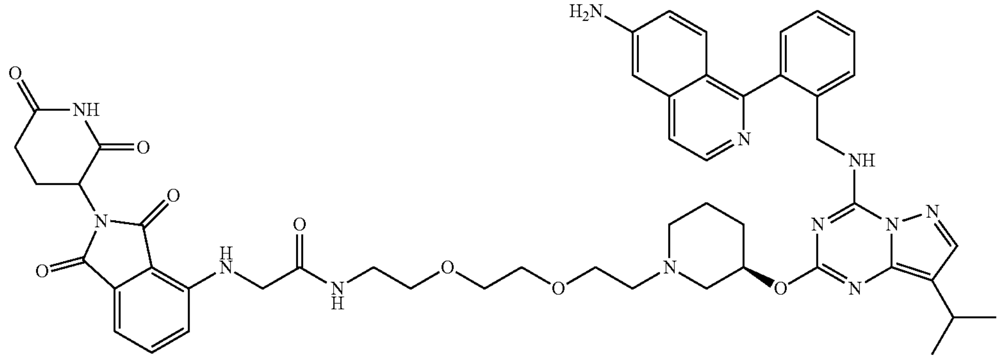 [SMILES: CC(C)c1cnn2c(NCc3ccccc3-c3nccc4cc(N)ccc34)nc(O[C@@H]3CCCN(CCOCCOCCNC(=O)CNc4cccc5c4C(=O)N(C4CCC(=O)NC4=O)C5=O)C3)nc12] |

-continued
| Cpd. No. | Structure |
| --- | --- |
| 6 | 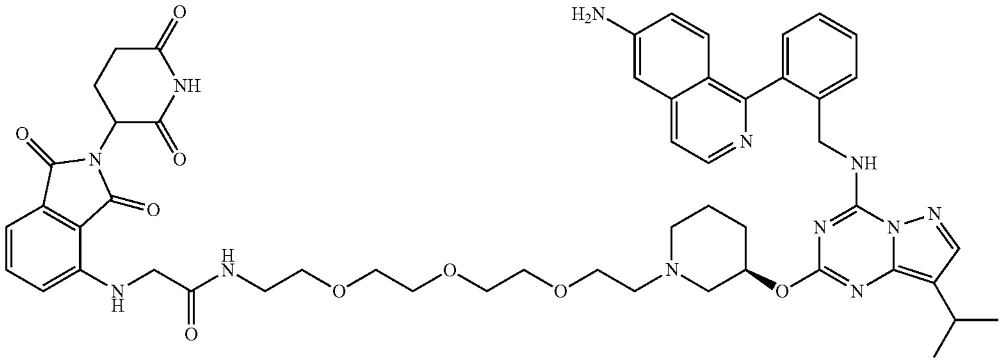 [SMILES: CC(C)c1cnn2c(NCc3ccccc3-c3nccc4cc(N)ccc34)nc(O[C@@H]3CCCN(CCOCCOCCOCCNC(=O)CNc4cccc5c4C(=O)N(C4CCC(=O)NC4=O)C5=O)C3)nc12] |
| 7 | 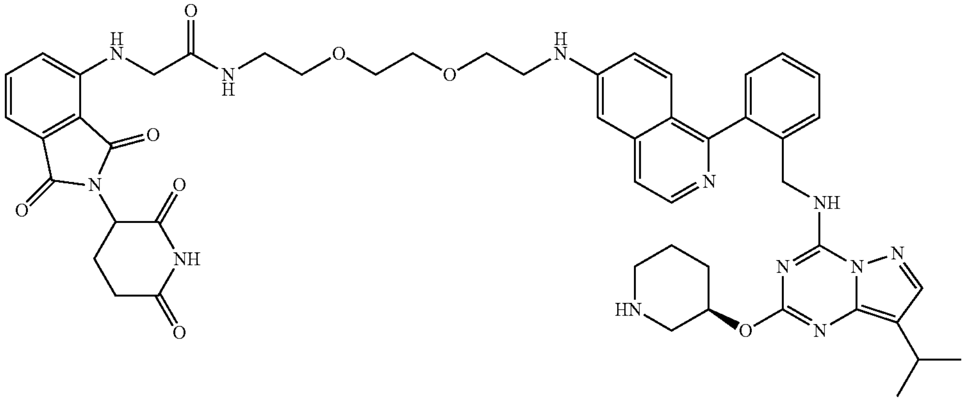 [SMILES: CC(C)c1cnn2c(NCc3ccccc3-c3nccc4cc(NCCOCCOCCNC(=O)CNc5cccc6c5C(=O)N(C5CCC(=O)NC5=O)C6=O)ccc34)nc(O[C@@H]3CCCNC3)nc12] |
| 8 | 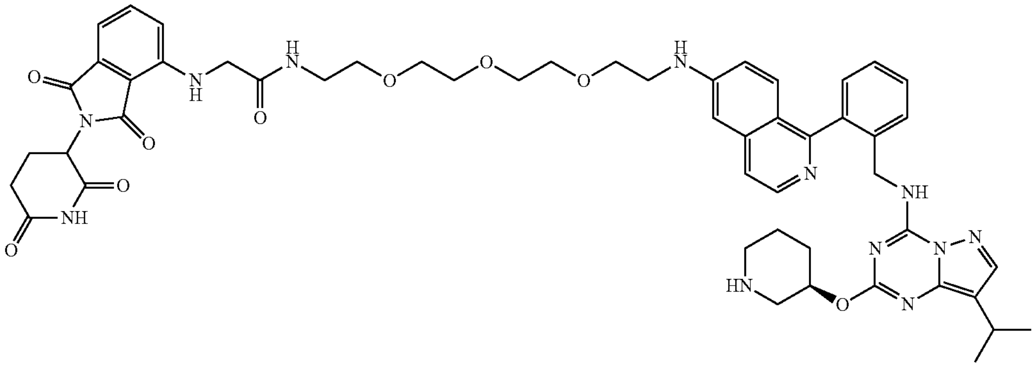 [SMILES: CC(C)c1cnn2c(NCc3ccccc3-c3nccc4cc(NCCOCCOCCOCCNC(=O)CNc5cccc6c5C(=O)N(C5CCC(=O)NC5=O)C6=O)ccc34)nc(O[C@@H]3CCCNC3)nc12] |
| 9 | 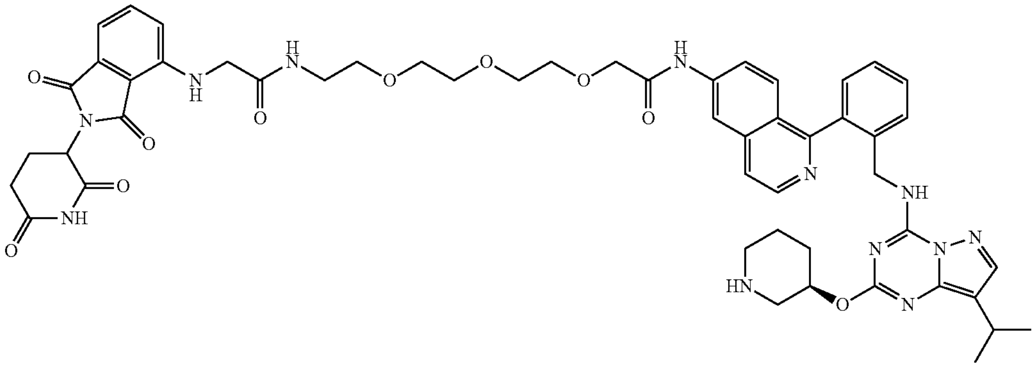 [SMILES: CC(C)c1cnn2c(NCc3ccccc3-c3nccc4cc(NC(=O)COCCOCCOCCNC(=O)CNc5cccc6c5C(=O)N(C5CCC(=O)NC5=O)C6=O)ccc34)nc(O[C@@H]3CCCNC3)nc12] |

-continued
| Cpd. No. | Structure |
| --- | --- |
| 10 | 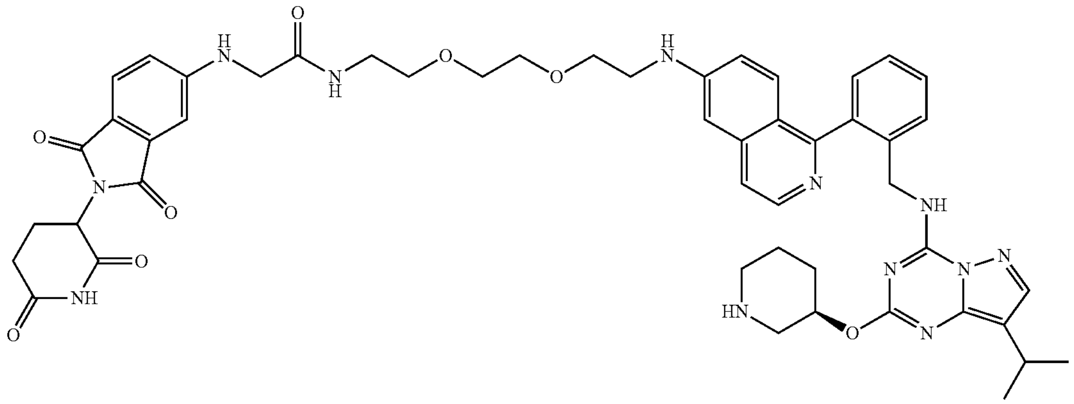 [SMILES: CC(C)c1cnn2c(NCc3ccccc3-c3nccc4cc(NCCOCCOCCNC(=O)CNc5ccc6c(c5)C(=O)N(C5CCC(=O)NC5=O)C6=O)ccc34)nc(O[C@@H]3CCCNC3)nc12] |
| 11 | 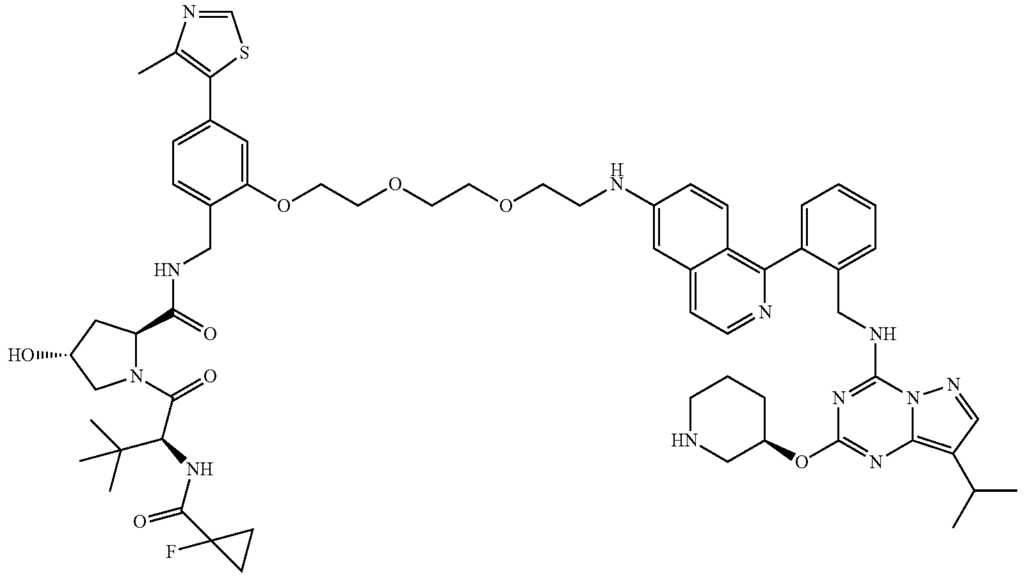 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCNc2ccc3c(-c4ccccc4CNc4nc(O[C@@H]5CCCNC5)nc5c(C(C)C)cnn45)nccc3c2)c1] |
| 12 | 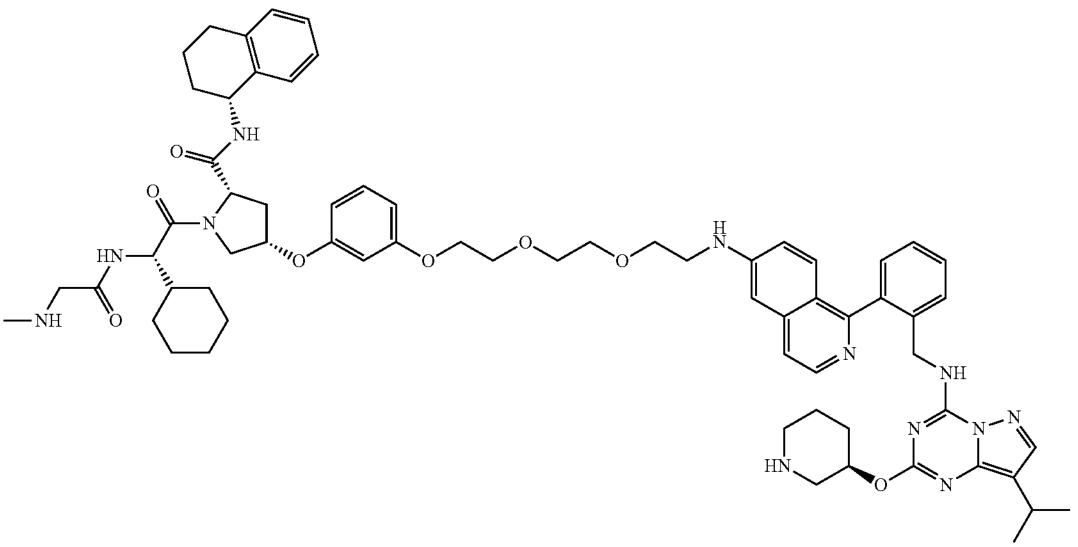 [SMILES: CNCC(=O)N[C@H](C(=O)N1C[C@@H](Oc2cccc(OCCOCCOCCNc3ccc4c(-c5ccccc5CNc5nc(O[C@@H]6CCCNC6)nc6c(C(C)C)cnn56)nccc4c3)c2)C[C@H]1C(=O)N[C@@H]1CCCc2ccccc21)C1CCCCC1] |

-continued
| Cpd. No. | Structure |
| --- | --- |
| 13 | 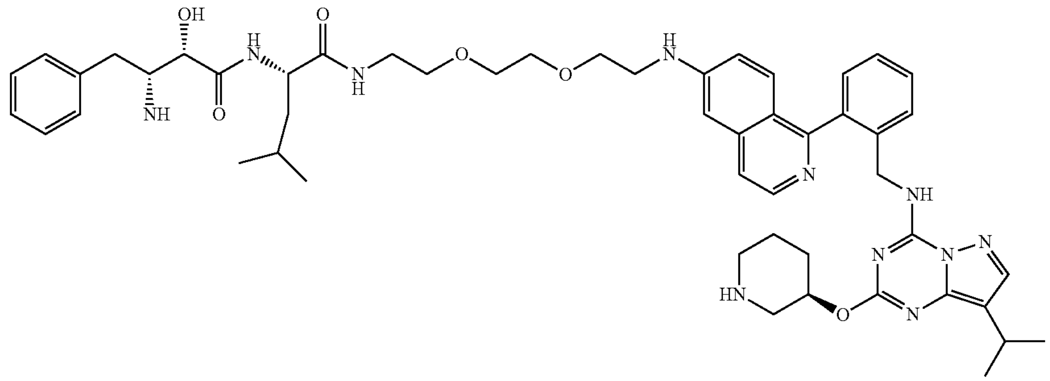 [SMILES: CC(C)C[C@H](NC(=O)[C@@H](O)[C@H](N)Cc1ccccc1)C(=O)NCCOCCOCCNc1ccc2c(-c3ccccc3CNc3nc(O[C@@H]4CCCNC4)nc4c(C(C)C)cnn34)nccc2c1] |
| 14 | 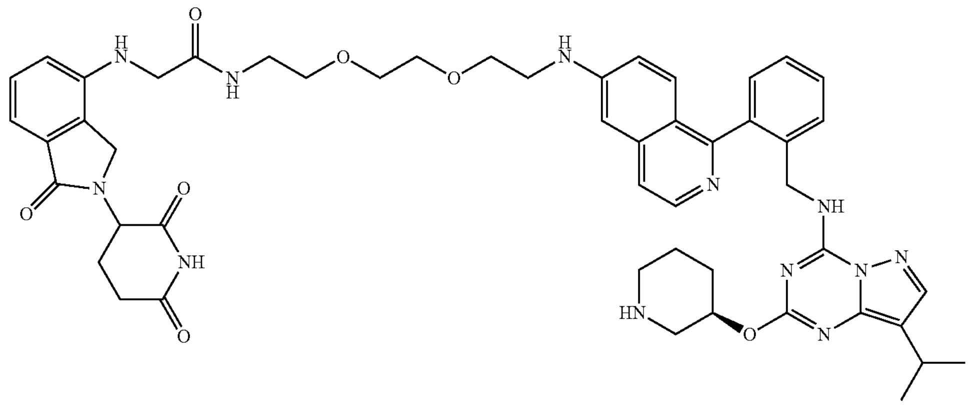 [SMILES: CC(C)c1cnn2c(NCc3ccccc3-c3nccc4cc(NCCOCCOCCNC(=O)CNc5cccc6c5CN(C5CCC(=O)NC5=O)C6=O)ccc34)nc(O[C@@H]3CCCNC3)nc12] |
| 15 | 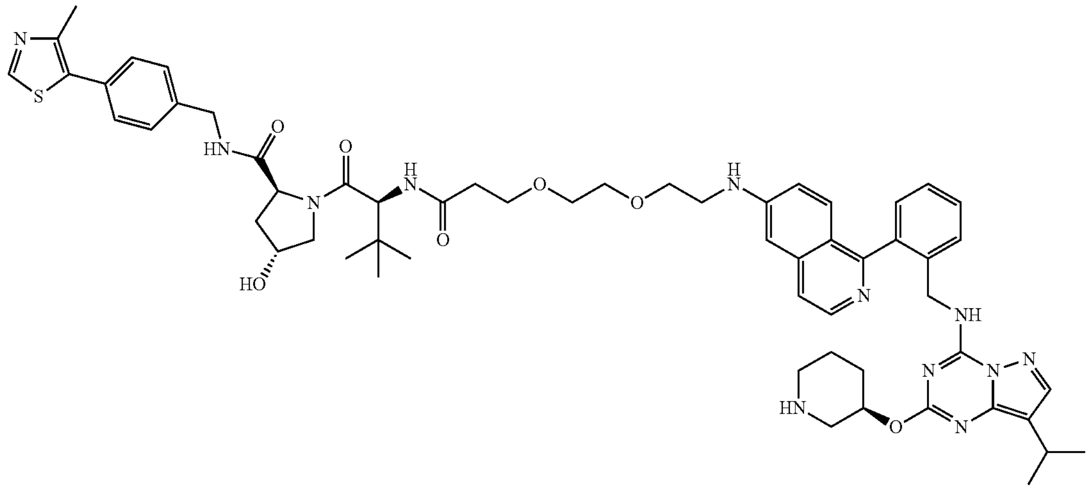 [SMILES: Cc1ncsc1-c1ccc(CNC(=O)[C@@H]2C[C@@H](O)CN2C(=O)[C@@H](NC(=O)CCOCCOCCNc2ccc3c(-c4ccccc4CNc4nc(O[C@@H]5CCCNC5)nc5c(C(C)C)cnn45)nccc3c2)C(C)(C)C)cc1] |

-continued
| Cpd. No. | Structure |
| --- | --- |
| 16 | 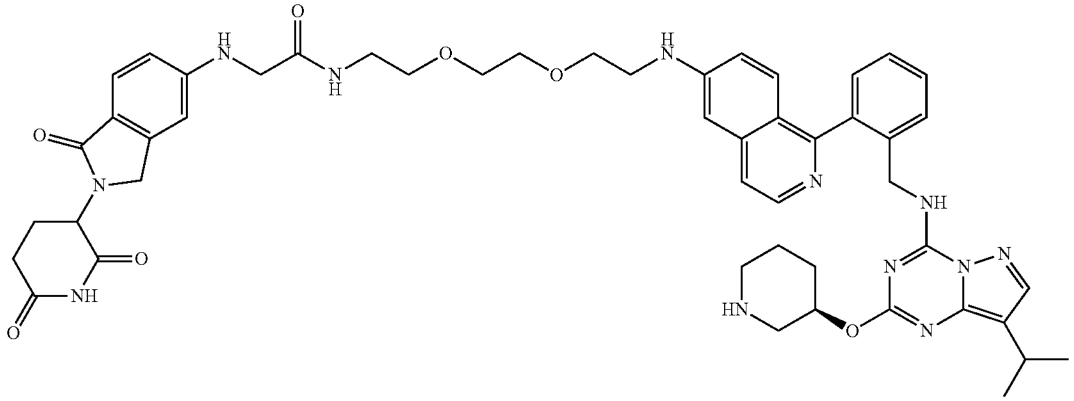 [SMILES: CC(C)c1cnn2c(NCc3ccccc3-c3nccc4cc(NCCOCCOCCNC(=O)CNc5ccc6c(c5)CN(C5CCC(=O)NC5=O)C6=O)ccc34)nc(O[C@@H]3CCCNC3)nc12] |
| 17 | 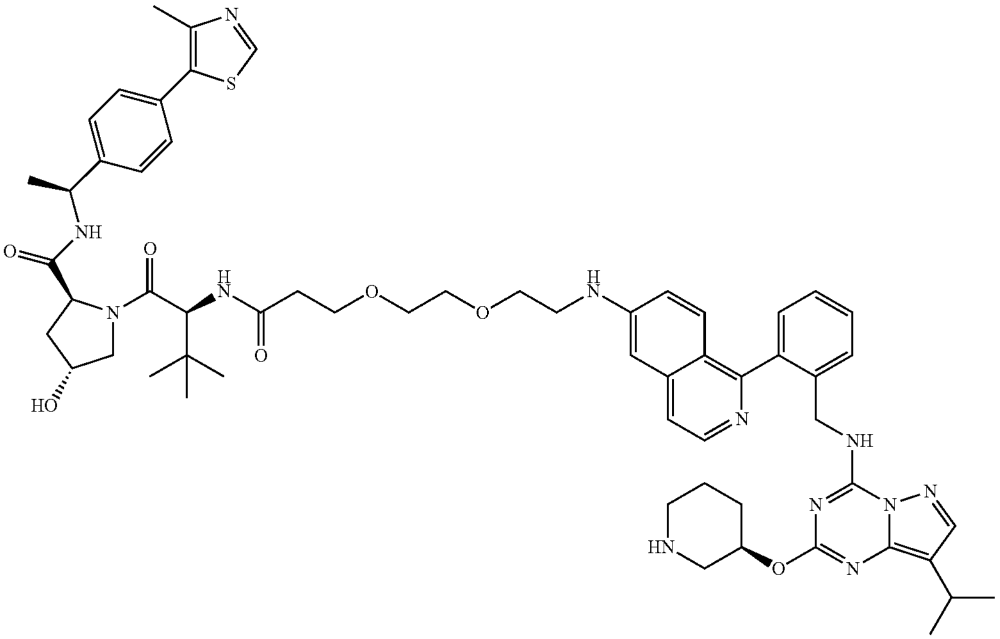 [SMILES: Cc1ncsc1-c1ccc([C@H](C)NC(=O)[C@@H]2C[C@@H](O)CN2C(=O)[C@@H](NC(=O)CCOCCOCCNc2ccc3c(-c4ccccc4CNc4nc(O[C@@H]5CCCNC5)nc5c(C(C)C)cnn45)nccc3c2)C(C)(C)C)cc1] |
| 18 | 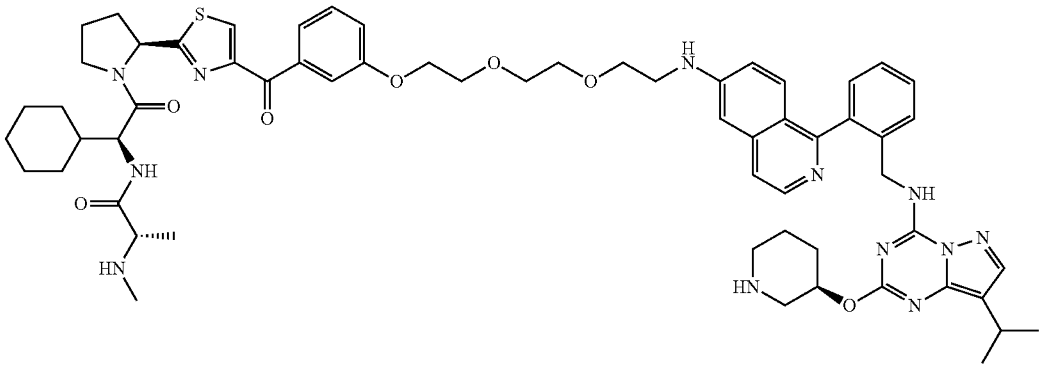 [SMILES: CN[C@@H](C)C(=O)N[C@H](C(=O)N1CCC[C@H]1c1nc(C(=O)c2cccc(OCCOCCOCCNc3ccc4c(-c5ccccc5CNc5nc(O[C@@H]6CCCNC6)nc6c(C(C)C)cnn56)nccc4c3)c2)cs1)C1CCCCC1] |

-continued
| Cpd. No. | Structure |
| --- | --- |
| 19 | 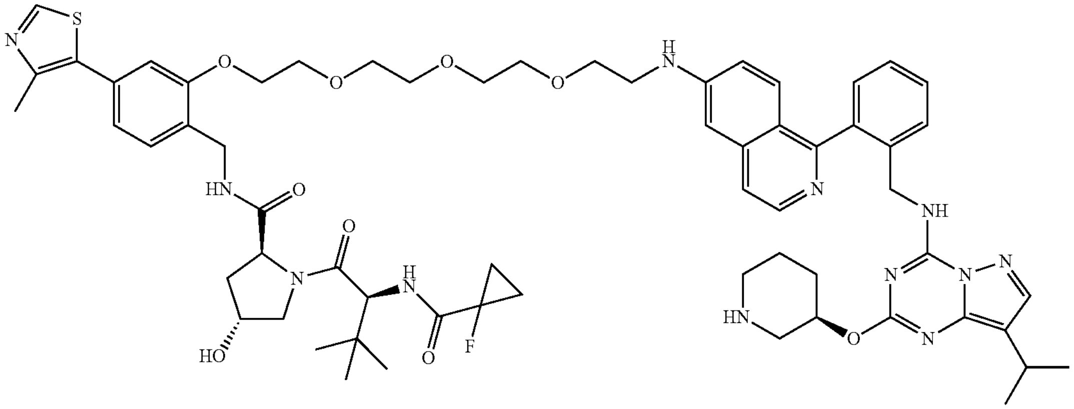 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCNc2ccc3c(-c4ccccc4CNc4nc(O[C@@H]5CCCNC5)nc5c(C(C)C)cnn45)nccc3c2)c1] |
| 20 | 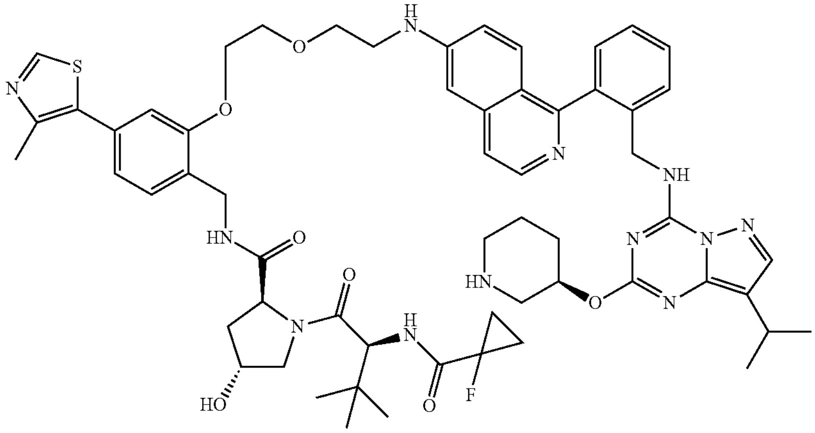 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCNc2ccc3c(-c4ccccc4CNc4nc(O[C@@H]5CCCNC5)nc5c(C(C)C)cnn45)nccc3c2)c1] |
| 21 | 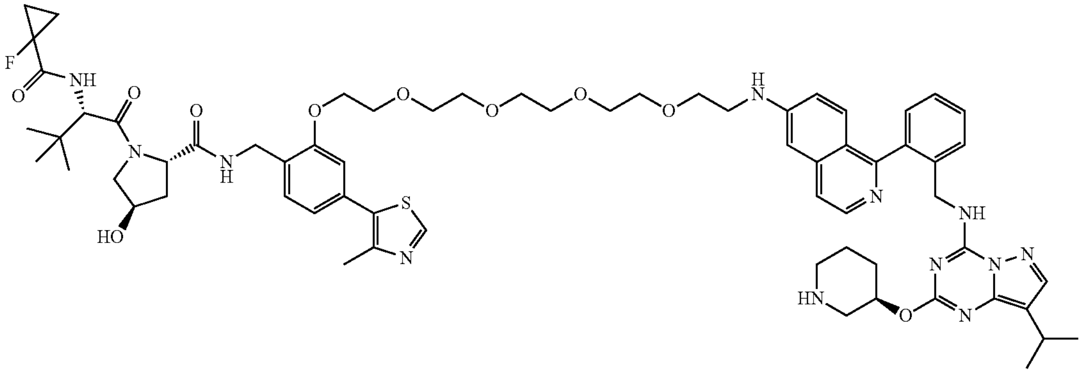 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCNc2ccc3c(-c4ccccc4CNc4nc(O[C@@H]5CCCNC5)nc5c(C(C)C)cnn45)nccc3c2)c1] |

-continued
| Cpd. No. | Structure |
|---|---|
| 22 | 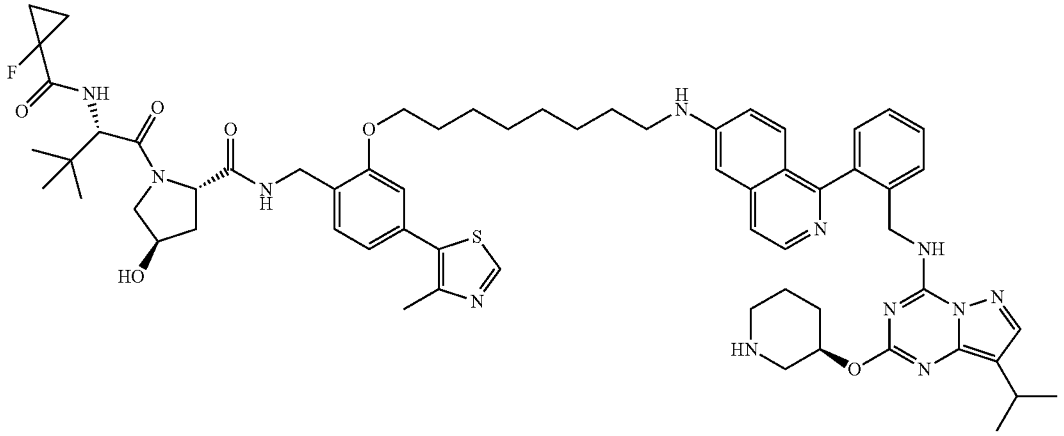 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCCNc2ccc3c(-c4ccccc4CNc4nc(O[C@@H]5CCCNC5)nc5c(C(C)C)cnn45)nccc3c2)c1] |
| 23 | 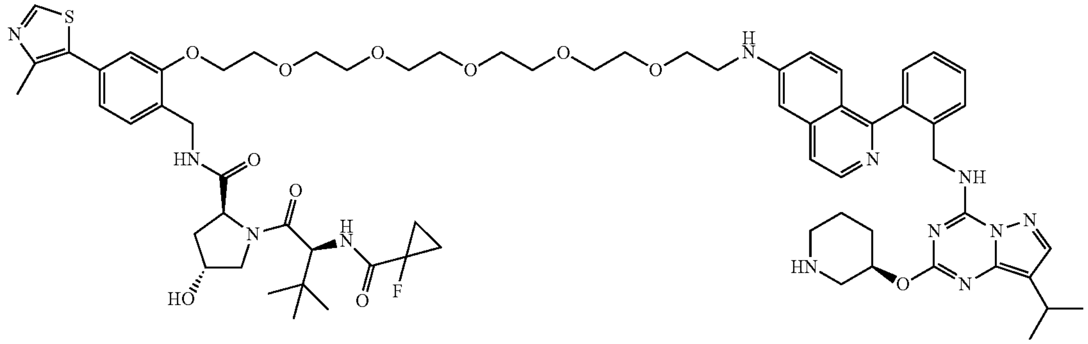 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCOCCNc2ccc3c(-c4ccccc4CNc4nc(O[C@@H]5CCCNC5)nc5c(C(C)C)cnn45)nccc3c2)c1] |
| 24 | 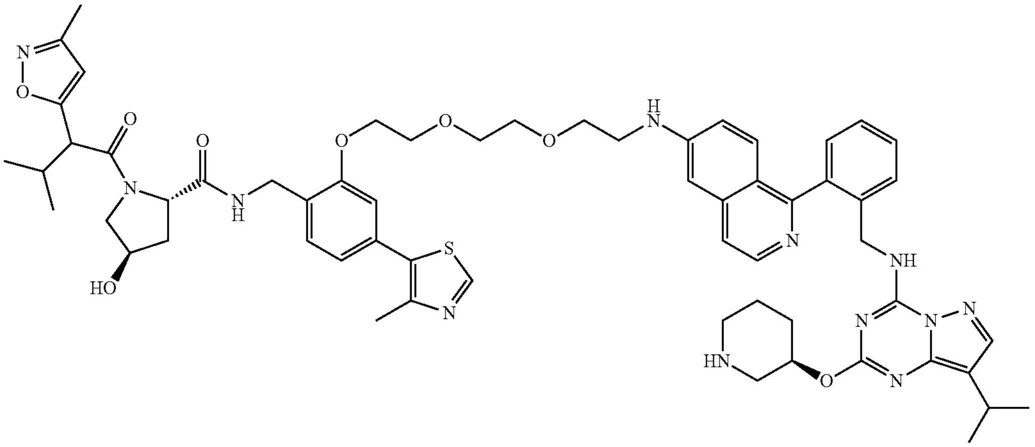 [SMILES: Cc1cc(C(C(=O)N2C[C@H](O)C[C@H]2C(=O)NCc2ccc(-c3scnc3C)cc2OCCOCCOCCNc2ccc3c(-c4ccccc4CNc4nc(O[C@@H]5CCCNC5)nc5c(C(C)C)cnn45)nccc3c2)C(C)C)on1] |

-continued
| Cpd. No. | Structure |
|---|---|
| 25 | 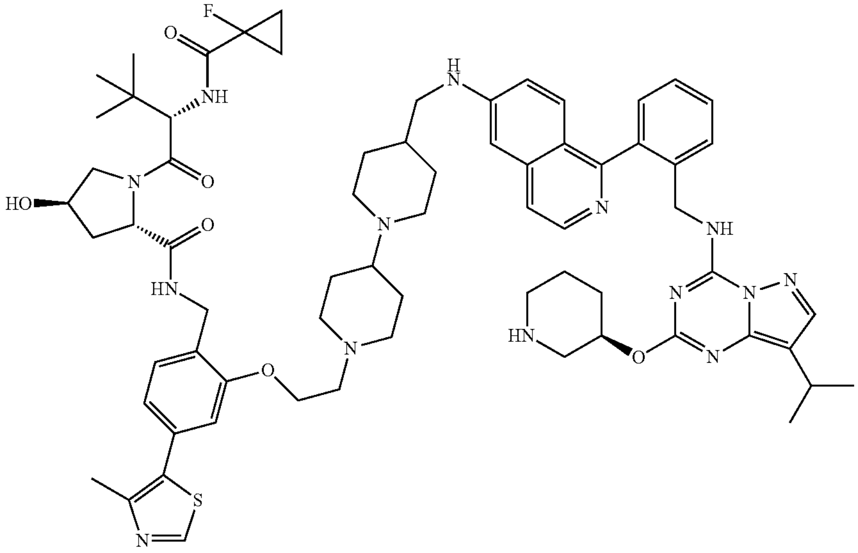 [SMILES: Cc1ncsc1-c1ccc(CNC(=O)[C@@H]2C[C@@H](O)CN2C(=O)[C@@H](NC(=O)C2(F)CC2)C(C)(C)C)c(OCCN2CCC(N3CCC(CNc4ccc5c(-c6ccccc6CNc6nc(O[C@@H]7CCCNC7)nc7c(C(C)C)cnn67)nccc5c4)CC3)CC2)c1] |
| 26 | 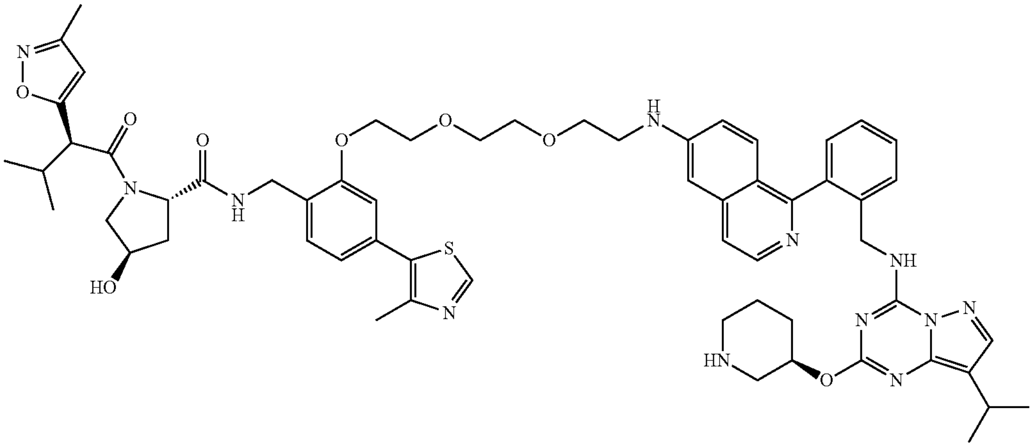 [SMILES: Cc1cc([C@@H](C(=O)N2C[C@H](O)C[C@H]2C(=O)NCc2ccc(-c3scnc3C)cc2OCCOCCOCCNc2ccc3c(-c4ccccc4CNc4nc(O[C@@H]5CCCNC5)nc5c(C(C)C)cnn45)nccc3c2)C(C)C)on1] |
| 27 | 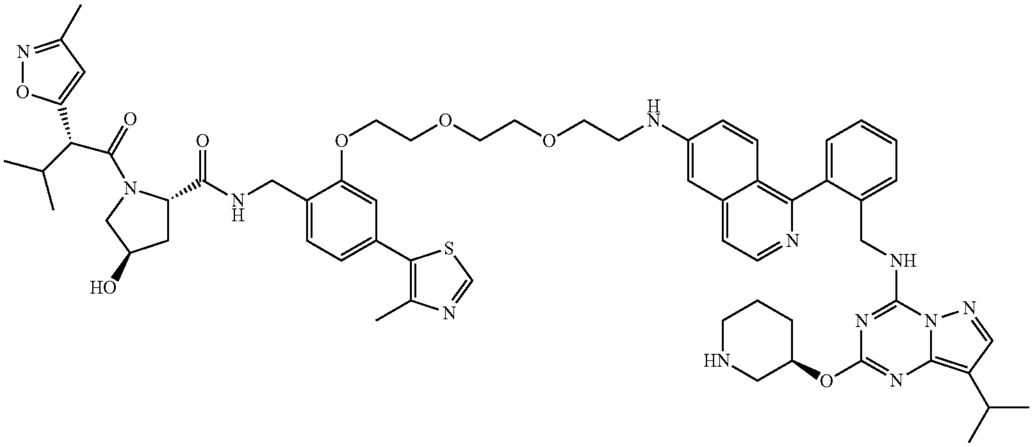 [SMILES: Cc1cc([C@H](C(=O)N2C[C@H](O)C[C@H]2C(=O)NCc2ccc(-c3scnc3C)cc2OCCOCCOCCNc2ccc3c(-c4ccccc4CNc4nc(O[C@@H]5CCCNC5)nc5c(C(C)C)cnn45)nccc3c2)C(C)C)on1] |

-continued
| Cpd. No. | Structure |
| --- | --- |
| 28 | 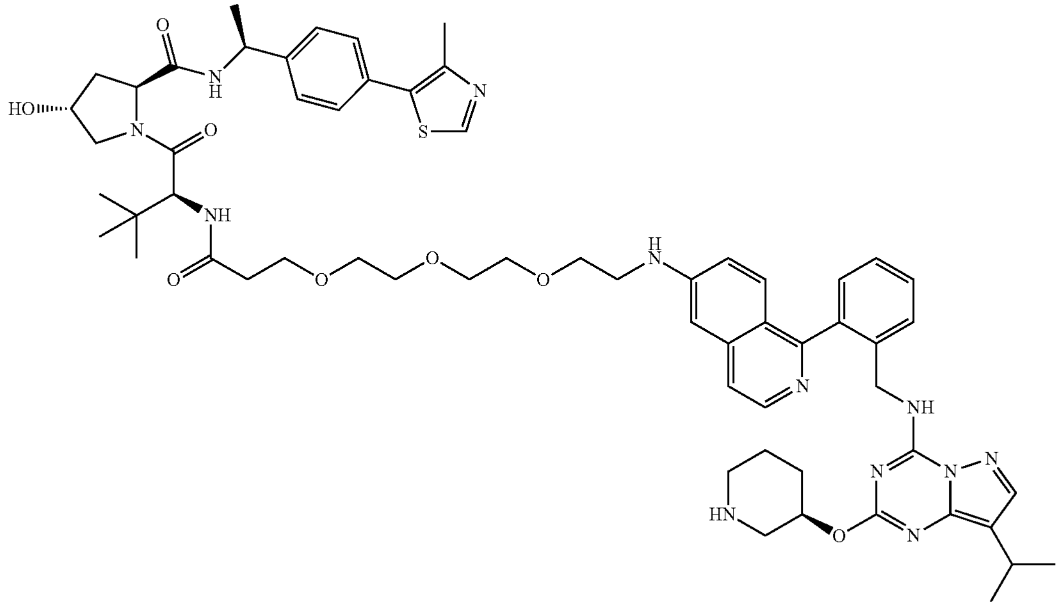 [SMILES: Cc1ncsc1-c1ccc([C@H](C)NC(=O)[C@@H]2C[C@@H](O)CN2C(=O)[C@@H](NC(=O)CCOCCOCCOCCNc2ccc3c(-c4ccccc4CNc4nc(O[C@@H]5CCCNC5)nc5c(C(C)C)cnn45)nccc3c2)C(C)(C)C)cc1] |
| 29 | 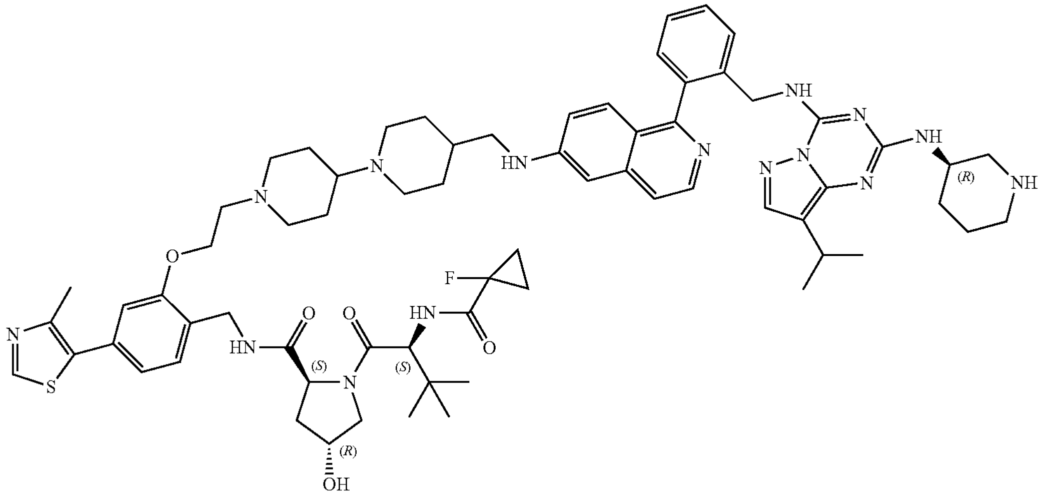 |
| 30 | 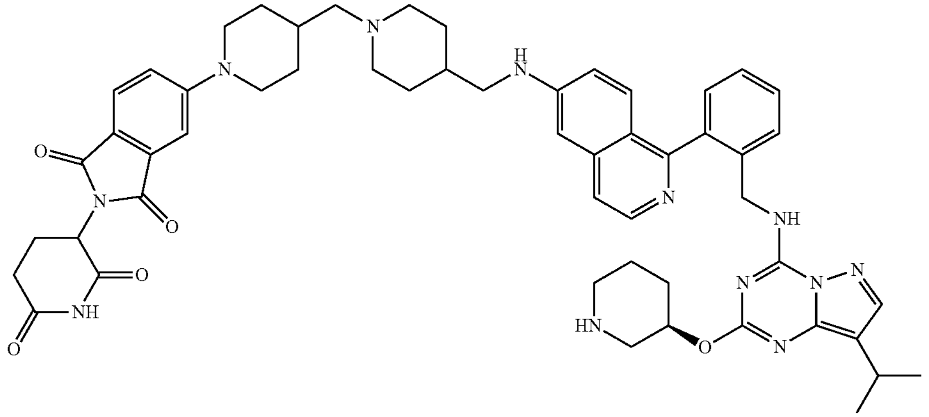 [SMILES: CC(C)c1cnn2c(NCc3ccccc3-c3nccc4cc(NCC5CCN(CC6CCN(c7ccc8c(c7)C(=O)N(C7CCC(=O)NC7=O)C8=O)CC6)CC5)ccc34)nc(O[C@@H]3CCCNC3)nc12] |

-continued
| Cpd. No. | Structure |
|---|---|
| 31 | 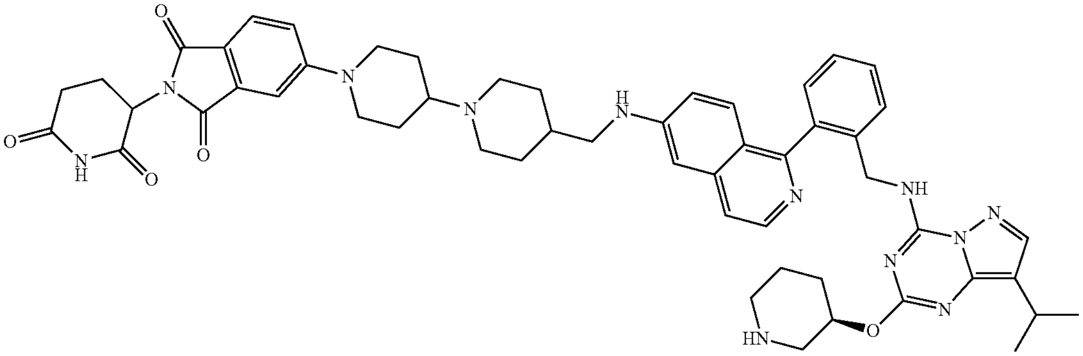 [SMILES: CC(C)c1cnn2c(NCc3ccccc3-c3nccc4cc(NCC5CCN(C6CCN(c7ccc8c(c7)C(=O)N(C7CCC(=O)NC7=O)C8=O)CC6)CC5)ccc34)nc(O[C@@H]3CCCNC3)nc12] |
| 32 | 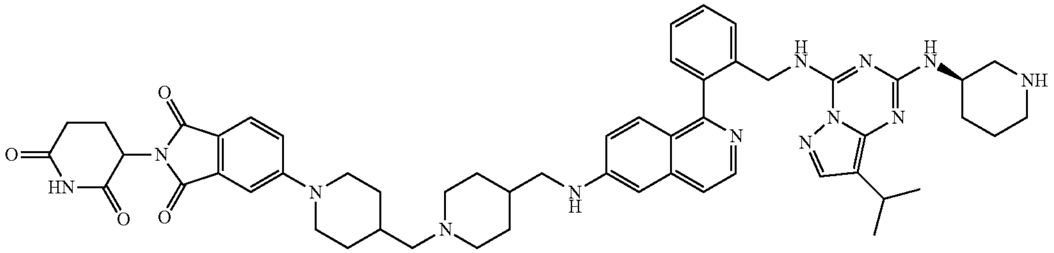 [SMILES: CC(C)c1cnn2c(NCc3ccccc3-c3nccc4cc(NCC5CCN(CC6CCN(c7ccc8c(c7)C(=O)N(C7CCC(=O)NC7=O)C8=O)CC6)CC5)ccc34)nc(N[C@@H]3CCCNC3)nc12] |
| 33 | 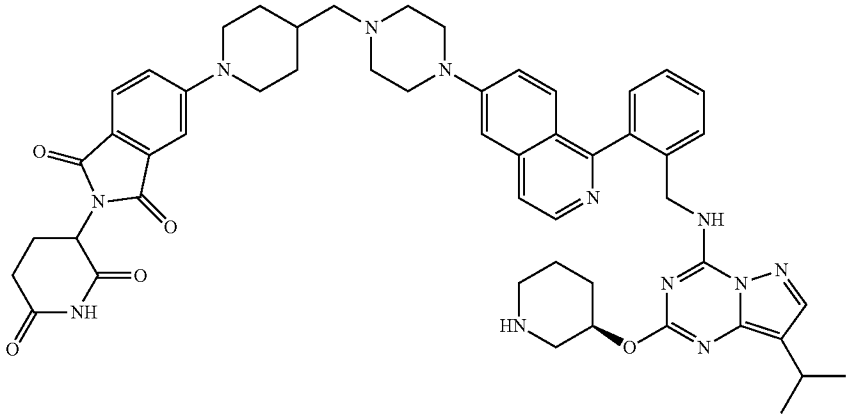 [SMILES: CC(C)c1cnn2c(NCc3ccccc3-c3nccc4cc(N5CCN(CC6CCN(c7ccc8c(c7)C(=O)N(C7CCC(=O)NC7=O)C8=O)CC6)CC5)ccc34)nc(O[C@@H]3CCCNC3)nc12] |
| 34 | 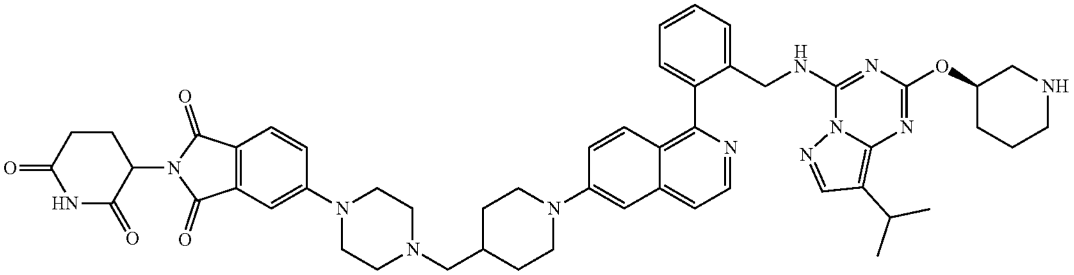 [SMILES: CC(C)c1cnn2c(NCc3ccccc3-c3nccc4cc(N5CCC(CN6CCN(c7ccc8c(c7)C(=O)N(C7CCC(=O)NC7=O)C8=O)CC6)CC5)ccc34)nc(O[C@@H]3CCCNC3)nc12] |

-continued

| Cpd. No. | Structure |
|---|---|
| 35 | 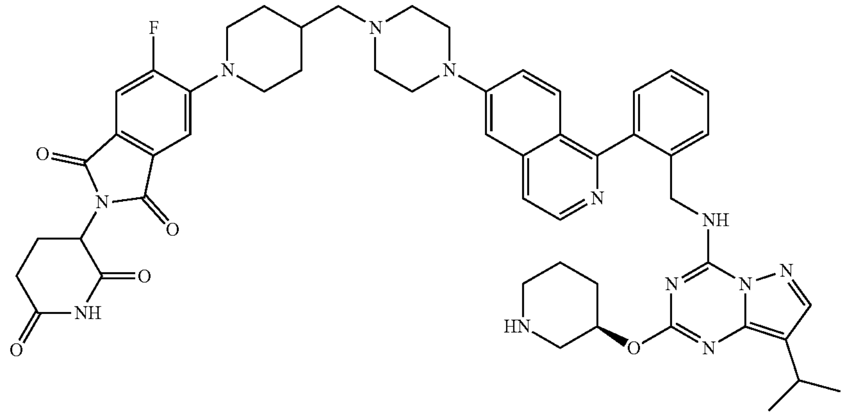 [SMILES: CC(C)c1cnn2c(NCc3ccccc3-c3nccc4cc(N5CCN(CC6CCN(c7cc8c(cc7F)C(=O)N(C7CCC(=O)NC7=O)C8=O)CC6)CC5)ccc34)nc(O[C@@H]3CCCNC3)nc12] |
| 36 | 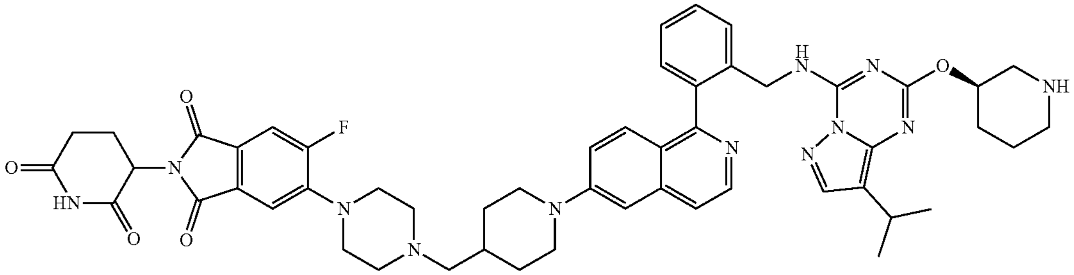 |

In a further aspect, the present invention also relates to a pharmaceutical composition comprising a compound according to the present invention as an active ingredient, together with at least one pharmaceutically acceptable carrier, excipient and/or diluent.

In a further aspect, the present invention also relates to a compound according to the present invention or a pharmaceutical composition according to the present invention, for use in a method of prevention and/or treatment of a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases.

In one embodiment, the proliferative disease is a cancer, preferably a cancer selected from the group comprising or consisting of: adenocarcinoma, choroidal melanoma, acute leukemia, acoustic neurinoma, ampullary carcinoma, anal carcinoma, astrocytoma, basal cell carcinoma, pancreatic cancer, Desmoid tumor, bladder cancer, bronchial carcinoma, estrogen dependent and independent breast cancer, Burkitt's lymphoma, corpus cancer, Carcinoma unknown primary tumor (CUP-syndrome), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic tumor, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymphomas, stomach cancer, malignant melanoma, malignant neoplasia, malignant tumors gastrointestinal tract, breast carcinoma, rectal cancer, medulloblastomas, melanoma, meningiomas, Hodgkin's/Non-Hodgkin's lymphoma, mycosis fungoides, nasal cancer, neurinoma, neuroblastoma, kidney cancer, renal cell carcinomas, oligodendroglioma, esophageal carcinoma, osteolytic carcinomas and osteoplastic carcinomas, osteosarcomas, ovarian carcinoma, pancreatic carcinoma, penile cancer, plasmacytoma, prostate cancer, pharyngeal cancer, rectal carcinoma, retinoblastoma, vaginal cancer, thyroid carcinoma, esophageal cancer, T-cell lymphoma, thymoma, tube carcinoma, eye tumors, urethral cancer, urologic tumors, urothelial carcinoma, vulva cancer, wart appearance, soft tissue tumors, soft tissue sarcoma, Nephroblastoma, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypothalamic glioma, cerebellar astrocytoma, cerebral astrocytoma, neuroectodermal tumor, pineal tumors, sarcoma of the uterus, salivary gland cancers, anal gland adenocarcinomas, mast cell tumors, pelvis tumor, ureter tumor, hereditary papillary renal cancers, sporadic papillary renal cancers, intraocular melanoma, hepatocellular carcinoma, cholangiocarcinoma, mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-cell lymphoma, lymphoma of the central nervous system, malignant fibrous histiocytoma, lymph sarcoma, rhabdomyosarcoma, malignant histiocytosis, fibroblastic sarcoma, hemangiosarcoma, hemangiopericytoma, leiomyosarcoma (LMS), canine mammary carcinoma, and feline mammary carcinoma.

In one embodiment, the infectious disease including opportunistic diseases is selected from the group comprising or consisting of AIDS, Adenovirus Infection, Alveolar Hydatid Disease (AHD), Amoebiasis, Angiostrongyliasis, Anisakiasis, Anthrax, Babesiosis, Balantidiasis, *Baylisascaris* Infection, *Bilharzia* (Schistosomiasis), *Blastocystis hominis* Infection, Lyme Borreliosis, Botulism, Brainerd Diarrhea, Brucellosis, Bovine Spongiform Encephalopathy (BSE), Candidiasis, Capillariasis, Chronic Fatigue Syndrome (CFS), Chagas Disease, Chickenpox, *Chlamydia pneumoniae* Infection, Cholera, Chronic Fatigue Syndrome, Creutzfeldt-Jakob Disease (CJD), Clonorchiasis, Cutaneous Larva migrans (CLM), Coccidioidomycosis, Conjunctivitis, Coxsackievirus A16 (Cox A16), Cryptococcal disease, Cryptosporidiosis, West Nile fever, Cyclosporiasis, Neurocysticercosis, Cytomegalovirus Infection, Dengue Fever, *Dipylidium caninum* Infection, Ebola Hemorrhagic Fever (EHF), Alveolar Echinococcosis (AE), Encephalitis, *Entamoeba coli* Infection, *Entamoeba dispar* Infection, *Entamoeba hartmanni* Infection, *Entamoeba polecki* Infection, Pinworm Infection, Enterovirus Infection (Polio/Non-Polio), Epstein Barr Virus Infection, *Escherichia coli* Infection, Foodborne Infection, Aphthae epizooticae, Fungal Dermatitis, Fungal Infections, Gastroenteritis, Group A streptococcal Disease, Group B streptococcal Disease, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis, Lassa Fever, Leishmaniasis, Visceral leishmaniasis (VL), Malaria, Marburg Hemorrhagic Fever, Measles, Meningitis, *Mycobacterium avium* Complex (MAC) Infection, *Naegleria* Infection, Nosocomial Infections, Nonpathogenic Intestinal Amebae Infection, Onchocerciasis, Opisthorchiasis, Papilloma virus Infection, Parvovirus Infection, Plague, *Pneumocystis* Pneumonia (PCP), Polyomavirus Infection, Q Fever, Rabies, Respiratory SyncytialVirus (RSV) Infection, Rheumatic Fever, Rift Valley Fever, Rotavirus Infection, Roundworms Infection, *Salmonellosis*, Scabies, Shigellosis, Shingles, Sleeping Sickness, Smallpox, Streptococcal Infection, Tapeworm Infection, Tetanus, Toxic Shock Syndrome, Tuberculosis, duodenum, *Vibrio parahaemolyticus* Infection, *Vibrio* septicemia, Viral Hemorrhagic Fever, Warts, Waterborne infectious Diseases, Varicella-Zoster Virus infection, Pertussis and Yellow Fever.

In one embodiment, the immunological disease and/or autoimmune disease is selected from the group comprising or consisting of: asthma, diabetes, rheumatic diseases, AIDS, rejection of transplanted organs and tissues, rhinitis, chronic obstructive pulmonary diseases, osteoporosis, ulcerative colitis, sinusitis, lupus erythematosus, recurrent infections, atopic dermatitis/eczema and occupational allergies, food allergies, drug allergies, severe anaphylactic reactions, anaphylaxis, manifestations of allergic diseases, primary immunodeficiencies, antibody deficiency states, cell mediated immunodeficiencies, severe combined immunodeficiency, DiGeorge syndrome, Hyper IgE syndrome (HIES), Wiskott-Aldrich syndrome (WAS), ataxia-telangiectasia, immune mediated cancers, white cell defects, autoimmune diseases, systemic lupus erythematosus (SLE), rheumatoid arthritis (RA), multiple sclerosis (MS), immune-mediated or Type 1 Diabetes Mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, Hashimoto's disease, dermatomyositis, Goodpasture syndrome (GPS), myasthenia gravis (MG), Sympathetic ophthalmia, Phakogene Uveitis, chronical aggressive hepatitis, primary biliary cirrhosis, autoimmune hemolytic anemia, and Werlhof's disease.

In one embodiment, the inflammatory disease is caused, induced, initiated and/or enhanced by bacteria, viruses, prions, parasites, fungi, and/or caused by irritative, traumatic, metabolic, allergic, autoimmune, or idiopathic agents.

In one embodiment, the inflammatory disease is selected from the group comprising or consisting of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, and inflammatory diseases of the larynx.

In one embodiment, the inflammatory disease is selected from inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx, wherein preferably said inflammatory diseases are selected from the group comprising abscessation, acanthamoeba infection, acne vulgaris, actinomycosis, acute inflammatory dermatoses, acute laryngeal infections of adults, acute multifocal placoid pigment epitheliopathy, acute (thermal) injury, acute retinal necrosis, acute suppurative otitis media, algal disorders, allergic contact dermatitis, amyloidosis angioedema, ankylosing spondylitis, aspergillosis, atopic dermatitis, pseudorabies, autoantibodies in vasculitis, bacterial disorders, bacterial laryngitis, bacterial meningitis, Beheet's disease (BD), birdshot choroidopathy, Gilchrist's disease, Borna disease, brucellosis, bullous myringitis, bursitis, candidiasis, canine distemper encephalomyelitis, canine distemper encephalomyelitis in immature animals, canine hemorrhagic fever, canine herpes virus encephalomyelitis, cholesteatoma, chronic granulomatous diseases (CGD), chronic inflammatory dermatoses, chronic relapsing encephalomyelitis, chronic suppurative otitis media, Ocular Cicatricial pemphigoid (OCP), common upper respiratory infection, granuloma, Crohn's disease, cryptococcal disease, dermatomyositis, diphtheria, discoid lupus erythematosus (DLE), drug-induced vasculitis, drug or hypersensitivity reaction, encephalitozoonosis, eosinophilic meningoencephalitis, Erythema multiforme (EM), feline leukemia virus, feline immunodeficiency virus, feline infectious peritonitis, feline Polioencephalitis, feline spongiform encephalopathy, fibromyalgia, Fuchs Heterochromic Uveitis, gastroesophageal (laryngopharyngeal) reflux disease, giant cell arteritis, glanders, glaucomatocyclitic crisis, gonorrhea granular myringitis, Granulomatous meningoencephalitis (GME), herpes simplex, histoplasmosis, idiopathic diseases, idiopathic inflammatory disorders, immune and idiopathic disorders, infections of the immunocompromised host, infectious canine hepatitis, inhalation laryngitis, interstitial nephritis, irritant contact dermatitis, juvenile rheumatoid arthritis, Kawasaki's disease, La Crosse virus encephalitis, laryngeal abscess, laryngotracheobronchitis, leishmaniasis, lens-induced uveitis, leprosy, leptospirosis, leukemia, lichen planus, lupus, lymphoma, meningitis, meningoencephalitis in greyhounds, miscellaneous meningitis/meningoencephalitis, microscopic polyangiitis, multifocal choroiditis, multifocal distemper encephalomyelitis in mature animals, multiple sclerosis, Muscle Tension Dysphonia (MTD), mycotic (fungal) diseases, mycotic diseases of the CNS, necrotizing encephalitis, neosporosis, old dog encephalitis, onchocerciasis, parasitic encephalomyelitis, parasitic infections, Pars planitis, parvovirus encephalitis, pediatric laryngitis, pollution and inhalant allergy, polymyositis, post-vaccinal canine distemper encephalitis, prion protein induced diseases, protothecosis, protozoal encephalitis-encephalomyelitis, psoriasis, psoriatic arthritis, pug dog encephalitis, radiation injury, radiation laryngitis, radionecrosis, relapsing polychondritis, Reiter's syndrome, retinitis pigmentosa, retinoblastoma, rheumatoid arthritis, Rickettsial disorders, rocky mountain spotted fever, salmon poisoning disease (SPD), Sarcocystosis, sarcoidosis, schistosomiasis, scleroderma, Rhinoscleroma, serpiginous choroiditis, shaker dog disease, Sjogren's syndrome, spasmodic croup, spirochetal (syphilis) diseases, spongiotic dermatitis, sporotrichosis, steroid responsive meningitis-arteritis, Stevens-Johnson syndrome (SJS, EM major), epiglottitis, sympathetic ophthalmia, Syngamosis, syphilis, systemic vasculitis in sarcoidosis, Takayasu's arteritis, tendinitis (tendonitis), Thromboangiitis obliterans (Buerger Disease), tick-borne encephalitis in dogs, toxic epidermal necrolysis (TEN), toxocariasis, toxoplasmosis, trauma, traumatic laryngitis, trichinosis, trypanosomiasis, tuberculosis, tularemia, ulcerative colitis, urticaria (hives), vasculitis, vasculitis and malignancy, vasculitis and rheumatoid arthritis, vasculitis in the idiopathic inflammatory myopathies, vasculitis of the central nervous system, vasculitis secondary to bacterial, fungal, and parasitic infection, viral disorders, viral laryngitis, vitiligo, vocal abuse, vocal-cord hemorrhage, Vogt-Koyanagi-Harada syndrome (VKH), Wegener's granulomatosis, and Whipple's disease.

In a further aspect, the present invention also relates to a method of preventing and/or treating a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases, said method comprising administering a compound or a pharmaceutical composition according to the present invention to a subject in need thereof.

In one embodiment, said proliferative diseases, infectious diseases, including opportunistic diseases, immunological diseases, autoimmune diseases, and inflammatory diseases are as defined herein.

In a further aspect, the present invention also relates to the use of a compound according to the present invention for the manufacture of a medicament for the prevention and/or treatment of a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases, such diseases being as defined herein.

DETAILED DESCRIPTION

The present inventors have surprisingly found that the compounds according to the present invention have a high specificity for cyclin-dependent kinase 7 over other cyclin-dependent kinases and moreover facilitate recruitment of the proteasome complex to cyclin-dependent kinase 7 (CDK7) through poly-ubiquitination and the subsequent degradation of cyclin-dependent kinase 7 by proteolysis through the proteasome complex. The compounds according to the present invention are therefore efficient CDK7-degraders. Without wishing to be bound by any theory, the present inventors believe that using compounds according to the present invention, it is possible to block downstream signaling of CDK7 through its degradation, and such blockage is much more efficient than when CDK7 was simply inhibited by an ordinary small molecule inhibitor on its own. This opens up the possibility of new treatment strategy for example in the field of cancer where cancer cells develop resistances to small molecule inhibitors on their own and maintain signaling cascades despite the respective kinase as such having been inhibited.

The compounds according to the present invention are highly selective in terms of their binding to cyclin-dependent kinase 7 versus its binding to other cyclin-dependent kinases. Moreover, the compounds according to the present invention show a very good target degradation behavior in that they result in target degradation of cyclin-dependent kinase 7. Moreover, they show a high binding affinity to E3 ubiquitin ligase. The compounds according to the present invention have high binding affinity to E3 ubiquitin ligase with dissociation constants (Kd) being typically $\leq$100 nM.

As used herein, the following terms shall refer to the following meanings:

The term "alkyl" refers to a monovalent straight, branched or cyclic chain, saturated aliphatic hydrocarbon radical having a number of carbon atoms in the specified range. Thus, for example, "$C_1$-$C_6$ alkyl" refers to any of the hexyl alkyl and pentyl alkyl isomers as well as n-, iso-, sec-, and t-butyl, n- and isopropyl, cyclic propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" refers to all of the hexenyl and pentenyl isomers as well as 1-butenyl, 2-butenyl, 3-butenyl, isobutenyl, 1-propenyl, 2-propenyl, and ethenyl (or vinyl).

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens. The term "haloalkyl" should be interpreted to include such substituents such as $-CHF_2$, $-CF_3$, $-CH_2-CH_2-F$, $-CH_2-CF_3$, and the like.

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., $-OCH_3$, etc.), an amine (e.g., $-NHCH_3$, $-N(CH_3)_2$, etc.), or thioalkyl group (e.g., $-SCH_3$, etc.). If a non-terminal carbon atom of the alkyl group which is not attached to the parent molecule is replaced with a heteroatom (e.g., O, N, or S) and the resulting heteroalkyl groups are, respectively, an alkyl ether (e.g., $-CH_2CH_2-O-CH_3$, etc.), alkyl amine (e.g., $-CH_2NHCH_3$, $-CH_2N(CH_3)_2$, etc.), or thioalkyl ether (e.g., $-CH_2-S-CH_3$).

The term "halogen" refers to fluorine, chlorine, bromine, or iodine.

The term "phenyl" as used herein is meant to indicate that optionally substituted or non-substituted phenyl group.

The term "benzyl" as used herein is meant to indicate that optionally substituted or non-substituted benzyl group.

The term "aryl" as used herein, is used in its regular understanding in the art, that is it refers to any functional group or substituent having an aromatic scaffold, for example an aromatic ring.

Typical examples of aryl groups are phenyl or naphthyl.

The term "heteroaryl" refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally S(O) or $S(O)_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl.

The term "heterocyclyl" or "heterocycle" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to S(O) or $S(O)_2$. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

The suffix "ene", when added to a designation of a monovalent radical, such as alkyl or aryl or cyclyl or heterocyclyl, is meant to indicate, in accordance with IUPAC-rules that such radical becomes a divalent radical accordingly. For example, an "alkylene" is meant to refer to a divalent functional group derived from an alkane by removal of two hydrogen atoms from different carbon atoms. A "heterocyclylene" is meant to refer to a divalent functional group derived from a heterocycle by removal of two hydrogen atoms from different carbon atoms. An "arylene" is meant to refer to a divalent aryl radical, derived from an aromatic ring by removal of two hydrogen atoms from different carbon atoms.

As used herein, the term "pharmaceutically acceptable salts" refers to any salt that is safe and non-toxic to use in the context of an active pharmaceutical ingredient (API). Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

The term "cereblon", or abbreviated "CRBN" is meant to refer to a protein encoded by the CRBN gene, which protein participates in the formation of a E3 ubiquitin ligase.

The term "inhibitor of apoptosis protein", abbreviated as "IAP" refers to a group of proteins which serve as endogenous inhibitors of programmed cell death (apoptosis). Typically, a common feature of all IAPs is the presence of a Baculovirus IAP Repeat (BIR).

The term "von Hippel-Landau tumor suppressor protein", abbreviated as "VHL", as used herein, is meant to refer to a protein encoded by the "VHL"-gene. It is also believed to have E3 ubiquitin ligase activity.

Further aspects of the present invention are illustrated and exemplified by the following schemes, examples, tables and procedural descriptions which are given merely to illustrate, not to limit the present invention. The scope of protection for the present invention is merely limited by the appended claims.

The terms "of the [present] invention", "in accordance with the invention", "according to the invention" and the like, as used herein, are intended to refer to all aspects and embodiments of the invention described and/or claim herein. As used herein, the term "comprising" is to be construed as encompassing both "including" and "consisting of", both meanings being specifically and explicitly intended, and hence, individually disclosed embodiments in accordance with the present invention. Where used herein, "and/or" is to be taken as a specific disclosure of each of the two specified features or components with or without the other. For example, "A" and/or "B" is to be taken as a specific disclosure of each of (i) A, (ii) B and (iii) A and B, just as if each is set out individually herein. Where an indefinite or definite article is used, wherein referring to a singular noun, e. g. "a", "an" or "the", this includes a plural of that noun unless something else is specifically stated. Likewise, such disclosure equally is meant to be taken as a specific disclosure of a single individual entity initiated by "a", "an" or "the".

BRIEF DESCRIPTION OF THE TABLES AND FIGURES

The present invention is now further described by reference to the following tables and FIGURES.

Table 1 shows the results of an enzyme binding assay of compounds according to the present invention in respect of cyclin-dependent kinases 1, 2, 5 and 7. Inhibition is indicated as $IC_{50}$ with the following key: A=$IC_{50}$ less than or equal to 100 nM; B=$IC_{50}$ greater than 100 nM, but less than or equal to 1000 nM; C=$IC_{50}$ greater than 1000 nM. Table 1 also shows selectivity data for the following relationships: CDK1/CDK7, CDK2/CDK7 and CDK5/CDK7 for selected compounds of the invention. Selectivity is indicated as CDK1/CDK7*, CDK2/CDK7, and CDK5/CDK7* with the selectivity range being indicated using the following key: A indicates >500-fold, B indicates selectivity being greater than 50-fold, but less than or equal to 500-fold, C indicates a selectivity being less than or equal to 50-fold.

Table 2 summarizes exemplary compounds 1-36 in terms of their structures and corresponding characteristics, as measured by 1H-NMR and mass spectrometry (MS(ESI)) as well as optical appearance.

Table 3 shows the results of a CDK7 protein degradation experiment in A2780 cells for exemplary compounds in accordance with Example 2. Degradation is indicated as $DC_{50}$ with the following key: A=$DC_{50}$ less than or equal to 100 nM; B=$DC_{50}$ greater than 100 nM, but less than or equal to 1000 nM; C=$DC_{50}$ greater than 1000 nM. "DC50", as used herein, refers to the compound concentration which causes 50% CDK7 protein degradation, preferably 50% CDK7 protein degradation in A2780 cells.

FIG. 1 shows the results of a CDK7 protein degradation experiment in A2780 cells which were treated with various concentrations of selected compounds according to the present invention, in accordance with Example 2.

In the following, reference is made to the examples, which are given to illustrate, not to limit the present invention.

EXAMPLES

Example 1: Binding Assay for CDK1 CDK2, CDK5 and CDK7

Inhibition activity of compound to CDK7 kinase was tested in a binding assay which was applied to the FRET (fluorescence resonance energy transfer) principle from the europium (Eu) donor fluorophore to the acceptor fluorophore on the kinase tracer. Test compounds were made to 1.125 mM of compound solution, and then this compound solution 4-fold serial diluted in 8 steps using an automated liquid handler (JANUS™, PerkinElmer). 80 nL/well of each diluted compound solution was added into the 384-well plate (Greiner, Cat #784075) first and 7.5 ul/well of working solution [5 nM of CDK7/CycH/MNAT1 (Invitrogen, Cat #PR6749B), 4 nM of Biotin anti-His Tag Antibody (Invitrogen, Cat #PV6090), and LanthaScreen® Eu-Streptavidin (Invitrogen, Cat #PV6025)] was added. After mixing the solution well, the same volume with the working solution of Tracer236 (Invitrogen, Cat #PV5592) was added into each well in the plate. The plate was incubated for 60 minutes at room temperature and then all the fluorescence were measured using Envision leader (Perkin Elmer, USA) [Laser as excitation light; APC 615 nm and Europium 665 as the first and the second emission filter]. Data was analysed using XL Fit software.

All of the synthesized compounds were screened in the above-mentioned assay procedure. To identify the inhibition activity of compounds for other CDKs including CDK1 (Invitrogen, Cat #PR4768C), CDK2 (Invitrogen, Cat #PR4448B) and CDK5 (Invitrogen, Cat #PR8543B) were tested using the same protocol under reasonable concentration of Tracer236 and kinases for each assay. The formula for the assay buffer summarized in below table.

| | Final assay concentration (nM) | | | |
|---|---|---|---|---|
| Reagents | CDK1 | CDK2 | CDK5 | CDK7 |
| Tracer 236 (2X) | 55 | 30 | 40 | 145 |
| Kinase | 5 | 2.5 | 5 | 2.5 |

-continued

| Reagents | Final assay concentration (nM) | | | |
|---|---|---|---|---|
| | CDK1 | CDK2 | CDK5 | CDK7 |
| Biotin anti-His Tag Antibody | 2 | 2 | 2 | 2 |
| LanthaScreen ®Eu-streptavidin | 2 | 2 | 2 | 2 |

The results for the binding assay and the selectivity in respect of cyclin-dependent kinase 7 (CDK7) are shown in table 1. From the results it is very clear that the compounds according to the present invention are highly selective for CDK7 versus CDK1; they are highly selective for CDK7 versus CDK2; and they are also highly selective for CDK7 versus CDK5.

Example 2: CDK7 Protein Degradation

Cell Culture

Human ovarian cancer cell line, A2780 (Cat #93112519) was obtained from ECACC. Cells were grown in RPMI-1640 media (Invitrogen, Cat #22400105) supplemented with 10% FBS (Hyclone, Cat #SH30084.03) and 1% penicillin/streptomycin (Hyclone, Cat #SV30010) and cultured at 37° C., 5% Co2 in a humidified chamber. All cell lines were routinely tested for mycoplasma.

Western Blot Assay for CDK7 Protein Degradation

To verify endogenous CDK7 protein degradation upon treatment of CDK7-specific degrader, the western blot assay was conducted a 24 hours' time period. $6\times10^5$ cells/well of A2780 cells were plated in 6-well plate. After 24 hours, the cells were treated with various concentrations of the compound corresponding range. DMSO solvent without compound served as a control and final DMSO concentration was not to exceed 0.1% of total volume. After 24 hours of incubation at 37° C., 5% Co2 incubator, cells were collected and lysed with 60 ul of lysis buffer. Collected lysates were incubated for 30 min on ice and collect supernatant through centrifugation at 12,000 rpm for 10 min at 4° C. The protein in lysates were quantified with BCA protein quantification kit (Pierce, Cat #23227) following manufacture's protocol. Cell lysates were diluted into 1 ug/ul of concentration with lysis buffer. 20 ug of protein was loaded to each well of 4~12% Bis-Tris gel (Invitrogen, Cat #NP0336BOX) with MOPS running buffer (Invitrogen, Cat #NP0001). The proteins were transferred from gel to membrane and incubated with primary antibody as followed at 4° C. overnight; CDK7 (CST, Cat #2090S) and β-actin (Santa Cruz, Cat #sc-47778) 1:20,000. The signals were developed and acquired with ImageQuant™ LAS 4000.

The results of the CDK7 protein degradation assay are shown in FIG. 1 and table 3. Whilst all the compounds tested show a CDK7 target degradation, compounds 7, 8, 9, 10, 11, 14, 15, 16, 17, 19, 20, 21, 22, 24, 25, 27, 28, 30, 31, 32, 33 and 34 are good compounds with degradative activity ranges of B or A, and, in particular, compounds 8, 11, 15, 17, 19, 20, 21, 24, 25, 27, 28, 30, 31, 32, 33 and 34 are very good compounds having a strong capability of degrading CDK7 protein, with a degradative activity range of A. For an explanation of these activity ranges (A, B and C), see the description of table 3 further above and the legend underneath table 3.

Example 3: Methods of Synthesis of Compounds According to the Present Invention

Scheme 1: General synthetic route 1
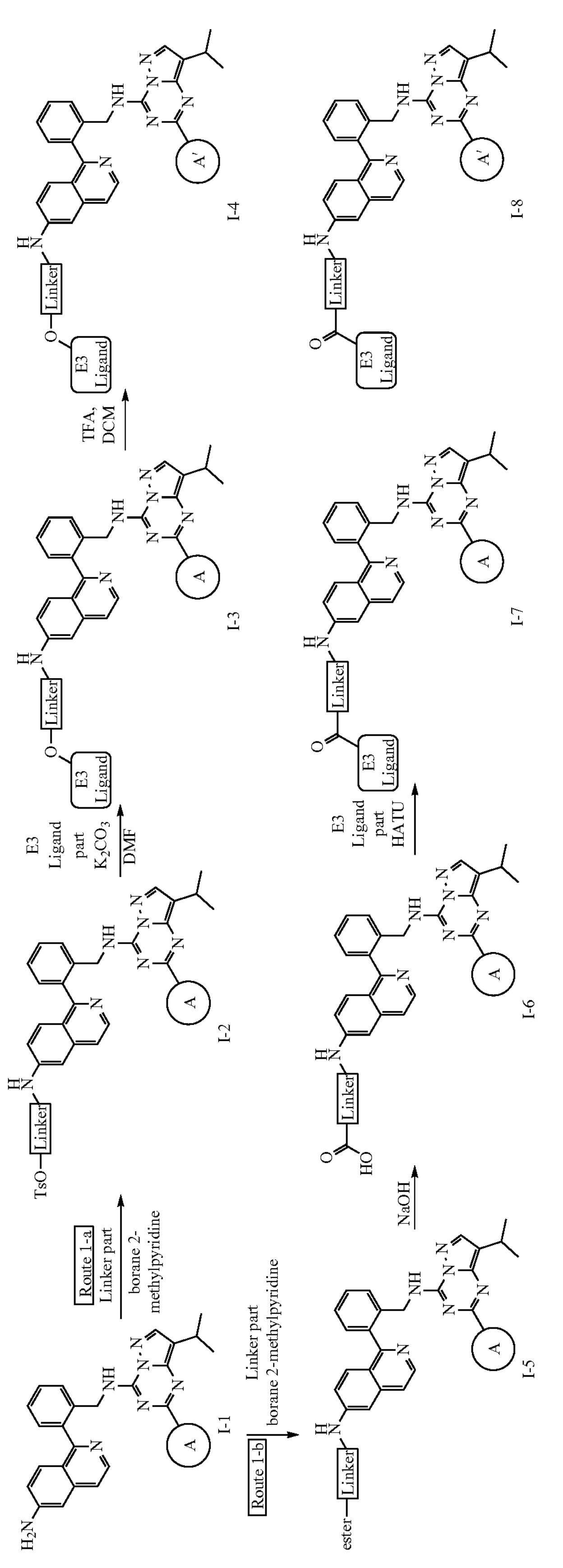
I-1 I-2 I-3 I-4 I-5 I-6 I-7 I-8

The Method to Prepare Compounds of Formula I-4 and I-8 Shown in Scheme 1

Route 1-a: Compounds of formula I-2 can be synthesized by I-1 and linker intermediates in presence of borane 2-methylpyridine. Compounds of formula I-3 can be prepared by E3 ligand intermediates in presence of potassium carbonate. Compounds of formula I-4 can be prepared in presence of trifluoroacetic acid.

Route 1-b: Compounds of formula I-5 can be synthesized by I-1 and linker intermediates in presence of borane 2-methylpyridine. Compounds of formula I-6 can be prepared in presence of Sodium hydroxide. Compounds of formula I-7 can be prepared by E3 ligand intermediates in presence of HATU. Compounds of formula I-8 can be prepared in presence of trifluoroacetic acid.

Wherein, A is any structure of aryl, heteroaryl and heterocyclyl; wherein, A is attached via —NH—, —O— or is directly attached without any intervening group or moiety;

Scheme 2: Synthesis of compound 11

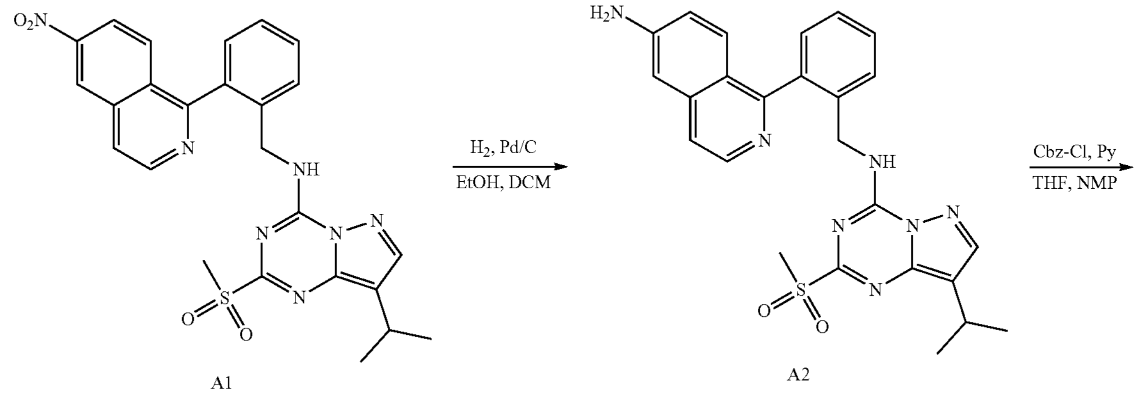

A1

A2

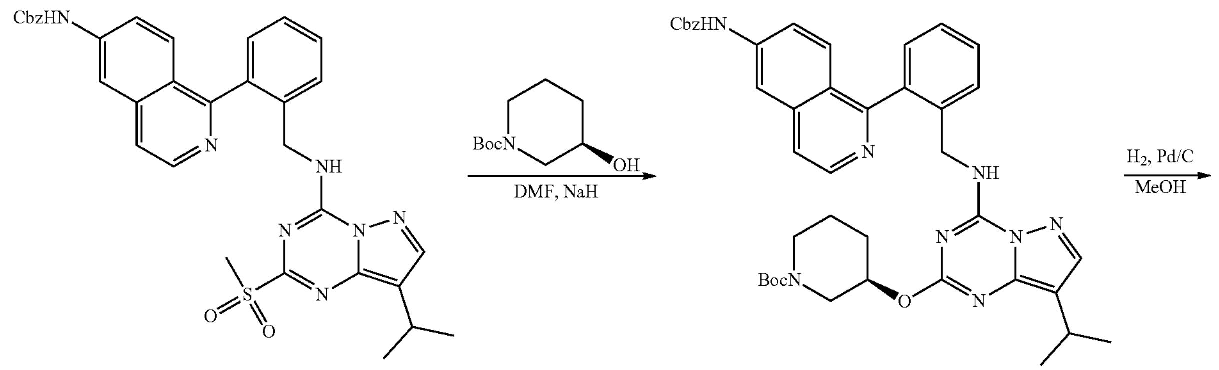

A3

A4

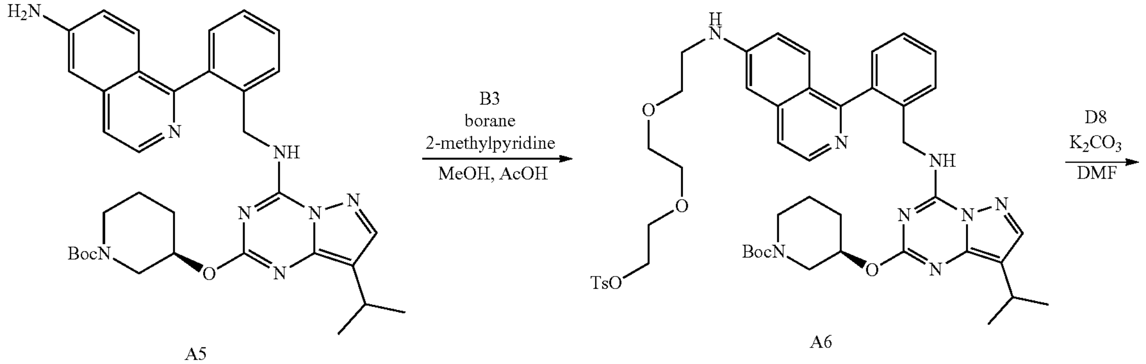

A5

A6

-continued

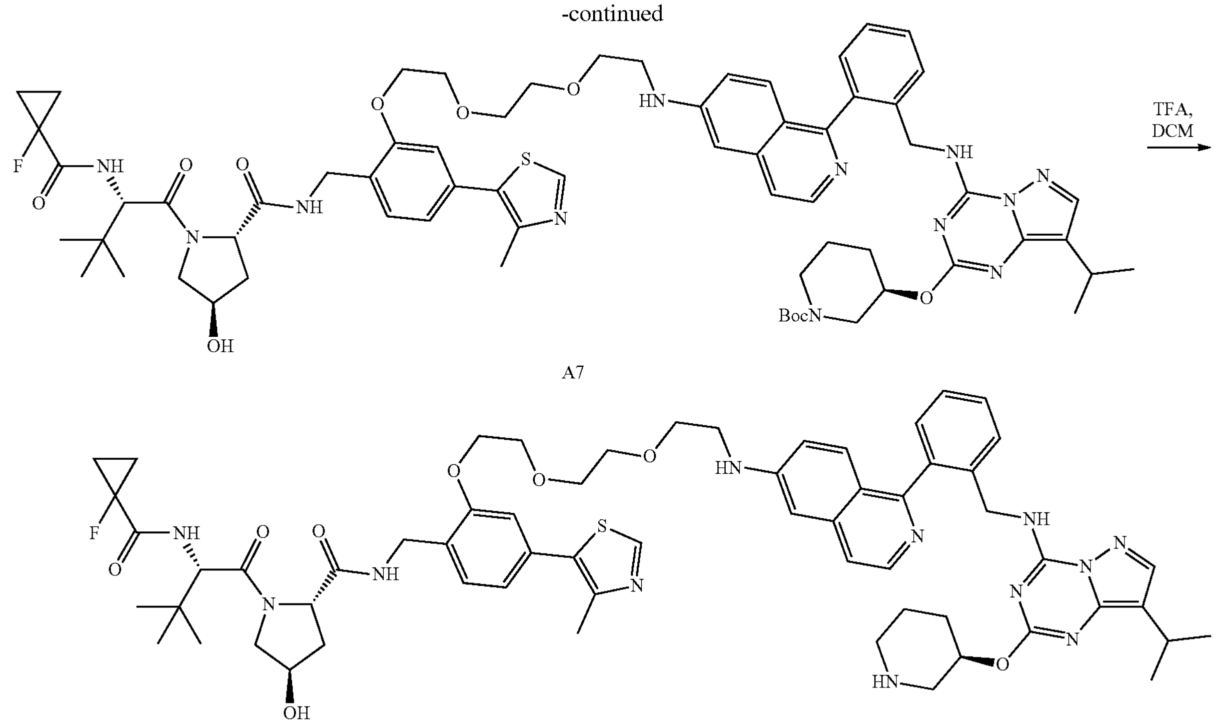

A7

Compound 11

Synthetic route of compound A1 is published in WO2019197546A1.

Procedure for Synthesis of A2

To a solution of A1 (10 g, 19.32 mmol) in DCM (150 mL) and EtOH (200 mL) was added 10% Pd/C (4 g). The suspension was degassed and purged with $H_2$ for 3 times. The mixture was stirred under $H_2$ (15 Psi) at 20° C. for 16 hr to give a black mixture. The suspension was filtered through a pad of Celite and the filter cake was washed with EtOH (20 mL×3). The combined filtrates were concentrated to afford A2 (9.3 g, 19.07 mmol, 98.7% yield) as yellow solid.

Procedure for Synthesis of A3

To a solution of A2 (4.64 g, 9.52 mmol) and Pyridine (4.52 g, 57.10 mmol) in THF (75 mL) and NMP (15 mL) was added benzyl carboformate (6.49 g, 38.07 mmol). The mixture was stirred at 50° C. for 6 hr to give a brown mixture. The mixture was partitioned between EtOAc (500 mL) and $H_2O$ (300 mL). The organic layer was washed with brine (200 mL×3), dried over anhydrous $Na_2SO_4$, filtered and concentrated under reduced pressure to give a crude product as yellow oil. The crude product was purified by column chromatography to give A3 (5.1 g, 8.20 mmol, 86.2% yield) as white solid.

Procedure for Synthesis of A4

To a mixture of NaH (1.29 g, 32.25 mmol, 60% purity) in DMF (5 mL) was added A3 (5.57 g, 8.96 mmol) in DMF (25 mL) at 0° C. The mixture was stirred at 20° C. for 30 min. Tert-butyl (3R)-3-hydroxypiperidine-1-carboxylate (6.67 g, 33.15 mmol) in DMF (25 mL) was added to the mixture. The reaction mixture was heated to 60° C. for 16 hr to give yellow mixture. TLC indicated the reaction was completed. Saturated $NH_4Cl$ (300 mL) was added to the reaction mixture, which followed by extraction with ethyl acetate (200 mL×2). The combined organic layers were washed with brine (200 mL×2), dried over anhydrous $Na_2SO_4$, filtered and concentrated under reduced pressure to give a crude product. The crude product was purified by column chromatography to afford A4 (4.86 g, 6.54 mmol, 73% yield) as white solid.

Procedure for Synthesis of A5

To a solution of A4 (500 mg, 673.07 umol) in MeOH (20 mL) was added wet Pd/C (230 mg). The mixture was stirred at 20° C. for 32 hr under $H_2$ (15 PSI) to give a black suspension. TLC showed the reaction was completed. The suspension was filtered through a pad of Celite and the filter cake was washed with EtOH (20 mL×3). The filtrate was concentrated to give the crude product. The residue was purified by flash silica gel chromatography to afford A5 (370 mg, 568.92 umol, 84.53% yield) as white solid.

Procedure for Synthesis of A6

A mixture of A5 (165 mg, 271 umol), B3 (122.9 mg, 406 umol) in MeOH (2.5 mL) and AcOH (250 uL) was treated with borane 2-methylpyridine (43.49 mg, 406 umol,), degassed and purged with $N_2$ for 3 times. Then the mixture was stirred at 20° C. for 16 hr under $N_2$ atmosphere to give a yellow mixture. The reaction mixture was treated with 1N HCl (0.5 mL), stirred at 20° C. for 0.5 hr. The pH was adjusted to around 9 by progressively adding saturated $NaHCO_3$. The mixture was extracted with EtOAc (20 mL×2). The combined extracts were washed with brine (20 mL), dried over anhydrous $Na_2SO_4$ and concentrated under reduced pressure to give the residue. The residue was purified by prep-TLC to afford A6 (185 mg, 204.62 umol, 75.5% yield) as light yellow solid.

Procedure for Synthesis of A7

A mixture of A6 (65 mg, 72.62 umol), D8 (50.28 mg, 94.41 umol), $K_2CO_3$ (20.07 mg, 145.24 umol) in DMF (0.5 mL) was degassed and purged with $N_2$ for 3 times, and then the mixture was stirred at 50° C. for 21 hr under $N_2$ atmosphere to give a yellow mixture. TLC showed the reaction was completed. The mixture was extracted with EtOAc (20 mL×2). The combined extracts were washed with brine (20 mL×2), dried over anhydrous $Na_2SO_4$ and concentrated under reduced pressure to give the residue. The residue was lyophilized to give a compound. The residue was purified by prep-TLC to afford A7 (44 mg, 34.80 umol, 47.9% yield) as light yellow solid.

Procedure for Synthesis of Compound 11

To a solution of A7 (73.94 mg, 58.89 umol) in DCM (1 mL) was added TFA (134.30 mg, 1.18 mmol) at 0° C. The mixture was stirred at 20° C. for 1 hr to give a yellow mixture. The reaction mixture was concentrated under reduced pressure to give a residue. The target is purified by prep-HPLC and lyophilized to afford compound 11 (72.8 mg, 51.2 umol, 87% yield) as yellow powder.

Synthesis of Compound 19

Compound 19

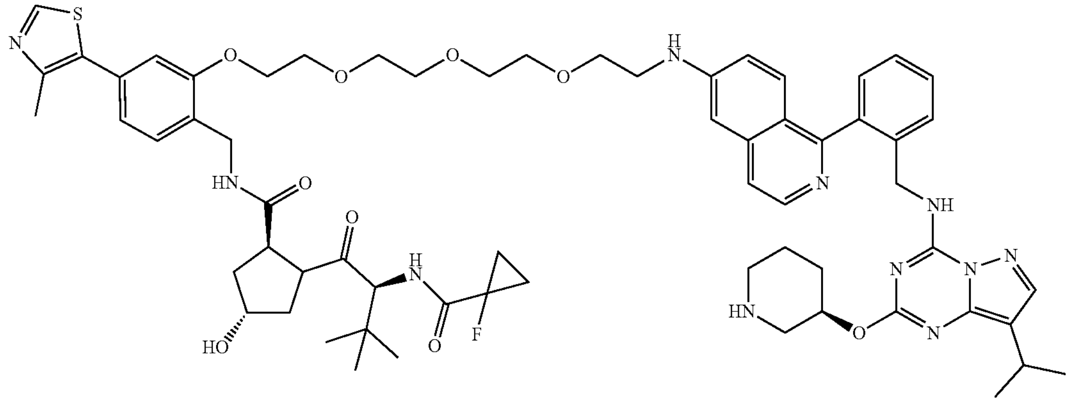

44.6 mg of Compound 19 was synthesized as yellow powder by using B4 and the same synthetic route of compound 11.

Synthesis of Compound 20

Compound 20

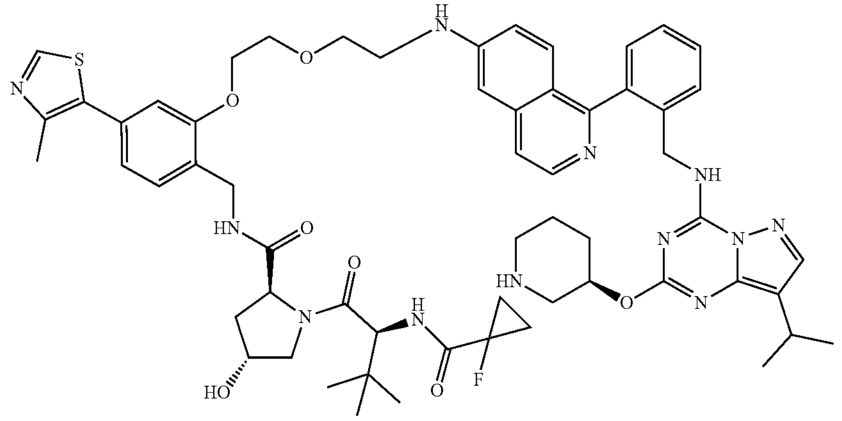

26.4 mg of Compound 20 was synthesized as yellow powder by using B5 and the same synthetic route of compound 11.

Synthesis of Compound 21
Compound 21
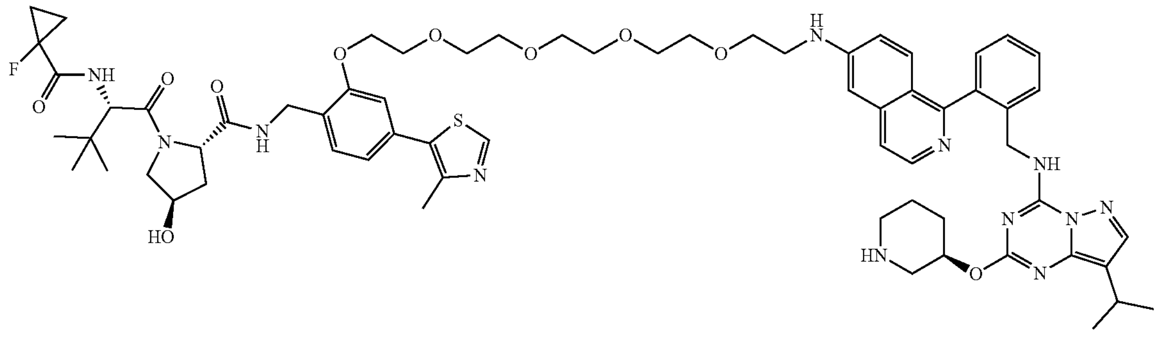
50.2 mg of Compound 21 was synthesized as yellow powder by using B6 and the same synthetic route of compound 11.
Synthesis of Compound 23
Compound 23
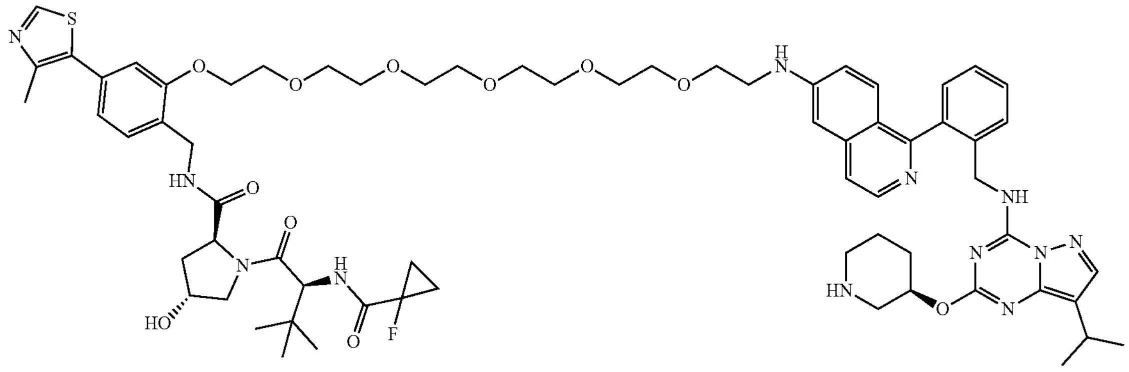
14 mg of Compound 23 was synthesized as yellow solid by using B7 and the same synthetic route of compound 11.
Synthesis of Compound 22
Compound 22
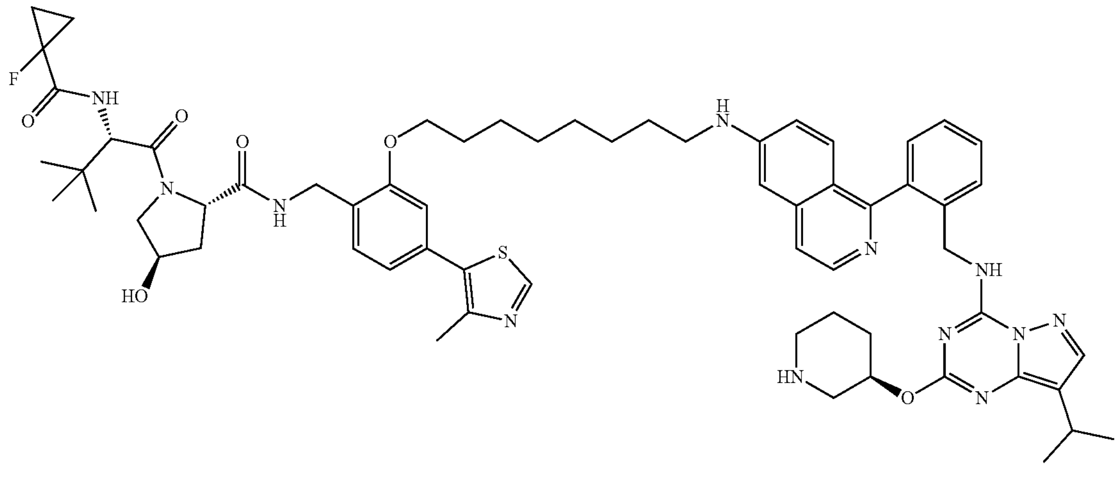

44.3 mg of Compound 22 was synthesized as yellow powder by using B8 and the same synthetic route of compound 11.
Synthesis of Compound 24, Compound 26 and Compound 27
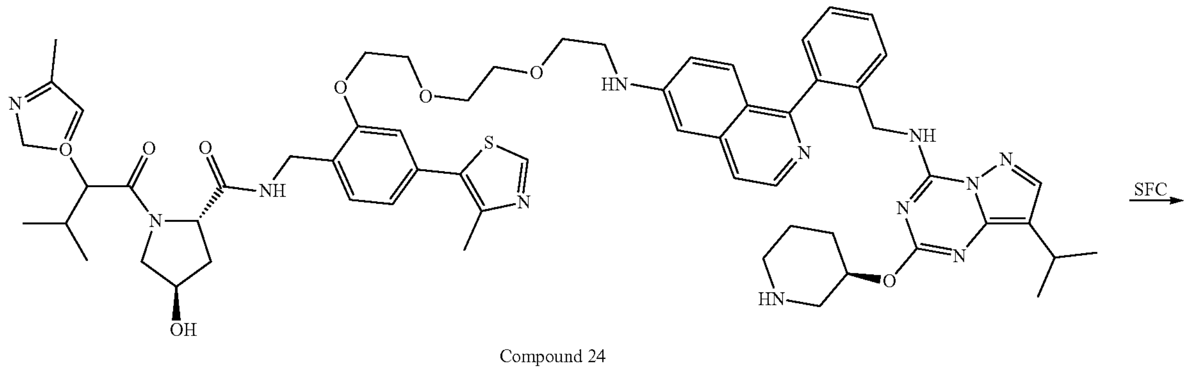
Compound 24
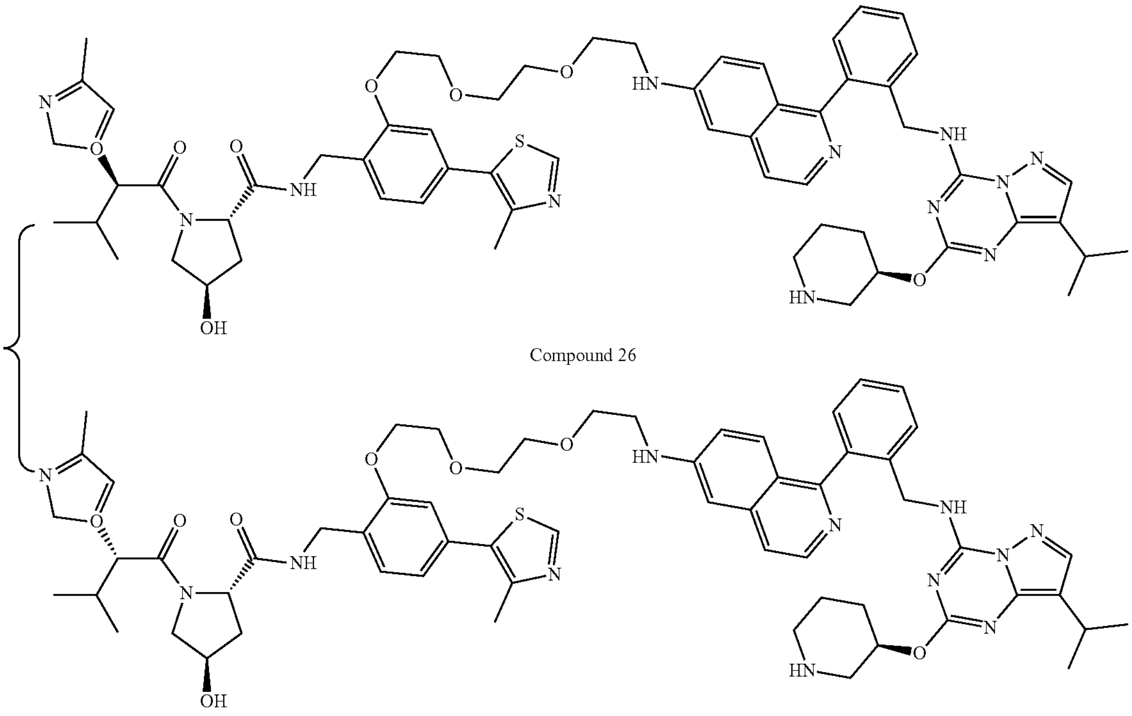
Compound 26
Compound 27
36.8 mg of Compound 24 was synthesized as yellow powder by using D13 and the same synthetic route of compound 11. Compound 26 and Compound 27 was obtained as each white powder by chiral SFC from Compound 24.

Synthesis of Compound 12
Compound 12
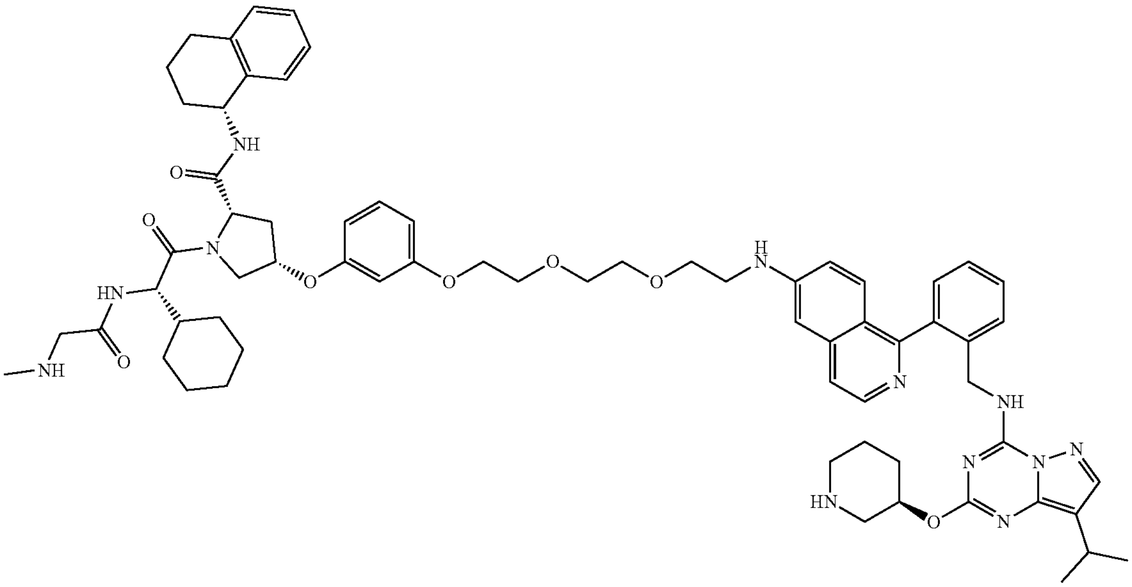
49.2 mg of Compound 12 was synthesized as yellow powder by using E10 and the same synthetic route of compound 11.
Synthesis of Compound 18
Compound 18
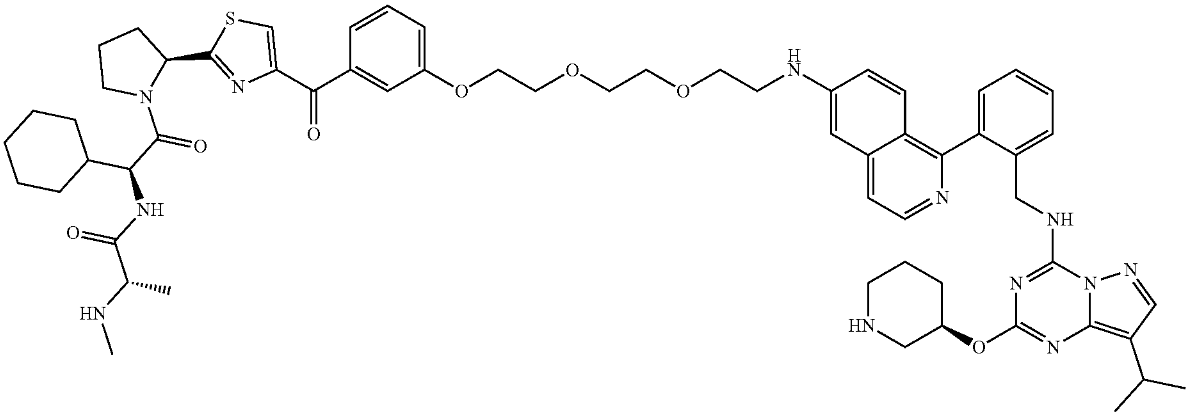
9.1 mg of Compound 18 was synthesized as yellow solid by using E22 and the same synthetic route of compound 11.

Scheme 3: Synthesis of compound 15
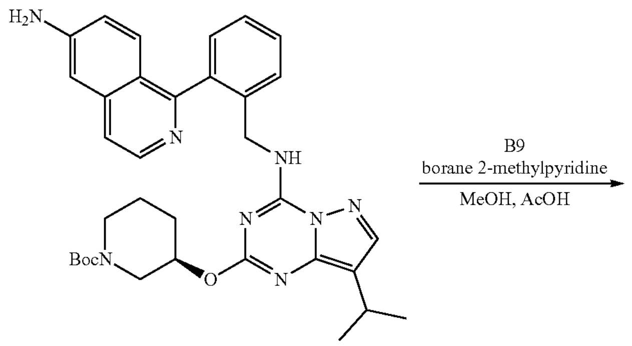
A5
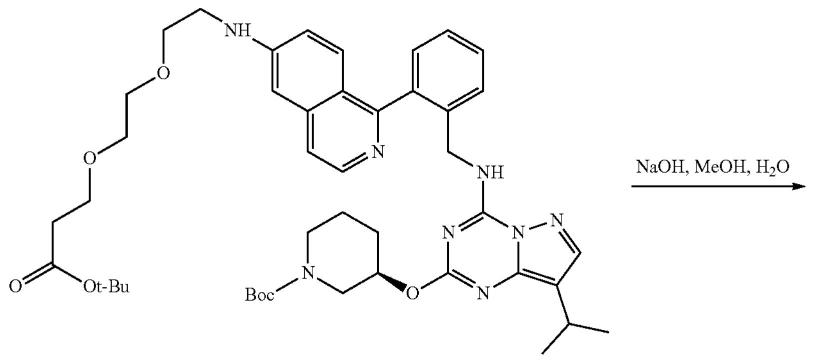
A8
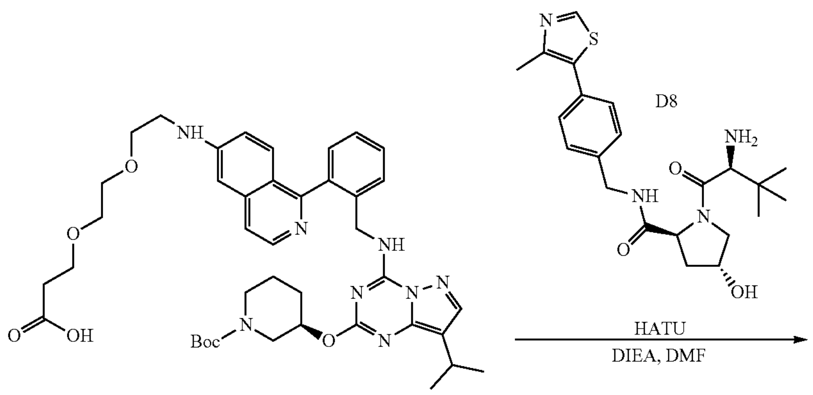
A9

-continued

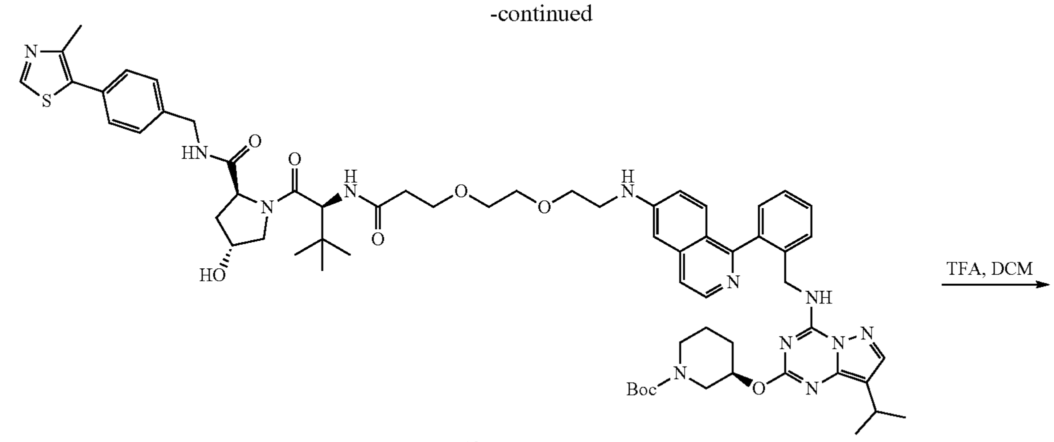

A10

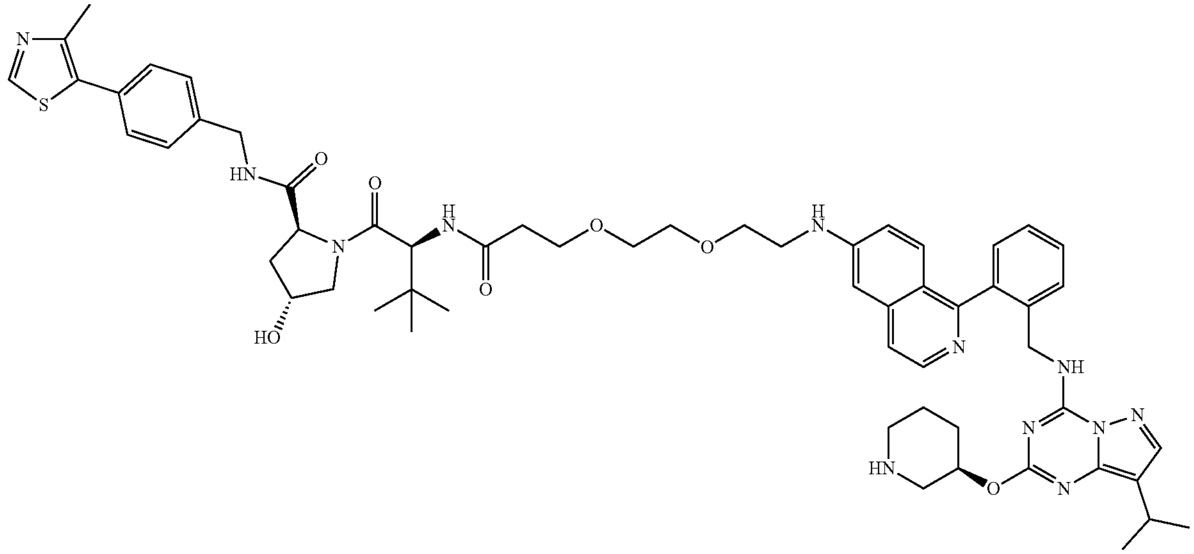

Compound 15

Procedure for Synthesis of A8

Intermediate A5 (100 mg, 164.28 umol) and B9 (57.24 mg, 246.41 umol) followed the same procedure of A6 to obtain 65 mg (78.79 umol, 47.96% yield) of A8 as yellow solid.

Procedure for Synthesis of A9

To a solution of A8 (65 mg, 78.79 umol) in MeOH (1 mL) and $H_2O$ (0.5 mL) and NaOH (9.45 mg, 236.36 umol). The mixture was stirred at 40° C. for 16 hr to give a yellow mixture. The mixture was diluted with water (10 mL), 10% HCl was used to adjust the pH to 4. Then the mixture was extracted with Ethylacetate (10 mL*3). The combined organic layers were washed with brine (10 mL*3), dried over $Na_2SO_4$, filtered and concentrated under reduced pressure to give A9 (50 mg, 65.03 umol, 82.54% yield) as yellow solid.

Procedure for Synthesis of A1

To a solution of A9 (100 mg, 130.05 umol) in DMF (1 mL) was added DIEA (25.22 mg, 195.08 umol) and HATU (54.4 mg, 143.06 umol). The mixture was stirred at 20° C. for 0.5 hr. Then D8 (61.6 mg, 143.06 umol) was added into the mixture. The mixture was stirred at 20° C. for 15 hr to give a yellow mixture. The mixture was diluted with water (10 mL) and extracted with Ethylacetate (10 mL*3). The combined organic layers were washed with brine (10 mL*3), dried over $Na_2SO_4$, filtered and concentrated under reduced pressure to give a yellow residue. The crude residue was purified by prep-TLC to give A10 (85 mg, 71.95 umol, 55.32% yield) as yellow solid.

Synthesis of Compound 15

Intermediate A10 (85 mg) followed the same procedure of compound 11 to obtain 33 mg of compound as yellow powder.

Synthesis of Compound 17
Compound 17
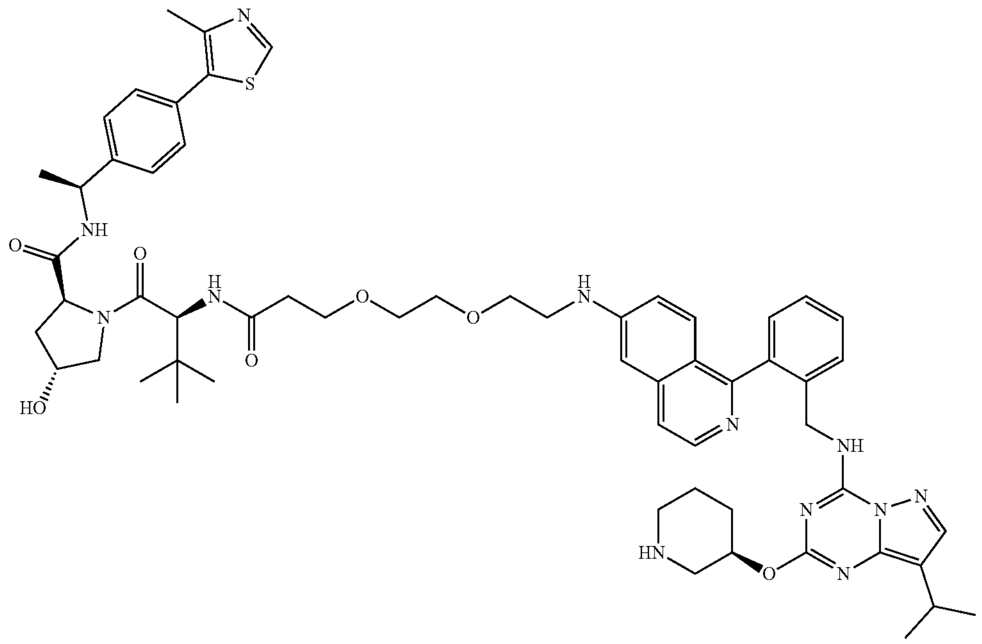
Compound 17 was synthesized as green powder by using D10 and the same synthetic route of compound 15.
Synthesis of Compound 28
Compound 28
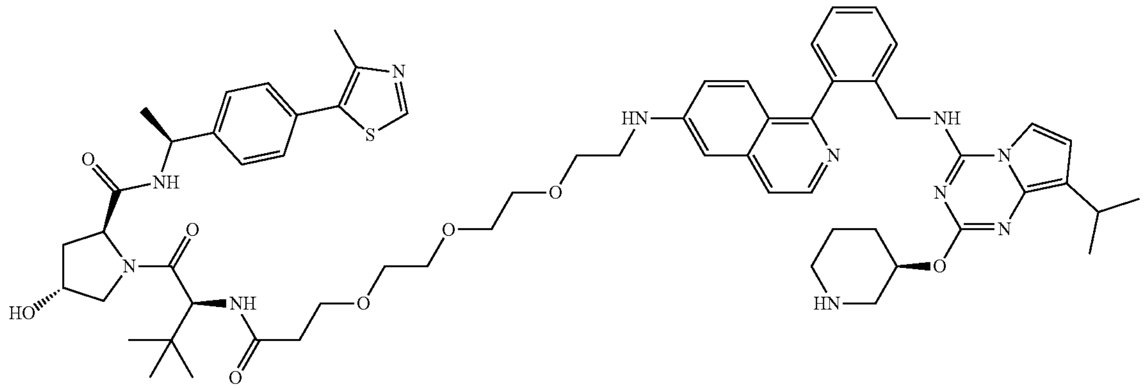
Compound 28 was synthesized as yellow powder by using B36, D10 and the same synthetic route of compound 15.

Scheme 4: General synthetic route 2

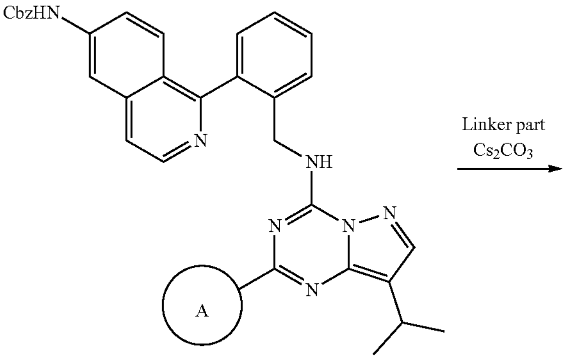

II-1

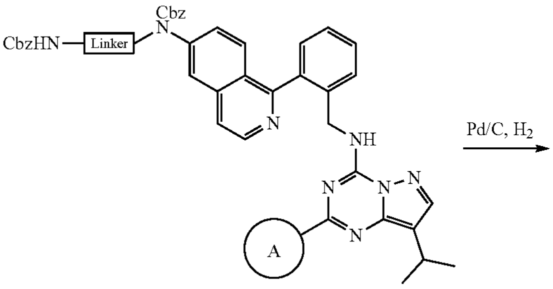

II-2

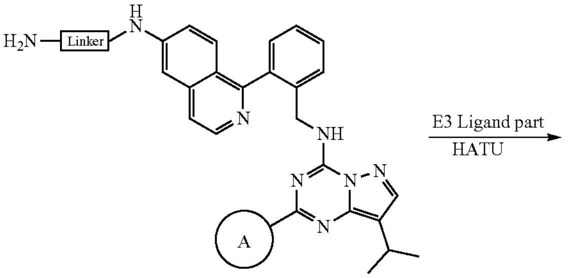

II-3

-continued

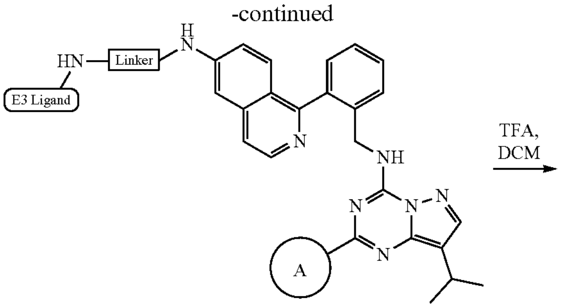

II-4

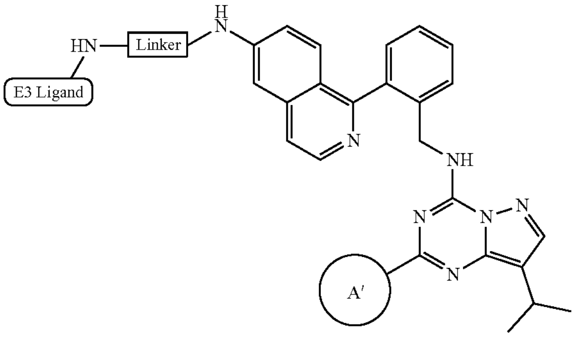

II-5

The Method to Prepare Compounds of Formula II-5 in Scheme 4

Compounds of formula II-2 can be synthesized by linker intermediates in presence of cesium carbonate. Compounds of formula II-3 can be prepared in presence of Pd/C and $H_2$ gas. Compounds of formula II-4 can be prepared by E3 ligand intermediates in presence of HATU condition. Compounds of formula II-5 can be prepared by in presence of trifluoroacetic acid.

Scheme 5: Synthesis of compound 7

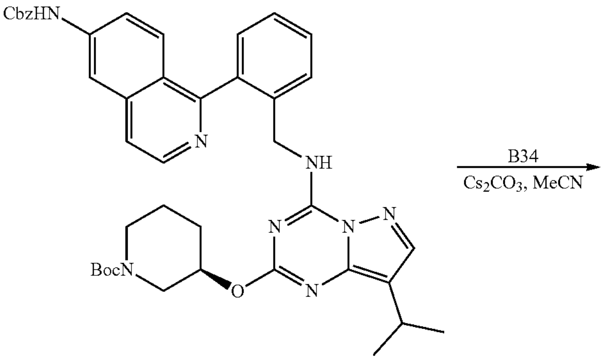

A4

-continued
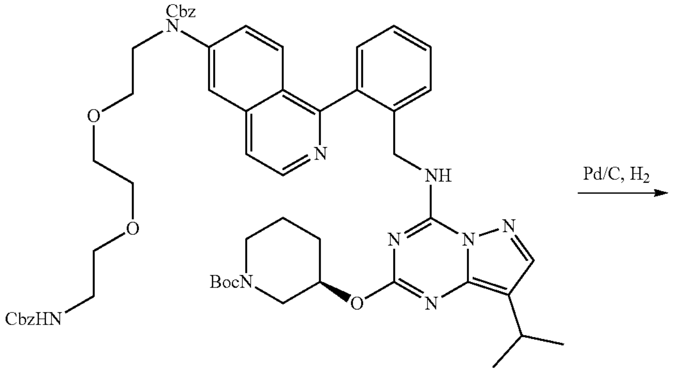
A11
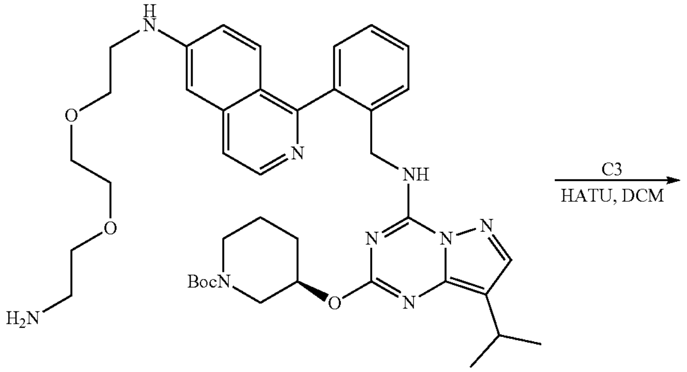
A12
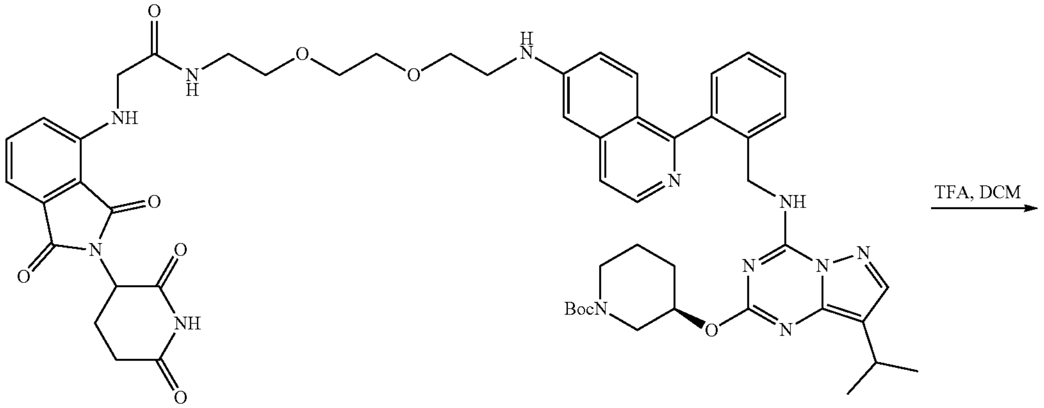
A13
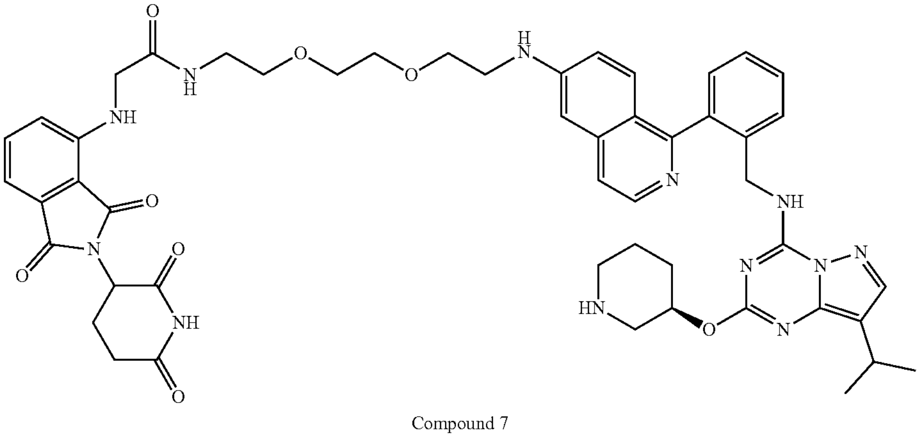
Compound 7

Procedure for Synthesis of A11

A mixture of A4 (300 mg, 403.84 umol), B34 (176.6 mg, 403.84 umol), $Cs_2CO_3$ (263.16 mg, 807.69 umol) in MeCN (2 mL) was degassed and purged with $N_2$ for 3 times, and then the mixture was stirred at 60° C. for 18 hr under $N_2$ atmosphere to give a yellow mixture. LCMS indicated the reaction was not completed. The B34 (53 mg, 121.14 umol) was added and the mixture was stirred at 60° C. for 24 hr. TLC indicated the reaction was completed. The reaction mixture diluted with water 20 mL and extracted with EtOAc (20 mL*2). The combined organic layers were washed with brine (20 mL*2), dried over $Na_2SO_4$, filtered and concentrated under reduced pressure to give a residue. The residue was purified by Silica Flash Column and prep-HPLC to afford A11 (90 mg, 89.27 umol, 22.1% yield) as white solid.

Procedure for Synthesis of A12

To a solution of A11 (90 mg, 89.27 umol) in MEOH (10 mL) was added wet Pd/C (60 mg, 46.25 umol). The mixture was stirred at 20° C. for 4 under $H_2$ (15 PSI) to give a black suspension. LCMS showed desired product was detected. The suspension was filtered through a pad of Celite and the filter cake was washed with EtOH (20 mL×3). The combined filtrates were concentrated to give A12 (63 mg, 85.15 umol, 95.38% yield) as white solid.

Procedure for Synthesis of A13

Intermediate A12 (65 mg, 87.85 umol) and C3 (34.9 mg, 105.42 umol) followed the same procedure of A10 to obtain 53 mg (50.3 umol, 57.28% yield) of A13 as yellow powder.

Synthesis of Compound 7

Intermediate A13 (101 mg) followed the same procedure of compound 11 to obtain 22 mg of compound 7 as yellow solid.

Synthesis of Compound 8

Compound 8

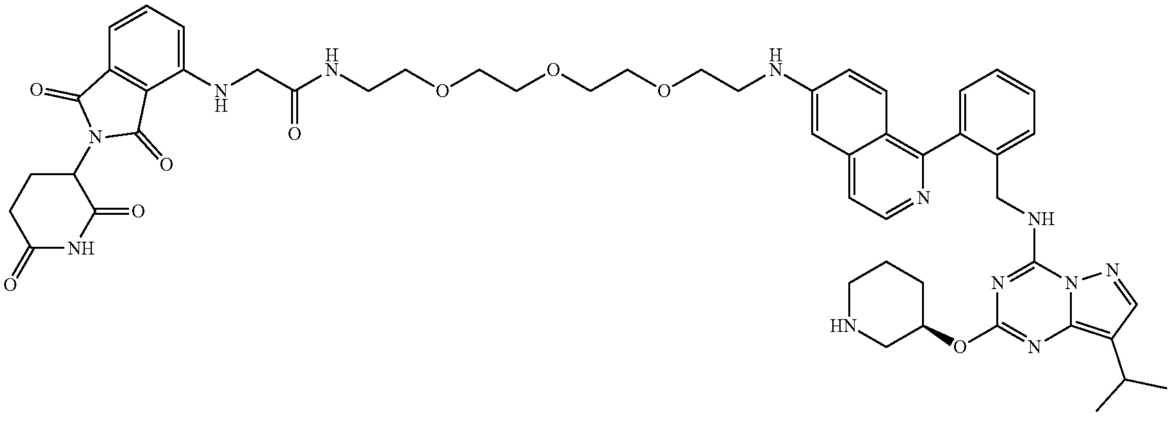

Compound 8 was synthesized as yellow powder by using B35 and the same synthetic route of compound 7.

Synthesis of Compound 10

Compound 10

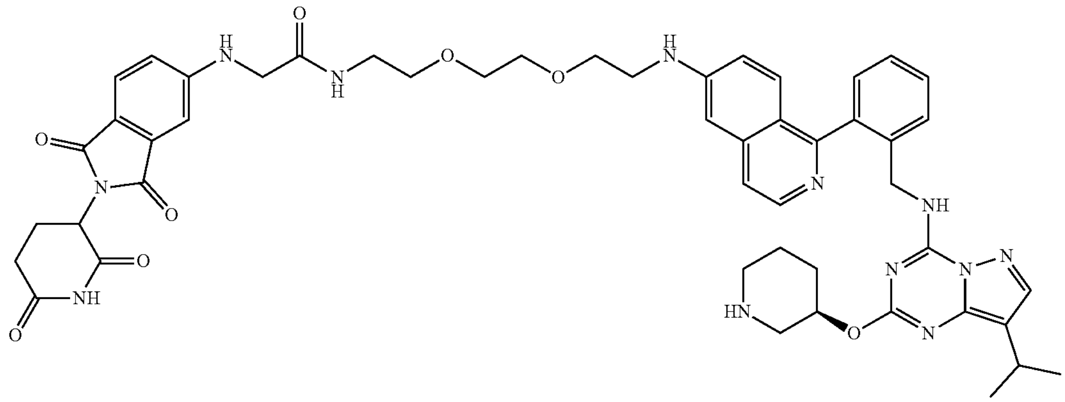

Compound 10 was synthesized as yellow solid by using C4 and the same synthetic route of compound 7.

Synthesis of Compound 14

Compound 14

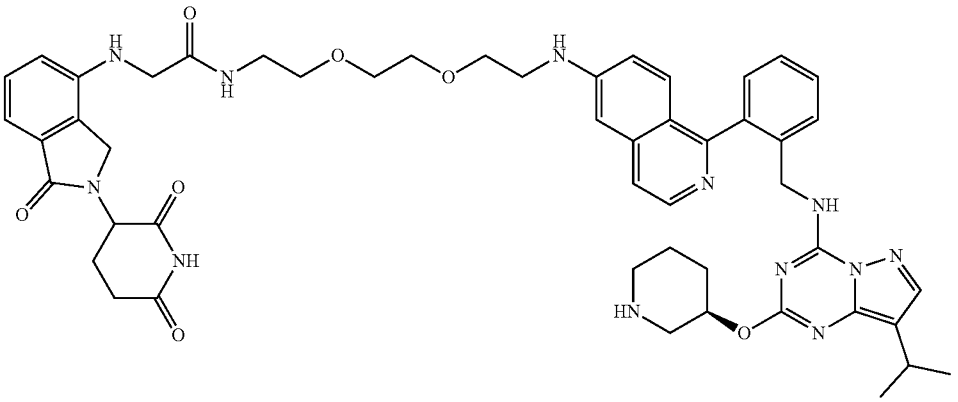

Compound 14 was synthesized as yellow solid by using C7 and the same synthetic route of compound 7.

Synthesis of Compound 16

Compound 16

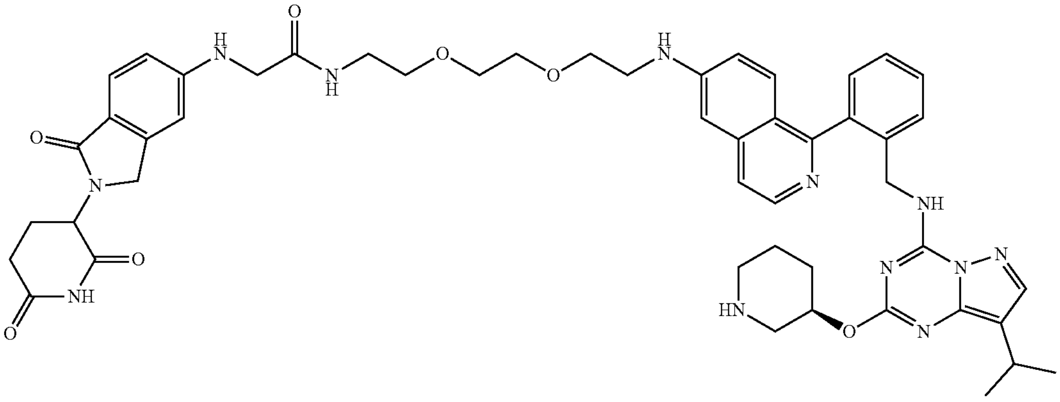

Compound 16 was synthesized as yellow powder by using C12 and the same synthetic route of compound 7.

Synthesis of Compound 13

Compound 13

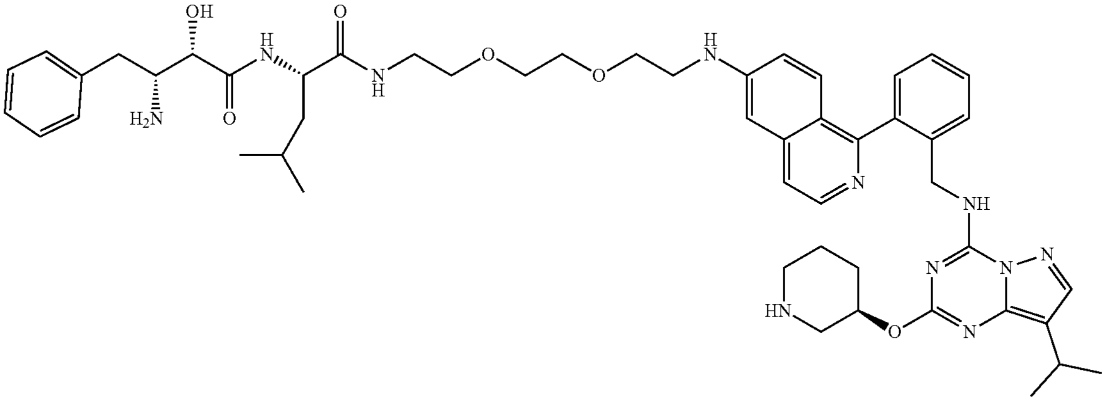

Compound 13 was synthesized as brown powder by using A12, E12 and the same synthetic route of compound 7.

Scheme 6: Synthesis of compound 1
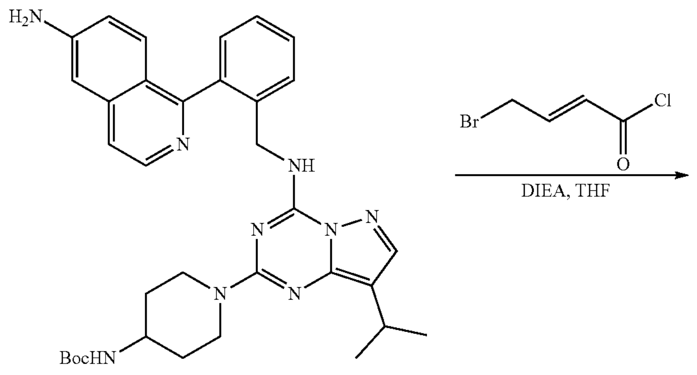
A14
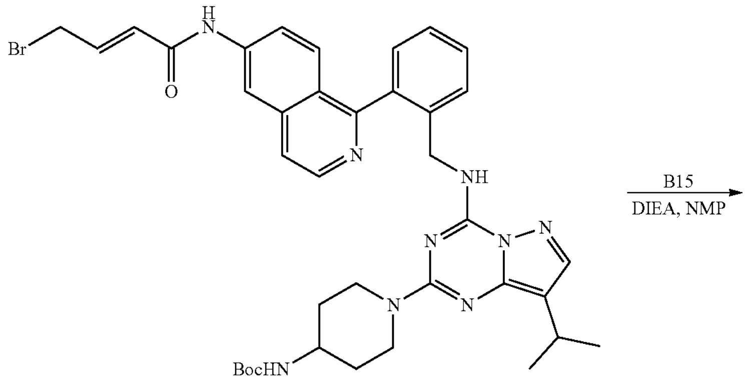
A15
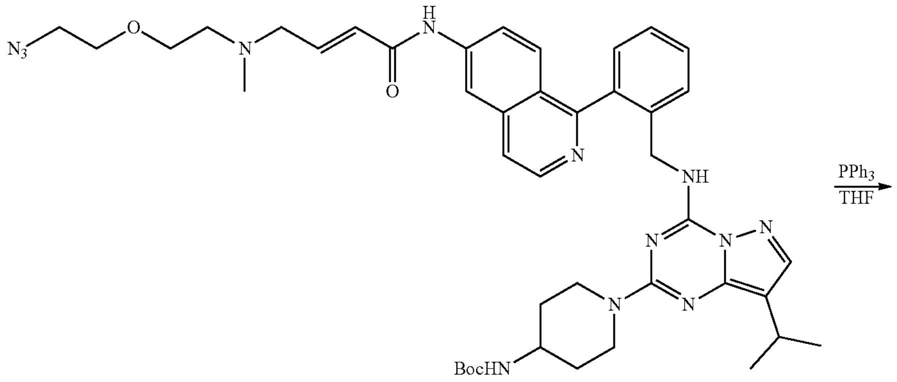
A16
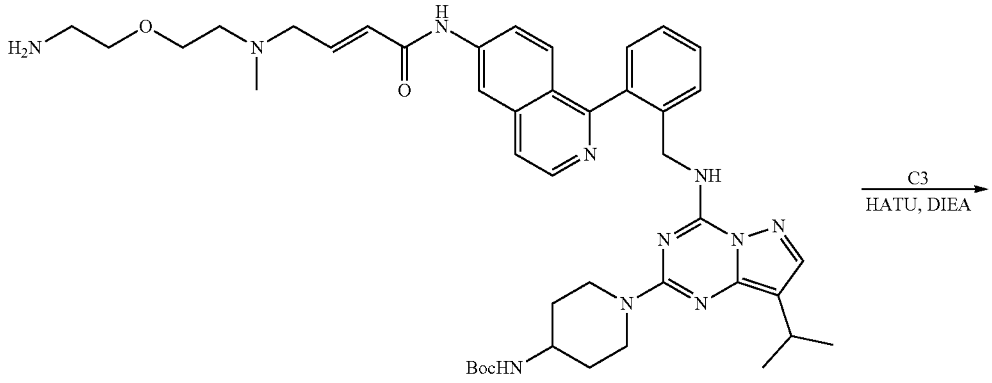
A17

-continued

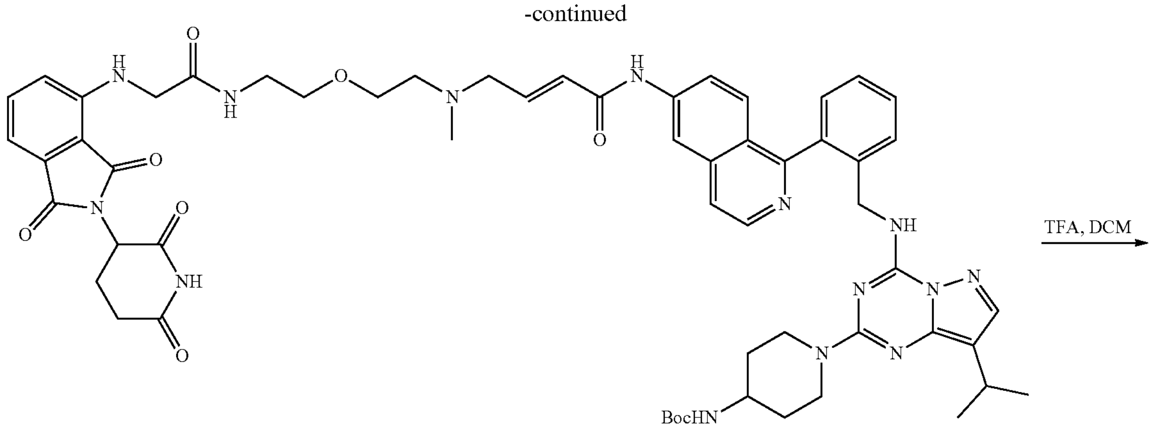

A18

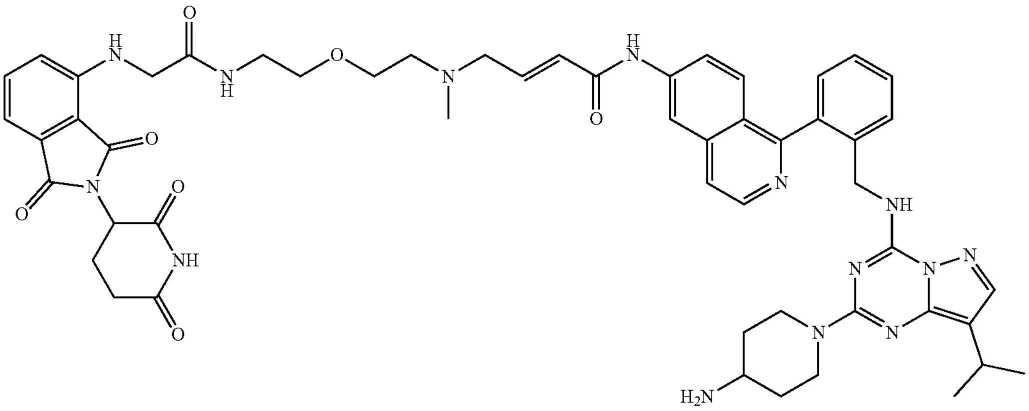 [SMILES: CC(C)c1cnn2c(NCc3ccccc3-c3nccc4cc(NC(=O)/C=C/CN(C)CCOCCNC(=O)CNc5cccc6c5C(=O)N(C5CCC(=O)NC5=O)C6=O)ccc34)nc(N3CCC(N)CC3)nc12]

Compound 1

Synthetic route of compound A14 is published in WO2019197546A1.

Procedure for Synthesis of A15

To a mixture of A14 (440 mg, 0.724 mmol) in THF (8 mL) was added DIEA (187.14 mg, 1.45 mmol) and (E)-4-bromobut-2-enoyl chloride (199.20 mg, 1.09 mmol, fresh prepared) at 0-5° C. The mixture was stirred at 0-5° C. for 10 min to give yellow mixture. The reaction mixture was diluted with EtOAc (10 mL), and it was washed with sat. aq. $NaHCO_3$ (10 mL), brine (10 mL), dried over anhydrous $Na_2SO_4$ and concentrated under reduced pressure to give A15 (580 mg, crude) as brown powder.

Procedure for Synthesis of A16

To a solution of A15 (150 mg, 198.75 umol) in NMP (1 mL) was added DIEA (256.87 mg, 1.99 mmol), B15 (57.31 mg, 0.397 mmol). The mixture was stirred at 20° C. for 16 hr to give a yellow mixture. LCMS indicated the desired product was detected. B15 (14 mg) and DIEA (184.63 uL) were added and the mixture was stirred at 20° C. for 48 hr. The reaction mixture was diluted with water 20 mL and extracted with EtOAc (20 mL*3). The combined organic layers were washed with brine (20 mL*3), dried over $Na_2SO_4$, filtered and concentrated under reduced pressure to give A16 (162 mg, crude) as yellow oil.

Procedure for Synthesis of A17

To a solution of A16 (162 mg, 198.05 umol) in THE (2 mL) and $H_2O$ (1 mL) was added $PPh_3$ (62.33 mg, 237.66 umol). The mixture was stirred at 60° C. for 16 hr to give a yellow mixture. LCMS indicated the reaction was completed. The reaction mixture was diluted with water 20 mL and extracted with EtOAc (20 mL*3). The combined organic layers were washed with brine, dried over $Na_2SO_4$, filtered and concentrated under reduced pressure to give A17 (156 mg, crude) as yellow oil.

Procedure for Synthesis of A18

Intermediate A17 (156 mg, 196.97 umol) and C3 (65.25 mg, 196.97 umol) followed the same procedure of A10 to obtain 58 mg (50.9 umol, 25.84% yield) of A18 as yellow solid.

Synthesis of Compound 1

Intermediate A18 (58 mg, 52.48 umol) followed the same procedure of compound 11 to obtain 43 mg of compound 1 as yellow solid.

Synthesis of Compound 3
Compound 3
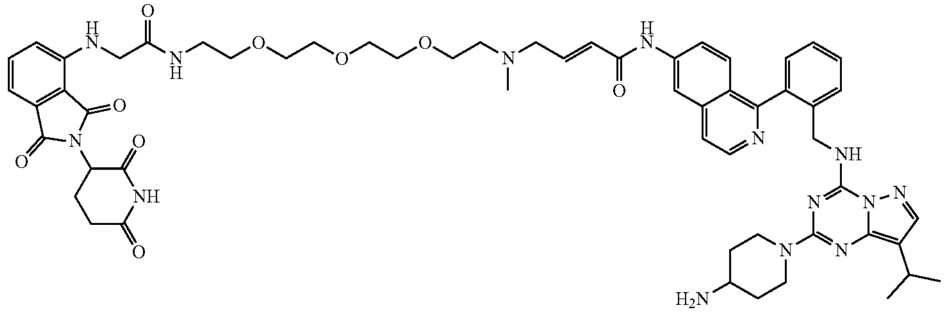
Compound 3 was synthesized as yellow solid by using B26 and the same synthetic route of compound 1.
Scheme 7: Synthesis of compound 2
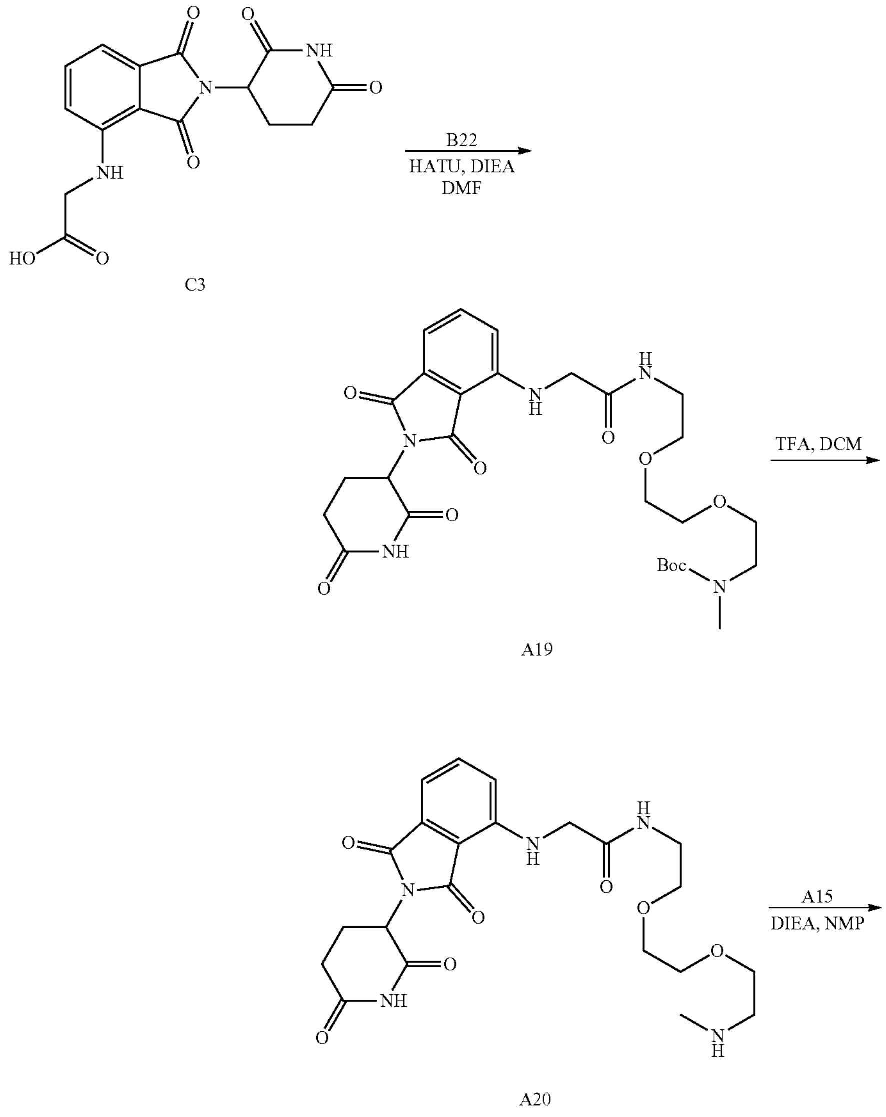
C3
A19
A20

-continued

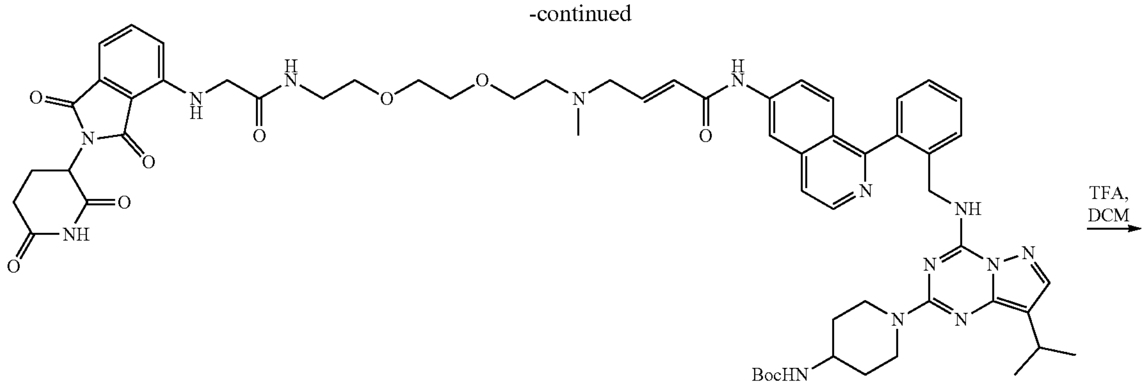

A21

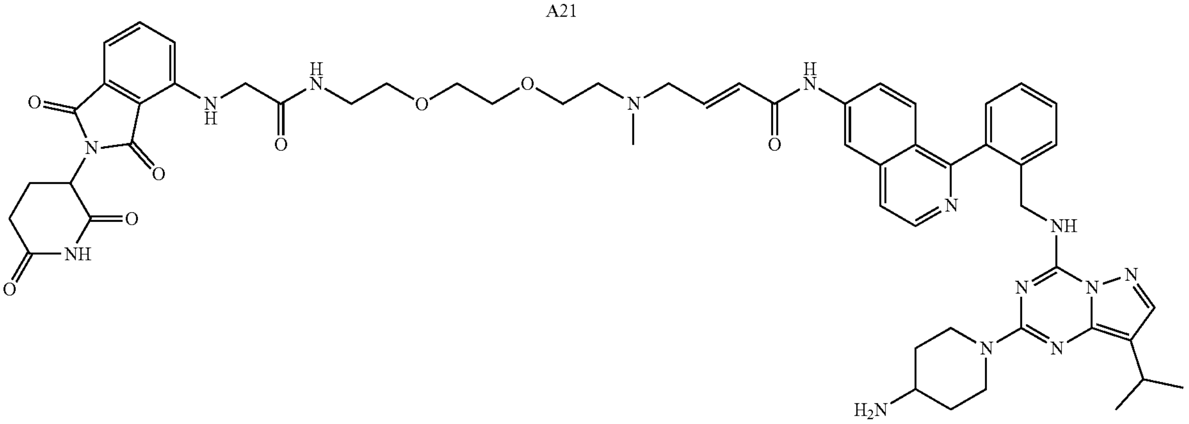

Compound 2

Procedure for Synthesis of A19

Intermediate C3 (300 mg, 905.5 umol) and B22 (237.57 mg, 905.58 umol) followed the same synthetic procedure of A10 to obtain 300 mg (524.2 umol, 57.9% yield) of A19 as yellow gum.

Procedure for Synthesis of A20

To a mixture of A19 (300 mg, 521.2 umol) in DCM (1 mL) was added TFA (356.56 mg, 3.13 mmol). Then the mixture was stirred at 20° C. for 2 hour to give a red suspension. LCMS showed the desired product was detected. The reaction mixture was concentrated under reduced pressure to give A20 (400 mg, crude) as red oil.

Procedure for Synthesis of A21

Intermediate A20 (100 mg, 169.63 umol) and A15 (128.02 mg, 169.63 umol) followed the same synthetic procedure of A16 to obtain 15 mg (13.05 umol, 7.7% yield) of A21 as yellow gum.

Synthesis of Compound 2

Intermediate A21 (15 mg) followed the same procedure of compound 11 to obtain 9 mg of compound 2 as yellow powder.

Scheme 8: Synthesis of compound 4

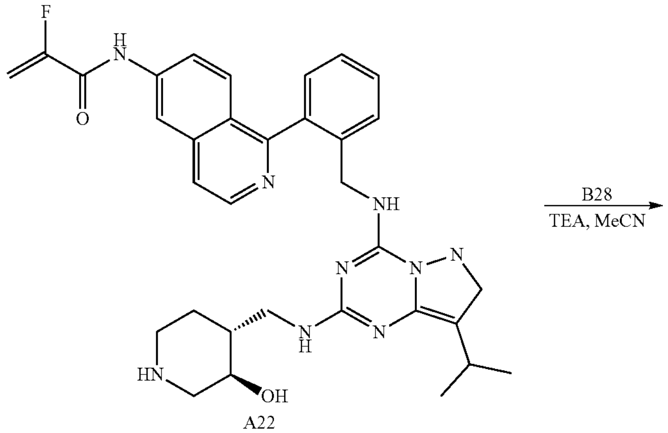

A22

-continued

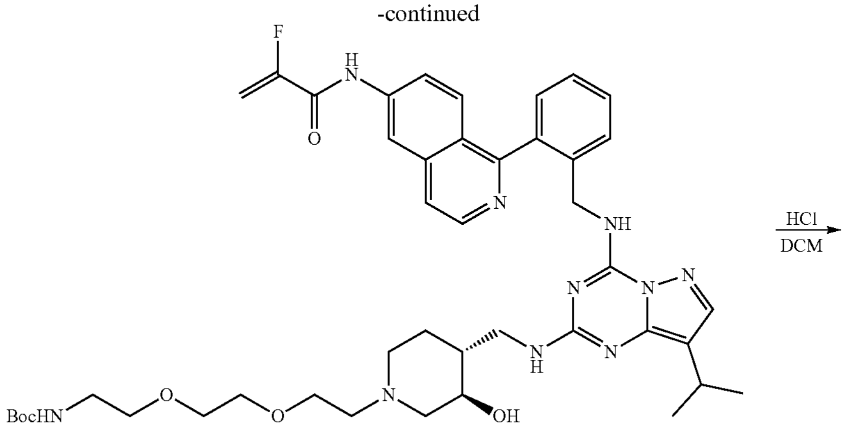

A23

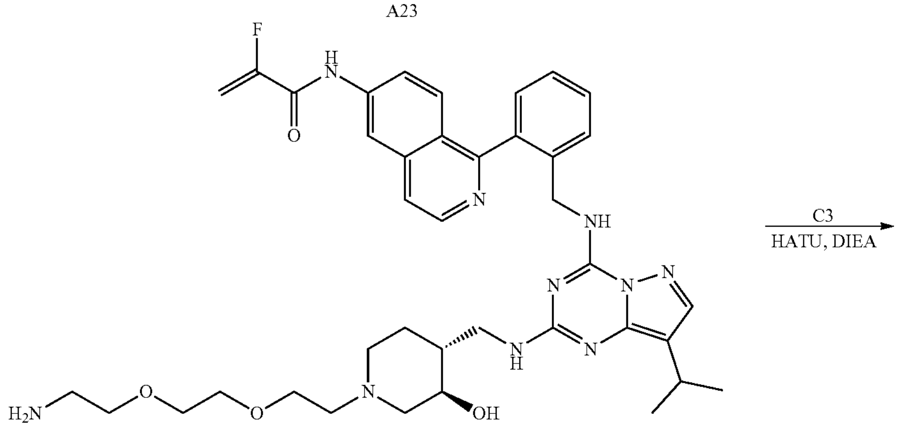

A24

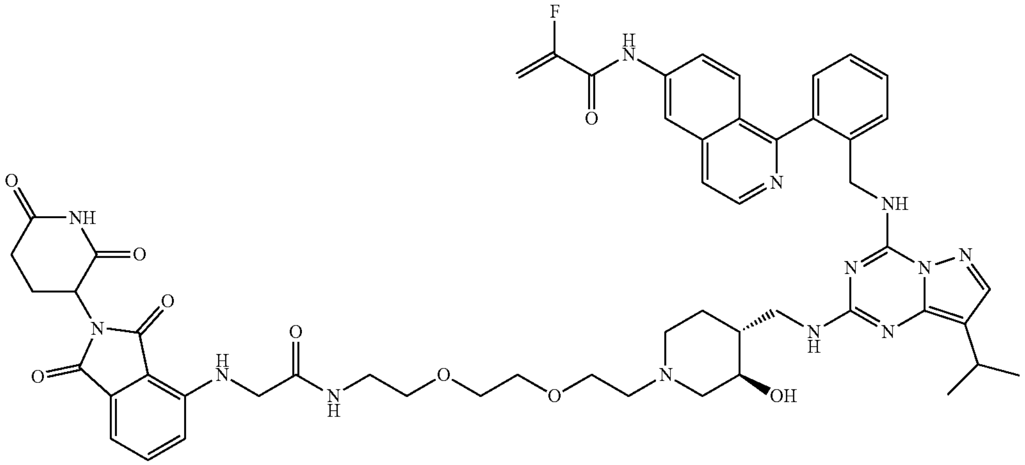

Compound 4

Synthetic route of compound A22 is published in WO2019197546A1.

Procedure for Synthesis of A23

A mixture of A22 (50 mg, 82.01 umol) and B28 (33.09 mg, 82.01 umol) with TEA (16.60 mg, 164.02 umol) in MeCN (0.5 mL)/DMF (0.5 mL) was heated to 80° C. for 48 hours to afford a brown mixture. The mixture was partitioned between DCM (10 mL) and water (10 mL). The aqueous layer was extracted with DCM (10 mL). The combined organic layers were dried over sodium sulfate as concentrated to afford A23 (80 mg, crude) as brown gum.

Procedure for Synthesis of A24

To a solution of A23 (80 mg, 95.13 umol) in DCM (1 mL) was added HCV/MeOH (4M, 1 mL) and the mixture was stirred at 15° C. for 1 hour to afford a brown solution. LCMS showed the reaction was completed. It was concentrated to give A24 (80 mg, crude) as brown gum.

Synthesis of Compound 4

Intermediate A24 (80 mg) and C3 (32.5 mg) followed the same procedure of A10 to obtain 4 mg of compound 4 as yellow powder.

Scheme 9: Synthesis of compound 5
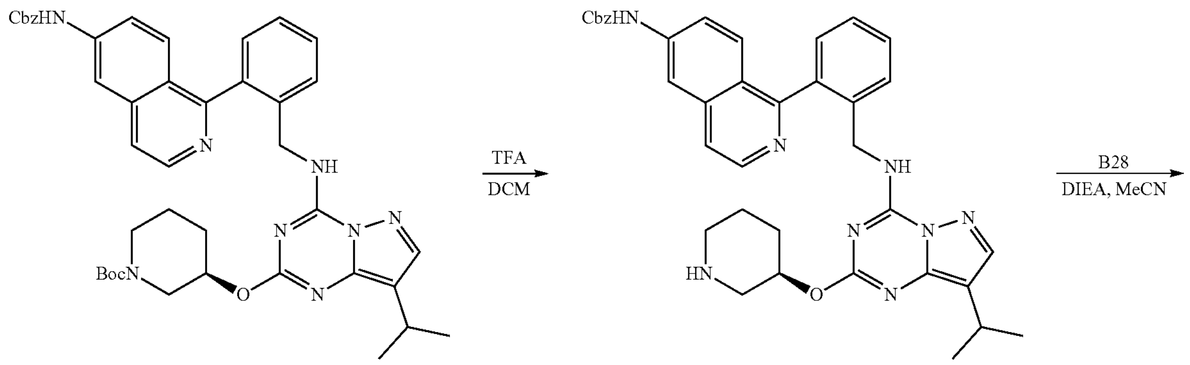
A4 A25
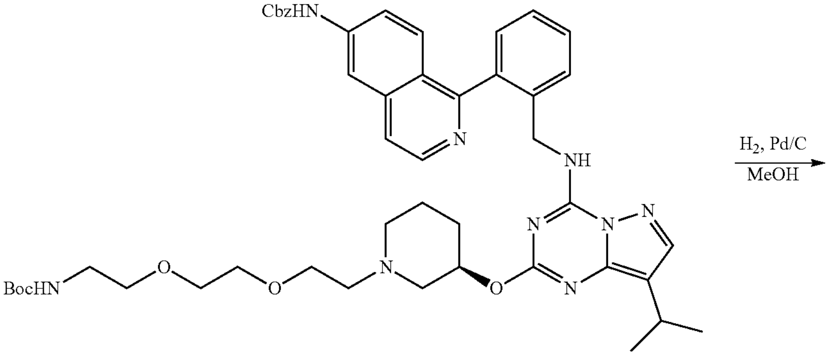
A26
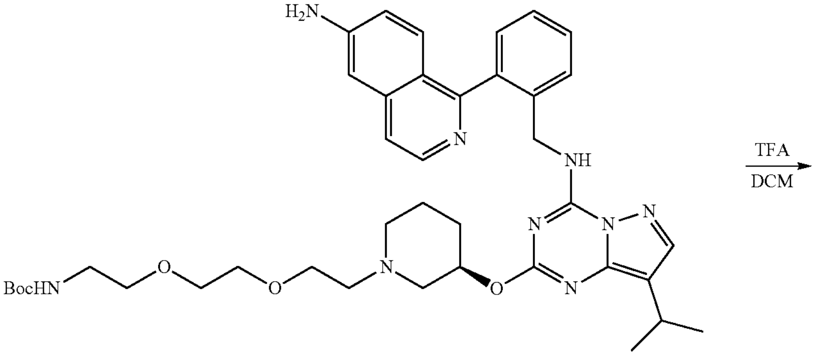
A27
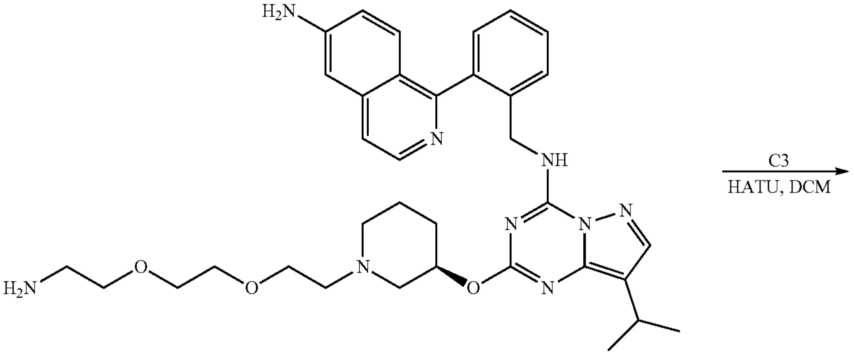
A28

-continued

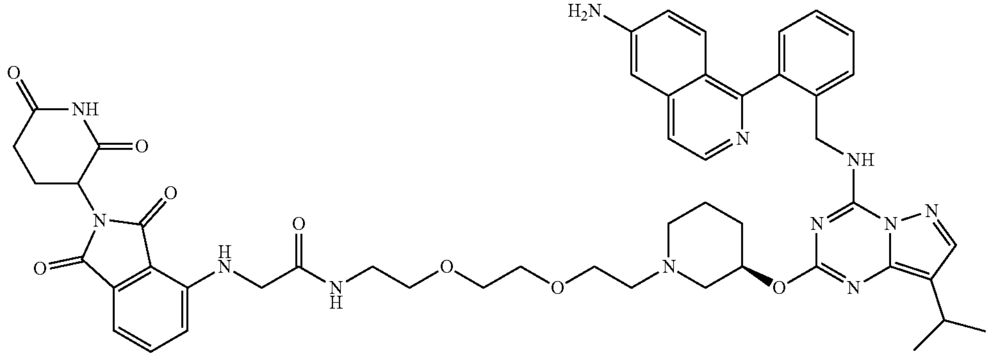

Compound 5

Procedure for Synthesis of A25

Intermediate A4 (150 mg, 201.92 umol) followed the same synthetic procedure of A20 to obtain 124 mg (crude) of A25 as colorless oil.

Procedure for Synthesis of A26

Intermediate A25 (124 mg, 192.92 umol) and B28 (77.84 mg, 192.92 umol) followed the same synthetic procedure of A23 to obtain 112 mg (112 mg, 128.14 umol, 66.42% yield) of A26 as white solid.

Procedure for Synthesis of A27

Intermediate A26 (112 mg, 128.14 umol) followed the same synthetic procedure of A12 to obtain 92 mg (crude) of A27 as white solid.

Procedure for Synthesis of A28

Intermediate A27 (92 mg) followed the same procedure of A20 to obtain 80 mg (crude) of A28 as colorless oil.

Synthesis of Compound 5

Intermediate A28 (crude 80 mg) followed the same procedure of compound 4 to obtain 10 mg of compound 5 as yellow solid.

Synthesis of Compound 6

Compound 6

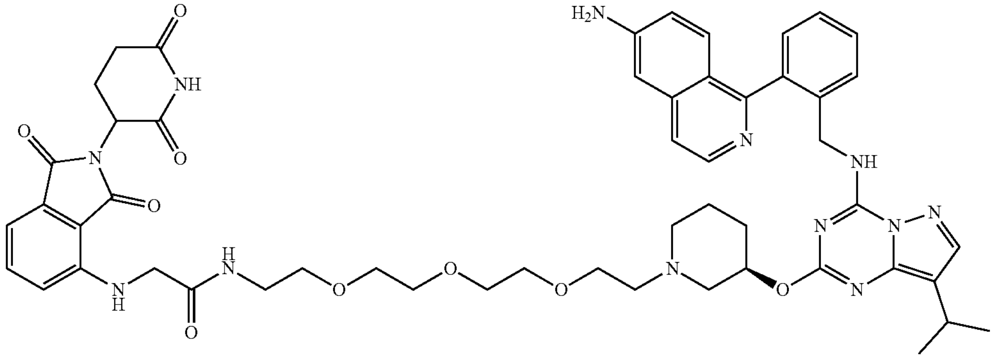

Compound 6 was synthesized as yellow solid by using B31 and the same synthetic route of compound 5.

Scheme 10: Synthesis of compound 9

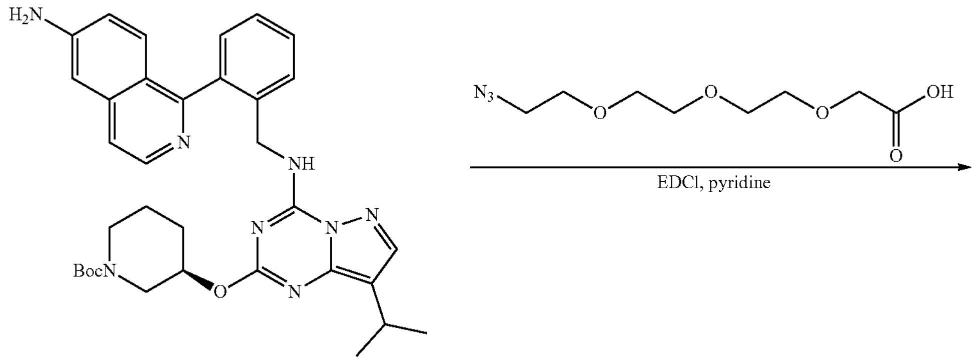

A5

-continued
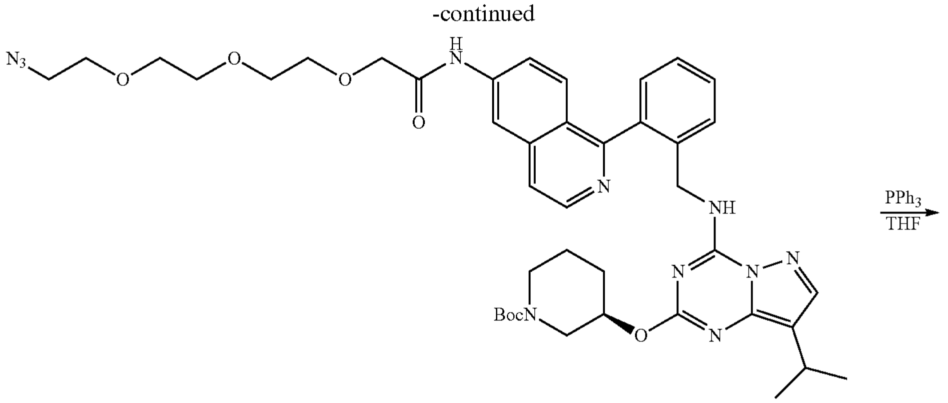
A29
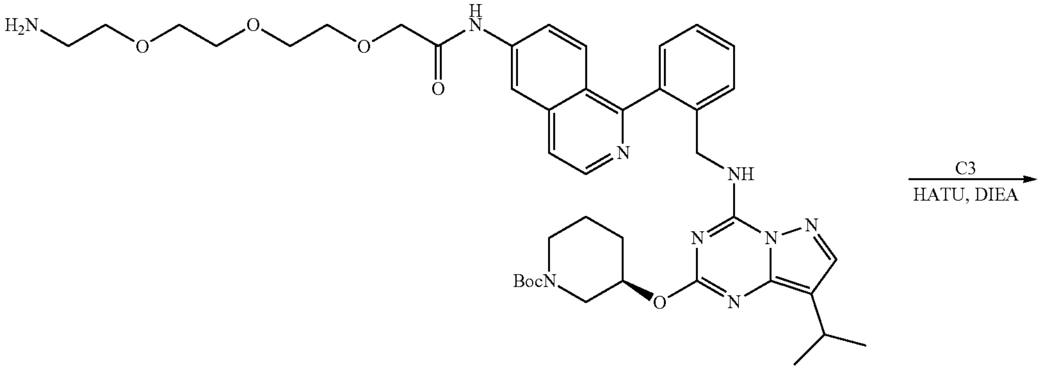
A30
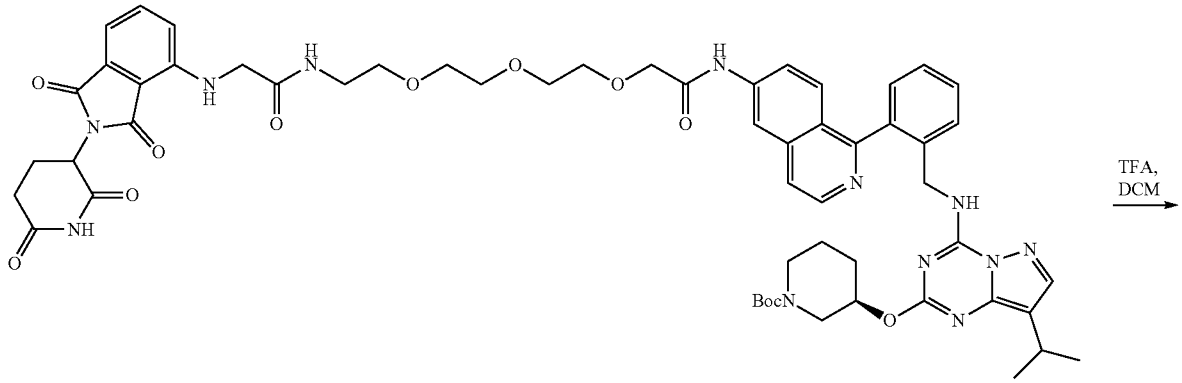
A31
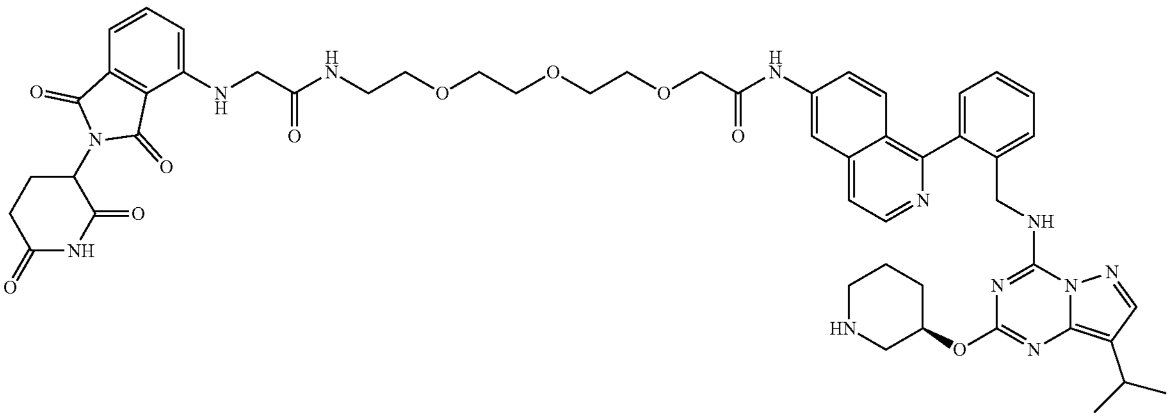
Compound 9

Procedure for Synthesis of A29

To a solution of 2-[2-[2-(2-azidoethoxy)ethoxy]ethoxy] acetic acid (160.91 mg, 689.96 umol) in Pyridine (5 mL) was added EDCI (176.36 mg, 919.95 umol) at 0° C. The mixture was stirred at 20° C. for 30 min. A5 (280 mg, 459.97 umol) was added and the mixture was stirred at 20° C. for 18 hr to give a yellow mixture. LCMS showed the reaction was completed. The reaction mixture diluted with water 20 mL and extracted with EtOAc (20 mL*3). The combined organic layers were washed with brine (20 mL*3), dried over $Na_2SO_4$, filtered and concentrated under reduced pressure to give a residue. The residue was purified by flash silica gel chromatography to afford A29 (330 mg, 400.52 umol, 87.07% yield) as white solid.

Procedure for Synthesis of A30

Intermediate A29 (165 mg, 200.26 umol) followed the same procedure of A17 to obtain 157 mg (196.76 umol, 98.25% yield) of A30 as yellow oil.

Procedure for Synthesis of A31

Intermediate A30 (156 mg, 196.97 umol) and C3 (65.25 mg, 196.97 umol) followed the same procedure of A10 to obtain 126 mg (111.69 umol, 54.08% yield) of A31 as yellow solid.

Synthesis of Compound 9

Intermediate A31 (126 mg) followed the same procedure of compound 11 to obtain 35.7 mg of compound 9 as yellow solid.

Scheme 11: Synthesis of compound 25

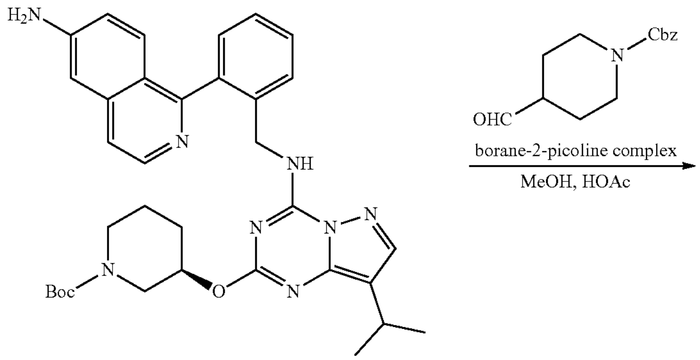

A5

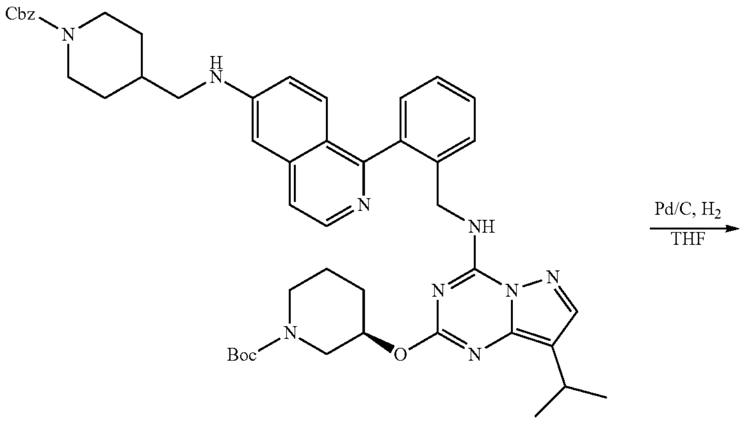

A32

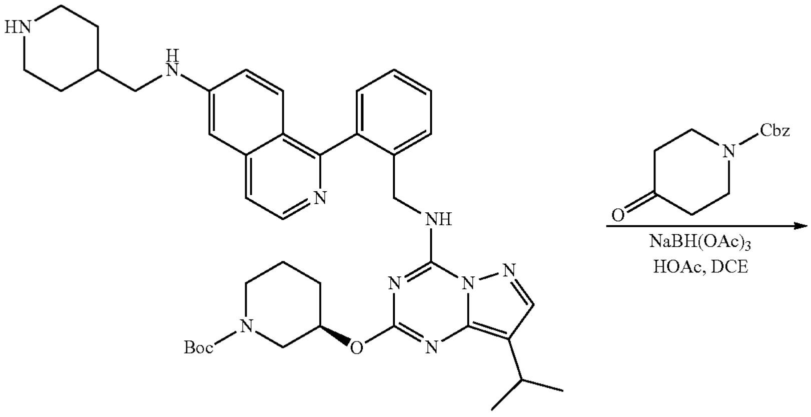

A33

-continued

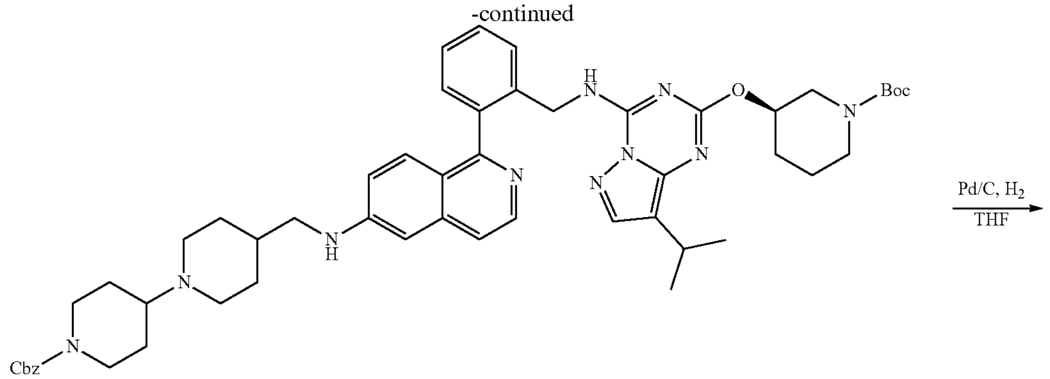

A34

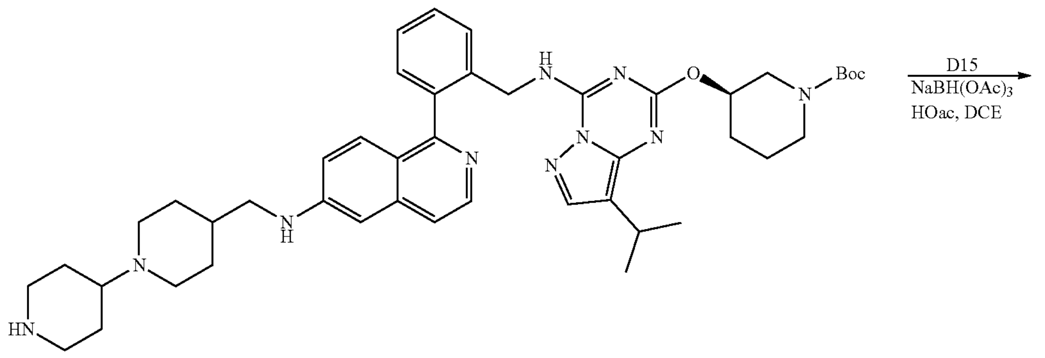

A35

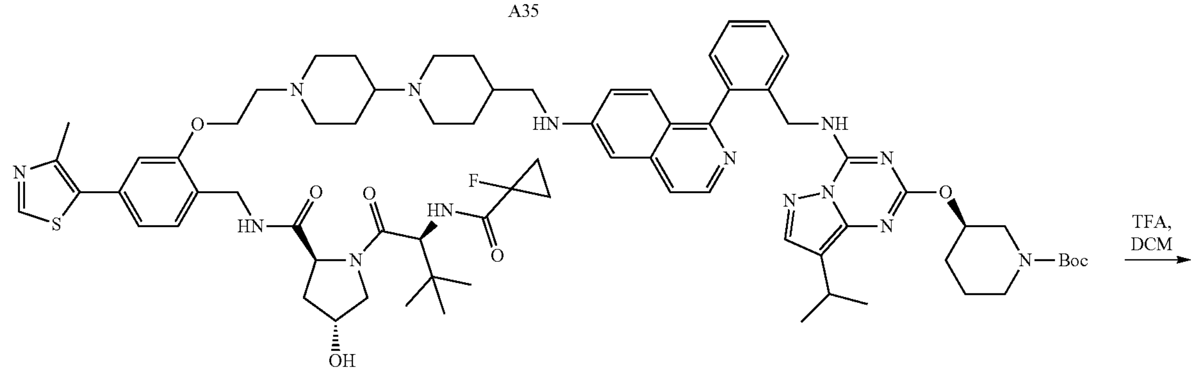

A36

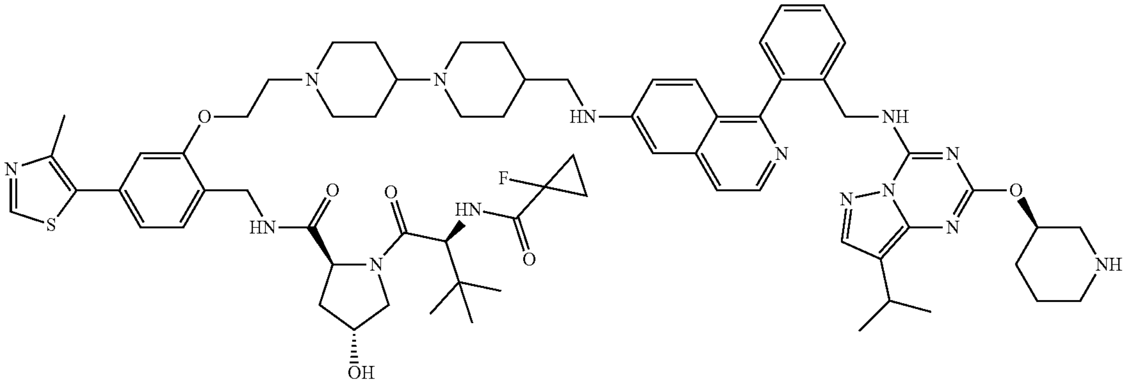

Compound 25

Procedure for Synthesis of A32

A mixture of A5 (300 mg, 492.83 umol), benzyl 4-formylpiperidine-1-carboxylate (182.81 mg, 739.24 umol) and borane-2-methylpyridine (79.07 mg, 739.24 umol) in MeOH (5 mL) was treated with HOAc (0.5 mL) at 20° C. The reaction mixture was stirred at 15° C. for 16 hours under $N_2$ to give brown mixture. Additional F4 (182.81 mg, 739.24 umol) and borane-2-methylpyridine (79.07 mg, 739.24 umol) were added, and the reaction was stirred at 15° C. under $N_2$ for 4 hous. The reaction was concentrated in vacuum. The residue was diluted with water (10 mL), stirred with 1M HCl (2 mL) for 5 min, then, basified with saturated $NaHCO_3$ (15 mL), extracted with ethyl acetate (20 mL×3). The organic layer was dried over $Na_2SO_4$, concentrated in vacuum to give crude product. The residue was purified by silica column to give A32 (368 mg, 438.08 umol, 88.89% yield) as brown oil.

Procedure for Synthesis of A33

Intermediate A32 (230 mg, 249.15 umol) followed the same synthetic procedure of A12 to obtain 166 mg (210.39 umol, 84.44% yield) of A33 as brown solid.

Procedure for Synthesis of A34

A mixture of A33 (290 mg, 410.83 umol) and benzyl 4-oxopiperidine-1-carboxylate (191.66 mg, 821.66 umol, 163.81 uL) and HOAc (24.67 mg, 410.83 umol, 23.50 uL) in DCE (4 mL) was treated with $NaBH(OAc)_3$ (304.75 mg, 1.44 mmol) at 15° C. The reaction mixture was stirred at 15° C. for 12 hours to give pale yellow mixture. The mixture was diluted with ethyl acetate (30 mL), stirred with saturated $NaHCO_3$ (20 mL) for 10 min. The organic layer was washed with brine (10 mL), dried over $Na_2SO_4$, concentrated in vacuum to give crude product. The residue was purified by prep-TLC to give A34 (200 mg, 216.65 umol, 52.73% yield) as yellow oil.

Procedure for Synthesis of A35

Intermediate A34 (350 mg, 339.3 umol) followed the same synthetic procedure of A12 to obtain 267 mg (crude) of A35 as yellow solid.

Procedure for Synthesis of A36

To a solution of A35 (25 mg, 31.68 umol) in DCE (0.5 mL) was added $NaBH(OAc)_3$ (20.15 mg, 95.05 umol), D15 (27.31 mg, 47.53 umol) and HOAc (4.97 mg, 82.78 umol, 4.73 uL). The mixture was stirred at 15° C. for 5 hours to give a yellow mixture. The mixture was added saturated $NaHCO_3$.aq (2 mL), partitioned between DCM (20 mL) and water (20 mL). The aqueous layer was extracted with DCM (20 mL×3). The organic layer was washed with saturated brine (30 mL), dried over anhydrous $Na_2SO_4$, filtered, and concentrated under reduced pressure to give crude product. The product was purified by prep-TLC to give A36 (27 mg, 20.03 umol, 63.23% yield) as yellow solid.

Synthesis of Compound 25

Intermediate A36 (65 mg) followed the same procedure of compound 11 to obtain 31.4 mg of compound as yellow solid.

Synthesis of Compound 29

Compound 29

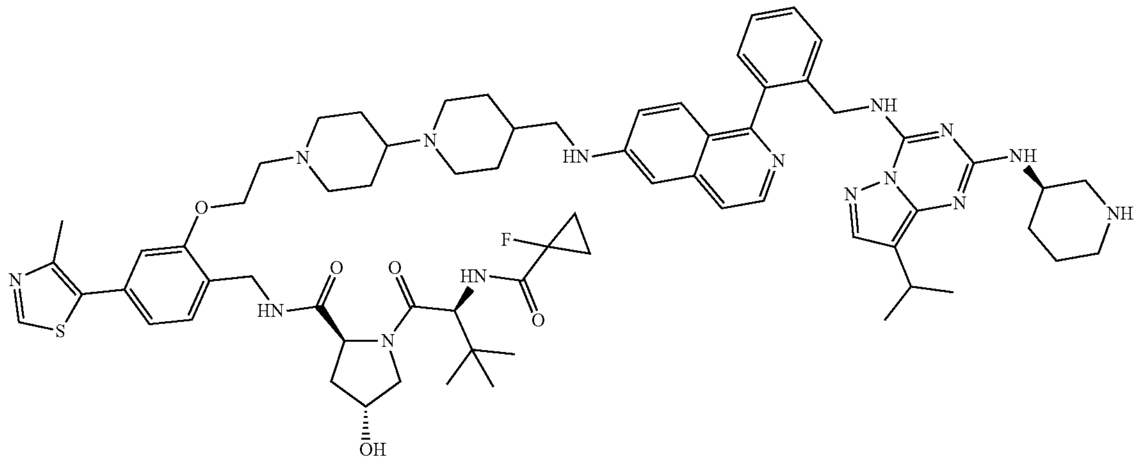

Compound 29 was synthesized as white solid by using F3 and the same synthetic route of compound 25.

Scheme 12: Synthesis of compound 30

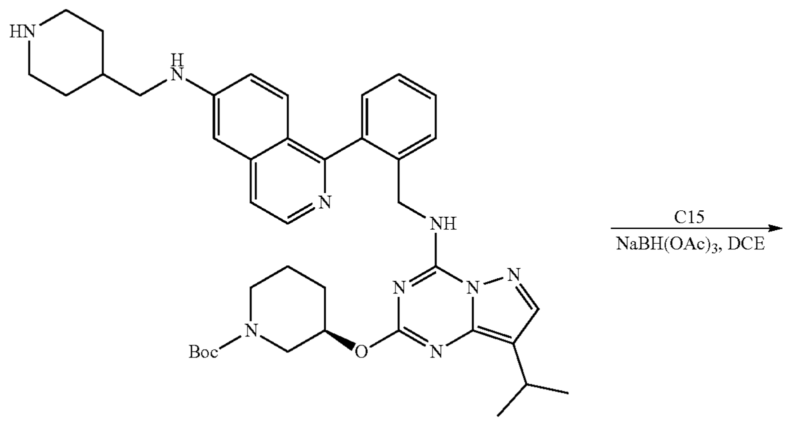

A33

-continued

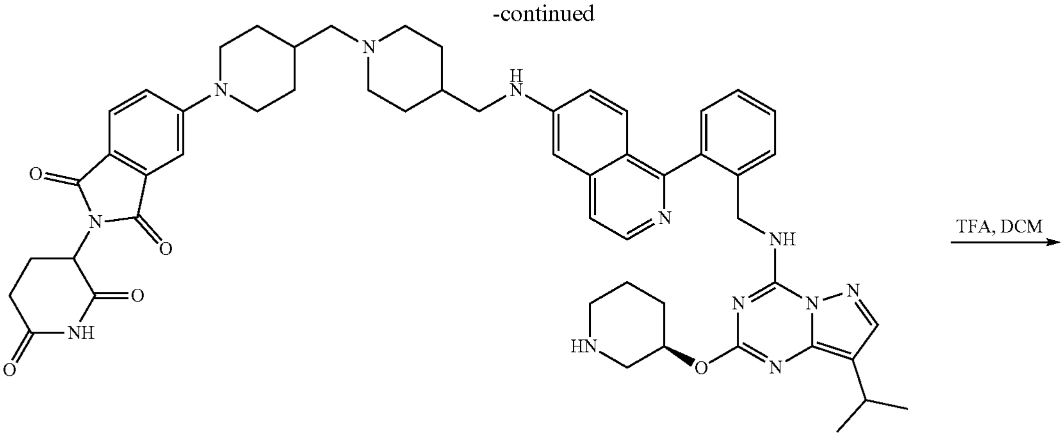

A37

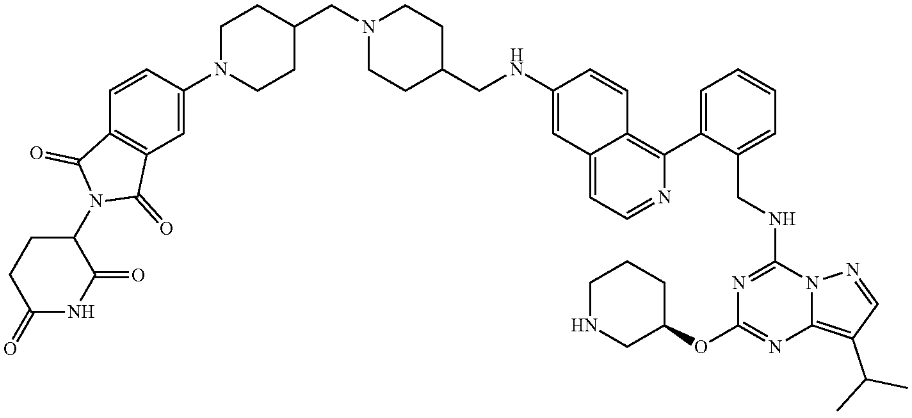

Compound 30

Procedure for Synthesis of A37

A solution of C15 (100.0 mg, 270.73 umol) and A33 (286.66 mg, 406.10 umol) in DCE (5 mL) was treated with $NaBH(OAc)_3$ (172.14 mg, 812.19 umol) at 0° C., then stirred at 20° C. for 12 hours to give yellow suspension. The reaction solution was used directly without further purification, A37 (280 mg, 264.34 umol, 97.64% yield) as a yellow suspension (in DCE).

Synthesis of Compound 30

Intermediate A37 (280 mg) followed the same procedure of compound 11 to obtain 50 mg of compound as yellow solid.

Synthesis of Compound 32

Compound 32

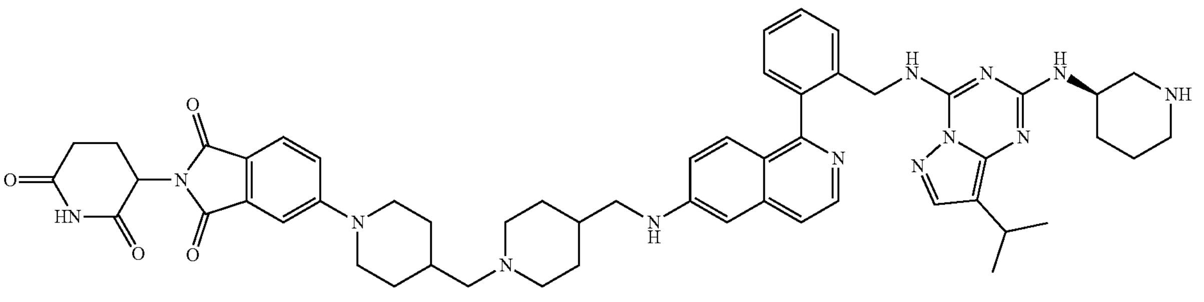

Compound 32 was synthesized as yellow solid by using F3, and the same synthetic route of A33 and compound 30.

Scheme 13: Synthesis compound 31

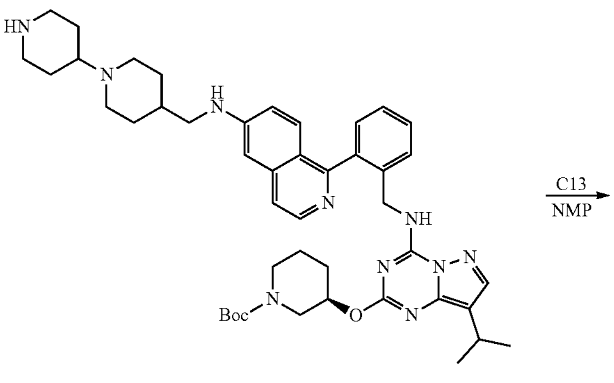

A35

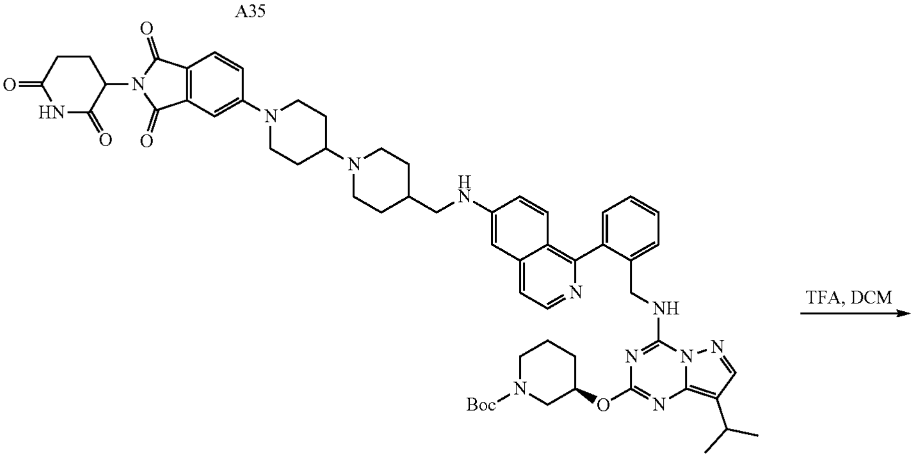

A38

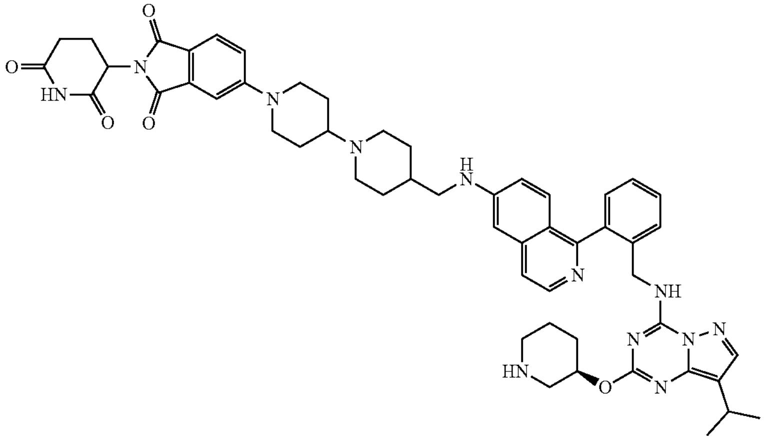

Compound 31

Procedure for Synthesis of A38

To a solution of C13 (55 mg, 199.12 umol) and A36 (141.40 mg, 179.21 umol) in DMF (2 mL) was added TEA (20.15 mg, 199.12 umol, 27.71 uL). The mixture stirred at 90° C. for 12 hours to give a yellow solution. Then 11 mg of C13 was added, the mixture stirred at 90° C. for 5 hours to give a yellow solution. The reaction mixture was concentrated directly to give A38 (300 mg, crude) as brown gum.

Synthesis of Compound 31

Intermediate A38 (300 mg) followed the same procedure of compound 11 to obtain 74.5 mg of compound 31 as yellow solid.

Scheme 14: Synthesis of compound 33
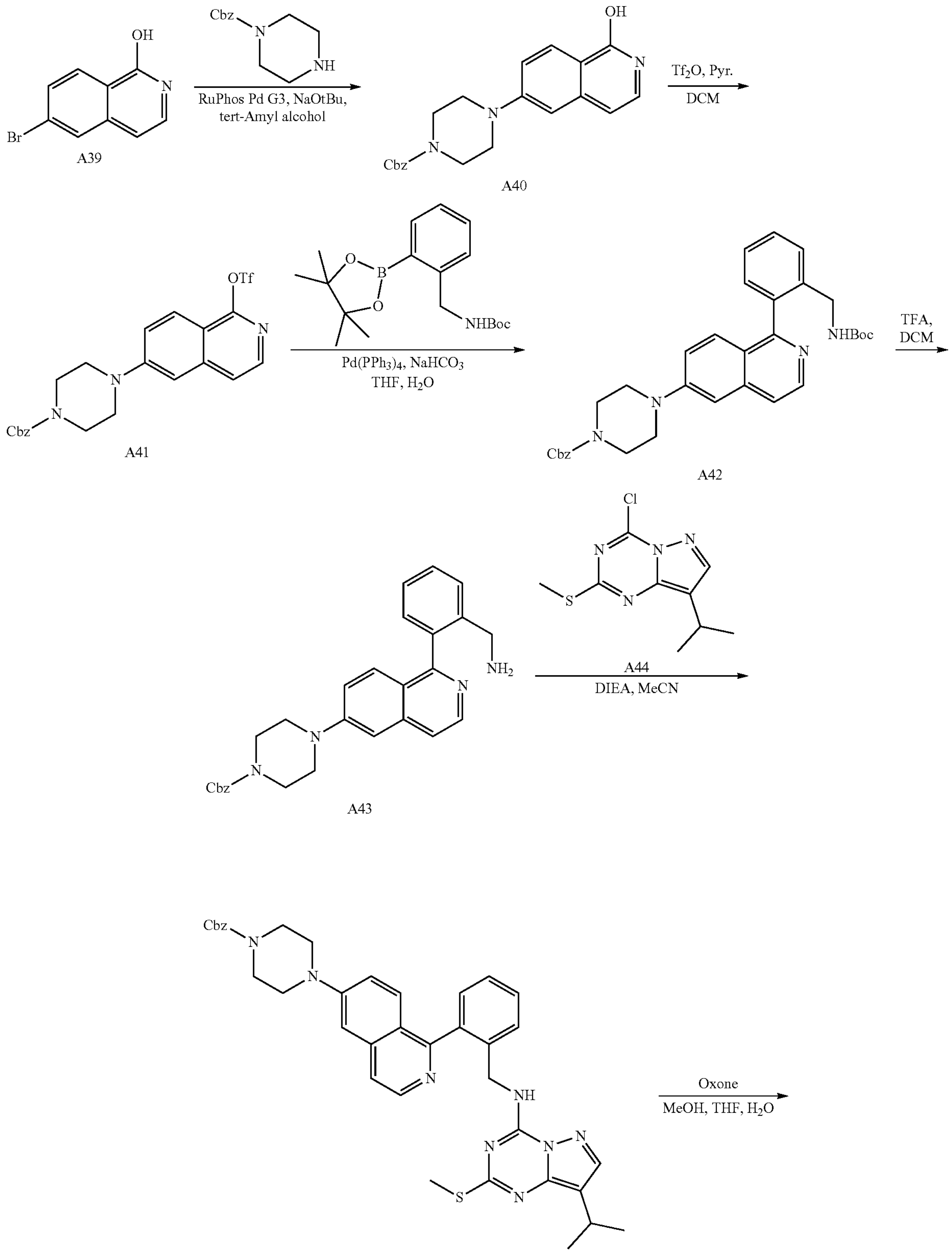
A39 A40 A41 A42 A43 A45

-continued
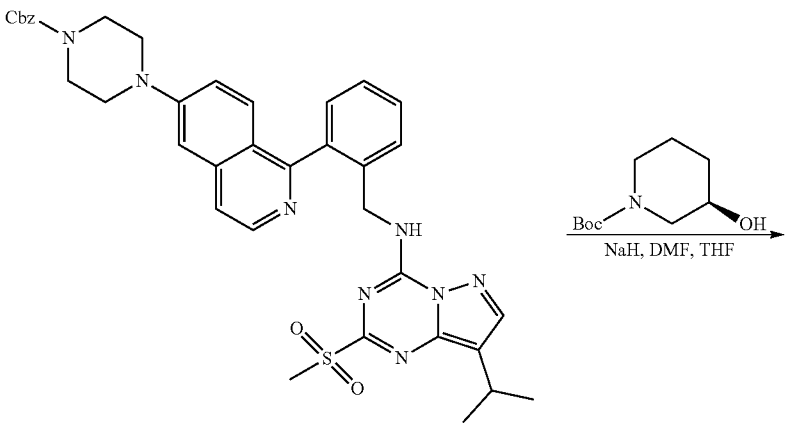
A46
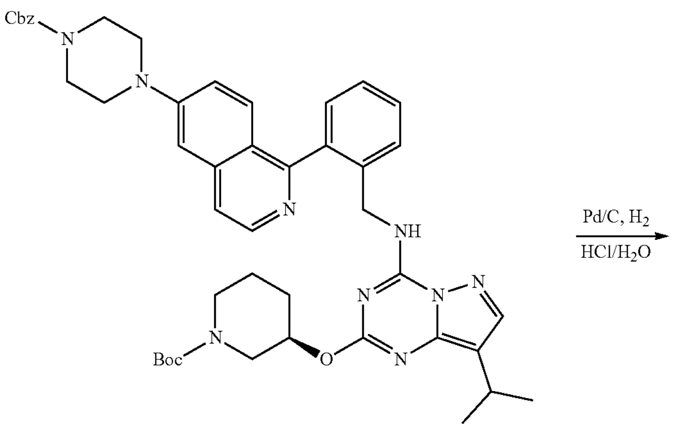
A47
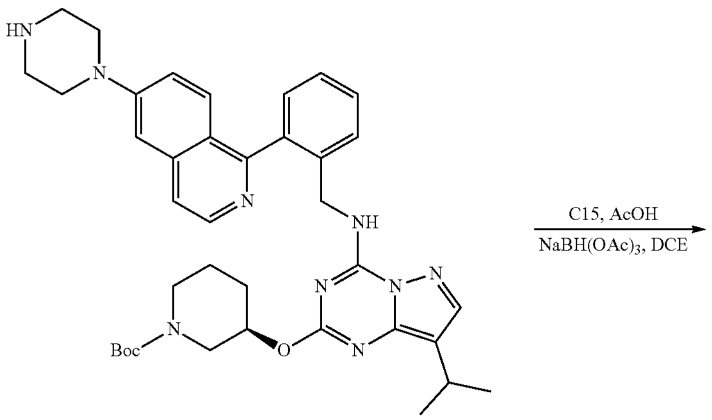
A48

-continued

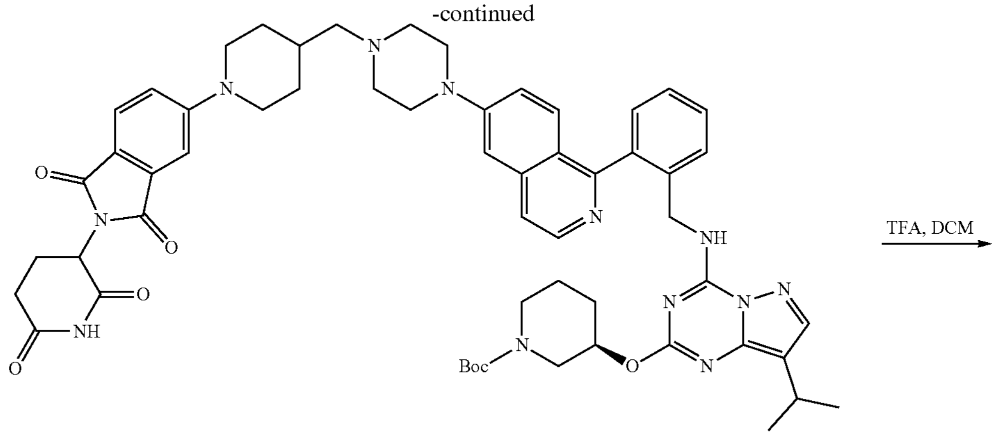

A49

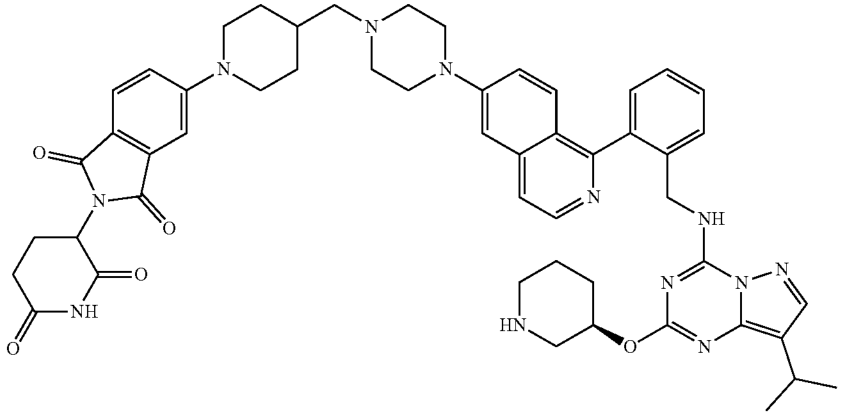

Compound 33

Synthetic route of compound A44 is published in WO2019197546A1.

Procedure for Synthesis of A40

To a solution of A39 (2 g, 8.93 mmol), benzyl piperazine-1-carboxylate (2.95 g, 13.39 mmol, 2.59 mL), NaOtBu (2.57 g, 26.78 mmol), RuPhos-Pd-G3 (746.58 mg, 892.64 umol) and in tert-Amyl alcohol (25 mL) was degassed and purged with $N_2$ for 3 times, and then the mixture was stirred at 100° C. for 16 hours under $N_2$ atmosphere. The reaction was diluted with water (30 mL), extracted with ethyl acetate (30 mL×3) and washed with brine (30 mL). The organic layer was concentrated in vacuum to give brown oil. The residue was purified by column chromatography to give A40 (1.1 g, 3.03 mmol, 33.91% yield) as white solid.

Procedure for Synthesis of A41

To a solution of A40 (1.1 g, 3.03 mmol) in DCM (15 mL) was added pyridine (1.20 g, 15.13 mmol, 1.22 mL) and $Tf_2O$ (1.02 g, 3.63 mmol, 599.30 uL) was added dropwised at 0° C. The reaction mixture was stirred at 0° C. under $N_2$ atmosphere protect for 1 hours to give a yellow mixture. The reaction mixture was diluted with water (20 mL) and extracted with ethyl acetate (20 mL×3). The combined organic layers were washed with brine (20 mL×3), dried over $Na_2SO_4$ filtered and concentrated under reduced pressure to give a residue. The residue was purified by column chromatography to give A41 (1.23 g, 2.48 mmol, 82.01% yield) as colorless oil.

Procedure for Synthesis of A42

To a solution of A41 (1.23 g, 2.48 mmol) in THF (12 mL) was added Pd(PPh3)4 (286.87 mg, 248.25 umol), the mixture was stirred at 20° C. for 30 min under $N_2$ atmosphere, $NaHCO_3$ (625.66 mg, 7.45 mmol, 289.66 uL) and tert-butyl (2-(4,4,5,5-tetramethyl-1,3,2-dioxaborolan-2-yl)benzyl)carbamate (827.24 mg, 2.48 mmol) in $H_2O$ (1.2 mL) was added. The reaction mixture was stirred at 80° C. under $N_2$ atmosphere protect for 16 hours to give a black mixture. The reaction mixture was diluted with water (20 mL) and extracted with ethyl acetate (20 mL×3). The combined organic layers were washed with brine (20 mL×3), dried over $Na_2SO_4$ filtered and concentrated under reduced pressure to give a residue. The residue was purified by column chromatography to give A42 (1.23 g, 2.23 mmol, 89.65% yield) as colorless oil.

Procedure for Synthesis of A43

To a solution of A42 (1.23 g, 2.23 mmol) in DCM (10 mL) was added TFA (3.81 g, 33.38 mmol, 2.47 mL). The mixture was stirred at 20° C. for 1 hour to give a yellow solution. TFA (1 mL) was added, and the mixture was stirred at 20° C. for 30 min. The reaction mixture was concentrated under reduced pressure to give A43 (1.26 g, crude, TFA) as yellow oil.

Procedure for Synthesis of A45

To a solution of A43 (1.26 g, 2.22 mmol, TFA) in MeCN (10 mL) was added DIEA (2.87 g, 22.24 mmol, 3.87 mL) and A44 (539.81 mg, 2.22 mmol). The mixture was stirred at 20° C. for 1 hour to give a yellow solution. The reaction mixture was diluted with water (20 mL) and extracted with ethyl acetate (20 mL×3). The combined organic layers were washed with brine (20 mL×3), dried over $Na_2SO_4$, filtered and concentrated under reduced pressure to give a residue.

The residue was purified by column chromatography to give A45 (1.22 g, 1.85 mmol, 83.27% yield) as white solid.

Procedure for Synthesis of A46

To a solution of A45 (1.22 g, 1.85 mmol) in THF (10 mL), MeOH (5 mL) and $H_2O$ (5 mL) was added Oxone (1.14 g, 1.85 mmol) at 0-5° C. and the mixture was stirred at 0-5° C. for 30 min. The mixture was treated with additional Oxone (569.22 mg, 925.91 umol) and stirred at 0-5° C. for another 30 min to give a yellow mixture. The mixture was added to another Oxone (569.22 mg, 925.91 umol) and stirred at 0-5° C. for another 30 min to give a yellow mixture. The mixture was added to another Oxone (569.22 mg, 925.91 umol) and stirred at 0-5° C. for another 30 min to give a yellow mixture. The reaction was then heated at 50° C. for 1 hour to give brown solution. LCMS indicated desired MS was detected, the mixture was stirred at 0° C. for 5 hours. The mixture was quenched by saturated $Na_2SO_3$ (10 mL) and then partitioned between ethyl acetate (30 mL) and $H_2O$ (30 mL). The aqueous phase was extracted with ethyl acetate (30 mL×2). The combined organic layers were dried over anhydrous $Na_2SO_4$, filtered and concentrated under reduced pressure to give a crude residue. The residue was purified by column chromatography to give A46 (820 mg, 1.19 mmol, 64.10% yield) as white solid.

Procedure for Synthesis of A47

To a solution of tert-butyl (3R)-3-hydroxypiperidine-1-carboxylate (58.27 mg, 289.51 umol) in THE (1 mL) was added NaH (11.58 mg, 289.51 umol, 60% purity) at 0° C. The mixture was heated to 50° C. A46 (100 mg, 144.76 umol) in DMF (0.5 mL) was added to the mixture. The reaction mixture was heated to 50° C. for 4 hours to give a yellow mixture. Saturated $NH_4Cl$ (10 mL) was added to the reaction mixture, which followed by extraction with ethyl acetate (20 mL×2). The combined organic layers were washed with brine (20 mL×4), dried over anhydrous $Na_2SO_4$, filtered and concentrated under reduced pressure to give a residue. The residue was purified by prep-TLC to give A47 (30 mg, 34.73 umol, 23.99% yield) as white solid.

Procedure for Synthesis of A48

To a solution of A47 (65 mg, 80.05 umol) and HCl (16.22 mg, 160.10 umol, 15.90 uL, 36% purity) in MeOH (10 mL) was added wet Pd/C (30 mg), the mixture was stirred at 20° C. under $H_2$ atmosphere for 7 hours to give a black mixture. The mixture was filtered and the pH was adjusted to around 8 by progressively adding saturate $Na_2CO_3$ was filtered and concentrated under reduced pressure to give A48 (55 mg, crude) as a white solid.

Procedure for Synthesis of A49

To a solution of A48 (44 mg, 64.91 umol, 1 eq), C15 (47.95 mg, 129.82 umol) in DCE (1.5 mL) and AcOH (779.62 ug) was added $NaBH(OAc)_3$ (41.27 mg, 194.74 umol), degassed and purged with $N_2$ for 3 times, and then the mixture was stirred at 20° C. for 17 hours under $N_2$ atmosphere to give a yellow mixture. C15 (16 mg) and $NaBH(OAc)_3$ (13.8 mg) was added, the mixture was stirred at 20° C. for 1 hour. The mixture was treated with 1N HCl (0.5 mL) and stirred at 20° C. for 30 min. The pH was adjusted to around 9 by progressively adding saturated $NaHCO_3$. The mixture was extracted with ethyl acetate (20 mL×2). The combined extracts were washed with brine (20 mL), dried over anhydrous $Na_2SO_4$ and concentrated under reduced pressure to give the residue. The residue was purified by prep-TLC to give A49 (36 mg, 31.52 umol, 48.56% yield) as yellow solid.

Synthesis of Compound 33

Intermediate A49 (36 mg) followed the same procedure of compound 11 to obtain 30.2 mg of compound 33 as yellow solid.

Synthesis of Compound 35

Compound 35

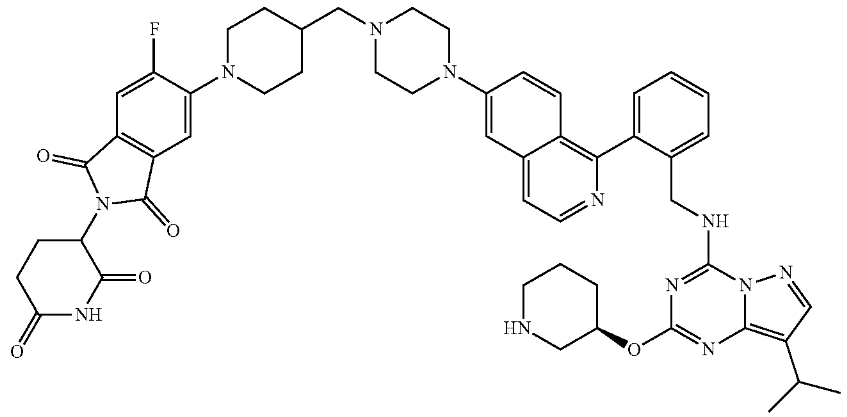

Compound 35 was synthesized as yellow powder by using 2-(2,6-dioxopiperidin-3-yl)-5,6-difluoroisoindoline-1,3-dione, and the same synthetic route of compound 33

Scheme 15: Synthesis of compound 34
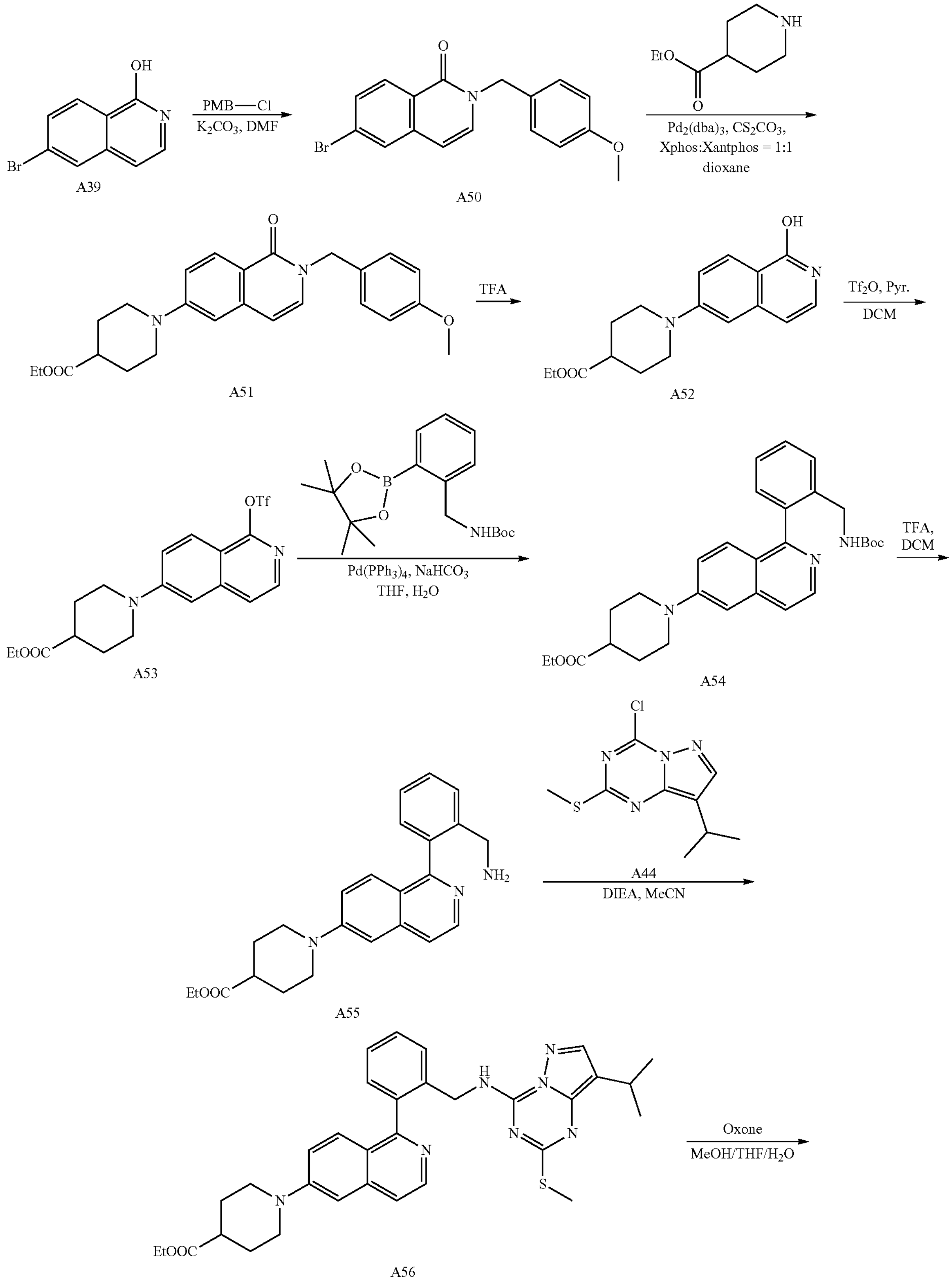

-continued
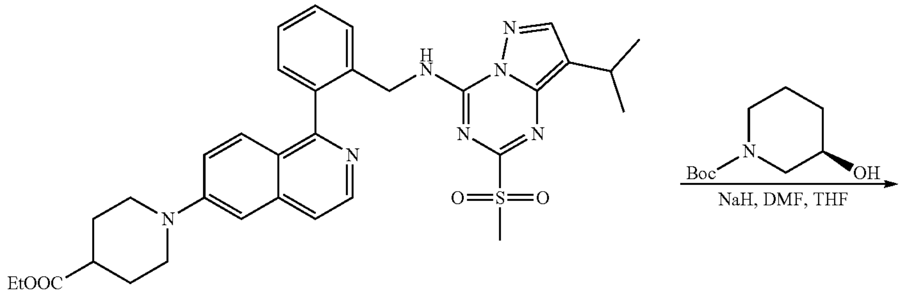
A57
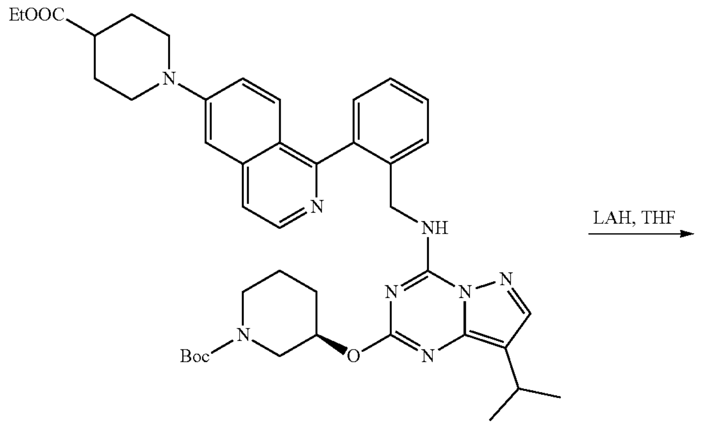
A58
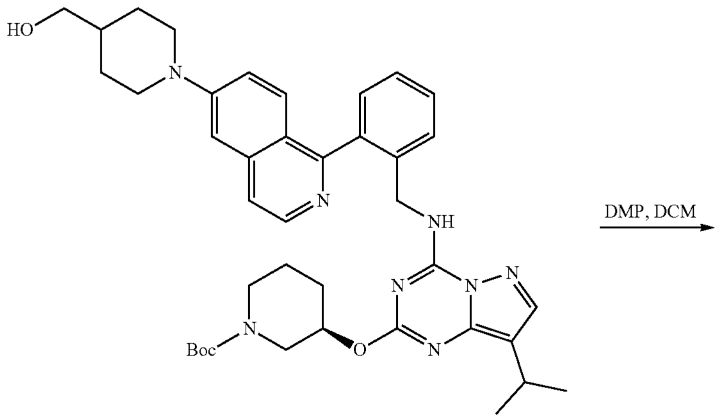
A59
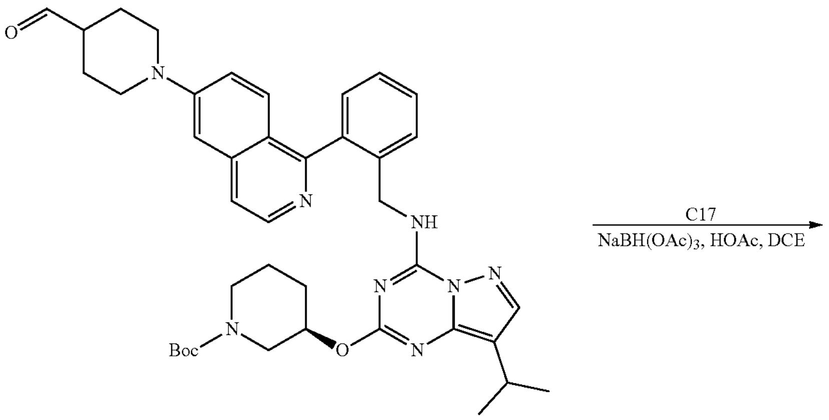
A60

-continued

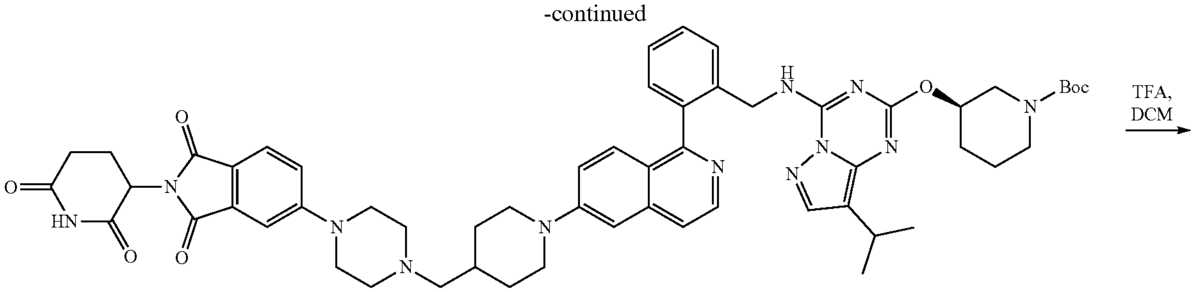

A61

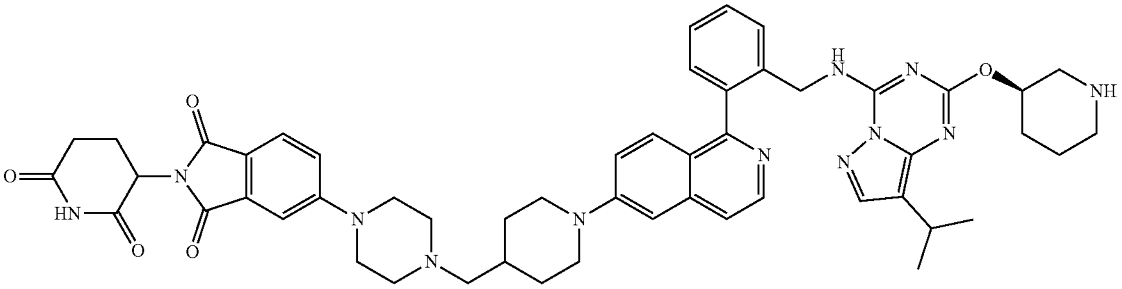

Compound 34

Procedure for Synthesis of A50

To a solution of A39 (200 mg, 892.64 umol) in DMF (4 mL) was added $K_2CO_3$ (246.74 mg, 1.79 mmol) and PMB-Cl (251.63 mg, 1.61 mmol, 218.81 uL). The mixture was heated to 80° C. and stirred for 16 hours to give a yellow mixture. The reaction mixture was diluted with water (30 mL), extracted with ethyl acetate (30 mL×3) and brine (30 mL×3). The organic layer was concentrated in vacuum to give a residue. The residue was purified by column chromatography to give A50 (200 mg, 581.05 umol, 65.09% yield) as white solid.

Procedure for Synthesis of A51

A mixture of A50 (150 mg, 435.79 umol), ethyl piperidine-4-carboxylate (102.77 mg, 653.69 umol, 100.75 uL), $Cs_2CO_3$ (425.97 mg, 1.31 mmol), XPhos (20.78 mg, 43.58 umol), Xantphos (25.22 mg, 43.58 umol) and $Pd_2(dba)_3$ (39.91 mg, 43.58 umol) in dioxane (3 mL) was degassed and purged with $N_2$ for 3 times, and then the mixture was heated at 120° C. for 1 hour under microwave to give a yellow mixture. The reaction mixture was diluted with water (30 mL), extracted with ethyl acetate (30 mL×3) and brine (30 mL). The organic layer was concentrated in vacuum to give brown oil. The residue was purified by prep-TLC to give A51 (110 mg, 261.59 umol, 60.03% yield) as white solid.

Procedure for Synthesis of A52

A mixture of A51 (1.8 g, 4.28 mmol) in TFA (6 mL) was stirred at 120° C. for 30 min under microwave to give a yellow mixture. The reaction mixture was diluted with water (10 mL) and the pH was adjusted to around 9 by adding $Na_2CO_3$, then extracted with DCM (20 mL×3). The combined organic layers dried over $Na_2SO_4$, filtered and concentrated under reduced pressure to give a residue. The residue was purified by column chromatography to give A52 (1 g, 3.33 mmol, 77.78% yield) as yellow oil.

Procedure for Synthesis of A53

Intermediate A52 (1 g, 3.33 mmol) followed the same procedure of A40 to obtain 1.1 g (2.54 mmol, 76.41% yield) of A53 as colorless oil.

Procedure for Synthesis of A54

Intermediate A53 (1.1 g, 2.54 mmol) followed the same procedure of A41 to obtain 250 mg (0.512 mmol, 20.14% yield) of A54 as yellow oil.

Procedure for Synthesis of A55

Intermediate A54 (660 mg, 1.35 mmol) followed the same procedure of A42 to obtain 680 mg (crude, TFA) of A55 as yellow oil.

Procedure for Synthesis of A56

Intermediate A55 (680 mg, 1.35 mmol, TFA) followed the same procedure of A43 to obtain 760 mg (1.28 mmol, 94.46% yield) of A56 as yellow oil.

Procedure for Synthesis of A57

Intermediate A56 (760 mg, 1.28 mmol) followed the same procedure of A45 to obtain 300 mg (0.478 mmol, 37.34% yield) of A57 as white solid.

Procedure for Synthesis of A58

Intermediate A57 (150 mg, 0.239 mmol) followed the same procedure of A46 to obtain 85 mg (0.114 mmol, 15.83% yield) of A58 as yellow solid.

Procedure for Synthesis of A59

To a solution of $LiAlH_4$ (6.59 mg, 173.59 umol) in THF (0.5 mL), A58 (65 mg, 86.79 umol) in THF (0.5 mL) was added dropwised at 0° C. After addition, the mixture was stirred at 0° C. for 30 min to give a yellow solution. The reaction was quenched with water (1 mL), and then 15% NaOH (1 mL) was added. After stirring for 10 min, water (1 mL) was added to the resulting mixture, and dried over $Na_2SO_4$ for 30 min. The mixture was filtered through celite and concentrated under reduced pressure to give a residue. The residue was purified by prep-TLC to give A59 (50 mg, 70.73 umol, 81.50% yield) as yellow solid.

Procedure for Synthesis of A60

To a solution of A59 (50 mg, 70.73 umol) in DCM (3 mL) was added Dess-Martin (60.00 mg, 141.47 umol). The mixture was stirred at 0° C. for 5 hours to give a yellow solution. The reaction mixture was quenched by saturated $Na_2SO_3$ aqueous solution at 0° C., and then diluted with water (5 mL) and extracted with DCM (20 mL×3). The combined organic layers were washed with brine (20 mL×3), dried over $Na_2SO_4$, filtered and concentrated under reduced pressure to give A60 (49 mg, crude) as yellow solid.

Procedure for Synthesis of A61

To a solution of A60 (49 mg, 69.52 umol) and C17 (23.80 mg, 69.52 umol) in DCE (1.5 mL) and AcOH (834.91 ug) was added $NaBH(OAc)_3$ (44.20 mg, 208.55 umol) degassed and purged with $N_2$ for 3 times, and then the mixture was stirred at 20° C. for 17 hours under $N_2$ atmosphere to give a yellow mixture. The mixture was treated with 1N HCl (0.5 mL), stirred at 20° C. for 30 min, and the pH was adjusted to around 9 by progressively adding saturated $NaHCO_3$. The mixture was extracted with ethyl acetate (20 mL×2). The combined extracts were washed with brine (20 mL), dried over anhydrous $Na_2SO_4$ and concentrated under reduced pressure to give the residue. The residue was purified by prep-TLC to give A61 (66 mg, 64.00 umol, 92.07% yield) as yellow solid.

Synthesis of Compound 34

Intermediate A61 (66 mg) followed the same procedure of compound 11 to obtain 31.3 mg of compound 34 as yellow powder.

Synthesis of Compound 36

Scheme 17: Synthesis of intermediate B3

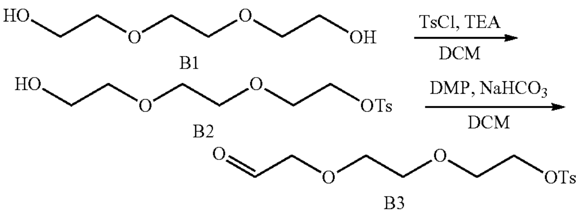

Procedure for Synthesis of B2

To a mixture of B1 (5 g, 33.30 mmol) in DCM (35 mL) was added TEA (5.05 g, 49.94 mmol). A solution of 4-methylbenzenesulfonyl chloride (6.35 g, 33.30 mmol) in DCM (15 mL) was dropwise added in the mixture. The resulting mixture was stirred at 20° C. under $N_2$ for 16 hr to give a yellow mixture. TLC indicated the reaction was completed. The reaction mixture was diluted with water 50 mL and extracted with DCM (50 mL*3). The combined organic layers were washed with brine (50 mL*3), dried over Compound 36

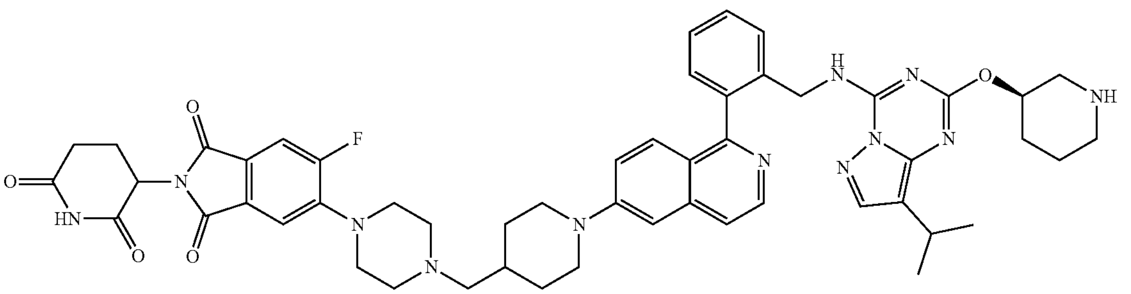

Compound 36 was synthesized as yellow powder by using 2-(2,6-dioxopiperidin-3-yl)-5,6-difluoroisoindoline-1,3-dione, and the same synthetic route of compound 34.

Synthesis of Linker Part Intermediates

Scheme 16: General synthetic route 3

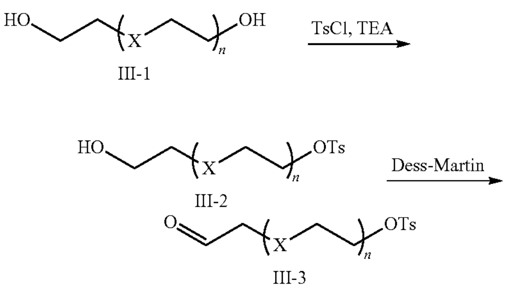

X: O, C
n: 1, 2, 3, 4, 5

The Method to Prepare Compounds of Formula III-3 Shown in Scheme 16

Compounds of formula III-2 can be synthesized by treating tosyl chloride in presence of triethylamine. Compound III-3 can be prepared by treating Dess-Martin periodinane in presence of sodium bicarbonate.

$Na_2SO_4$, filtered and concentrated under reduced pressure to give a residue. The residue was purified by column chromatography to afford B2 (4.16 g, 13.67 mmol, 41% yield) as white solid.

Procedure for Synthesis of Intermediate B3

To a solution of B2 (1.5 g, 4.93 mmol) in DCM (30 mL) was added Dess-Martin periodinane (2.72 g, 6.41 mmol) and $NaHCO_3$ (4.14 g, 49.28 mmol). The mixture was stirred at 20° C. for 3 hr to give a white suspension. The reaction mixture was diluted with water 20 mL and extracted with DCM (20 mL*2). The combined organic layers were washed with brine (20 mL*2), dried over $Na_2SO_4$, filtered and concentrated under reduced pressure to give a residue. The residue was purified by flash silica gel chromatography to afford B3 (700 mg, 2.32 mmol, 47% yield) as white solid.

Synthesis of Intermediate B4

B4

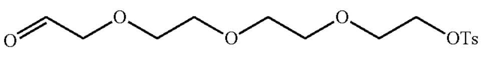

Intermediate B4 was synthesized as colorless oil by using 2,2'-((oxybis(ethane-2,1-diyl))bis(oxy))bis(ethan-1-ol) and the same synthetic route of B3.

Synthesis of Intermediate B5

B5

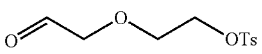

Intermediate B5 was synthesized as colorless oil by using 2,2'-oxybis(ethan-1-ol) and the same synthetic route of B3.

Synthesis of Intermediate B6

B6

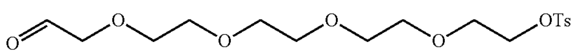

Intermediate B6 was synthesized as colorless oil by using 3,6,9,12-tetraoxatetradecane-1,14-diol and the same synthetic route of B3.

Synthesis of Intermediate B7

B7

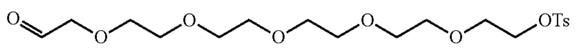

Intermediate B7 was synthesized as colorless oil by using 3,6,9,12,15-pentaoxaheptadecane-1,17-diol and the same synthetic route of B3.

Synthesis of Intermediate B8

B8

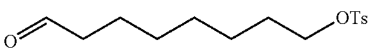

Intermediate B8 was synthesized as colorless oil by using octane-1,8-diol and the same synthetic route of B3.

Synthesis of Intermediate B9

B9

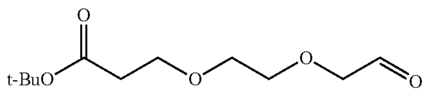

tert-butyl 3-(2-(2-hydroxyethoxy)ethoxy)propanoate (200 mg, 853.65 umol) followed the same synthetic procedure of B3 to obtain 120 mg (516.63 umol, 60.5% yield) of B9 as colorless oil.

Synthesis of Intermediate B36

B36

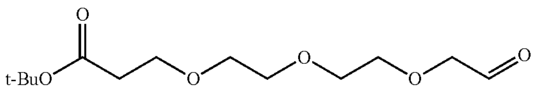

tert-butyl 3-(2-(2-(2-hydroxyethoxy)ethoxy)ethoxy)propanoate (200 mg, 718.52 umol) followed the same synthetic procedure of B3 to obtain 110 mg (396.07 umol, 55.1% yield) of B36 as colorless oil.

Scheme 18: Synthesis of intermediate B15

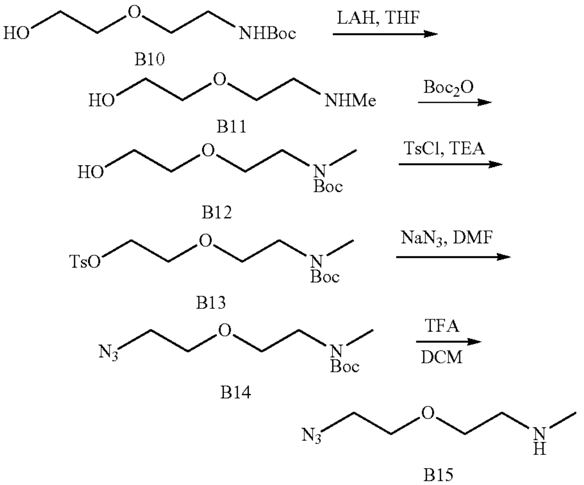

Procedure for Synthesis of B11

To a solution of $LiAlH_4$ (565.78 mg, 14.91 mmol) in THF (20 mL), B10 (1.53 g, 7.45 mmol) in THF (20 mL) was added drop-wised at 0° C. The mixture was stirred at 70° C. for 2 hr to give a white mixture. The mixture solution was treated with water (0.4 mL), 15% NaOH solution (0.4 mL) and water (1.2 mL). The, the mixture was dried over $Na_2SO_4$, filtered and concentrated under reduced pressure to give Bit (880 mg, 7.38 mmol, 99% yield) as colorless oil.

Procedure for Synthesis of B12

To a solution of B11 (230 mg, 1.93 mmol) in MeOH (3 mL) was added $(Boc)_2O$ (631.87 mg, 2.90 mmol). The mixture was stirred at 20° C. for 16 hr. The reaction mixture was concentrated under reduced pressure to remove MeOH. The residue was diluted with water 20 mL and extracted with EtOAc (20 mL*3). The combined organic layers were washed with aqueous $NaHCO_3$ and aqueous NaCl, dried over $Na_2SO_4$, filtered and concentrated under reduced pressure to give B12 (400 mg, 1.82 mmol, 94% yield) as colorless oil.

Procedure for Synthesis of B13

To a solution of B12 (400 mg, 1.82 mmol) in DCM (8 mL) was added TEA (553.76 mg, 5.47 mmol). Then, 4-methylbenzene-1-sulfonyl chloride (695.56 mg, 3.65 mmol) was added drop-wise at 0° C. The mixture was stirred at 20° C. for 16 hr to give a yellow mixture. The mixture was diluted with water (10 mL), extracted with EtOAc (10 mL×3). The combined organic extract was washed with $NaHCO_3$ aq. (10 mL) and brine (20 mL), dried over $Na_2SO_4$, filtered, concentrated under reduced pressure to give crude residue, which was purified by flash silica gel chromatography to give B13 (700 mg, crude) as colorless oil.

Procedure for Synthesis of B14

To a solution of B13 (700 mg, 1.87 mmol) in DMF (10 mL) was added $NaN_3$ (121.85 mg, 1.87 mmol) at 20° C. The was degassed and purged with $N_2$ for 3 times, and then the mixture was stirred at 50° C. for hr under $N_2$ atmosphere to give a yellow mixture. The mixture was cooled to 20° C., poured into water (20 mL), and extracted with EtOAc (20 mL*2). The combined organic layers were concentrated to B14 (440 mg, 1.80 mmol, 96% yield) as colorless oil.

Procedure for Synthesis of Intermediate B15

To a solution of B14 (100 mg, 409.35 umol) in DCM (1 mL) was added TFA (616.00 mg, 5.40 mmol) at 0° C. The mixture was stirred at 20° C. for 1 hr to give a yellow mixture. TLC indicated the reaction was completed. The reaction mixture was concentrated under reduced pressure to give B15 (106 mg, crude) as colorless oil.

Scheme 19: Synthesis of intermediate B22

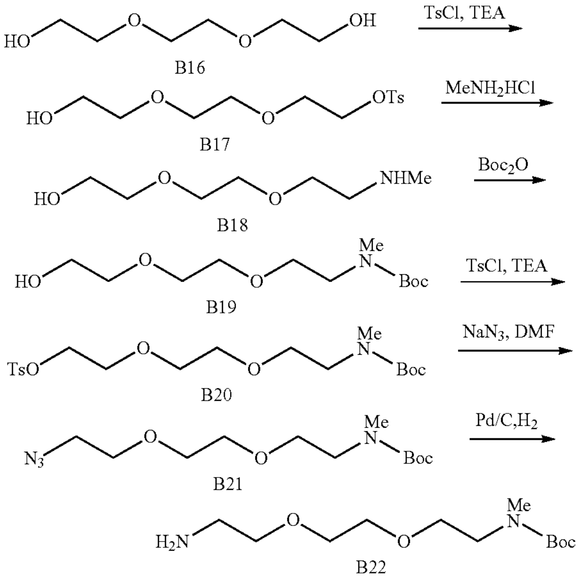

Procedure for Synthesis of B17

B16 (5 g, 33.29 mmol) followed the same synthetic procedure of B13 to obtain 3.5 g (11.5 mmol, 34.5% yield) of B17 as yellow oil.

Procedure for Synthesis of B18

To a mixture of B17 (500 mg, 1.64 mmol) and $K_2CO_3$ (681.13 mg, 4.93 mmol, 3 eq) in dioxane (10 mL) was added $MeNH_2$ (221.84 mg, 3.29 mmol) and the result mixture was heated to 40° C. for 18 hours to afford a white mixture. The mixture was diluted with 10 mL of water and then concentrated to afford B18 (2 g, crude) as white gum.

Procedure for Synthesis of B19

Intermediate B18 (2 g, 1.72 mmol) followed the same synthetic procedure of B12 to obtain 240 mg (0.911 mmol, 53.1% yield) of B19 as brown oil.

Procedure for Synthesis of B20

Intermediate B19 (240 mg, 0.911 mmol) followed the same synthetic procedure of B13 to obtain 120 mg (0.287 mmol, 31.5% yield) of B20 as colorless oil.

Procedure for Synthesis of B21

Intermediate B20 (120 mg, 0.287 mmol) followed the same synthetic procedure of B14 to obtain 70 mg (0.242 mmol, 84.4% yield) of B21 as yellow oil.

Procedure for Synthesis of Intermediate B22

To a mixture of B21 (300 mg, 1.04 mmol) in MeOH (5 mL) was added Pd/C (50 mg, 1.04 mmol) was stirred at 20° C. under $H_2$ for 16 hours to give a black mixture. TLC showed the new spot was formed. The reaction mixture was filtered and concentrated under reduced pressure to afford B22 (230 mg, 876.71 umol, 84.26% yield) as yellow gum.

Scheme 20: Synthesis of intermediate B26

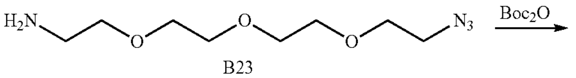

-continued

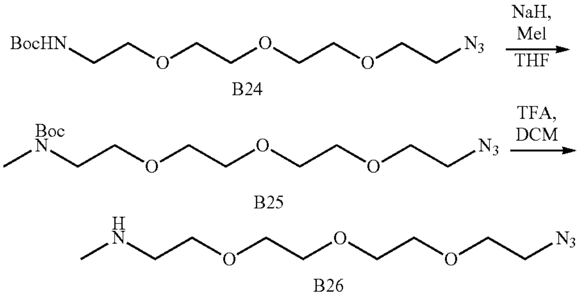

Procedure for Synthesis of B24

Intermediate B23 (400 mg, 1.83 mmol) followed the same synthetic procedure of B12 to obtain 580 mg (1.82 mmol, 99.4% yield) of B24 as colorless oil.

Procedure for Synthesis of B25

To a solution of B24 (580 mg, 1.82 mmol) in DMF (6 mL) was added NaH (145.73 mg, 3.64 mmol) drop-wise at 0° C., and the mixture was stirred at 0° C. for 0.5 hr. Then MeI (2.59 g, 18.22 mmol) was added at 0° C. The mixture was stirred at 20° C. for 16 hr to give a white suspension. TLC indicated the reaction was completed. The mixture was poured onto ice water (20 mL) and extracted with EtOAc (20 mL*4). The combined organic layer was washed with brine (20 mL*2). The solution was dried over $Na_2SO_4$, filtered and concentrated under reduced pressure to give a residue. The residue was purified by column chromatography to give B25 (400 mg, 1.20 mmol, 66.06% yield) as colorless oil.

Synthesis of Intermediate B26

Intermediate B25 (100 mg, 0.301 mmol) followed the same synthetic procedure of B15 to obtain 104 mg (0.300 mmol, 99.8% yield) of B26 as colorless oil.

Scheme 21: Synthesis of intermediate B28

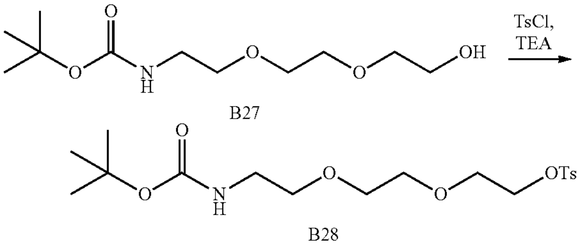

B27 (100 mg, 0.401 mmol) followed the same synthetic procedure of B13 to obtain 120 mg (0.297 mmol, 74.1% yield) of B28 as colorless oil.

Scheme 22: Synthesis of intermediate B31

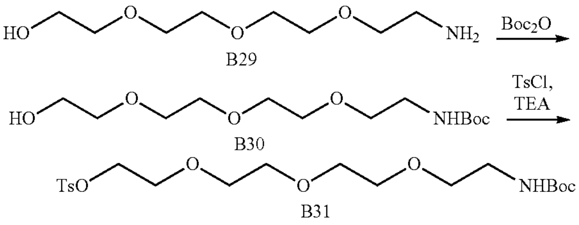

Procedure for Synthesis of B30

B29 (250 mg, 1.29 mmol) followed the same synthetic procedure of B12 to obtain 360 mg (1.23 mmol, 94.8% yield) of B30 as colorless oil.

Procedure for Synthesis of B31

Intermediate B30 (360 mg, 1.23 mmol) followed the same synthetic procedure of B13 to obtain 370 mg (0.826 mmol, 67.3% yield) of B31 as colorless oil.

Scheme 23: Synthesis of intermediate B34

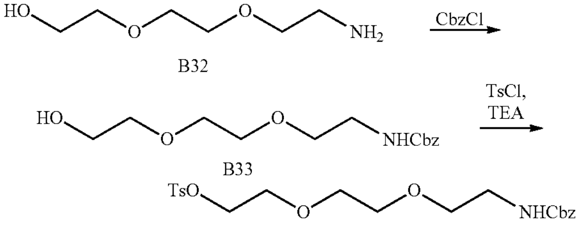

B32

B33

B34

Procedure for Synthesis of B33

To a solution of B33 (1 g, 6.70 mmol) in MeOH (10 mL) was added TEA (1.56 g, 15.42 mmol). Then, benzyl chloroformate (1.26 g, 7.37 mmol) in MeOH (5 mL) was added and the mixture was stirred at 20° C. for 16 hr to give a yellow mixture. TLC and LCMS indicated the reaction was completed. The reaction mixture was concentrated under reduced pressure to remove MeOH. The residue was diluted with water 20 mL and extracted with DCM (20 mL*2). The combined organic layers were washed with brine 20 mL, dried over $Na_2SO_4$, filtered and concentrated under reduced pressure to afford B33 (1.45 g, 5.12 mmol, 76.3% yield) as colorless oil.

Synthesis of Intermediate B34

Intermediate B33 (1.45 g, 5.12 mmol) followed the same synthetic procedure of B13 to obtain 1.57 g (3.59 mmol, 70.1% yield) of B34 as colorless oil.

Synthesis of Intermediate B35

B35

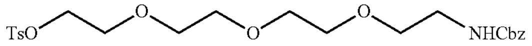

Intermediate B35 was synthesized as colorless oil by using 2-(2-(2-(2-aminoethoxy)ethoxy)ethoxy)ethan-1-ol and the same synthetic route of B34.

Synthesis of E3 Ligand Part Intermediates

Scheme 24: Synthesis of intermediate C3

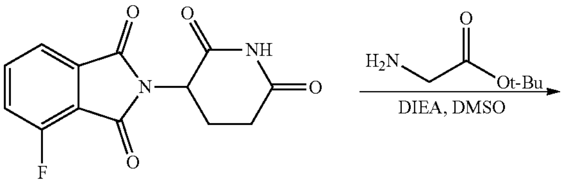

C1

-continued

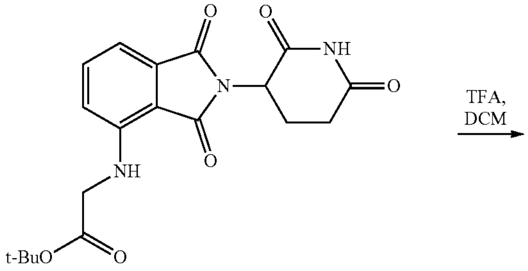

C2

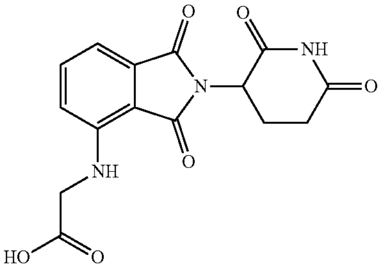

C3

Procedure for Synthesis of C2

To a mixture of C1 (500 mg, 1.81 mmol) and tert-butyl 2-aminoacetate (237.44 mg, 1.81 mmol) in DMSO (15 mL) was added DIEA (467.90 mg, 3.62 mmol), the mixture was stirred at 90° C. for 16 hours to give a green mixture. The mixture was partitioned between EtOAc (20 ml) and water (20 mL). The aqueous phase was extracted with EtOAc (20 mL×2). The combined organic extract was washed with brine (50 mL×3), dried over $Na_2SO_4$, filtered, concentrated under reduced pressure to give crude product. The crude product was purified by combi flash to afford C2 (440 mg, 1.14 mmol, 62.75% yield) as yellow solid.

Procedure for Synthesis of Intermediate C3

To a solution of C2 (430 mg, 1.11 mmol) in DCM (20 mL) was added TFA (3.08 g, 27.01 mmol) and the resulting mixture was stirred at r.t. for 18 hours to afford a brown mixture. The reaction mixture was concentrated under reduced pressure to give C3 (360 mg, 1.09 mmol, 97.90% yield) as yellow powder.

Synthesis of Intermediate C4

C4

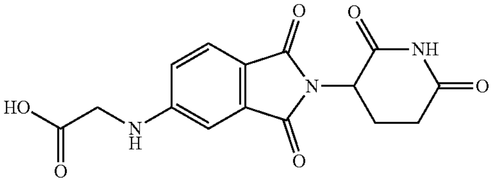

Intermediate C4 was synthesized as yellow powder by using 2-(2,6-dioxopiperidin-3-yl)-5-fluoroisoindoline-1,3-dione and the same synthetic route of C3.

Scheme 25: Synthesis of intermediate C7

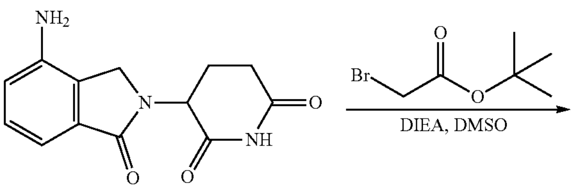

C5

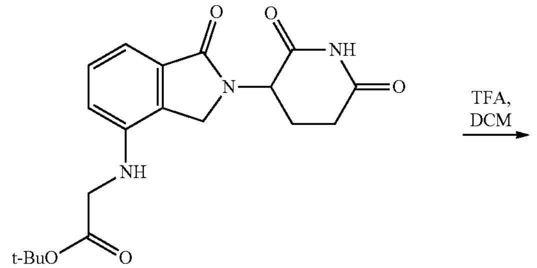

C6

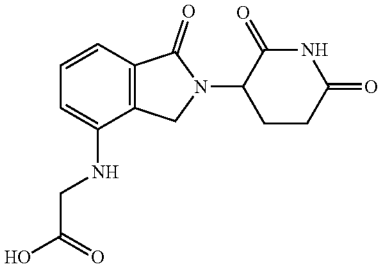

C7

Procedure for Synthesis of C6

To a solution of C5 (950 mg, 3.66 mmol) in NMP (18 mL) was added DIEA (1.42 g, 10.99 mmol) and tert-butyl 2-bromoacetate (714.73 mg, 3.66 mmol). The solution was stirred at 110° C. for 12 hr to give a brown solution. The mixture was partitioned between EtOAc (100 mL) and water (100 mL). The organic layer was washed with water (50 mL*5) and saturated brine (50 mL), dried over anhydrous $Na_2SO_4$, filtered, and concentrated under reduced pressure to give compound as a crude product. The residue was purified by column chromatography to give C6 (572 mg, 1.53 mmol, 41.81% yield) as yellow solid.

Synthesis of Intermediate C7

Intermediate C6 (352 mg, 0.942 mmol) followed the same synthetic procedure of C3 to obtain 274 mg (0.863 mmol, 91% yield) of C7 as yellow powder.

Scheme 26: Synthesis of intermediate C12

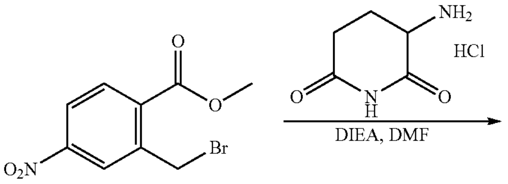

C8

-continued

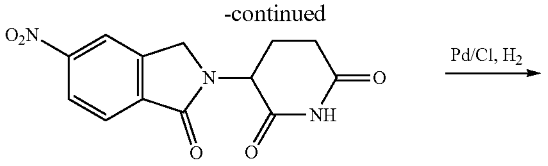

C9

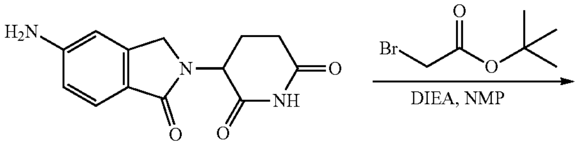

C10

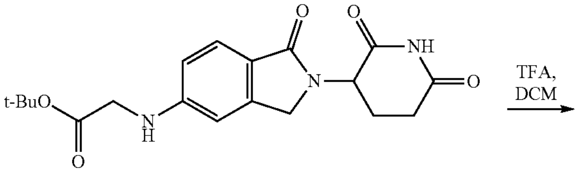

C11

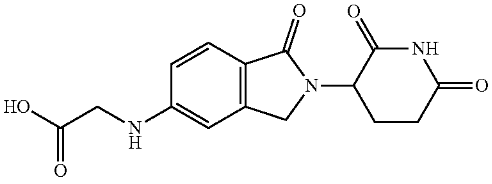

C12

Procedure for Synthesis of C9

To a solution of 3-aminopiperidine-2, 6-dione (161.39 mg, 0.80 mmol) and C8 (200 mg, 0.729 mmol) in DMF (4 mL) was added DIEA (282.94 mg, 2.19 mmol). The solution was stirred at 80° C. for 12 h to give a yellow solution. The mixture was treated with 1M HCl (3 mL). The solvent was removed under reduced pressure. Then DCM (50 mL) was added and the mixture was filtered and concentrated under reduced pressure to give crude product. The crude product was purified by column chromatography to give C9 (46 mg, 159.04 umol, 21.79% yield) as brown solid.

Procedure for Synthesis of C10

To a solution of C9 (280 mg, 968.04 umol) in MeOH (20 mL) was added Pd/C (50 mg). The mixture was stirred at 15° C. under $H_2$ (15 psi) for 12 hr to give a black mixture. The mixture was filtered. The filtrated was concentrated under reduced pressure to give C10 (108 mg, 416.57 umol, 43.03% yield) as blue solid.

Procedure for Synthesis of C11

Intermediate C10 (400 mg, 1.54 mmol) followed the same synthetic procedure of C6 to obtain 140 mg (0.374 mmol, 24% yield) of C11 as yellow solid.

Synthesis of Intermediate C12

Intermediate C6 (140 mg, 0.374 mmol) followed the same synthetic procedure of C3 to obtain 70 mg (0.197 mmol, 52.7% yield) of C12 as pale brown solid.

Scheme 27: Synthesis of intermediate C15

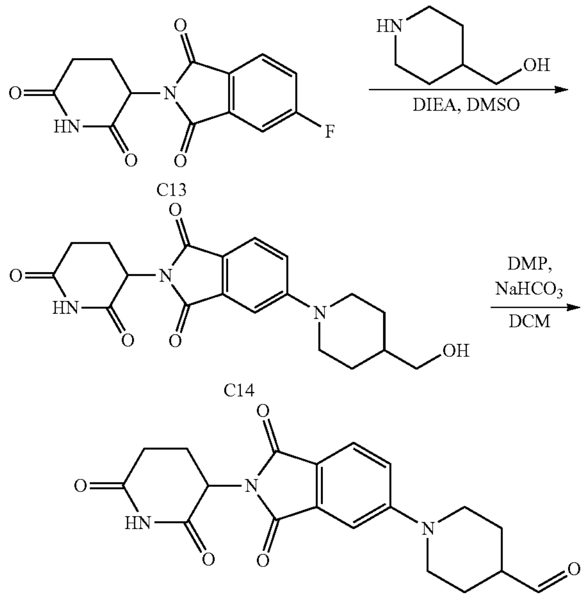

C13

C14

C15

Procedure for Synthesis of C14

A mixture of C13 (500 mg, 1.81 mmol) and DIEA (701.83 mg, 5.43 mmol, 945.87 uL) in NMP (5 mL) was treated with 4-piperidylmethanol (218.90 mg, 1.90 mmol), then, stirred at 80° C. for 12 hours to give yellow solution. The reaction was diluted with water (40 mL) and ethyl acetate (60 ml). The organic layer was washed with water (40 mL) and brine (40 mL), dried over $Na_2SO_4$, concentrated in vacuum to give C14 (530 mg, 1.43 mmol, 78.84% yield) as yellow gum.

Procedure for Synthesis of C15

A solution of C14 (0.45 g, 1.21 mmol) in DCM (10 mL) was added DMP (1.03 g, 2.42 mmol, 1.03 g) at 0° C., then stirred at 20° C. for 2 hours to give yellow suspension. The reaction was quenched with saturated aqueous $NaHSO_3$ solution (20 ml) and triturated with saturated aqueous $NaHCO_3$ solution (20 ml), extracted with EtOAc (30 ml×6). The organic phase was washed with brine (50 mL), dried over $Na_2SO_4$, filtered and concentrated, purified by flash column chromatography to give C15 (200 mg, 541.46 umol, 44.69% yield) as yellow solid.

Scheme 28: Synthesis of intermediate C17

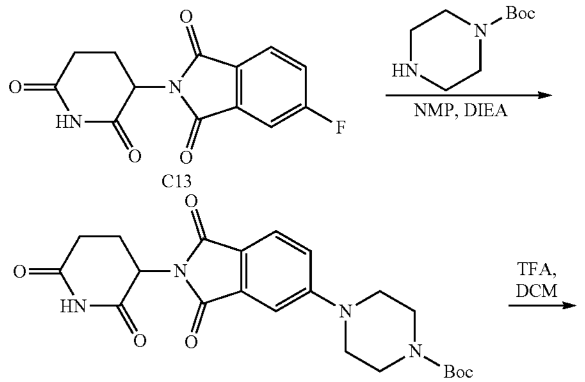

C13

C16

-continued

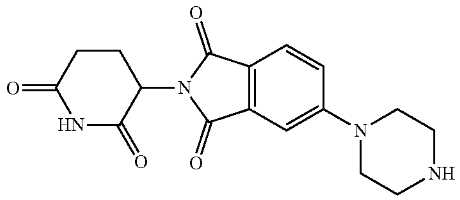

C17

Procedure for Synthesis of C16

To a solution of C13 (400 mg, 1.45 mmol), tert-butyl piperazine-1-carboxylate (323.66 mg, 1.74 mmol,), DIEA (187.16 mg, 1.45 mmol, 252.24 uL) in NMP (5 mL) was degassed and purged with $N_2$ for 3 times, and then the mixture was stirred at 80° C. for 16 hours under $N_2$ atmosphere. The reaction mixture was diluted with water (20 mL) and extracted with Ethyl acetate (20 mL×3). The combined organic layers were washed with brine (20 mL×3), dried over $Na_2SO_4$ filtered and concentrated under reduced pressure to give a residue. The residue was purified by column chromatography to give C16 (450 mg, 1.02 mmol, 70.23% yield) as yellow solid.

Synthesis of Intermediate C17

Intermediate C16 (450 mg, 1.02 mmol) followed the same synthetic procedure of C3 to obtain 300 mg (0.876 mmol, 86.2% yield) of C17 as yellow solid.

Scheme 29: Synthesis of intermediate D8

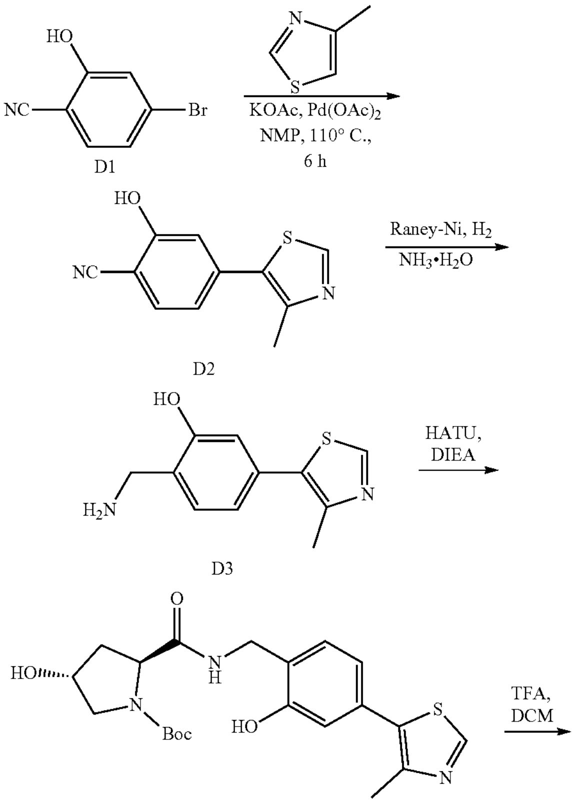

D1

D2

D3

D4

-continued

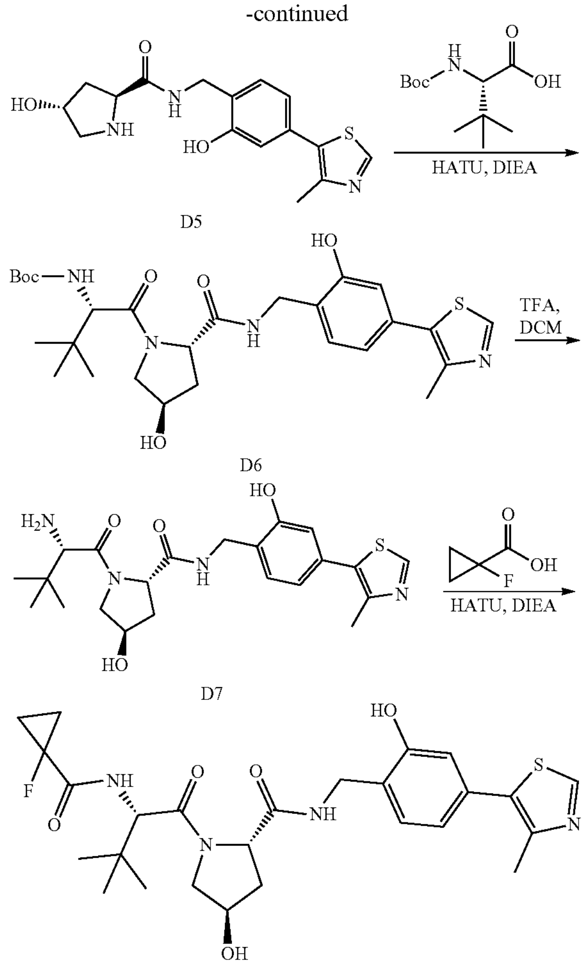

D5

D6

D7

D8

Procedure for Synthesis of D2

To a solution of D1 (4.8 g, 24.24 mmol) and 4-methylthiazole (4.81 g, 48.48 mmol) in NMP (50 mL) was added KOAc (4.76 g, 48.48 mmol) and $Pd(OAc)_2$ (272.11 mg, 1.21 mmol), the resulting mixture was stirred at 110° C. for 6 hours to give yellow solution. LCMS showed desired product was detected. The reaction mixture was poured into diluted with water (50 mL) and extracted with EtOAc (50 mL×3). The combined organic layers were washed with water (50 mL×5) and brine (50 mL×2), dried over $Na_2SO_4$, filtered and concentrated under reduced pressure. The crude product was purified by flash to afford D2 (3.8 g, 16.82 mmol, 69.37% yield) as yellow solid.

Procedure for Synthesis of D3

To a solution of LiAlH4 (1.97 g, 51.79 mmol) in THE (35 mL) was added D2 (2.8 g, 12.95 mmol) at 0° C., the resulting mixture was stirred at 20° C. for 3 hours to give yellow solution. The reaction mixture was quenched by water (2 mL) at 0° C., and then 15% NaOH solution (2 mL) was added, diluted with water (6 mL) and the mixture was stirred at 20° C. for 0.5 hr. The mixture was filtered, the filter cake was washed with 50 mL (DCM/MeOH=4:1). The combined filter was concentrated under reduced pressure to give D3 (2.8 g, 12.71 mmol, 98.17% yield) as yellow solid.

Procedure for Synthesis of D4

To a solution of (2S,4R)-1-tert-butoxycarbonyl-4-hydroxy-pyrrolidine-2-carboxylic acid (2.73 g, 11.80 mmol, 1 eq) in DMF (20 mL) was added HOBt (1.59 g, 11.80 mmol, 1 eq) and HATU (4.94 g, 12.98 mmol, 1.1 eq). The mixture was stirred at 20° C. for 0.5 hr. DIEA (4.58 g, 35.41 mmol, 6.17 mL, 3 eq) and D3 (2.6 g, 11.8 mmol, 1 eq.) was added. The mixture was stirred at 20° C. for 1.5 hr. The reaction mixture was treated with $K_2CO_3$ (4.89 g), the mixture was stirred at 20° C. for 16 hr. TLC showed the reaction was completed. The mixture was diluted with water 50 mL and extracted with EtOAc (50 mL*3). The combined organic layers were washed with brine (50 mL*3), dried over $Na_2SO_4$, filtered and concentrated under reduced pressure to give a residue. The residue was purified by column chromatography to give D4 (3.07 g, 7.08 mmol, 60% yield) as white solid.

Procedure for Synthesis of D5

To a solution of D4 (1 g, 2.31 mmol) in DCM (8 mL) was added TFA (2.63 g, 23.07 mmol) at 0° C. The mixture was stirred at 20° C. for 1 hr to give yellow mixture. TLC indicated the reaction was completed. The reaction mixture was concentrated under reduced pressure to give D5 (1.05 g, crude) as yellow oil.

Procedure for Synthesis of D6

Intermediate D5 (1.04 g, 2.33 mmol) and (S)-2-((tert-butoxycarbonyl)amino)-3,3-dimethylbutanoic acid (540 mg, 2.33 mmol) followed the same synthetic procedure of D4 to obtain 720 mg (1.32 mmol, 56.4% yield) of D6 as yellow solid.

Procedure for Synthesis of D7

Intermediate D6 (720 mg, 1.32 mmol) followed the same synthetic procedure of D5 to obtain 740 mg (crude) of D7 as yellow oil.

Synthesis of Intermediate D8

Intermediate D7 (737 mg, 1.32 mmol) and 1-fluorocyclopropane-1-carboxylic acid (137 mg, 1.32 mmol) followed the same synthetic procedure of D4 to obtain 450 mg (0.844 mmol, 64.2% yield) of D8 as white solid.

Scheme 30: Synthesis of intermediate D10

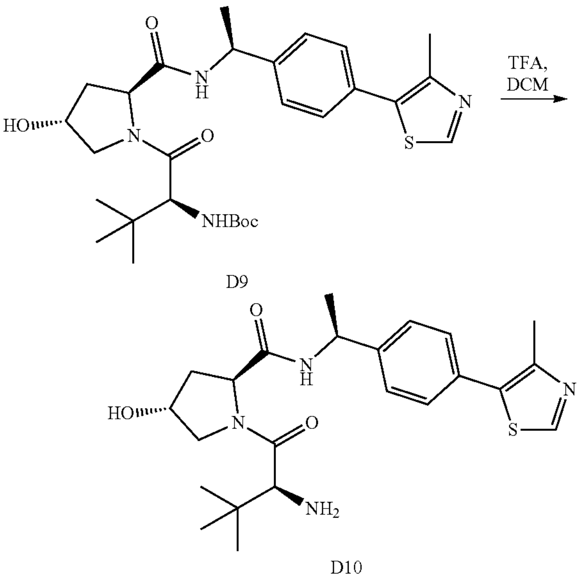

D9

D10

Procedure for Synthesis of D10

To a solution of D9 (300 mg, 0.55 mmol) in DCM (3 mL) was added TFA (1.26 g, 11.02 mmol). The mixture was stirred at 0-5° C. for 3 hr to give a yellow mixture. The mixture was concentrated under reduced pressure to give D10 (400 mg, crude) as yellow solid.

Scheme 31: Synthesis of intermediate D13

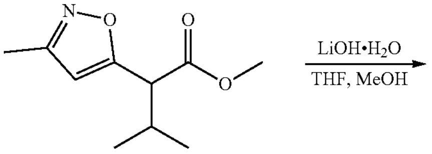

D11

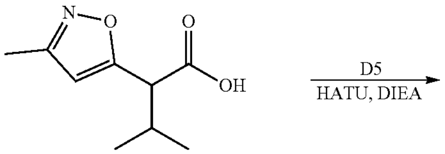

D12

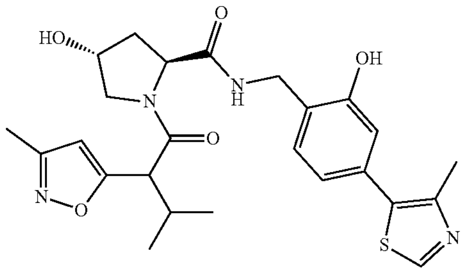

D13

Procedure for Synthesis of D12

To a solution of methyl D11 (370 mg, 1.88 mmol) in $H_2O$ (1 mL) and MeOH (2 mL) was added LiOH·$H_2O$ (236.17 mg, 5.63 mmol). The mixture was stirred at 20° C. for 16 hours to give a yellow mixture. The mixture was concentrated under reduced pressure to remove MeOH. Then the residue was diluted with $H_2O$ (5 mL), and extracted with Ethyl acetate (10 mL) to remove impurity. The aqueous phase was adjusted to pH to 2 by 10% HCl solution, then extracted with ethyl acetate/MeOH (15 mL×6). The combined organic layers were dried over $Na_2SO_4$, concentrated under reduced pressure to give D12 (260 mg, 1.42 mmol, 75.65% yield) as white solid.

Procedure for Synthesis of D13

To a solution of D12 (170 mg, 927.93 umol) in DCM (4 mL) was added HATU (458.67 mg, 1.21 mmol,) and DIEA (359.78 mg, 2.78 mmol, 484.87 uL). The mixture was stirred at 20° C. for 15 min. Then D5 (414.56 mg, 1.24 mmol) was added into the mixture. The mixture was stirred at 20° C. for 16 hours to give a yellow mixture. The mixture was diluted with water (10 mL) and extracted with Ethyl acetate (10 mL×3). The combined organic layers were washed with brine (10 mL×3), dried over $Na_2SO_4$, filtered and concentrated under reduced pressure to give a yellow residue. The residue was purified by prep-TLC to give D13 (101 mg, 202.57 umol, 21.83% yield) as yellow solid.

Scheme 32: Synthesis of intermediate D15

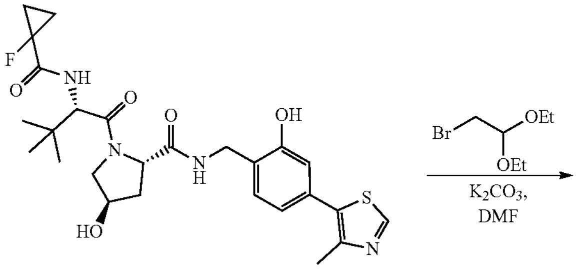

D8

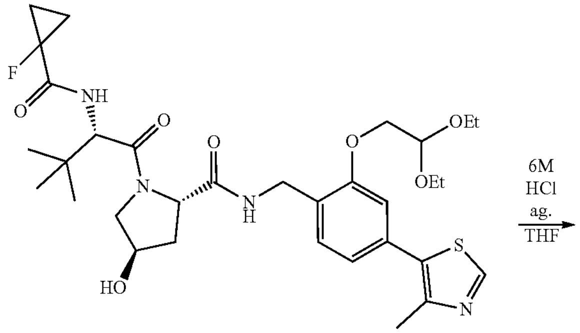

D14

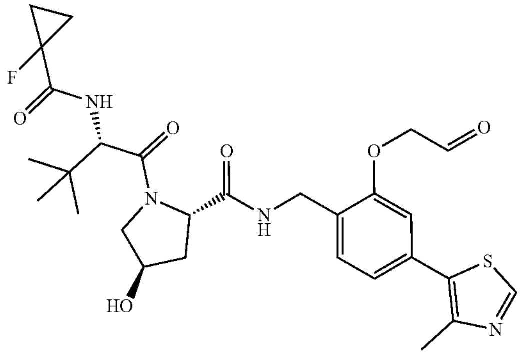

D15

Procedure for Synthesis of D14

A mixture of D8 (150 mg, 281.62 umol), $K_2CO_3$ (97.31 mg, 704.06 umol) in DMF (2 mL) was stirred at 15° C. for 10 min. Then, 2-bromo-1,1-diethoxyethane (142.80 mg, 844.87 umol, 99.16 uL) was added and the mixture was stirred at 60° C. for 12 hours to give pale yellow mixture. Additional 2-bromo-1,1-dimethoxy-ethane (0.99 mL) and $K_2CO_3$ (97 mg) were added and the mixture was stirred at 60° C. for 12 hours. The reaction was diluted with ethyl acetate (20 mL), washed with water (10 mL×3) and brine (10 mL). The organic layer was dried over $Na_2SO_4$, concentrated under reduced pressure to give crude residue. The residue was purified by prep-TLC to give D14 (120 mg, 193.32 umol, 68.65% yield) as colorless oil.

Procedure for Synthesis of D15

To a solution of D14 (30 mg, 48.33 umol) in THF (0.5 mL) was added 6M HCl/$H_2O$ (0.5 mL) dropwise at 0° C. The solution was stirred at 20° C. for 5 hours to give a colorless solution. The reaction was diluted with $NaHCO_3$ (5 mL). The mixture was partitioned between ethyl acetate (2 mL) and water (2 mL). The aqueous layer was extracted with ethyl acetate (2 mL×3). The organic layer was concentrated under reduced pressure to give D15 (27 mg, crude) as white solid.

Scheme 33: Synthesis of intermediate E10
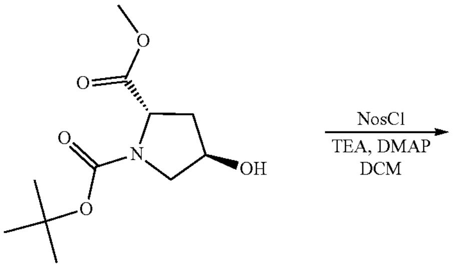
E1
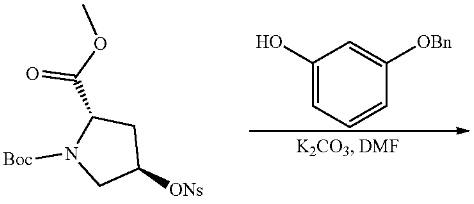
E2
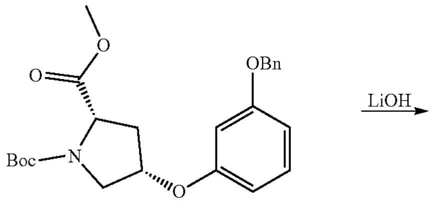
E3
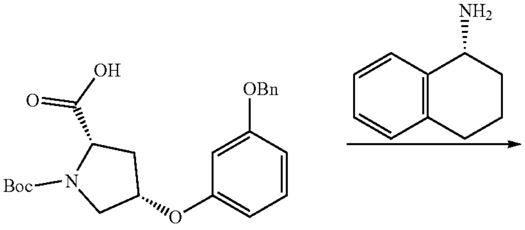
E4
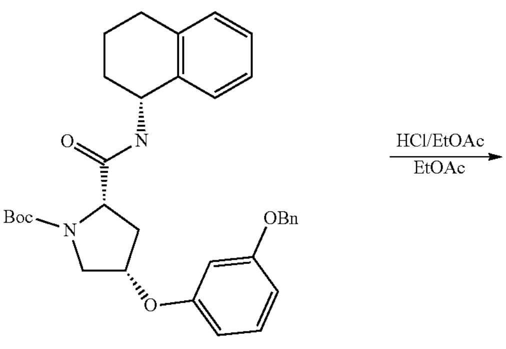
E5
-continued
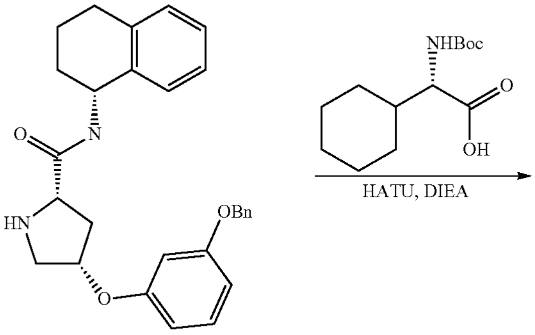
E6
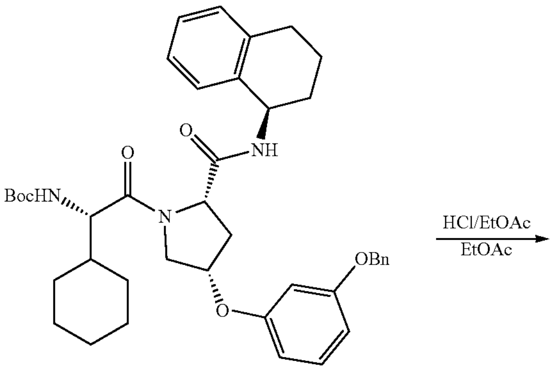
E7
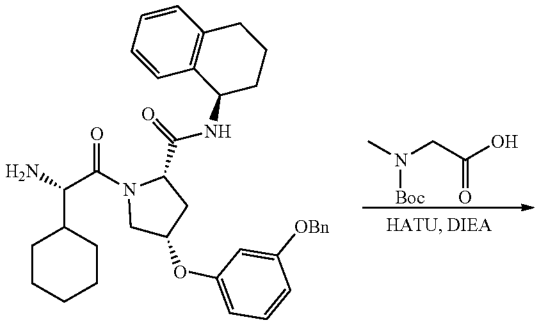
E8
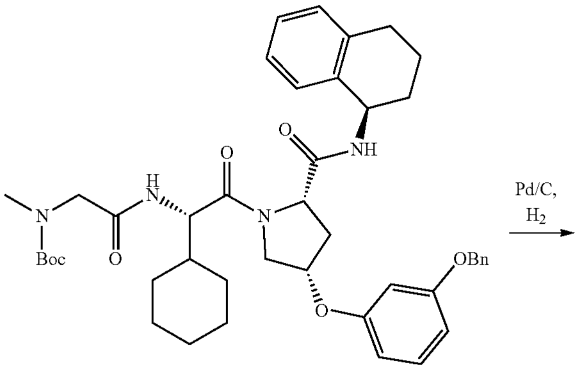
E9

-continued

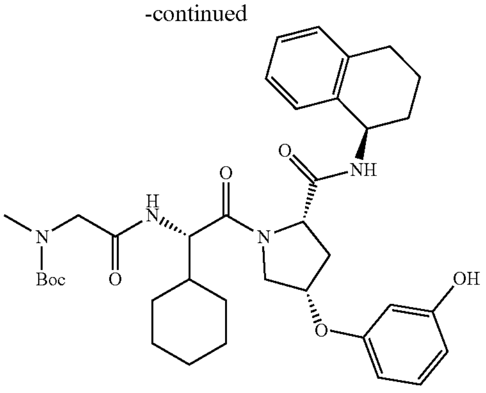

E10

Procedure for Synthesis of E2

To a solution of E1 (5 g, 20.39 mmol), 2-nitrobenzenesulfonyl chloride (9.04 g, 40.77 mmol) in DCM (100 mL) was added triethylamine (6.19 g, 61.16 mmol), N,N-dimethylpyridin-4-amine (249.05 mg, 2.04 mmol) and the mixture was stirred at 15° C. for 16 hr to give a yellow solution. TLC showed new spot. The mixture was quenched by water and extracted with DCM (50 ml*3), washed with 0.1M HCl (50 ml*3). The organic layer was washed with $NaHCO_3$ (50 ml*3) and brine (50 ml*3), concentrated under reduced pressure to give a crude product. The residue was purified by column to give E2 (4 g, 9.29 mmol, 45.59% yield) as yellow oil.

Procedure for Synthesis of E3

To a solution of E2 (4 g, 9.25 mmol), 3-benzyloxyphenol (2.22 g, 11.10 mmol) in NMP (40 mL) was added $Cs_2CO_3$ (15.07 g, 46.25 mmol), the mixture was stirred at 40° C. for 16 hr to give a yellow solution. TLC showed new spot. The mixture was quenched by water, extracted with EtOAc (30 ml*3), the organic layer was washed with brine (30 ml*3), concentrated under reduced pressure to give a crude product. The residue was purified by column chromatography to give E3 (1.7 g, 3.98 mmol, 42.99% yield) as yellow oil.

Procedure for Synthesis of E4

To a solution of E3 (1.2 g, 2.81 mmol) in THF (30 mL) was added lithium hydroxide hydrate (353.39 mg, 8.42 mmol) in $H_2O$ (12 mL). The mixture was stirred at 15° C. for 16 hr to give a yellow solution. The mixture was partitioned with 1N HCl (20 mL) and EtOAc (50 mL). The aqueous layer was extracted with EtOAc (50 mL) and the organic layer was washed with brine (30 mL), dried over sodium sulfate and concentrated under reduced pressure to give E4 as crude product.

Procedure for Synthesis of E5

Intermediate E4 (3.4 g, 8.22 mmol) and (R)-1,2,3,4-tetrahydronaphthalen-1-amine (1.21 g, 8.22 mmol) followed the same synthetic procedure of D4 to obtain 4.2 g (7.74 mmol, 94.1% yield) of E5 as white solid.

Procedure for Synthesis of E6

A solution of HCl/EtOAc (4 mL) in EtOAc (4 mL) was added to E5 (360 mg, 663.39 umol). The mixture was stirred at 15° C. for 32 hr to give a yellow solution. Additional 3 ml of HCl/EtOAc was added and the mixture was stirred at 15° C. for further 2 hr. The mixture was stirred under reduced pressure to give E6 (230 mg, crude) as yellow oil.

Procedure for Synthesis of E7

Intermediate E6 (680 mg, 1.42 mmol, HCl) and (2S)-2-(tert-butoxycarbonylamino)-2-cyclohexyl-acetic acid (730.60 mg, 2.84 mmol) followed the same synthetic procedure of D4 to obtain 300 mg (0.439 mmol, 31% yield) of E7 as colorless gum.

Procedure for Synthesis of E8

To a mixture of E7 (300 mg, 439.97 umol) in EtOAc (2 mL) was added HCl/EtOAc (4M, 1 mL). The mixture was stirred at 25° C. for 1 hr to give a colorless mixture. The mixture was concentrated under reduced pressure to give E8 (260 mg, crude) as colorless gum.

Procedure for Synthesis of E9

Intermediate E8 (260 mg, 0.421 mmol, HCl) and N-(tert-butoxycarbonyl)-N-methylglycine (119.36 mg, 0.631 mmol) followed the same synthetic procedure of D4 to obtain 180 mg (0.217 mmol, 51% yield) of E9 as colorless gum.

Procedure for Synthesis of Intermediate E10

To a mixture of E9 (140 mg, 0.185 mmol) in EtOH (5 mL) was Pd/C (80 mg). The mixture was stirred at 25° C. under $H_2$ (15 psi) for 2 hours to give a yellow mixture. The reaction mixture was filtered and concentrated under reduced pressure to give E10 (98 mg, 0.131 mmol, 70.77% yield) as colorless gum.

Scheme 34: Synthesis of intermediate E12

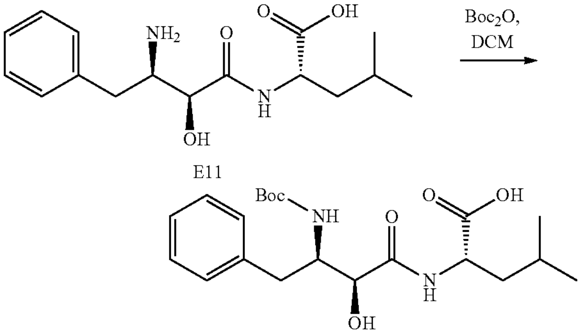

E11

E12

Procedure for Synthesis of Intermediate E12

E11 (500 mg, 1.45 mmol, HCl) was stirred in 1M NaOH (1.59 mL) under an ice bath (0-5° C.). $(Boc)_2O$ (332.28 mg, 1.52 mmol) dissolved in THF (0.8 mL) was then added into the solution. After 2 h, the ice bath was removed. The mixture was stirred at 25° C. for 16 hour to give a white mixture. After removing THF under vacuum, the solution was acidified to pH 3 with 1N HCL. The solution was washed with EtOAc (10 ml×3). The organic layer was collected and dried over sodium sulfate. After evaporating the solvent, the residue was dried in vacuum to obtain E12 (630 mg, crude) as white solid.

Scheme 35: Synthesis of intermediate E22

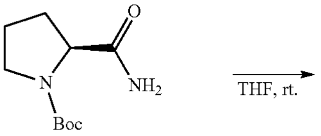

E13

-continued

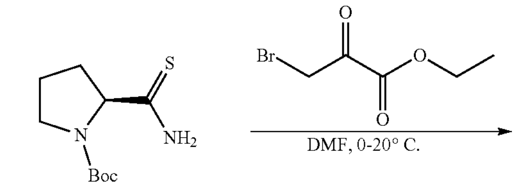

E14

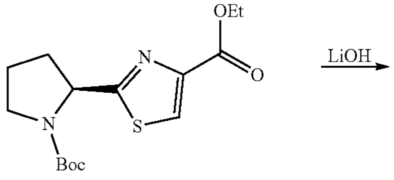

E15

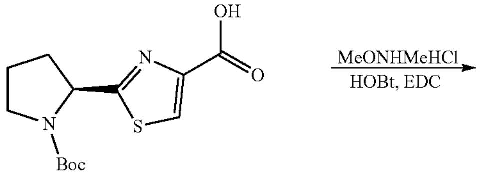

E16

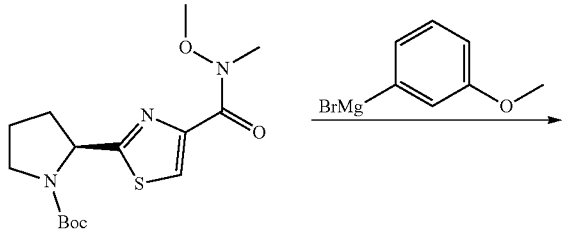

E17

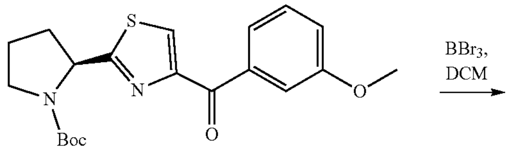

E18

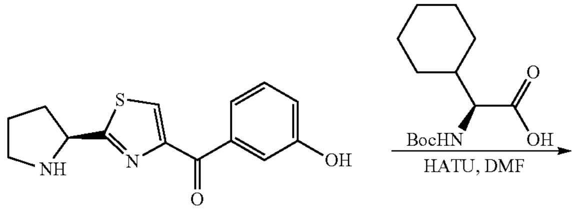

E19

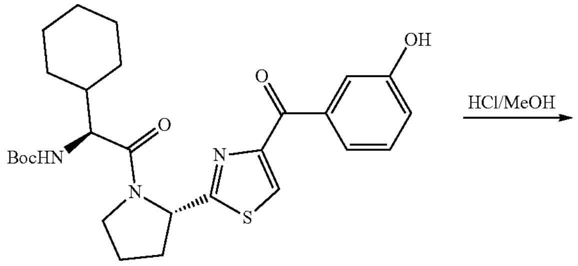

E20

-continued

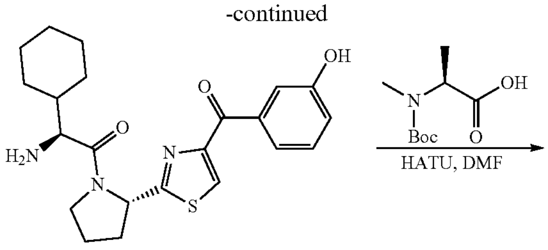

E21

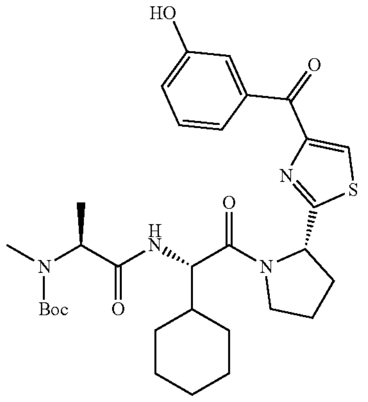

E22

Procedure for Synthesis of E14

To a solution of E13 (7.5 g, 35.00 mmol) in THF (45 mL) was added Lawesson's reagent (7.08 g, 17.50 mmol). The resulting mixture was stirred at 20° C. under $N_2$ for 4 hours to give yellow solution. The solvent was removed under reduced pressure. Saturated aqueous $NaHCO_3$ (50 mL) was added and the mixture stirred for 1 hr. The aqueous suspension was extracted with EtOAc (50 mL×2). The organic fraction was washed with saturated aqueous $NaHCO_3$ (100 mL×2) and the combined aqueous fractions were extracted with EtOAc (200 mL×2). The combined organics extracts were dried over $Na_2SO_4$ and then concentrated in vacuum to give E14 (6.9 g, crude) as white solid.

Procedure for Synthesis of E15

To a solution of E14 (6.4 g, 27.79 mmol) in EtOH (30 mL) at 0° C. was added dropwise a solution of ethyl 3-bromo-2-oxo-propanoate (5.96 g, 30.57 mmol) in EtOH (30 mL). The resulting mixture was stirred at 20° C. for 14 hours to give yellow solution. The reaction mixture was concentrated under reduced pressure. The residue was diluted with water (30 mL) and extracted with EtOAc (20 mL×4). The combined organic layers were washed with brine (30 mL×2), dried over $Na_2SO_4$, filtered and concentrated under reduced pressure to give 6 g of crude product. The water layer was basified with sat. $NaHCO_3$ aq. to pH=8, and then treated with $(Boc)_2O$ (20 mL), stirred at 25° C. for 2 hr. The reaction mixture was extracted with EtOAc (50 mL×3). The combined organic layers were washed with brine (50 mL×2), dried over $Na_2SO_4$, filtered and concentrated under reduced pressure to give 4 g of crude product impure. Total 10 g of crude product was purified by flash column to afford E15 (5.6 g, 16.81 mmol, 60.51% yield) as yellow solid.

Procedure for Synthesis of E16

To a solution of E15 (4.6 g, 14.09 mmol) in $H_2O$ (46 mL) and THE (23 mL) was added $LiOH{\cdot}H_2O$ (1.77 g, 42.28 mmol). The resulting mixture was stirred at 20° C. for 14 hours to give yellow solution. The reaction mixture was diluted with water 20 mL and extracted with EtOAc (20 mL×3). The reaction mixture was acidified with 1 N HCl aq. to pH=4-5, extracted with EtOAc (50 mL×4). The combined organic layers were washed with brine (50 mL×2), dried over $Na_2SO_4$, filtered and concentrated under reduced pressure to afford E16 (3.5 g, 11.73 mmol, 83.24% yield) as yellow solid.

Procedure for Synthesis of E17

To a solution of E16 (4 g, 13.41 mmol) in DMF (40 mL) was added HATU (7.65 g, 20.11 mmol) at 0° C. DIEA (8.66 g, 67.03 mmol) and N-methoxymethanamine (1.57 g, 16.09 mmol, HCl) were added in sequence to the reaction mixture prepared above at 0° C. The resulting mixture is allowed to stir at 0° C. for 1 hour, then at 20° C. for 3 hours to give brown solution. The reaction is then concentrated to a brown oil. This residue is partitioned between ethyl acetate (50 mL) and water (100 mL). The organic phase was separated and the aqueous phase is further extracted with ethyl acetate (50 mL×2). The organic phases are combined, washed with saturated sodium bicarbonate solution (100 mL), washed with 5% citric acid solution (100 mL) and brine (100 mL×2), then, dried over anhydrous sodium sulfate to give E17 (4 g, 11.48 mmol, 85.64% yield) as brown oil.

Procedure for Synthesis of E18

To a solution of E17 (200 mg, 0.585 mmol) in THE (2 mL) was added bromo-(3-methoxyphenyl)magnesium (1 M, 878.67 uL, 1.5 eq) at 0° C. The mixture stirred at 0° C. for 1 hr under $N_2$ to give yellow solution. The reaction mixture was diluted with sat. $NH_4Cl$ aq. (10 mL) and extracted with EtOAc (10 mL×3). The combined organic layers were washed with brine (15 mL×2), dried over $Na_2SO_4$, filtered and concentrated under reduced pressure. The crude product was purified by flash column to give E18 (150 mg, 0.386 mmol, 65.92% yield) as white solid.

Procedure for Synthesis of E19

To a solution of E18 (440 mg, 1.13 mmol) in DCM (4 mL), a solution of $BBr_3$ (1.42 g, 5.66 mmol) in DCM (1 mL) was added at −45° C. The resulting mixture was stirred at −45° C. for 1 hour to give red solution. Then another solution of $BBr_3$ (1.42 g, 5.66 mmol) in DCM (1 mL) was added at −45° C. The resulting mixture was stirred at −45° C. for 1 hour to give red solution. The mixture was quenched with methanol (15 ml) at −40° C. After warmed to room temperature, the resulting mixture was basified by $NaCO_3$ to PH=7-8. The mixture was diluted with water, extracted with DCM (20 ml×3). The organic layer was collected, washed with brine (30 ml), dried over anhydrous sodium sulfate, and concentrated under reduced pressure. The residue was purified by silica column to afford E19 (200 mg, 0.729 mmol, 64.37% yield) as yellow gum.

Procedure for Synthesis of E20

Intermediate E19 (200 mg, 0.729 mmol, HCl) and (S)-2-((tert-butoxycarbonyl)amino)-2-cyclohexylacetic acid (225.12 mg, 0.874 mmol) followed the same synthetic procedure of D4 to obtain 240 mg (0.449 mmol, 61.5% yield) of E20 as colorless gum.

Procedure for Synthesis of E21

To a mixture of E20 (140 mg, 272.56 umol) in EtOAc (1 mL) was added HCl/EtOAc (2 mL). The mixture was stirred at 25° C. for 1 hour to give colorless mixture. The mixture was concentrated under reduced pressure to give E21 (140 mg, crude) as colorless gum.

Synthesis of Intermediate E22

Intermediate E21 (235 mg, 0.568 mmol) and N-(tert-butoxycarbonyl)-N-methyl-L-alanine (138.59 mg, 0.682 mmol) followed the same synthetic procedure of D4 to obtain 105 mg (0.175 mmol, 30.8% yield) of E22 as colorless gum.

Exceptional Synthetic Route

Scheme 36: Synthesis of intermediate F3

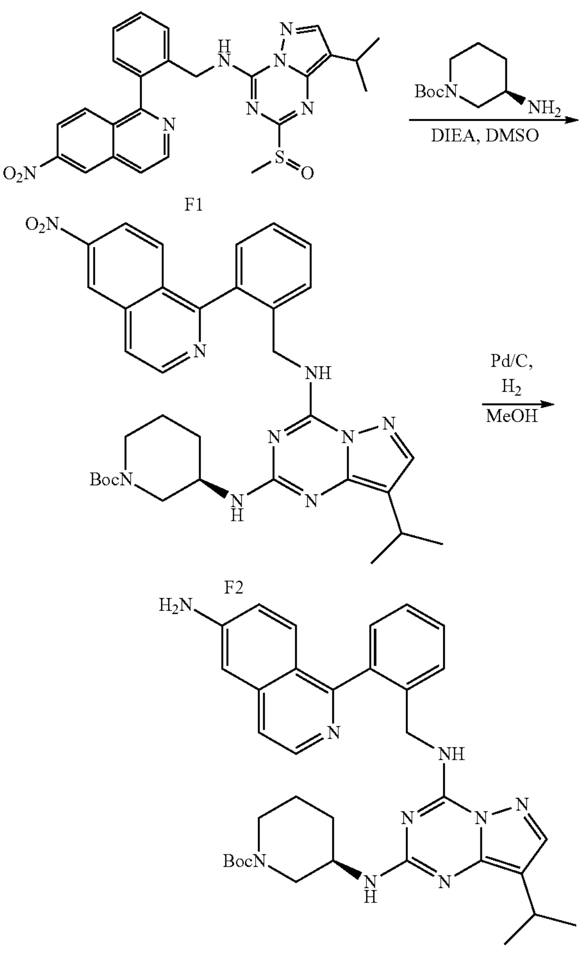

F1

F2

F3

Procedure for Synthesis of F2

A solution of F1 (500 mg, 996.89 umol) and tert-butyl (3R)-3-aminopiperidine-1-carboxylate (399.31 mg, 1.99 mmol) and DIEA (386.51 mg, 2.99 mmol, 520.91 uL) in DMSO (7 mL) was stirred at 120° C. for 12 hours to give yellow solution. The mixture was partitioned between ethyl acetate (100 mL) and water (100 mL). The organic layer was washed with water (50 mL×3) and saturated brine (50 mL), dried over anhydrous $Na_2SO_4$, filtered, and concentrated under reduced pressure. The residue was purified by column chromatography to give F2 (457 mg, 716.60 umol, 71.88% yield) as yellow solid.

Procedure for Synthesis of F3

To a solution of F2 (457 mg, 716.60 umol) in THF (30 mL) was added Pd/C (300 mg, 716.60 umol, 10% purity), the mixture was stirred at 20° C. for 12 h under $H_2$ (15 psi) to give black mixture. The mixture was filtered, the filter cake was washed with DCM (50 mL). The filtrated was concentrated under reduced pressure to give F3 (435 mg, 715.76 umol, 99.88% yield) as yellow solid.

Reference is now made to the following table showing the results of Example 1:

TABLE 1

Enzyme binding assay of CDKs (1, 2, 5 and 7) and selectivity of CDK7

| # cpds | CDK1 | CDK2 | CDK5 | CDK7 | CDK1/ CDK7* | CDK2/ CDK7** | CDK5/ CDK7*** |
|---|---|---|---|---|---|---|---|
| 1 | C | C | C | A | A | A | A |
| 2 | C | C | C | A | A | A | A |
| 3 | C | C | C | A | A | A | A |
| 4 | C | C | C | B | A | C | B |
| 5 | C | C | C | A | A | A | A |
| 6 | C | C | C | A | A | A | A |
| 7 | C | C | C | A | A | A | A |
| 8 | C | C | C | A | A | A | B |
| 9 | C | C | C | A | A | A | A |
| 10 | C | C | C | A | A | A | A |
| 11 | C | C | C | A | A | A | A |
| 12 | C | C | C | A | A | A | A |
| 13 | C | C | C | A | A | A | A |
| 14 | C | C | C | A | A | A | A |
| 15 | C | C | C | A | A | A | A |
| 16 | C | C | C | A | A | A | A |
| 17 | C | C | C | A | A | A | A |
| 18 | C | C | C | A | A | A | A |
| 19 | C | C | C | A | A | A | A |
| 20 | C | C | C | A | A | A | A |
| 21 | C | C | C | A | A | A | A |
| 22 | C | C | C | B | A | A | B |
| 23 | C | C | C | A | A | A | A |
| 24 | C | C | C | A | A | A | A |
| 25 | C | C | C | A | A | A | A |
| 26 | C | C | C | A | A | A | A |
| 27 | C | C | C | B | B | B | B |
| 28 | C | C | C | A | A | A | A |
| 29 | C | C | C | A | B | B | B |
| 30 | C | C | C | A | A | B | B |
| 31 | C | C | C | A | A | A | B |
| 32 | C | C | C | A | A | A | B |
| 33 | C | C | C | A | A | A | B |
| 34 | C | C | C | A | A | A | A |
| 35 | C | C | C | B | B | B | B |
| 36 | C | C | C | A | B | B | B |

Activity range: A indicates $IC_{50} \leq 100$ nM, B indicates $100 < IC_{50} \leq 1{,}000$ nM, C indicates $IC_{50} > 1{,}000$ nM
*CDK1/CDK7: Selectivity of CDK7 inhibition over CDK1 inhibition [fold]
**CDK2/CDK7: Selectivity of CDK7 inhibition over CDK2 inhibition [fold]
***CDK5/CDK7: Selectivity of CDK7 inhibition over CDK5 inhibition [fold]
Selectivity range: A indicates [fold] > 500, B indicates 50 < [fold] ≤ 500, C indicates [fold] ≤ 50

TABLE 2

Summary of compounds 1-36 in terms of their structures and corresponding characteristics.

| #cpd | Structure | Characterization |
| --- | --- | --- |
| 1 | 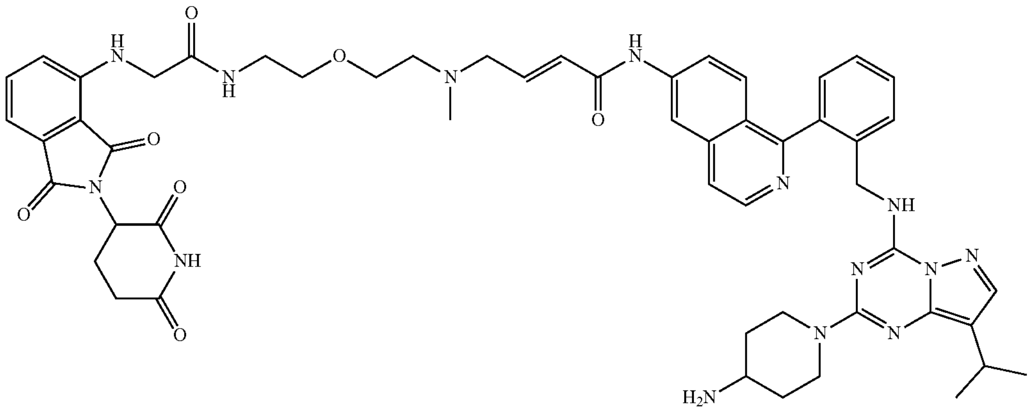 | Yellow solid; $^1$H-NMR (400 MHz, DMSO-$d_6$) δ 11.25 (brs, 1H), 11.11 (brs, 1H), 10.88 (brs, 1 H), 8.56 (s, 2 H), 8.47 (d, J = 6.4 Hz, 1H), 8.40 (s, 1H), 8.20 (s, 2H), 8.02 (s, 1H), 7.56-7.69 (m, 4H), 7.43-7.51 (m, 3 H), 7.04 (d, J = 7.2 Hz, 1H), 6.87-7.00 (m, 2H), 6.67 (d, J = 15.2 Hz, 1H), 5.06 (dd, J = 12.0, 4.8 Hz, 1H), 4.64 (s, 1H), 4.42 (d, J = 16.0 Hz, 4H), 3.90-4.19 (m, 6H), 3.12-3.31 (m, 6H), 2.72-2.93 (m, 8H), 1.80-2.13 (m, 4 H), 1.21-1.46 (m, 2H), 1.14 (d, J = 6.8 Hz, 6H); MS (ESI): m/z 1005.6 $[M + H]^+$ |
| 2 | 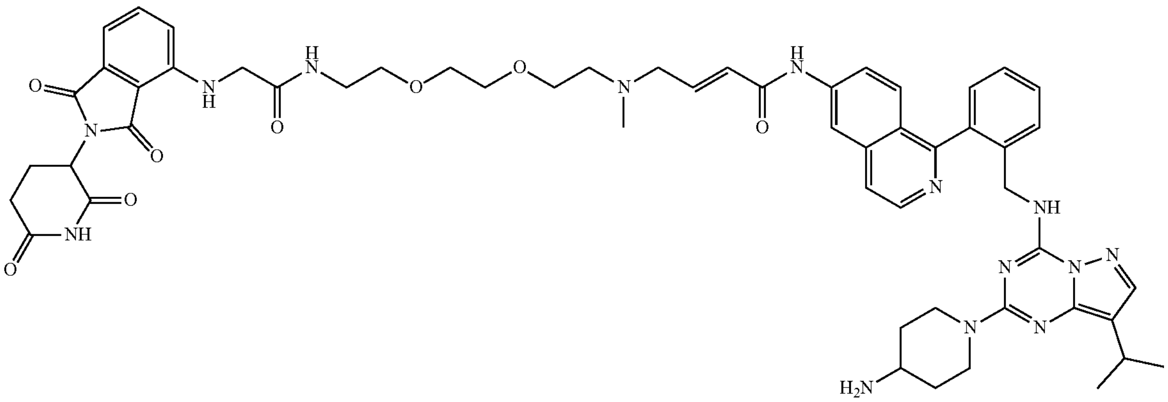 [SMILES: CC(C)c1cnn2c(NCc3ccccc3-c3nccc4cc(NC(=O)/C=C/CN(C)CCOCCOCCNC(=O)CNc5cccc6c5C(=O)N(C5CCC(=O)NC5=O)C6=O)ccc34)nc(N3CCC(N)CC3)nc12] | Pale yellow powder; $^1$H-NMR (400 MHz, MeOD-$d_4$) δ 8.63 (brs, 1H), 8.41 (d, J = 6.0 Hz, 1H), 8.20 (d, J = 6.4 Hz, 1H), 7.76-7.89 (m, 4H), 7.65-7.70 (m, 1H), 7.56-7.62 (m, 2H), 7.47-7.53 (m, 1H), 6.99-7.14 (m, 2H), 6.89 (d, J = 8.4 Hz, 1H), 6.74 (d, J = 14.8 Hz, 1 H), 4.96-5.14 (m, 1 H), 4.50 (d, J = 12.8 Hz, 2H), 4.14-4.25 (m, 1H), 4.00-4.14 (m, 3H), 3.83 (d, J = 4.4 Hz, 2H), 3.61-3.68 (m, 5H), 3.45-3.60 (m, 7H), 3.18-3.29 (m, 2H), 3.04-3.15 (m, 1H), 2.96 (s, 3H), 2.81-2.91 (m, 1H), 2.59-2.80 (m, 2H), 2.05-2.20 (m, 3H), 1.52-1.80 (m, 2H), 1.23-1.36 (m, 1H), 1.17 (d, J = 6.8 Hz, 6H); MS (ESI): m/z 1049.8 $[M + H]^+$ |

TABLE 2-continued
| Summary of compounds 1-36 in terms of their structures and corresponding characteristics. | | |
|---|---|---|
| #cpd | Structure | Characterization |
| 3 | 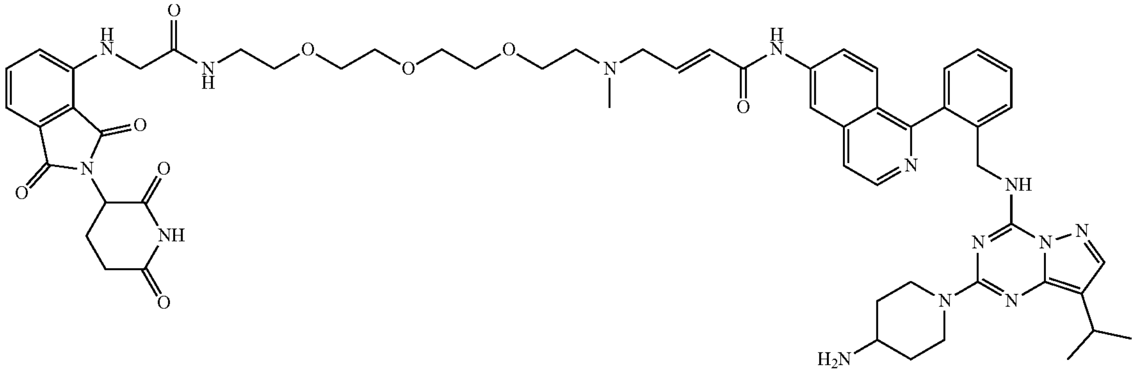 [SMILES: CC(C)c1cnn2c(NCc3ccccc3-c3nccc4cc(NC(=O)/C=C/CN(C)CCOCCOCCOCCNC(=O)CNc5cccc6c5C(=O)N(C5CCC(=O)NC5=O)C6=O)ccc34)nc(N3CCC(N)CC3)nc12] | Yellow solid; $^1$H-NMR (400 MHz, DMSO-$d_6$) δ 11.11 (brs, 1H), 8.41-8.51 (m, 3H), 8.11-8.22 (m, 3H), 7.93-8.03 (m, 1H), 7.35-7.69 (m, 8H), 6.91-7.21 (m, 3H), 5.01-5.09 (m, 1H), 4.53-4.61 (m, 1H), 4.31-4.52 (m, 4H), 4.17-4.28 (m, 3H), 3.88-4.02 (m, 4H), 3.61-3.89 (m, 6H), 3.21-3.27 (m, 1H), 2.86-3.08 (m, 5H), 2.70-2.84 (m, 5H), 2.55-2.62 (m, 4H), 2.51-2.52 (m, 1H), 1.95-2.03 (m, 1H), 1.84-2.01 (m, 2H), 1.22-1.41 (m, 2H), 1.17 (s, 6H); MS (ESI): m/z 1093.6 [M + H] $^+$ |
| 4 | 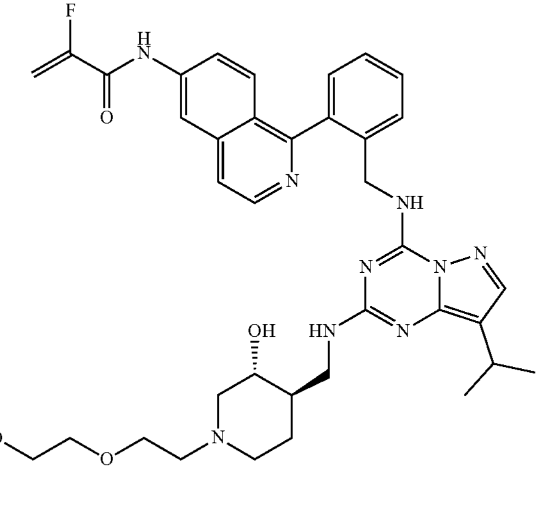 | yellow powder; $^1$H-NMR (400 MHz, MeOD-$d_4$) δ 8.38-8.56 (m, 2H), 7.85-8.08 (m, 1H), 7.70-7.81 (m, 3H), 7.50-7.69 (m, 5H), 7.05-7.08 (m, 1H), 6.89-6.96 (m, 1H), 5.90 (dd, J = 46, 2.8 Hz, 1H), 5.44 (dd, J = 15.2, 3.2 Hz, 1H), 5.02-5.08 (m, 2H), 3.93-4.06 (m, 2H), 3.77-3.83 (m, 3 H), 3.51-3.72 (m, 8H), 3.38-3.50 (m, 5H), 2.56-3.12 (m, 8H), 2.03-2.08 (m, 1H), 1.94-2.05 (m, 1H), 1.55-1.87 (m, 2H), 1.20 (d, J = 6.4 Hz, 6 H); MS (ESI): m/z 507.3 [M/2 + H] $^+$ |

TABLE 2-continued

| Summary of compounds 1-36 in terms of their structures and corresponding characteristics. | | |
|---|---|---|
| #cpd | Structure | Characterization |
| 5 | 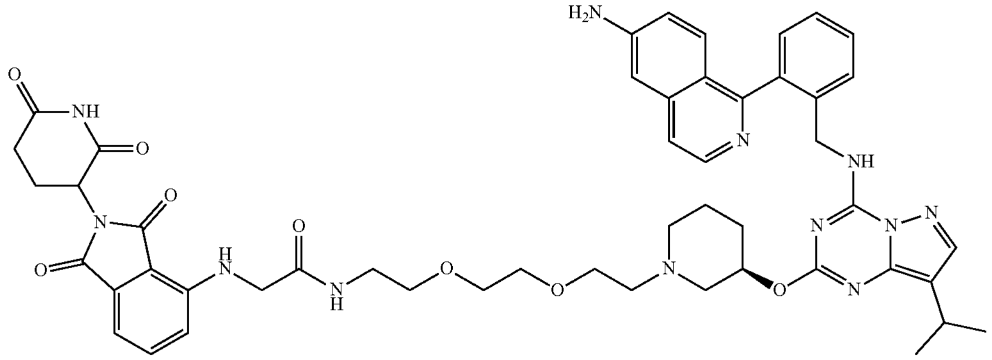 [SMILES: CC(C)c1cnn2c(NCc3ccccc3-c3nccc4cc(N)ccc34)nc(O[C@@H]3CCCN(CCOCCOCCNC(=O)CNc4cccc5c4C(=O)N(C4CCC(=O)NC4=O)C5=O)C3)nc12] | Yellow solid; $^1$H-NMR (400 MHz, DMSO-$d_6$) δ 10.81 (brs, 1H), 8.69 (brs, 1H), 8.17 (d, J = 6.0 Hz, 1H), 7.92 (brs, 1H), 7.81 (s, 1H), 7.48-7.61 (m, 3H), 7.42-7.46 (m, 2H), 7.33-7.40 (m, 2H), 7.07 (d, J = 7.2 Hz, 1H), 6.90 (d, J = 8.8 Hz, 1H), 6.86-6.93 (m, 3H), 5.08-5.16 (m, 1H), 4.99-5.06 (m, 1H), 4.52 (s, 2H), 3.94 (d, J = 5.2 Hz, 1H), 3.67-3.75 (m, 2H), 3.44-3.55 (m, 5H), 3.39-3.43 (m, 3H), 3.24-3.30 (m, 4H), 3.01-3.09 (m, 1H), 2.65-2.77 (m, 2H), 2.61-2.70 (m, 2H), 2.28-2.31 (m, 1H), 1.88-2.07 (m, 4H), 1.64-1.81 (m, 2H), 1.28 (d, J = 6.8 H, 6H); MS (ESI): m/z 953.4 [M + H] $^+$ |
| 6 | 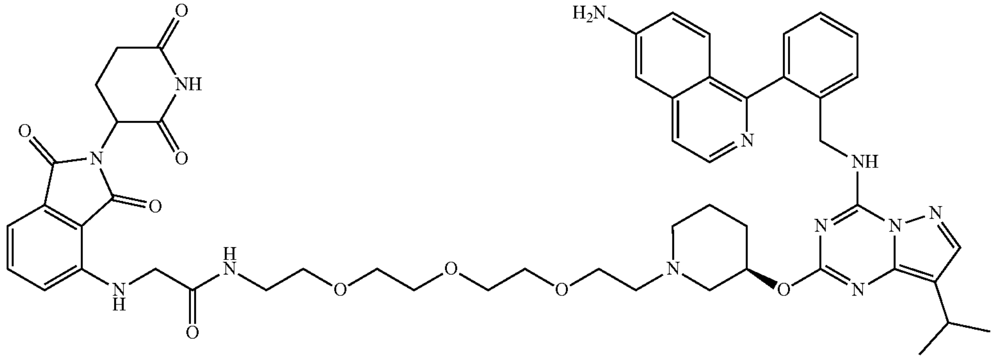 [SMILES: CC(C)c1cnn2c(NCc3ccccc3-c3nccc4cc(N)ccc34)nc(O[C@@H]3CCCN(CCOCCOCCOCCNC(=O)CNc4cccc5c4C(=O)N(C4CCC(=O)NC4=O)C5=O)C3)nc12] | Yellow solid; $^1$H-NMR (400 MHz, DMSO-$d_6$) δ 10.82 (brs, 1H), 8.69 (brs, 1H), 8.04 (d, J = 6.4 Hz, 1H), 7.97 (brs, 1H), 7.64-7.78 (m, 4H), 7.53-7.61 (m, 2H), 7.45 (d, J = 7.2 Hz, 1H), 7.32 (d, J = 6.0 Hz, 1H), 7.05-7.12 (m, 2H), 6.84-6.94 (m, 2H), 5.26 (s, 1H), 5.03-5.07 (m, 1H), 4.64-4.68 (m, 1H), 4.53-4.56 (m, 1H), 3.95 (s, 2H), 3.85 (s, 2H), 3.50-3.61 (m, 6H), 3.48 (s, 5H), 3.41-3.48 (m, 3H), 3.24-3.35 (m, 2H), 2.81-3.03 (m, 2H), 2.52-2.67 (m, 3H), 1.93-2.21 (m, 4H), 1.39-1.92 (m, 2H), 1.27 (d, J = 6.8 Hz, 6H); MS (ESI): m/z 997.4 [M + H] $^+$ |

TABLE 2-continued

| Summary of compounds 1-36 in terms of their structures and corresponding characteristics. | | |
|---|---|---|
| #cpd | Structure | Characterization |
| 7 | 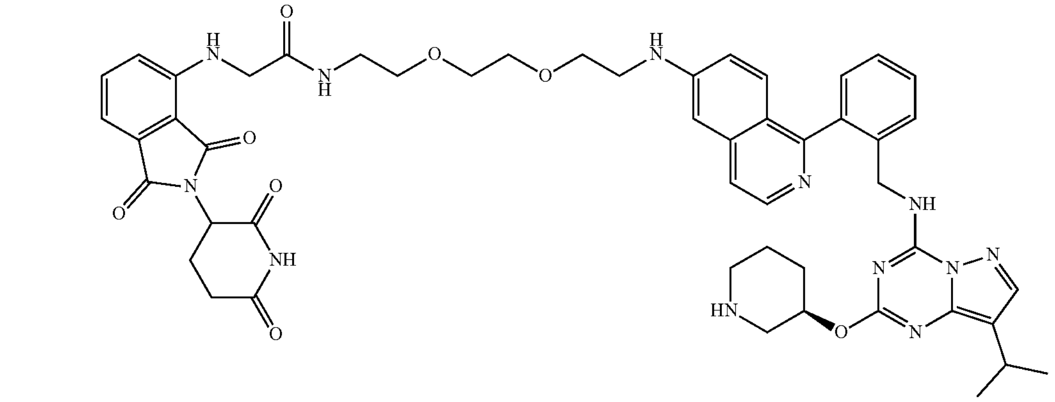 [SMILES: CC(C)c1cnn2c(NCc3ccccc3-c3nccc4cc(NCCOCCOCCNC(=O)CNc5cccc6c5C(=O)N(C5CCC(=O)NC5=O)C6=O)ccc34)nc(O[C@@H]3CCCNC3)nc12] | Yellow solid; $^1$H-NMR (400 MHz, DMSO-$d_6$) δ 10.82 (brs, 1H), 9.60 (brs, 1H), 9.08 (brs, 1H), 8.69 (brs, 1H), 8.09 (d, J = 6.8 Hz, 1H), 8.01 (brs, 1H), 7.71-7.77 (m, 3H), 7.65-7.70 (m, 1H), 7.51-7.60 (m, 2H), 7.44 (d, J = 7.2 Hz, 1H), 7.30 (d, J = 9.2 Hz, 1H), 7.19 (d, J = 9.2 Hz, 1H), 7.05 (d, J = 7.2 Hz, 1H), 6.86-6.95 (m, 2H), 5.10-5.18 (m, 1H), 4.97-5.05 (m, 1H), 4.62-4.75 (m, 1H), 4.48-4.58 (m, 1H), 3.93-3.93 (m, 1H), 3.95 (s, 1H), 3.61-3.72 (m, 2H), 3.54-3.61 (m, 4H), 3.36-3.49 (m, 5H), 3.26-3.31 (m, 2H), 3.03-3.09 (m, 4H), 2.83-2.99 (m, 2H), 2.53-2.65 (m, 2H), 1.99-2.10 (m, 2H), 1.89-1.92 (m, 1H), 1.76-1.86 (m, 1H), 1.25 (d, J = 7.2 Hz, 6H); MS (ESI): m/z 953.5 $[M + H]^+$ |
| 8 | 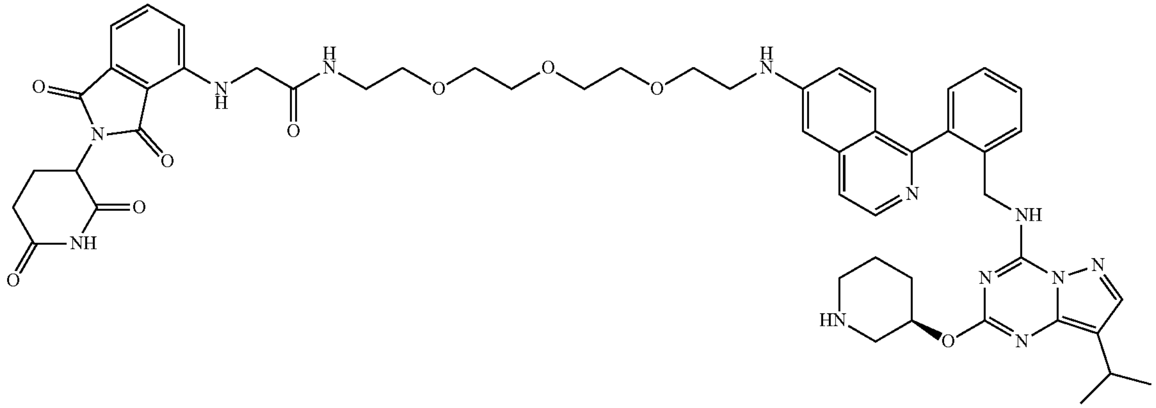 [SMILES: CC(C)c1cnn2c(NCc3ccccc3-c3nccc4cc(NCCOCCOCCOCCNC(=O)CNc5cccc6c5C(=O)N(C5CCC(=O)NC5=O)C6=O)ccc34)nc(O[C@@H]3CCCNC3)nc12] | Yellow powder; $^1$H-NMR (400 MHz, DMSO-$d_6$) δ 10.88 (brs, 1H), 9.34 (brs, 1H), 8.90 (brs, 1H), 8.74 (brs, 1H), 8.08 (d, J = 6.8 Hz, 1H), 7.99 (brs, 1H), 7.65-7.76 (m, 4H), 7.53-7.59 (m, 2H), 7.44 (d, J = 7.8 Hz, 1H), 7.24-7.33 (m, 1H), 7.11-7.22 (m, 1H), 7.06 (d, J = 6.8 Hz, 1H), 6.89 (d, J = 8.8 Hz, 2H), 5.06-5.12 (m, 1H), 5.03 (dd, J = 12.4, 5.6 Hz, 1H), 4.62-4.71 (m, 1H), 4.48-4.54 (m, 1H), 3.94 (s, 2H), 3.63-3.70 (m, 2H), 3.54-3.60 (m, 4H), 3.46-3.53 (m, 5H), 3.03-3.10 (m, 3H), 2.81-2.99 (m, 4H), 2.53-2.65 (m, 3H), 2.43-2.47 (m, 2H), 1.74-2.08 (m, 6H), 1.24 (d, J = 6.8 Hz, 6H); MS (ESI): m/z 997.5 $[M + H]^+$ |

TABLE 2-continued

| Summary of compounds 1-36 in terms of their structures and corresponding characteristics. | | |
|---|---|---|
| #cpd | Structure | Characterization |
| 9 | 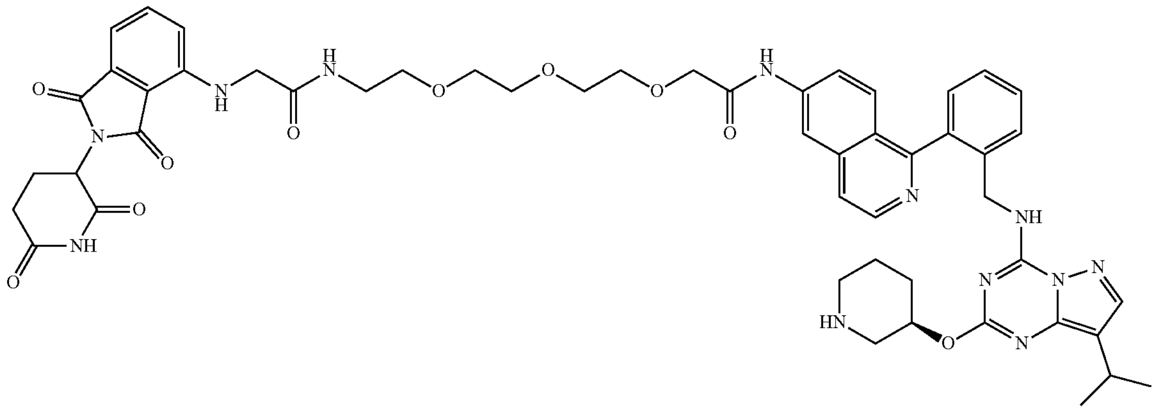 [SMILES: CC(C)c1cnn2c(NCc3ccccc3-c3nccc4cc(NC(=O)COCCOCCOCCNC(=O)CNc5cccc6c5C(=O)N(C5CCC(=O)NC5=O)C6=O)ccc34)nc(O[C@@H]3CCCNC3)nc12] | Yellow powder; $^{1}$H-NMR (400 MHz, DMSO-$d_6$) δ 1H NMR (DMSO-d6, 400 MHz) δ 10.82 (brs, 1H), 10.43 (brs, 1H), 9.43 (brs, 1H), 8.93 (brs, 1H), 8.62 (brs, 1H), 8.51 (s, 1H), 8.45 (d, J = 6.0 Hz, 1H), 8.10 (d, J = 6.4 Hz, 1H), 7.96 (s, 1H), 7.83 (d, J = 9.6 Hz, 1H), 7.65-7.76 (m, 3H), 7.52-7.62 (m, 2H), 7.29-7.50 (m, 1H), 7.02-7.12 (m, 1H), 6.82-6.94 (m, 1H), 5.09-5.16 (m, 1H), 4.98-5.06 (m, 1H), 4.49-4.74 (m, 2H), 4.22 (s, 2H), 3.95 (s, 2H), 3.70-3.75 (m, 2H), 3.60-3.66 (m, 2H), 3.51-3.59 (m, 4H), 3.14-3.25 (m, 4H), 3.02-3.12 (m, 3H), 2.82-2.98 (m, 2H), 2.54-2.65 (m, 2H), 1.74-2.09 (m, 6H), 1.21-1.28 (m, 6H); MS (ESI): m/z 1011.5 $[M + H]^+$ |
| 10 | 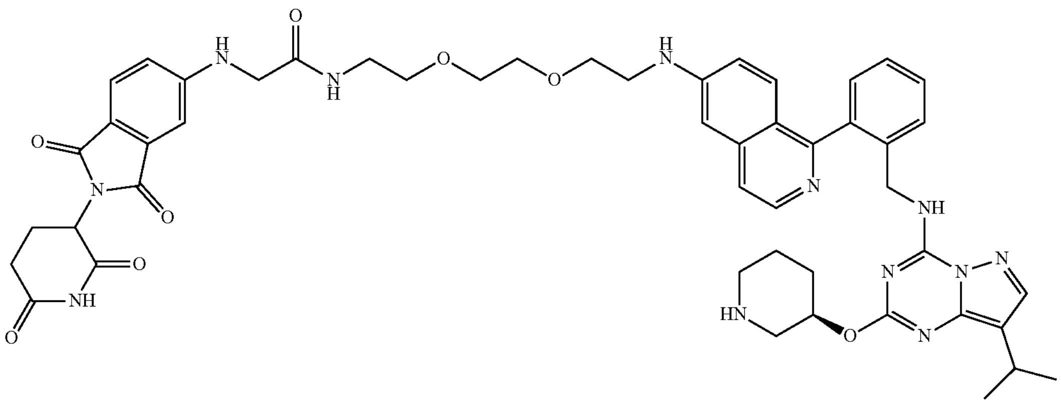 [SMILES: CC(C)c1cnn2c(NCc3ccccc3-c3nccc4cc(NCCOCCOCCNC(=O)CNc5ccc6c(c5)C(=O)N(C5CCC(=O)NC5=O)C6=O)ccc34)nc(O[C@@H]3CCCNC3)nc12] | Yellow solid; $^{1}$H-NMR (400 MHz, DMSO-$d_6$) δ 11.07 (brs, 1H), 9.10 (brs, 1H), 8.93 (brs, 1H), 8.84 (brs, 1H), 8.59 (brs, 1H), 8.05-8.18 (m, 2H), 7.64-7.87 (m, 4H), 7.44-7.60 (m, 3H), 7.15-7.27 (m, 1H), 7.00-7.14 (m, 1H), 6.76-6.95 (m, 2H), 5.03 (m, 2H), 4.54-4.73 (m, 1H), 4.34-4.50 (m, 1H), 3.49-3.67 (m, 9H), 3.31-3.46 (m, 6H), 3.18-3.28 (m, 3H), 3.04-3.08 (m, 2H), 2.81-2.95 (m, 3H), 1.79-2.04 (m, 3H), 1.70-1.73 (m, 1H), 1.21-1.23 (m, 6H); MS (ESI): m/z 953.5 $[M + H]^+$ |

TABLE 2-continued
Summary of compounds 1-36 in terms of their structures and corresponding characteristics.
| #cpd | Structure | Characterization |
| --- | --- | --- |
| 11 | 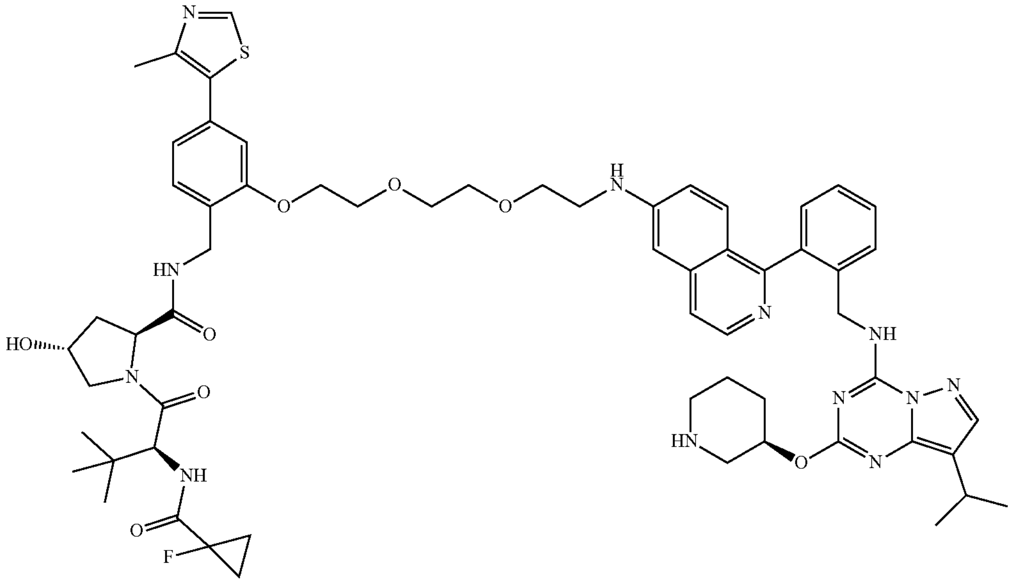 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCNc2ccc3c(-c4ccccc4CNc4nc(O[C@@H]5CCCNC5)nc5c(C(C)C)cnn45)nccc3c2)c1] | Yellow powder; $^1$H-NMR (400 MHz, DMSO-$d_6$) δ 8.92 (brs, 1H), 8.71 (brs, 1H), 8.17 (brs, 1H), 8.08 (d, J = 6.8 Hz, 1H), 7.62-7.77 (m, 4H), 7.54 (t, J = 7.2 Hz, 1H), 7.36-7.46 (m, 2H), 7.23-7.34 (m, 1H), 7.09-7.18 (m, 2H), 7.03 (s, 1H), 6.98 (d, J = 7.6 Hz, 1H), 6.88 (s, 1H), 5.07-5.11 (m, 1H), 4.53-4.64 (m, 3H), 4.34-4.37 (m, 2H), 4.28-4.33 (m, 3H), 4.17-4.21 (m, 4H), 3.79-3.84 (m, 2H), 3.58-3.71 (m, 7H), 3.35-3.52 (m, 3H), 3.18-3.21 (m, 1H), 3.07-3.10 (m, 2H), 2.91-2.94 (m, 1H), 2.45 (s, 3H), 2.03-2.14 (m, 1H), 1.71-2.02 (m, 5H), 1.30-1.34 (m, 2H), 1.25 (d, J = 6.8 Hz, 6H), 0.97 (s, 9H); MS (ESI): m/z 1155.7 $[M + H]^+$ |

TABLE 2-continued

| Summary of compounds 1-36 in terms of their structures and corresponding characteristics. | | |
|---|---|---|
| #cpd | Structure | Characterization |
| 12 | 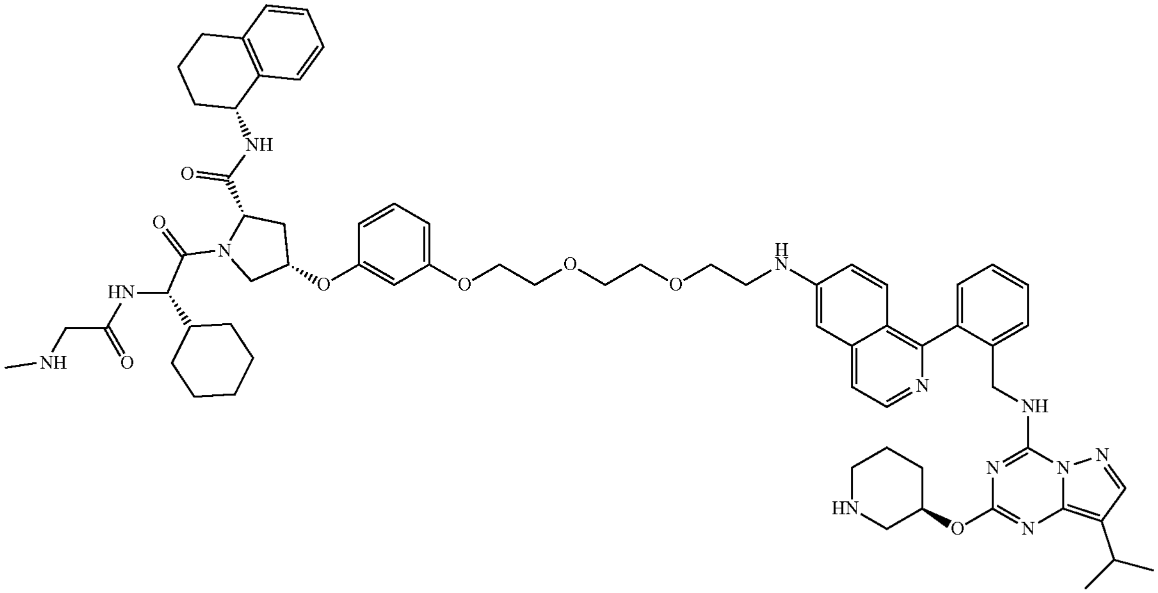 [SMILES: CNCC(=O)N[C@H](C(=O)N1C[C@@H](Oc2cccc(OCCOCCOCCNc3ccc4c(-c5ccccc5CNc5nc(O[C@@H]6CCCNC6)nc6c(C(C)C)cnn56)nccc4c3)c2)C[C@H]1C(=O)N[C@@H]1CCCc2ccccc21)C1CCCCC1] | Yellow powder; $^1$H-NMR (400 MHz, DMSO-$d_6$) δ 8.72 (brs, 2H), 8.52 (brs, 1 H), 8.09 (d, J = 6.8 Hz, 1 H), 7.65-7.81 (m, 4H), 7.52-7.56 (m, 2H), 7.41-7.44 (m, 1H), 7.24-7.28 (m, 2H), 7.08-7.20 (m, 5H), 6.89 (s, 1H), 6.47-6.60 (m, 2H), 6.41-6.46 (m, 1H), 4.95-5.14 (m, 3H), 4.45-4.54 (m, 2H), 4.21-4.25 (m, 1H), 4.05-4.08 (m, 4H), 3.70-3.81 (m, 7H), 3.64 (s, 6H), 3.41-3.44 (m, 2H), 3.31-3.37 (m, 1H), 3.21-3.28 (m, 1H), 3.07-3.10 (m, 2H), 2.91-2.95 (m, 1H), 2.67-2.78 (m, 2H), 2.59 (s, 3H), 2.21-2.24 (m, 1H), 1.59-1.95 (m, 14H), 1.26 (d, J = 6.8 Hz, 6H), 0.98-1.19 (m, 4H); MS (ESI): m/z 1185.8 $[M + H]^+$ |
| 13 | 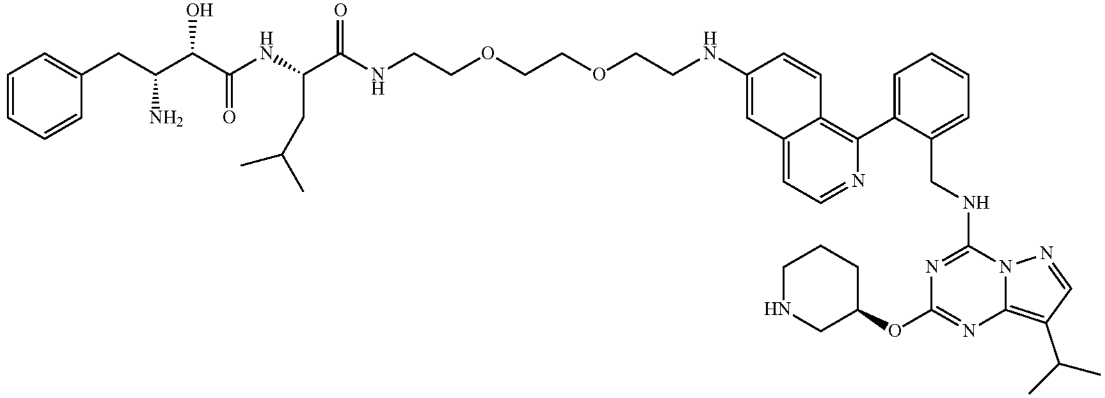 [SMILES: CC(C)C[C@H](NC(=O)[C@@H](O)[C@H](N)Cc1ccccc1)C(=O)NCCOCCOCCNc1ccc2c(-c3ccccc3CNc3nc(O[C@@H]4CCCNC4)nc4c(C(C)C)cnn34)nccc2c1] | Brown powder; $^1$H-NMR (400 MHz, DMSO-$d_6$) δ 8.73 (brs, 1H), 8.12 (d, J = 6.4 Hz, 1H), 7.99 (brs, 1H), 7.74-7.93 (m, 3H), 7.60-7.73 (m, 3H), 7.55 (m, 1H), 7.44 (m, 1H), 7.26-7.38 (m, 5H), 7.12 (m, 1H), 6.88 (s, 1H), 5.08-5.11 (m, 1H), 4.51-4.54 (m, 1H), 4.24-4.39 (m, 1H), 3.97-4.10 (m, 1H), 3.62-3.67 (m, 2H), 3.52-3.62 (m, 5H), 3.42-3.48 (m, 4H), 2.84-3.11 (m, 8H), 1.72-2.05 (m, 5H), 1.47-1.70 (m, 2H), 1.24-1.30 (m, 8H), 0.85-0.90 (m, 6H); MS (ESI): m/z 930.6 $[M + H]^+$ |

TABLE 2-continued

Summary of compounds 1-36 in terms of their structures and corresponding characteristics.

| #cpd | Structure | Characterization |
|---|---|---|
| 14 | 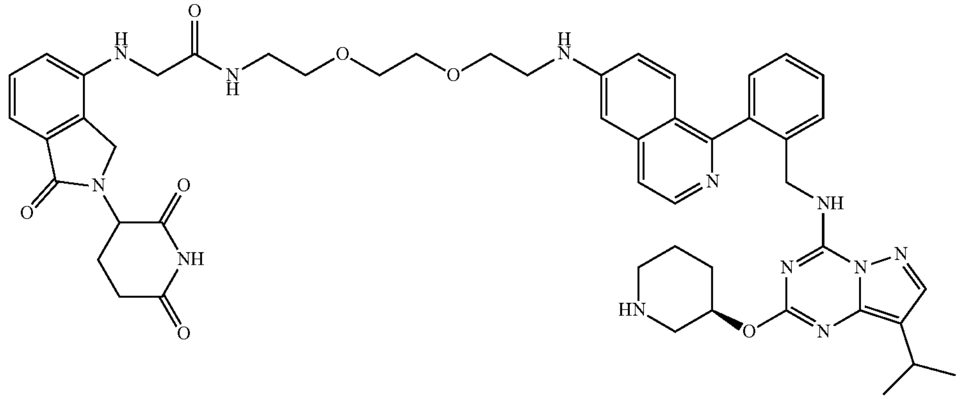 [SMILES: CC(C)c1cnn2c(NCc3ccccc3-c3nccc4cc(NCCOCCOCCNC(=O)CNc5cccc6c5CN(C5CCC(=O)NC5=O)C6=O)ccc34)nc(O[C@@H]3CCCNC3)nc12] | Yellow solid; $^{1}$H-NMR (400 MHz, DMSO-$d_6$) δ 10.73 (brs, 1H), 8.72 (brs, 1H), 8.10 (d, J = 6.4 Hz, 1H), 7.59-7.80 (m, 5H), 7.49-7.52 (m, 1H), 7.39-7.42 (m, 1H), 7.19-7.33 (m, 2H), 7.09 (d, J = 8.8 Hz, 1H), 6.98 (d, J = 7.2 Hz, 1H), 6.85 (s, 1H), 6.81-6.89 (m, 1H), 6.61 (d, J = 8.0 Hz, 1H), 4.95-5.15 (m, 2H), 4.19-4.52 (m, 2H), 4.18-4.35 (m, 2H), 3.75 (s, 2H), 3.61-3.66 (m, 2H), 3.49-3.55 (m, 2H), 3.42-3.45 (m, 2H), 3.41 (m, 2H), 3.34-3.38 (m, 2H), 3.33 (s, 3H), 3.09-3.13 (m, 1H), 2.83-2.99 (m, 2H), 2.58-2.68 (m, 1H), 2.33 (m, 2H), 1.81-2.09 (m, 5H), 1.74-1.76 (m, 1H), 1.25 (d, J = 6.8 Hz, 6H); MS (ESI): m/z 938.4 [M + H]+ |
| 15 | 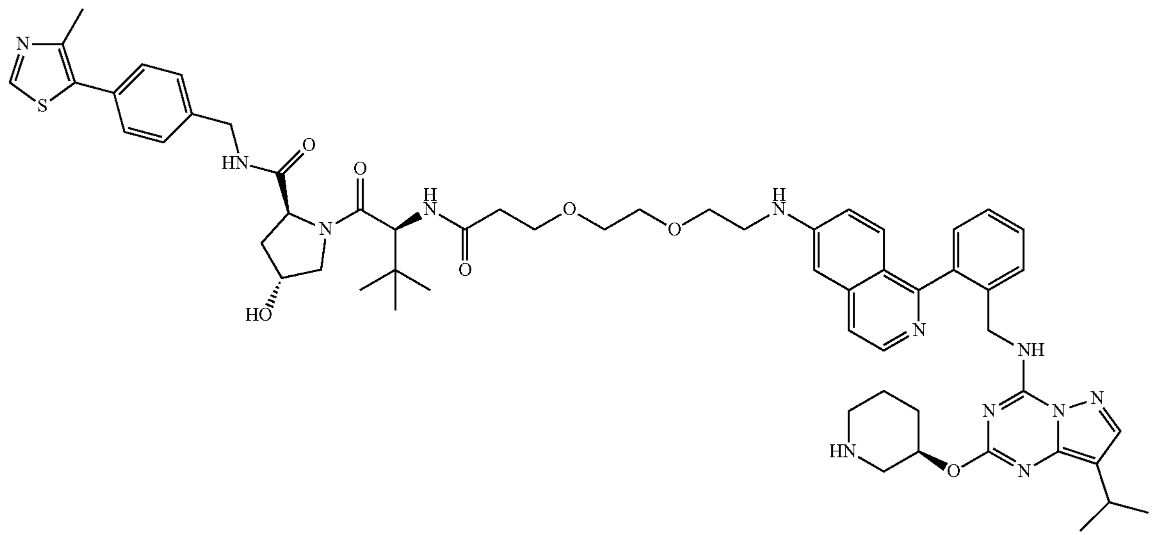 [SMILES: Cc1ncsc1-c1ccc(CNC(=O)[C@@H]2C[C@@H](O)CN2C(=O)[C@@H](NC(=O)CCOCCOCCNc2ccc3c(-c4ccccc4CNc4nc(O[C@@H]5CCCNC5)nc5c(C(C)C)cnn45)nccc3c2)C(C)(C)C)cc1] | Yellow powder; $^{1}$H-NMR (400 MHz, DMSO-$d_6$) δ 8.92 (brs, 1H), 8.73 (brs, 1H), 8.24 (brs, 1H), 8.09 (d, J = 6.4 Hz, 1H), 7.77 (s, 1H), 7.64-7.74 (m, 3H), 7.52-7.60 (m, 2H), 7.45 (m, 1H), 7.35-7.41 (m, 4H), 7.26-7.29 (m, 1H), 7.09-7.12 (m, 1H), 6.88 (s, 1H), 5.07-5.10 (m, 1H), 4.51-4.55 (m, 1H), 4.44-4.47 (m, 2H), 4.39-4.42 (m, 1H), 4.34-4.38 (m, 1H), 4.24-4.28 (m, 1H), 4.21-4.24 (m, 1H), 3.62-3.73 (m, 4H), 3.58-3.62 (m, 3H), 3.51-3.57 (m, 3H), 3.33-3.45 (m, 3H), 3.19-3.26 (m, 1H), 3.06-3.13 (m, 2H), 2.93-2.96 (m, 1H), 2.44 (s, 3H), 2.35-2.41 (m, 1H), 1.82-2.08 (m, 6H), 1.72-1.75 (m, 1H), 1.26 (d, J = 6.8 Hz, 6H), 0.94 (s, 9H); MS (ESI): m/z 1081.6 $[M + H]^+$ |

TABLE 2-continued
Summary of compounds 1-36 in terms of their structures and corresponding characteristics.
| #cpd | Structure | Characterization |
|---|---|---|
| 16 | 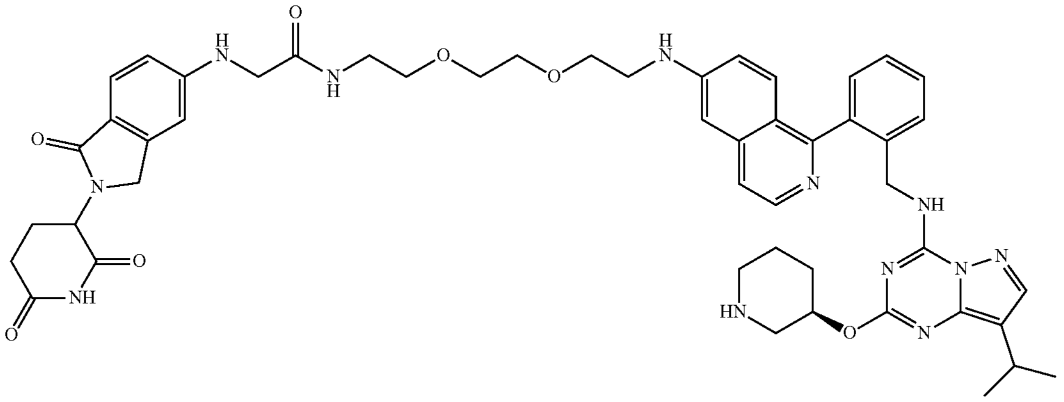 [SMILES: CC(C)c1cnn2c(NCc3ccccc3-c3nccc4cc(NCCOCCOCCNC(=O)CNc5ccc6c(c5)CN(C5CCC(=O)NC5=O)C6=O)ccc34)nc(O[C@@H]3CCCNC3)nc12] | Pale yellow powder; $^1$H-NMR (400 MHz, DMSO-$d_6$) δ 10.66 (brs, 1H), 8.72 (brs, 1H), 8.09 (d, J = 6.4 Hz, 1H), 7.77 (s, 1H), 7.64-7.74 (m, 3H), 7.51-7.55 (m, 1H), 7.39-7.48 (m, 2H), 7.29 (m, 1H), 7.11 (m, 1H), 6.87 (s, 1H), 6.57-6.72 (m, 2H), 5.07-5.10 (m, 1H), 4.95-4.97 (m, 1H), 4.49-4.53 (m, 2H), 4.12-4.34 (m, 2H), 3.74 (s, 1H), 3.61-3.65 (m, 2H), 3.51-3.58 (m, 4H), 3.44-3.47 (m, 2H), 3.41-3.43 (m, 2H), 3.35-3.40 (m, 3H), 3.21-3.29 (m, 2H), 2.94-2.97 (m, 1H), 2.82-2.92 (m, 2H), 2.53-2.66 (m, 2H), 2.32-2.37 (m, 1H), 1.80-2.03 (m, 4H), 1.71-1.77 (m, 1H), 1.26 (d, J = 6.8 Hz, 6H); LCMS: 100%, MS (ESI): m/z 939.4 $[M + H]^+$ |

TABLE 2-continued
| Summary of compounds 1-36 in terms of their structures and corresponding characteristics. | | |
|---|---|---|
| #cpd | Structure | Characterization |
| 17 | 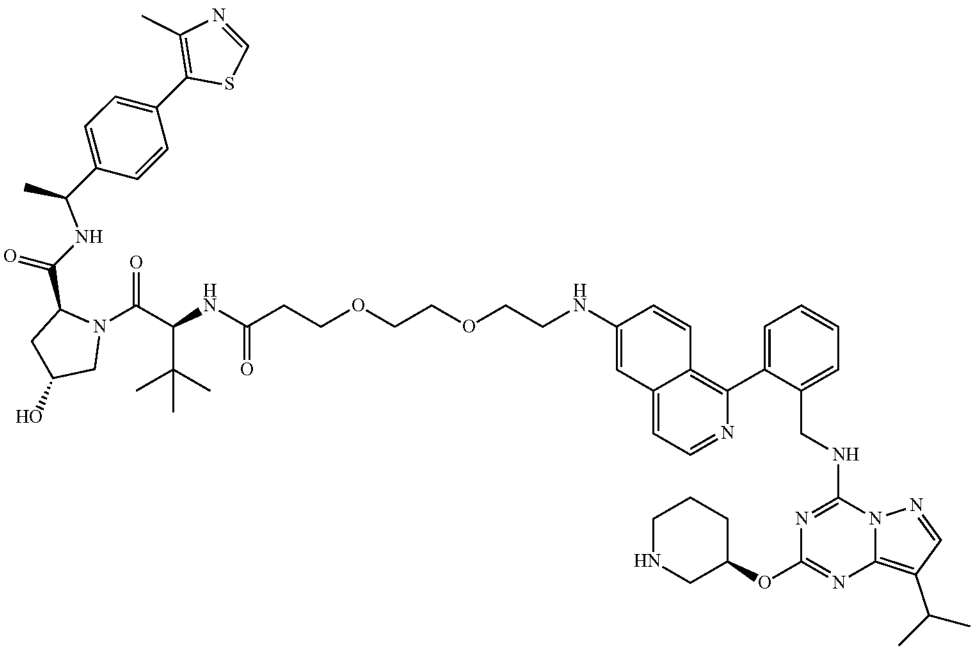 [SMILES: Cc1ncsc1-c1ccc([C@H](C)NC(=O)[C@@H]2C[C@@H](O)CN2C(=O)[C@@H](NC(=O)CCOCCOCCNc2ccc3c(-c4ccccc4CNc4nc(O[C@@H]5CCCNC5)nc5c(C(C)C)cnn45)nccc3c2)C(C)(C)C)cc1] | Green powder; $^1$H-NMR (400 MHz, DMSO-$d_6$) δ 8.93 (brs, 1H), 8.72 (brs, 1H), 8.69-8.75 (m, 1H), 8.03-8.11 (m, 2H), 7.66-7.78 (m, 4H), 7.52-7.59 (m, 2H), 7.36-7.47 (m, 5H), 7.25-7.29 (m, 1H), 7.14 (brs, 1H), 6.89 (s, 1H), 5.07-5.10 (m, 1H), 4.89-4.93 (m, 1H), 4.45-4.56 (m, 3H), 4.29-4.32 (m, 1H), 3.63-3.70 (m, 4H), 3.58-3.62 (m, 4H), 3.53-3.58 (m, 3H), 3.35-3.47 (m, 3H), 3.19-3.25 (m, 1H), 3.06-3.10 (m, 3H), 2.91-2.94 (m, 1H), 2.45 (s, 3H), 2.35-2.42 (m, 1H), 1.95-2.03 (m, 2H), 1.83-1.94 (m, 3H), 1.70-1.81 (m, 1H), 1.36-1.42 (m, 3H), 1.23-1.28 (m, 6H), 0.97 (s, 9H); MS (ESI): m/z 1095.4 $[M + H]^+$ |

TABLE 2-continued

| Summary of compounds 1-36 in terms of their structures and corresponding characteristics. | | |
|---|---|---|
| #cpd | Structure | Characterization |
| 18 | 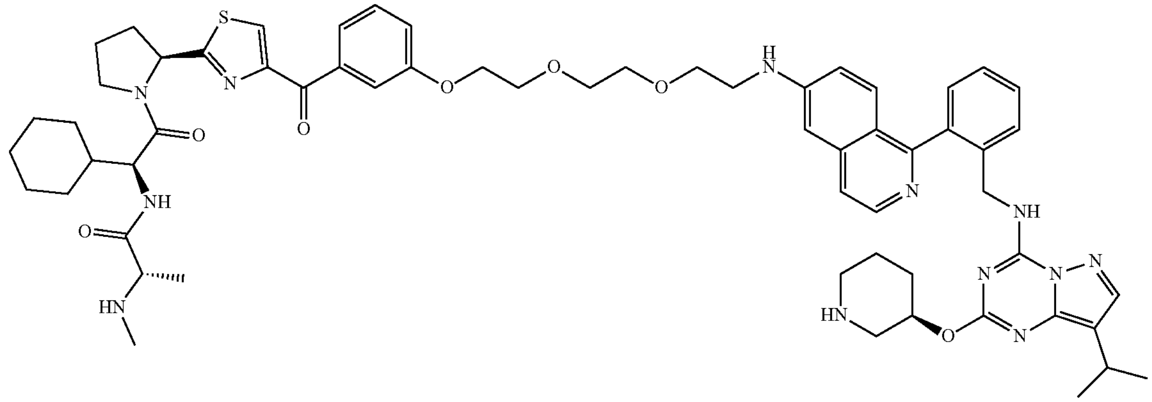 [SMILES: CN[C@@H](C)C(=O)N[C@H](C(=O)N1CCC[C@H]1c1nc(C(=O)c2cccc(OCCOCCOCCNc3ccc4c(-c5ccccc5CNc5nc(O[C@@H]6CCCNC6)nc6c(C(C)C)cnn56)nccc4c3)c2)cs1)C1CCCCC1] | Yellow solid; $^1$H-NMR (400 MHz, DMSO-$d_6$) δ 8.75 (brs, 1H), 8.49 (brs, 1H), 8.41 (s, 1H), 8.11-8.14 (m, 1H), 7.79 (s, 1H), 7.56-7.73 (m, 6H), 7.46-7.50 (m, 1H), 7.36-7.47 (m, 3H), 7.26-7.29 (m, 1H), 7.19-7.22 (m, 1H), 7.05-7.08 (m, 1H), 6.84 (s, 1H), 5.37-5.41 (m, 1H), 5.07-5.11 (m, 1H), 4.43-4.57 (m, 3H), 4.16-4.22 (m, 2H), 3.86-3.98 (m, 1H), 3.76-3.85 (m, 4H), 3.61-3.71 (m, 4H), 3.38-3.44 (m, 3H), 3.06-3.10 (m, 2H), 2.92-2.96 (m, 1H), 2.65-2.69 (m, 1H), 2.55-2.58 (m, 1H), 2.53 (s, 3H), 2.29-2.32 (m, 1H), 2.21-2.25 (m, 3H), 1.82-2.12 (m, 4H), 1.54-1.79 (m, 6H), 1.34-1.37 (m, 3H), 1.23-1.26 (m, 8H), 1.08-1.11 (m, 4H); MS (ESI): m/z 1021.5 $[M + H]^+$ |
| 19 | 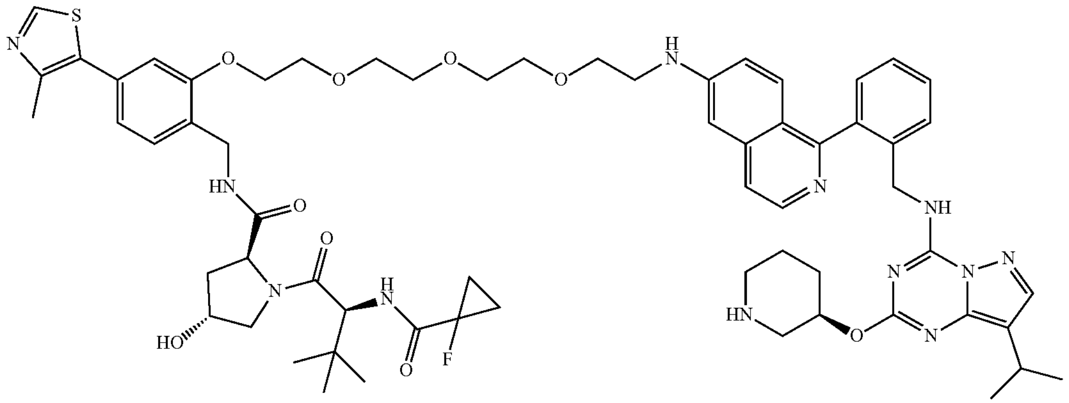 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCNc2ccc3c(-c4ccccc4CNc4nc(O[C@@H]5CCCNC5)nc5c(C(C)C)cnn45)nccc3c2)c1] | Yellow powder; $^1$H-NMR (400 MHz, DMSO-$d_6$) δ 8.92 (brs, 1H), 8.70 (brs, 1H), 8.15 (brs, 1H), 8.08 (d, J = 6.8 Hz, 1H), 7.65-7.78 (m, 4H), 7.54 (t, J = 7.6 Hz, 1H), 7.35-7.45 (m, 2H), 7.23-7.31 (m, 1H), 7.07-7.18 (m, 2H), 7.03 (s, 1H), 6.95-7.00 (m, 1H), 6.88 (s, 1H), 5.06-5.09 (m, 1H), 4.53-4.63 (m, 4H), 4.47-4.49 (m, 1H), 4.35-4.38 (m, 1H), 4.26-4.33 (m, 2H), 4.17-4.21 (m, 2H), 3.77-3.83 (m, 2H), 3.61-3.71 (m, 6H), 3.55-3.59 (m, 5H), 3.33-3.47 (m, 3H), 3.18-3.21 (m, 1H), 3.07-3.09 (m, 2H), 2.90-2.94 (m, 1H), 2.45 (s, 3H), 2.05-2.15 (m, 1H), 1.87-2.03 (m, 3H), 1.70-1.87 (m, 3H), 1.28-1.39 (m, 3H), 1.25 (d, J = 6.8 Hz, 6H), 0.97 (s, 9H); MS (ESI): m/z 1199.6 $[M + H]^+$ |

TABLE 2-continued

Summary of compounds 1-36 in terms of their structures and corresponding characteristics.

| #cpd | Structure | Characterization |
|---|---|---|
| 20 | 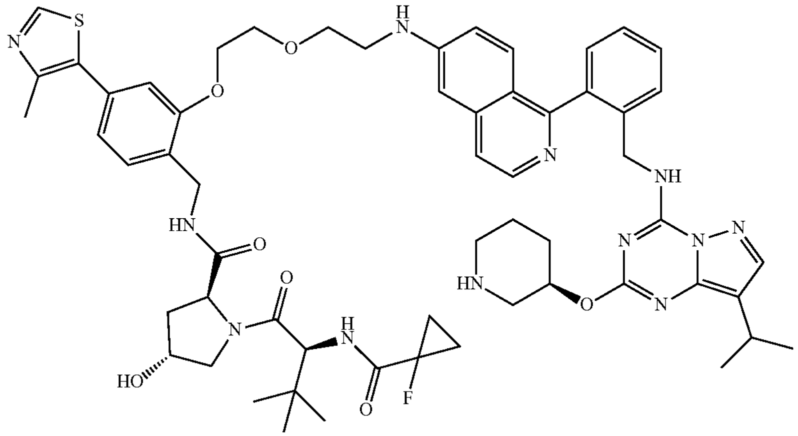 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCNc2ccc3c(-c4ccccc4CNc4nc(O[C@@H]5CCCNC5)nc5c(C(C)C)cnn45)nccc3c2)c1] | Yellow powder; $^1$H-NMR (400 MHz, DMSO-$d_6$) δ 8.91 (brs, 1H), 8.72 (brs, 1H), 8.18 (brs, 1H), 8.07 (d, J = 6.8 Hz, 1H), 7.65-7.79 (m, 4H), 7.52-7.55 (m, 1H), 7.36-7.46 (m, 2H), 7.27 (d, J = 9.2 Hz, 1H), 7.10-7.16 (m, 2H), 6.94-7.04 (m, 2H), 6.88 (s, 1H), 5.07-5.09 (m, 1H), 4.53-4.63 (m, 1H), 4.34-4.39 (m, 1H), 4.30 (t, J = 6.0 Hz, 2H), 4.20-4.25 (m, 2H), 3.84-3.90 (m, 2H), 3.75-3.80 (m, 2H), 3.66-3.71 (m, 1H), 3.57-3.61 (m, 2H), 3.40-3.46 (m, 5H), 3.23-3.25 (m, 3H), 3.06-3.09 (m, 2H), 2.89-3.00 (m, 1H), 2.44 (s, 3H), 2.04-2.11 (m, 1H), 1.83-2.00 (m, 4H), 1.74-1.78 (m, 1H), 1.30-1.39 (m, 2H), 1.25 (d, J = 6.8 Hz, 6H), 0.96 (s, 9H); MS (ESI): m/z 1111.5 [M + H]$^+$ |
| 21 | 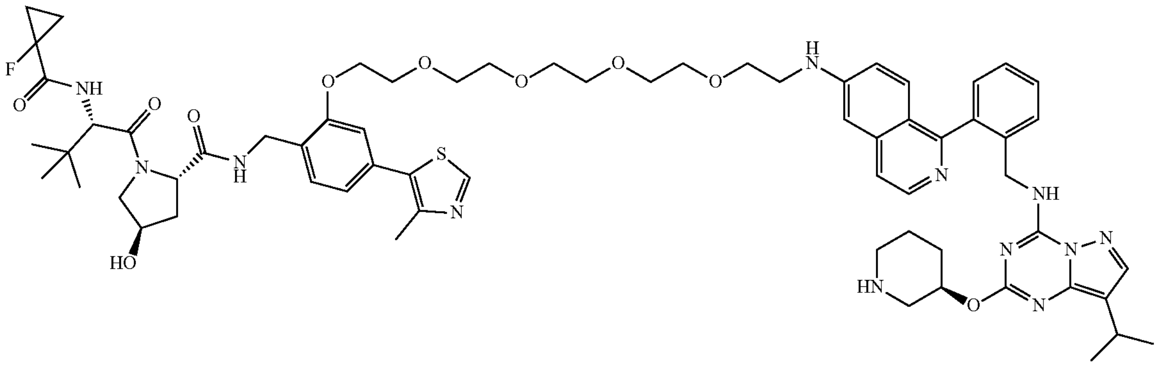 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCNc2ccc3c(-c4ccccc4CNc4nc(O[C@@H]5CCCNC5)nc5c(C(C)C)cnn45)nccc3c2)c1] | Yellow powder; $^1$H-NMR (400 MHz, DMSO-$d_6$) δ 8.92 (brs, 1H), 8.71 (brs, 1H), 8.15 (brs, 1H), 8.09 (d, J = 6.8 Hz, 1H), 7.65-7.76 (m, 4H), 7.54 (t, J = 7.6 Hz, 1H), 7.44 (d, J = 7.2 Hz, 1H), 7.39 (d, J = 8.0 Hz, 1H), 7.22-7.32 (m, 1H), 7.10-7.14 (m, 2H), 7.03 (s, 1H), 6.97 (dd, J = 8.0, 1.2 Hz, 1H), 6.88 (s, 1H), 5.05-5.13 (m, 1H), 4.57-4.60 (m, 1H), 4.51-4.56 (m, 1H), 4.41-4.48 (m, 1H), 4.35-4.38 (m, 1H), 4.27-4.32 (m, 3H), 4.22-4.25 (m, 1H), 4.17-4.20 (m, 3H), 3.78-3.82 (m, 2H), 3.65-3.71 (m, 3H), 3.60-3.64 (m, 3H), 3.55-3.59 (m, 5H), 5.49-3.52 (m, 4H), 3.38-3.42 (m, 3H), 3.35-3.38 (m, 1H), 3.16-3.20 (m, 1H), 3.07-3.13 (m, 2H), 2.91-2.98 (m, 1H), 2.46 (s, 3H), 2.05-2.13 (m, 1H), 1.89-2.02 (m, 3H), 1.81-1.89 (m, 1H), 1.71-1.80 (m, 1H), 1.34-1.39 (m, 1H), 1.29-1.33 (m, 1H), 1.25 (d, J = 6.8 Hz, 6H), 0.97 (s, 9H); MS (ESI): m/z 1143.6 [M + H]$^+$ |

TABLE 2-continued

Summary of compounds 1-36 in terms of their structures and corresponding characteristics.

| #cpd | Structure | Characterization |
|---|---|---|
| 22 | 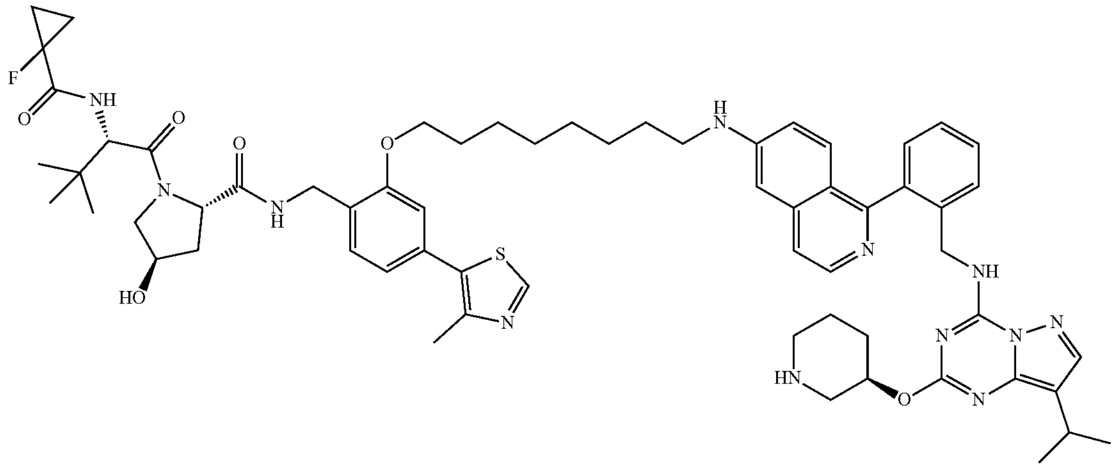 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCCNc2ccc3c(-c4ccccc4CNc4nc(O[C@@H]5CCCNC5)nc5c(C(C)C)cnn45)nccc3c2)c1] | Yellow powder; $^1$H-NMR (400 MHz, DMSO-$d_6$) δ 8.92 (brs, 1H), 8.68 (brs, 1H), 8.20 (brs, 1H), 8.06 (d, J = 6.8 Hz, 1H), 7.65-7.76 (m, 4H), 7.55 (td, J = 7.6, 1.2 Hz, 1H), 7.44 (d, J = 6.8 Hz, 1H), 7.39 (d, J = 7.2 Hz, 1H), 7.21-7.30 (m, 1H), 7.15 (d, J = 6.8 Hz, 1H), 7.03-7.11 (m, 1H), 7.00 (d, J = 1.2 Hz, 1H), 6.96 (dd, J = 7.6, 1.2 Hz, 1H), 6.80 (d, J = 7.6 Hz, 1H), 5.05-5.09 (m, 1H), 4.54-4.62 (m, 4H), 4.42-4.52 (m, 3H), 4.34-4.41 (m, 2H), 4.23-4.32 (m, 2H), 4.07 (t, J = 6.0 Hz, 2H), 3.66-3.71 (m, 1H), 3.57-3.64 (m, 1H), 3.31-3.39 (m, 1H), 3.19-3.24 (m, 3H), 3.06-3.14 (m, 2H), 2.89-2.98 (m, 1H), 2.46 (s, 3H), 2.05-2.13 (m, 1H), 1.90-2.03 (m, 3H), 1.74-1.89 (m, 4H), 1.61-1.70 (m, 2H), 1.46-1.52 (m, 2H), 1.39-1.45 (m, 4H), 1.30-1.38 (m, 2H), 1.25 (d, J = 6.8 Hz, 6H), 0.97 (s, 9H); MS (ESI): m/z 1151.6 $[M + H]^+$ |
| 23 | 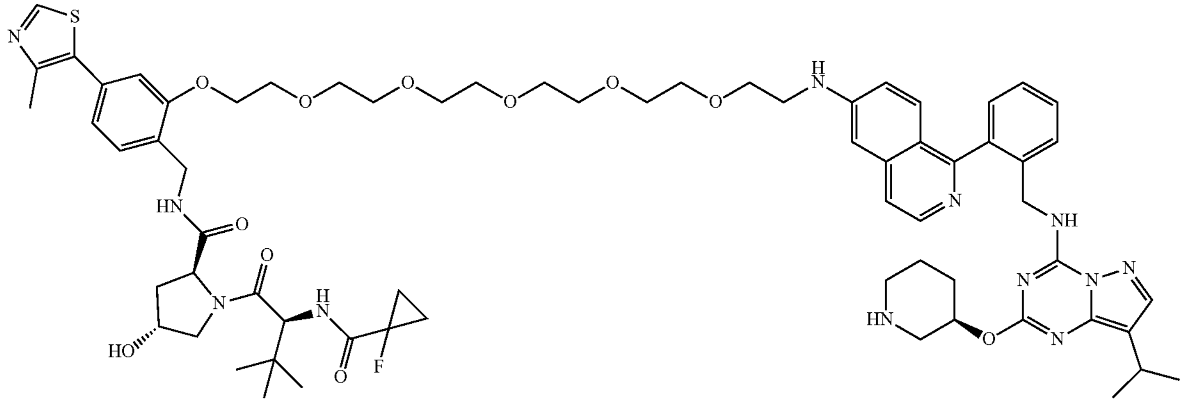 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCOCCNc2ccc3c(-c4ccccc4CNc4nc(O[C@@H]5CCCNC5)nc5c(C(C)C)cnn45)nccc3c2)c1] | Yellow solid; $^1$H-NMR (400 MHz, DMSO-$d_6$) δ 8.93 (brs, 1H), 8.76 (brs, 1H), 8.18 (brs, 1H), 8.09 (d, J = 6.8 Hz, 1H), 7.77 (s, 1H), 7.64-7.74 (m, 3H), 7.52-7.56 (m, 1H), 7.36-7.47 (m, 2H), 7.26-7.29 (m, 1H), 7.08-7.19 (m, 2H), 7.03 (s, 1H), 6.98 (d, J = 7.6 Hz, 1H), 6.88 (s, 1H), 5.07-5.10 (m, 1H), 4.51-4.64 (m, 3H), 4.35-4.38 (m, 1H), 4.25-4.29 (m, 2H), 4.16-4.22 (m, 2H), 3.76-3.82 (m, 2H), 3.64-3.68 (m, 4H), 3.61-3.63 (m, 2H), 3.53-3.60 (m, 8H), 3.48-3.53 (m, 8H), 3.07-3.10 (m, 2H), 2.92-2.95 (m, 2H), 2.48 (s, 3H), 2.04-2.13 (m, 2H), 1.93-2.02 (m, 3H), 1.69-1.92 (m, 4H), 1.31-1.36 (m, 2H), 1.20-1.28 (m, 7H), 0.97 (s, 9H); MS (ESI): m/z 1286.6 $[M + H]^+$ |

TABLE 2-continued
| Summary of compounds 1-36 in terms of their structures and corresponding characteristics. | | |
|---|---|---|
| #cpd | Structure | Characterization |
| 24 | 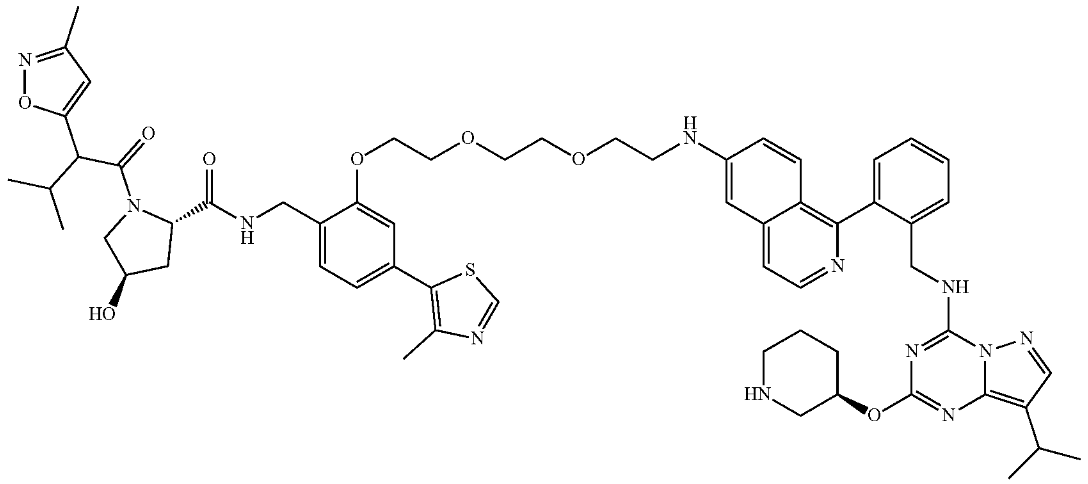 [SMILES: Cc1cc(C(C(=O)N2C[C@H](O)C[C@H]2C(=O)NCc2ccc(-c3scnc3C)cc2OCCOCCOCCNc2ccc3c(-c4ccccc4CNc4nc(O[C@@H]5CCCNC5)nc5c(C(C)C)cnn45)nccc3c2)C(C)C)on1] | Yellow powder; $^1$H-NMR (400 MHz, DMSO-$d_6$) δ 8.92 (s, 1H), 8.72 (brs, 1H), 8.08 (d, J = 6.8Hz, 1H), 7.76 (s, 1H), 7.73-7.62 (m, 3H), 7.57-7.51 (m, 1H), 7.43 (d, J = 7.5 Hz, 1H), 7.37-7.23 (m, 2H), 7.13-6.95 (m, 3H), 6.87 (brs, 1H), 6.21-6.14 (m, 1H), 5.10 (brs, 1H), 4.55-4.42 (m, 2H), 4.37-4.26 (m, 3H), 4.24-4.15 (m, 2H), 3.86-3.77 (m, 2H), 3.69-3.64 (m, 6H), 3.57 (brs, 1H), 3.43-3.39 (m, 4H), 3.35-3.32 (m, 2H), 2.97-2.94 (m, 1H), 2.45 (s, 3H), 2.20-2.13 (m, 2H), 2.08-2.03 (m, 1H), 1.99-1.81 (m, 4H), 1.78-1.76 (m, 2H), 1.52-1.50 (m, 1H), 1.32-1.21 (m, 9H), 1.04-0.90 (m, 3H), 0.87-0.78 (m, 3H); MS (ESI): m/z 1121.6 $[M + H]^+$ |

TABLE 2-continued
| Summary of compounds 1-36 in terms of their structures and corresponding characteristics. | | |
|---|---|---|
| #cpd | Structure | Characterization |
| 25 | 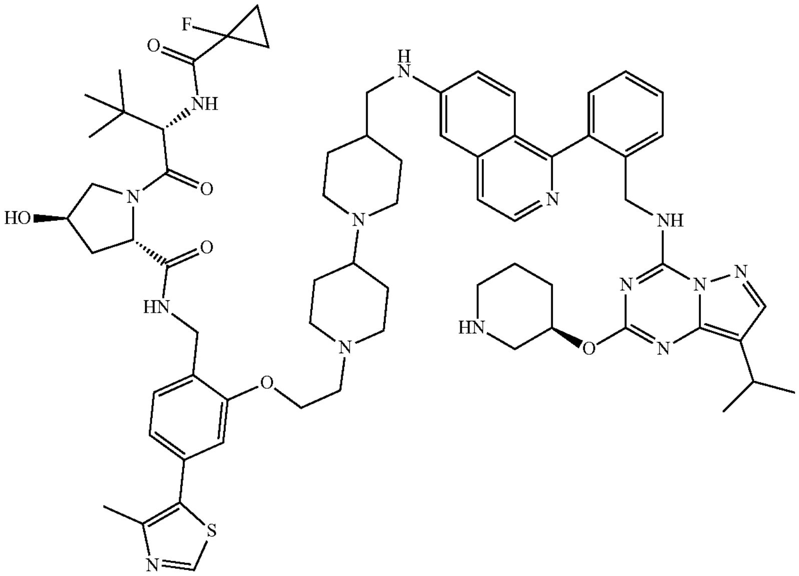 [SMILES: Cc1ncsc1-c1ccc(CNC(=O)[C@@H]2C[C@@H](O)CN2C(=O)[C@@H](NC(=O)C2(F)CC2)C(C)(C)C)c(OCCN2CCC(N3CCC(CNc4ccc5c(-c6ccccc6CNc6nc(O[C@@H]7CCCNC7)nc7c(C(C)C)cnn67)nccc5c4)CC3)CC2)c1] | Yellow solid; $^{1}$H-NMR (400 MHz, DMSO-$d_6$) δ 8.96 (s, 1H), 8.78 (brs, 1H), 8.27-8.11 (m, 2H), 7.80 (s, 1H), 7.74-7.61 (m, 3H), 7.54 (t, J = 6.7 Hz, 1H), 7.45-7.41 (m, 2H), 7.33 (d, J = 9.5 Hz, 1H), 7.19-7.02 (m, 4H), 6.88 (s, 1H), 5.14-5.10 (m, 2H), 4.64-4.49 (m, 4H), 4.42-4.30 (m, 5H), 3.75-3.57 (m, 7 H), 2.99-2.90 (m, 2H), 2.70-2.64 (m, 1H) 2.47 (s, 3H), 2.35-2.31 (m, 1H), 2.25-2.20 (m, 3H), 2.08-1.85 (m, 11H), 1.64-1.52 (m, 5H), 1.36-1.19 (m, 13H), 0.96 (s, 9H); MS (ESI): m/z 1247.8 $[M + H]^+$ |

TABLE 2-continued

| Summary of compounds 1-36 in terms of their structures and corresponding characteristics. | | |
|---|---|---|
| #cpd | Structure | Characterization |
| 26 | 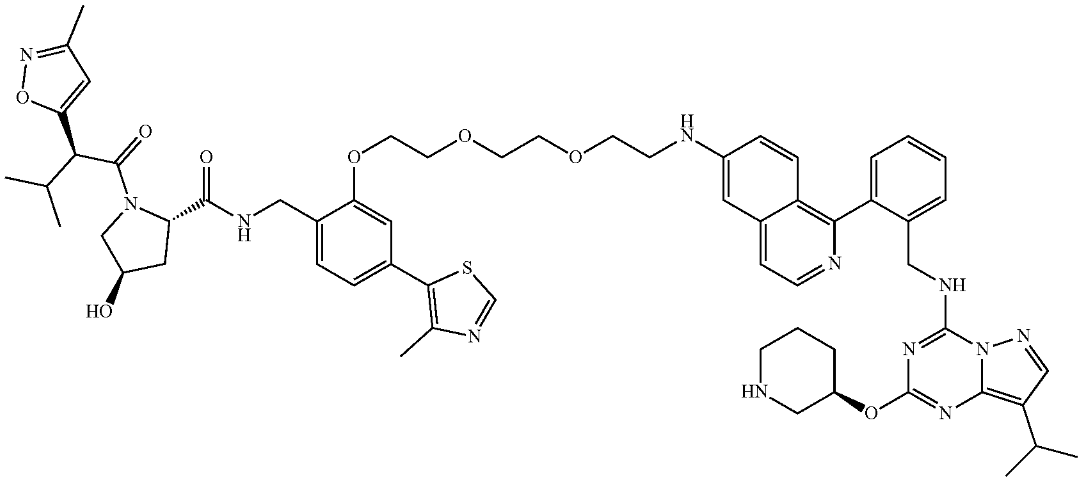 [SMILES: Cc1cc([C@@H](C(=O)N2C[C@H](O)C[C@H]2C(=O)NCc2ccc(-c3scnc3C)cc2OCCOCCOCCNc2ccc3c(-c4ccccc4CNc4nc(O[C@@H]5CCCNC5)nc5c(C(C)C)cnn45)nccc3c2)C(C)C)on1] | White powder; $^1$H-NMR (400 MHz, DMSO-$d_6$) δ 8.91 (s, 1H), 8.24 (d, J = 6.0 Hz, 1H), 8.08 (s, 1H), 7.81 (brs, 1H), 7.46-7.29 (m, 7H), 7.06-6.98 (m, 4H), 6.75 (s, 1H), 6.28 (brs, 1H), 6.18 (s, 1H), 5.34 (brs, 1H), 4.74-4.72 (m, 1H), 4.46-4.20 (m, 8H), 3.94 (d, J = 6.0 Hz, 1H), 3.82-3.55 (m, 10H), 3.35-3.32 (m, 2H), 2.97-2.95 (m, 1H), 2.45 (s, 3H), 2.29-1.96 (m, 7H), 1.53-1.49 (m, 3H), 1.30-1.24 (m, 9H), 0.96-0.81 (m, 6H); MS (ESI): m/z 1121.4 $[M + H]^+$ |
| 27 | 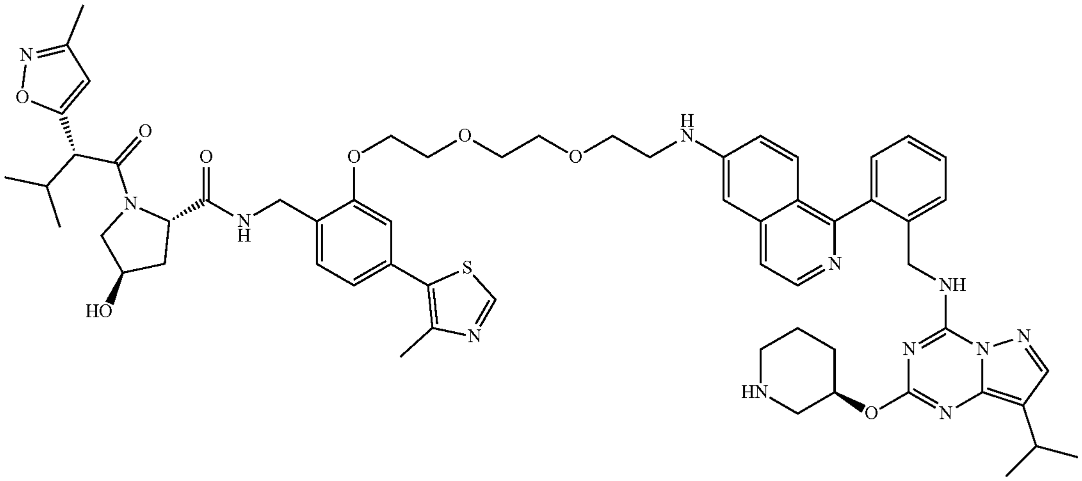 [SMILES: Cc1cc([C@H](C(=O)N2C[C@H](O)C[C@H]2C(=O)NCc2ccc(-c3scnc3C)cc2OCCOCCOCCNc2ccc3c(-c4ccccc4CNc4nc(O[C@@H]5CCCNC5)nc5c(C(C)C)cnn45)nccc3c2)C(C)C)on1] | White powder; $^1$H-NMR (400 MHz, DMSO-$d_6$) δ 8.91 (s, 1H), 8.24 (d, J = 6.0 Hz, 1H), 7.94 (brs, 1H), 7.81 (s, 1H), 7.47-7.25 (m, 7H), 7.08-6.99 (m, 4H), 6.75 (s, 1H), 6.24 (brs, 1H), 6.17 (s, 1H), 5.34 (brs, 1H), 4.76-4.74 (m, 1H), 4.51-4.18 (m, 8H), 3.95 (d, J = 5.6 Hz, 1H), 3.83-3.79 (m, 2H), 3.69-3.60 (m, 6H), 3.57-3.54 (m, 2H), 3.35-3.33 (m, 2H), 2.97-2.95 (m, 1H), 2.45 (s, 3H), 2.29-1.99 (m, 7H), 1.56-1.52 (m, 3H), 1.30-1.24 (m, 9H), 0.99-0.80 (m, 6H); MS (ESI): m/z 1121.4 $[M + H]^+$ |

TABLE 2-continued
Summary of compounds 1-36 in terms of their structures and corresponding characteristics.
| #cpd | Structure | Characterization |
|---|---|---|
| 28 | 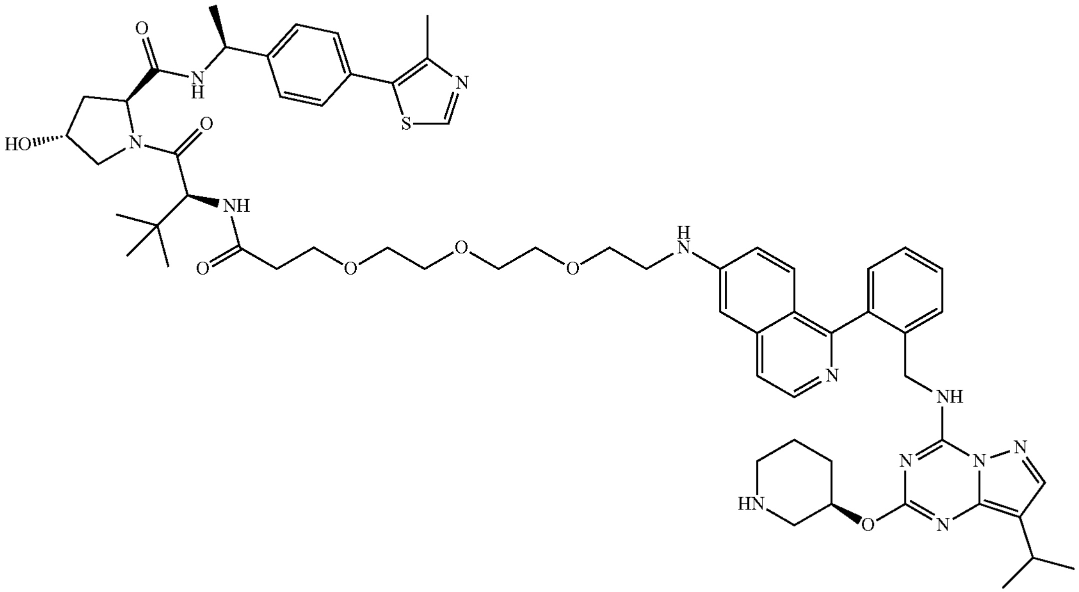 [SMILES: Cc1ncsc1-c1ccc([C@H](C)NC(=O)[C@@H]2C[C@@H](O)CN2C(=O)[C@@H](NC(=O)CCOCCOCCOCCNc2ccc3c(-c4ccccc4CNc4nc(O[C@@H]5CCCNC5)nc5c(C(C)C)cnn45)nccc3c2)C(C)(C)C)cc1] | Yellow powder; $^{1}$H-NMR (400 MHz, DMSO-$d_6$) δ 8.91 (s, 1H), 8.66 (brs, 1H), 8.05 (d, J = 6.5 Hz, 2H), 7.73-7.68 (m, 4H), 7.57-7.53 (m, 2H), 7.42-7.38 (m, 5H), 7.26-7.24 (m, 1H), 7.09 (brs, 1H), 6.86 (brs, 1H), 5.07 (brs, 1H), 4.94-4.90 (m, 1H), 4.54-4.43 (m, 3H), 4.31 (brs, 1H), 3.67-3.62 (m, 5H), 3.61-3.56 (m, 10H), 3.53-3.50 (m, 4H), 3.11-3.09 (m, 2H), 2.95-2.90 (m, 1H), 2.44 (s, 3H), 2.35-2.31 (m, 1H), 2.10-1.85 (m, 5H), 1.77-1.74 (m, 1H), 1.49-1.45 (m, 1H), 1.39 (d, J = 7.0 Hz, 3H), 1.25 (d, J = 6.4 Hz, 6H), 0.94 (s, 9H); MS (ESI): m/z 1139.5 $[M + H]^+$ |

TABLE 2-continued

| Summary of compounds 1-36 in terms of their structures and corresponding characteristics. | | |
|---|---|---|
| #cpd | Structure | Characterization |
| 29 | 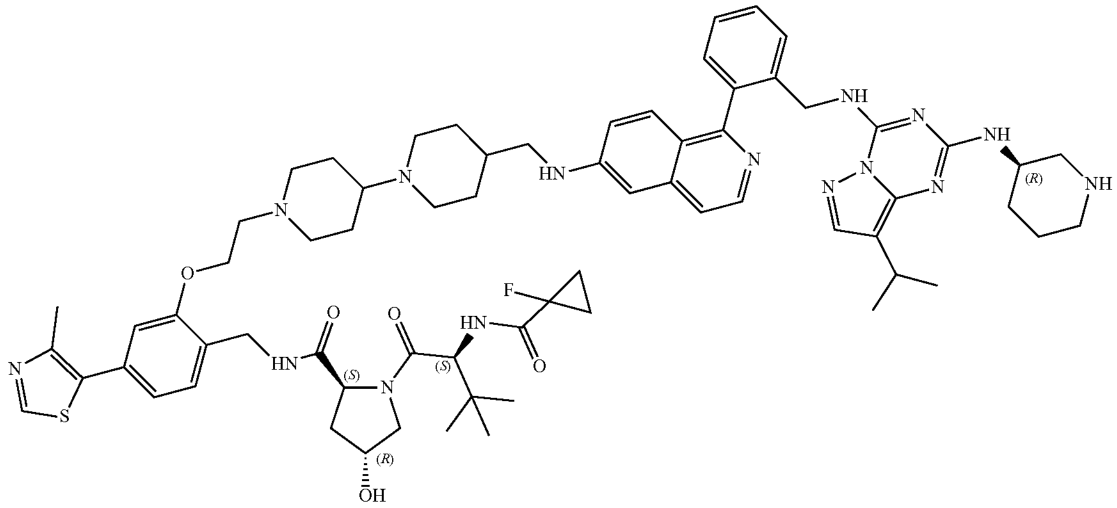 | Yellow solid; $^1$H-NMR (400 MHz, DMSO-$d_6$) δ 8.96 (s, 1H), 8.78 (brs, 1H), 8.27-8.11 (m, 2H), 7.80 (s, 1H), 7.74-7.61 (m, 3H), 7.55-7.53 (m, 1H), 7.44-7.42 (m, 2H), 7.34-7.32 (m, 1H), 7.19-7.02 (m, 4H), 6.88 (s, 1H), 5.12 (brs, 2H), 4.64-4.49 (m, 4H), 4.42-4.30 (m, 5H), 3.75-3.57 (m, 7H), 2.99-2.90 (m, 1H) 2.70-2.64 (m, 1H), 2.35-2.31 (m, 2H), 2.24 (s, 3H), 2.06-1.94 (m, 11H), 1.63-1.61 (m, 4H) 1.36-1.19 (m, 12H) 0.96 (s, 9H); MS (ESI): m/z 1247.8 $[M + H]^+$ |
| 30 | 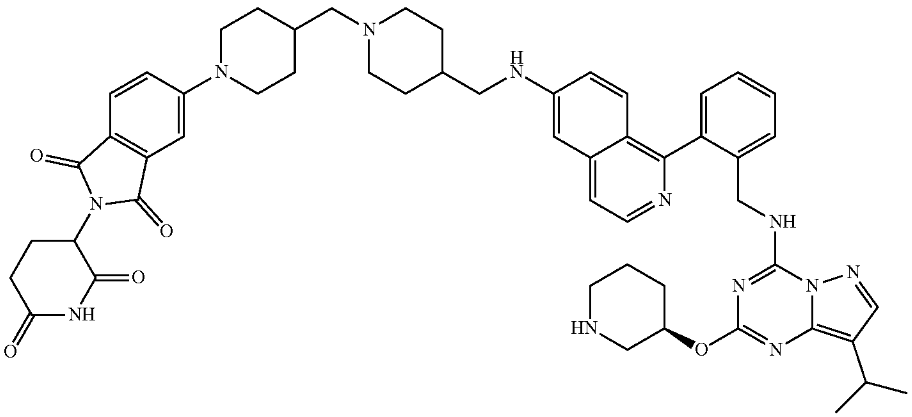 [SMILES: CC(C)c1cnn2c(NCc3ccccc3-c3nccc4cc(NCC5CCN(CC6CCN(c7ccc8c(c7)C(=O)N(C7CCC(=O)NC7=O)C8=O)CC6)CC5)ccc34)nc(O[C@@H]3CCCNC3)nc12] | Yellow solid; $^1$H-NMR (400 MHz, DMSO-$d_6$), δ 10.82 (s, 1H), 10.57 (brs, 1H), 9.63 (brs, 1H), 9.14 (brs, 1H), 8.75 (s, 1H), 8.13-8.11 (m, 1H), 7.78-7.65 (m, 5H), 7.55 (t, J = 4.8 Hz, 1H), 7.47-7.45 (m, 1H), 7.35-7.20 (m, 3H), 7.20-7.26 (m, 1H) 6.96-6.92 (m, 1H), 5.14-5.10 (m, 1H), 5.03 (dd, J = 12.4, 6.0 Hz, 1H), 4.70-4.56 (m, 2H), 3.56 (d, J = 12.8 Hz, 2H), 3.40-3.30 (m, 2H), 3.28-2.85 (m, 12H), 2.70-2.56 (m, 2H), 2.47-2.44 (m, 1H), 2.30-2.15 (m, 2H), 2.10-1.87 (m, 8H), 1.85-1.77 (m, 2H), 1.37 (q, J = 10.8 Hz, 2H), 1.27 (d, J = 6.8 Hz, 6H); MS (ESI): m/z 959.7 $[M + H]^+$. |

TABLE 2-continued

Summary of compounds 1-36 in terms of their structures and corresponding characteristics.

| #cpd | Structure | Characterization |
|---|---|---|
| 31 | 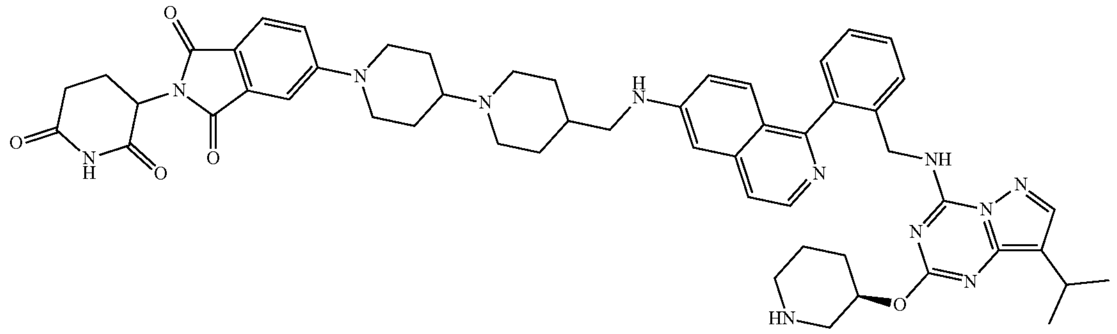 | Yellow solid; $^1$H-NMR (400 MHz, DMSO-$d_6$) δ 10.91 (brs, 1H), 10.83 (brs, 1H), 9.46 (brs, 1H), 8.99 (brs, 1H), 8.75 (brs, 1H), 8.11 (d, J = 6.5 Hz, 1H), 7.80-7.66 (m, 5H), 7.55 (t, J = 7.3 Hz, 1H), 7.46-7.44 (m, 1H), 7.36-7.26 (m, 3H), 7.21-7.14 (m, 1H), 6.95-6.91 (m, 1H), 5.13-5.11 (m, 1H), 5.03 (dd, J = 12.7, 5.4 Hz, 1H), 4.46-4.71 (m, 2H), 4.19 (d, J = 13.0 Hz, 2H), 3.57-3.35 (m, 4H), 3.24-2.83 (m, 12H), 2.67-2.55 (m, 2H), 2.33-2.30 (m, 1H), 2.25 (d, J = 13.0 Hz, 2H), 2.09-1.90 (m, 5H), 1.86-1.80 (m, 5H), 1.26 (d, J = 6.8 Hz, 6H); MS (ESI): m/z 945.7 $[M + H]^+$ |
| 32 | 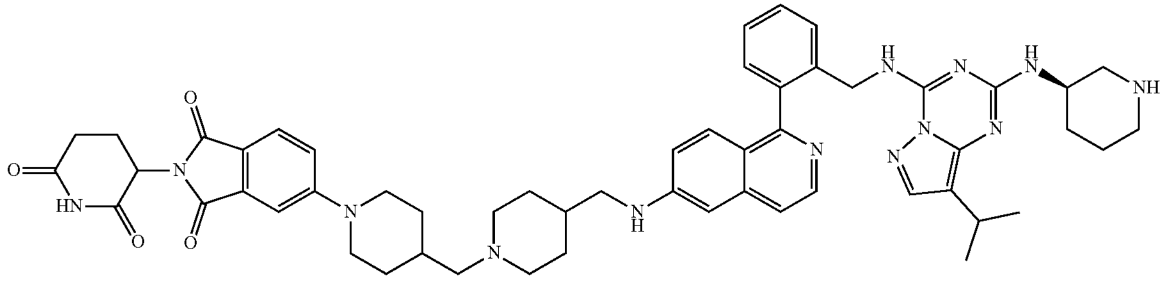 [SMILES: CC(C)c1cnn2c(NCc3ccccc3-c3nccc4cc(NCC5CCN(CC6CCN(c7ccc8c(c7)C(=O)N(C7CCC(=O)NC7=O)C8=O)CC6)CC5)ccc34)nc(N[C@@H]3CCCNC3)nc12] | Yellow powder; $^1$H-NMR (400 MHz, DMSO-$d_6$), δ 8.28 (d, J = 6.0 Hz, 1H), 8.18 (brs, 1H), 7.65-7.63 (m, 2H), 7.54 (d, J = 7.6 Hz, 1H), 7.47-7.27 (m, 6H), 7.21 (dd, J = 8.4, 2.5 Hz, 1H), 7.03 (dd, J = 9.2, 2.5 Hz, 1H), 6.75 (d, J = 2.5 Hz, 1H), 5.02 (dd, J = 12.4, 6.0 Hz, 1H), 4.43 (brs, 2H), 3.99 (d, J = 13.2 Hz, 2H), 3.72 (brs, 1H), 2.96-2.85 (m, 8H), 2.68-2.56 (m, 2H), 2.34-2.32 (m, 1H), 2.18 (d, J 6.8 Hz, 2H), 2.06-2.02 (m, 2H), 1.97-1.92 (m, 2H), 1.84-1.78 (m, 6H), 1.65-1.63 (m, 2H), 1.45-1.42 (m, 2H), 1.32-1.18 (m, 12H); MS (ESI): m/z 958.7 $[M + H]^+$. |

TABLE 2-continued

Summary of compounds 1-36 in terms of their structures and corresponding characteristics.

| #cpd | Structure | Characterization |
| --- | --- | --- |
| 33 | 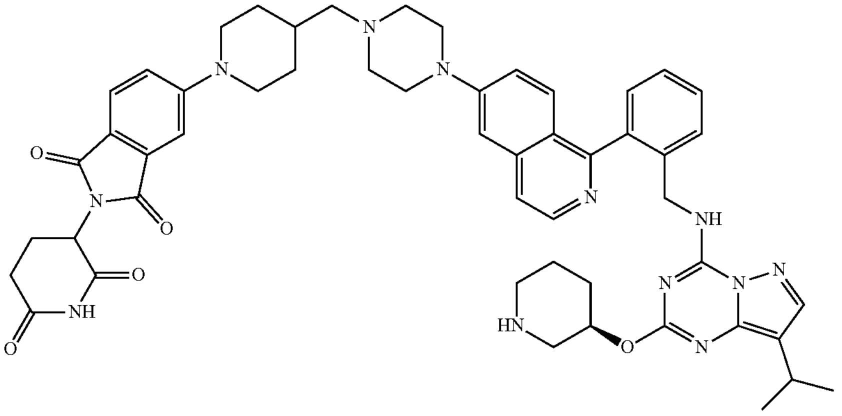 [SMILES: CC(C)c1cnn2c(NCc3ccccc3-c3nccc4cc(N5CCN(CC6CCN(c7ccc8c(c7)C(=O)N(C7CCC(=O)NC7=O)C8=O)CC6)CC5)ccc34)nc(O[C@@H]3CCCNC3)nc12] | Yellow solid; $^1$H-NMR (400 MHz, DMSO-$d_6$) δ 10.80 (brs, 1H), 8.58 (brs, 1H), 8.34 (d, J = 5.8 Hz, 1H), 7.81 (s, 1H), 7.65 (d, J = 8.5 Hz, 1H), 7.56-7.40 (m, 5H), 7.35-7.28 (m, 3H), 7.23 (dd, J = 8.5, 2.3 Hz, 1H), 7.14 (d, J = 2.3 Hz, 1H), 5.02 (dd, J = 12.7, 5.4 Hz, 1H), 4.88-4.80 (m, 1H), 4.49 (brs, 2H), 4.01 (d, J = 12.6 Hz, 2H), 3.38-3.36 (m, 4H), 3.02-2.91 (m, 3H), 2.90-2.82 (m, 2H), 2.79-2.65 (m, 3H), 2.61-2.55 (m, 5H), 2.38 (brs, 1H), 2.27 (d, J = 6.8 Hz, 2H), 2.09-1.94 (m, 4H), 1.92-1.84 (m, 2H), 1.75-1.52 (m, 4H) 1.27 (d, J = 6.8 Hz, 6H); MS (ESI): m/z 931.7 $[M + H]^+$. |
| 34 | 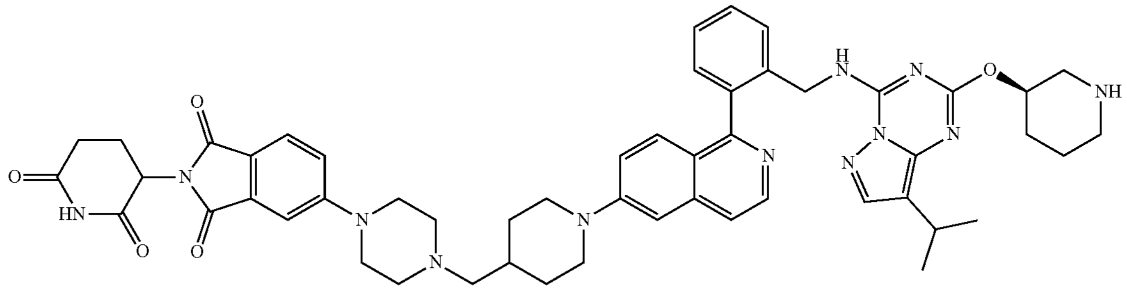 [SMILES: CC(C)c1cnn2c(NCc3ccccc3-c3nccc4cc(N5CCC(CN6CCN(c7ccc8c(c7)C(=O)N(C7CCC(=O)NC7=O)C8=O)CC6)CC5)ccc34)nc(O[C@@H]3CCCNC3)nc12] | Yellow powder; $^1$H-NMR (400 MHz, DMSO-$d_6$) δ 8.60 (brs, 1H), 8.32 (d, J = 5.8 Hz, 1H), 7.80 (s, 1H), 7.67 (d, J = 8.5 Hz, 1H), 7.54-7.46 (m, 5H), 7.36-7.29 (m, 3H) 7.25 (dd, J = 8.8, 2.3 Hz, 1H), 7.14 (d, J = 2.5 Hz, 1H), 5.03 (dd, J = 12.4, 5.4 Hz, 1H), 4.80-4.69 (m, 1H), 4.49 (brs, 2H), 3.94 (d, J = 13.3 Hz, 2H), 3.52-3.38 (m, 4H), 2.99-2.88 (m, 5H), 2.84-2.76 (m, 3H) 2.64-2.55 (m, 5H), 2.44 (brs, 1H), 2.27 (d, J = 6.5 Hz, 2H), 2.06-1.99 (m, 2H), 1.90-1.80 (m, 3H), 1.68-1.35 (m, 4H), 1.27 (d, J = 7.0 Hz, 6H); MS (ESI): m/z 931.6 $[M + H]^+$ |

TABLE 2-continued

Summary of compounds 1-36 in terms of their structures and corresponding characteristics.

| #cpd | Structure | Characterization |
| --- | --- | --- |
| 35 | 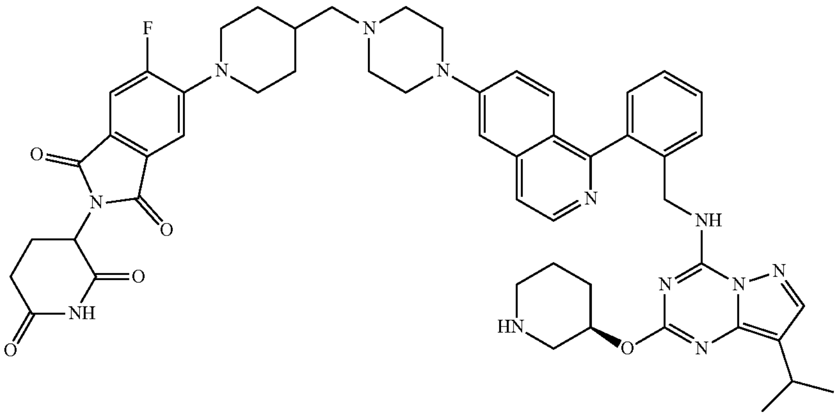 [SMILES: CC(C)c1cnn2c(NCc3ccccc3-c3nccc4cc(N5CCN(CC6CCN(c7cc8c(cc7F)C(=O)N(C7CCC(=O)NC7=O)C8=O)CC6)CC5)ccc34)nc(O[C@@H]3CCCNC3)nc12] | Yellow powder; $^{1}$H-NMR (400 MHz, DMSO-$d_6$) δ 10.84 (brs, 1H), 8.73 (brs, 1H), 8.34 (d, J = 6.0 Hz, 1H), 7.85 (s, 1H), 7.63-7.33 (m, 9H), 7.14 (d, J = 2.4 Hz, 1H), 5.11-5.03 (m, 2H), 4.45 (brs, 2H), 3.66-3.63 (m, 2H), 3.40-3.37 (m, 4H), 2.97-2.70 (m, 7H), 2.68-2.65 (m, 2H), 2.60-2.57 (m, 4H), 2.34-2.31 (m, 3H), 2.06-2.02 (m, 2H), 1.92-1.85 (m, 4H), 1.74-1.68 (m, 1H), 1.37-1.32 (m, 1H), 1.31-1.26 (m, 8H); MS (ESI): m/z 949.9 $[M + H]^+$. |
| 36 | 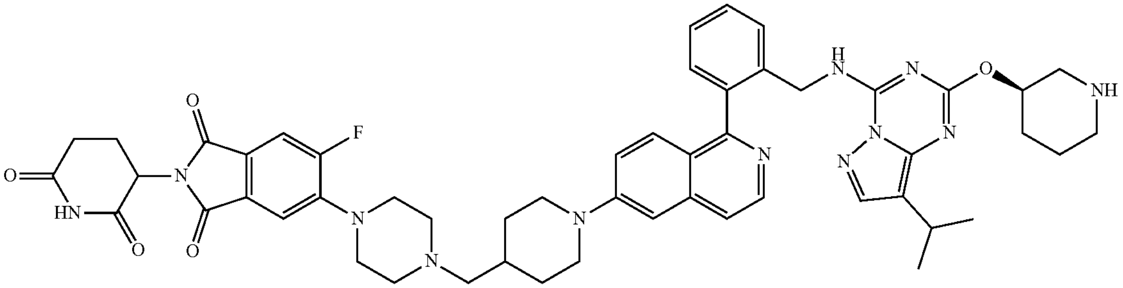 | Yellow powder; $^{1}$H-NMR (400 MHz, DMSO-$d_6$) δ 10.80 (brs, 1H), 8.79 (brs, 1H), 8.26 (d, J = 5.6 Hz, 1H), 7.82 (s, 1H), 7.73-7.51 (m, 9H), 7.22 (d, J = 2.4 Hz, 1H), 5.14-5.06 (m, 2H), 4.54 (brs, 2H), 4.05 (d, J = 12.4 Hz, 2H), 3.53-3.45 (m, 4H), 3.15-2.86 (m, 5H), 2.84-2.76 (m, 2H), 2.64-2.54 (m, 5H), 2.42-2.30 (m, 3H), 2.10-2.07 (m, 2H), 1.97-1.90 (m, 4H), 1.78-1.74 (m, 2H), 1.34 (q, J = 10.4 Hz, 2H), 1.27 (d, J = 6.8 Hz, 6H); ; MS (ESI): m/z 949.9 $[M + H]^+$. |

TABLE 3

Results of a CDK7 protein degradation experiment in A2780 cells for exemplary compounds in accordance with Example 2.

| # cpds | Compound concentration that caused 50% CDK7 protein degradation in A2780 cells ($DC_{50}$, nM) |
|---|---|
| 7 | B |
| 10 | B |
| 11 | A |
| 12 | C |
| 13 | C |
| 14 | B |
| 15 | A |
| 16 | B |
| 17 | A |
| 19 | A |
| 20 | A |
| 21 | A |
| 22 | B |
| 24 | A |
| 25 | A |
| 26 | C |
| 27 | A |
| 28 | A |
| 30 | A |
| 31 | A |
| 32 | A |
| 33 | A |
| 34 | A |

Activity range: A indicates $DC_{50} \leq 100$ nM, B indicates 100 nM < $DC_{50} \leq 1{,}000$ nM, C indicates $DC_{50} > 1{,}000$ nM The features of the present invention disclosed in the specification, the claims, and/or in the accompanying FIGURES may, both separately and in any combination thereof, be material for realizing the invention in various forms thereof.

The invention claimed is:

1. A compound having the general formula I

Formula I

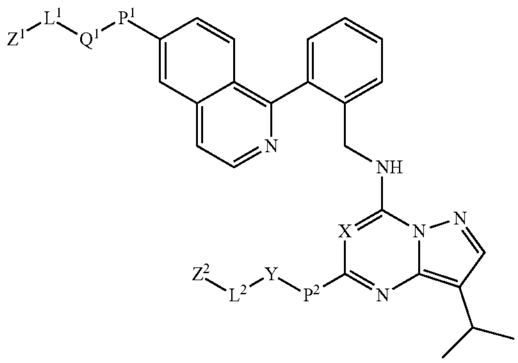

wherein

X is, at each occurrence, independently selected from CH and N;

$P^1$ is either absent or independently, at each occurrence, selected from the group consisting of —$NR^1$—, —O—, $k^a$-$CH_2$O-$k^b$, $k^a$-O$CH_2$-$k^b$, $k^a$-C(═O)O-$k^b$ and $k^a$-O(O═)C-$k^b$;

$k^a$ indicates the point of attachment to an aromatic ring;

$Q^1$ is either absent or is independently selected from hydrogen, —C(═O)—, any structure of (a-1) to (a-5) and any structure of (a-6) to (a-18) of Group A:

Group A (a-1)

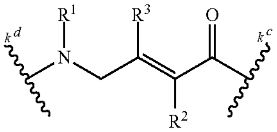

(a-2)

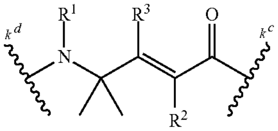

(a-3)

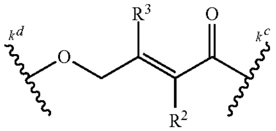

(a-4)

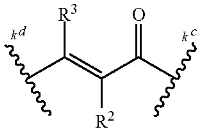

(a-5)

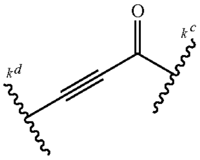

(a-6)

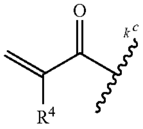

(a-7)

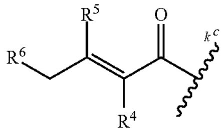

(a-8)

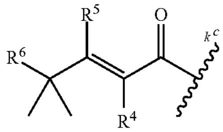

(a-9)

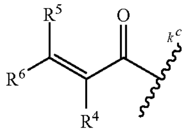

(a-10)

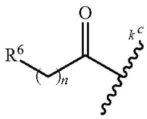

(a-11)

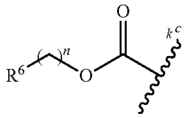

-continued (a-12)

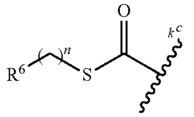

(a-13)

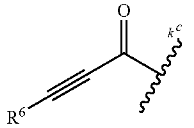

(a-14)

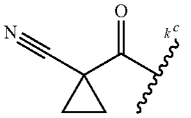

(a-15)

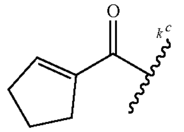

(a-16)

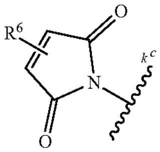

(a-17)

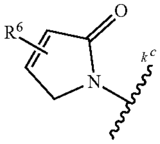

(a-18)

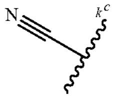

wherein n is 1, 2 or 3; $k^c$ indicates the point of attachment to $P^1$ and $k^d$ indicates the point of attachment to $L^1$ or $Z^1$;

$R^1$ is, independently at each occurrence, selected from hydrogen, C1-C3 alkyl and C3-C6 cycloalkyl;

$R^2$ and $R^3$ are, at each occurrence, independently selected from the group consisting of hydrogen, halogen, C1-C6 alkyl, C1-C3 haloalkyl, heterocyclyl and —CN;

$R^4$ and $R^5$ are, at each occurrence, independently selected from the group consisting of hydrogen, halogen, C1-C6 alkyl, C1-C3 haloalkyl, heterocyclyl and —CN;

$R^6$ is selected from the group consisting of hydrogen, halogen, C1-C6 alkyl, C3-C10 cycloalkyl, —$NR^7R^8$, —$OR^7$, —CN and heterocyclyl;

$R^7$ and $R^8$ are, at each occurrence, independently selected from hydrogen, C1-C3 alkyl and C3-C6 cycloalkyl;

wherein, if $Q^1$ is selected from hydrogen and any structure of (a-6) to (a-18), then $L^1$ and $Z^1$ are absent;

$L^1$ is either absent or is a linker;

$Z^1$ is either absent or is an E3 ubiquitin ligase binding group;

$P^2$ is either absent or is independently, at each occurrence, selected from the group consisting of —$NR^1$—, $k^e$-$NR^1CH_2$-$k^f$, —O— and $k^e$-$CH_2$-$k^f$;

$R^1$ being as defined above;

$k^e$ indicates the point of attachment to an aromatic ring, and $k^f$ indicates the point of attachment to Y;

Y is at each occurrence, independently, selected from the group consisting of halogen, C1-C6 alkyl, C1-C6 alkylene, C1-C3 haloalkyl, C1-C3 haloalkylene, C3-C8 cycloalkyl, C3-C8 cycloalkylene, aryl, arylene, heteroaryl, heteroarylene, heterocyclyl, heterocyclylene, heterocyclyl substituted with one or two of $R^9$, and heterocyclylene substituted with one or two of $R^9$;

$R^9$ is, at each occurrence independently, selected from the group consisting of halogen, —$NR^7R^8$, —$OR^7$, C1-C3 alkyl and C1-C3 haloalkyl;

$R^7$ and $R^8$ being as defined above;

$L^2$ is either absent or is a linker;

$Z^2$ is either absent or is an $E^3$ ubiquitin ligase binding group;

wherein, if $Q^1$ is absent, $L^1$ is absent and $Z^1$ is absent, then $L^2$ is a linker and $Z^2$ is an E3 ubiquitin ligase binding group;

wherein, if $Q^1$ is any structure of (a-6) to (a-18) or H, $L^1$ is absent and $Z^1$ is absent, then $L^2$ is a linker and Z is an E3 ubiquitin ligase binding group; and wherein, if $L^2$ is absent and $Z^2$ is absent, then $Q^1$ is either absent or any structure of (a-1) to (a-5), and $L^1$ is a linker, and $Z^1$ is an E3 ubiquitin ligase binding group;

wherein the E3 ubiquitin ligase binding group binds to von Hippel-Landau tumor suppressor protein (VHL) and is selected from any structure of Group C;

Group C (c-1)

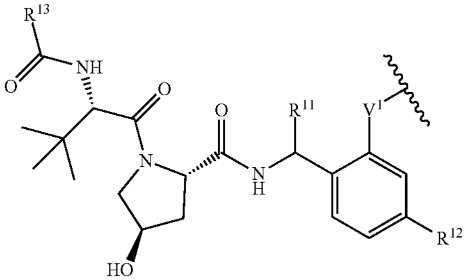

(c-2)

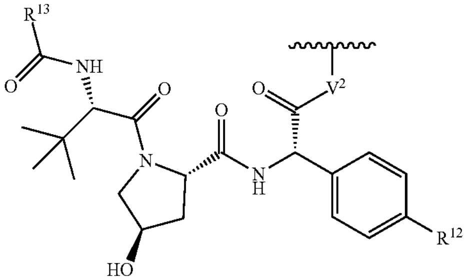

(c-3)

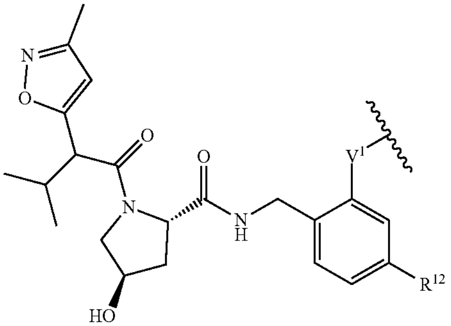

-continued (c-4)

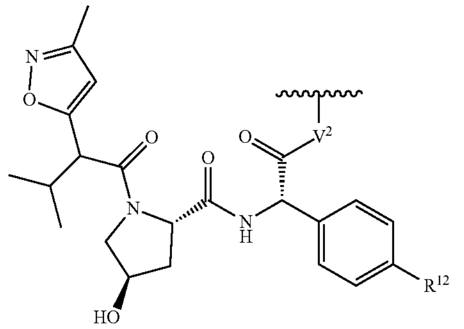

(c-5)

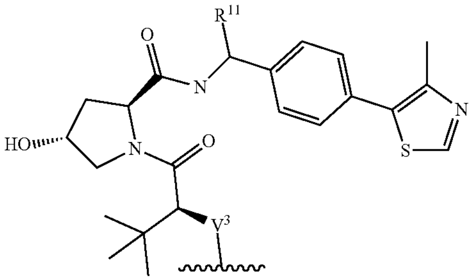

(c-6)

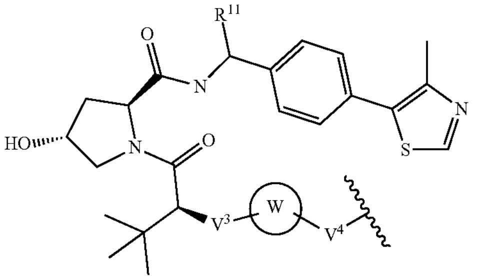

wherein $R^{11}$ is hydrogen or C1-C3 alkyl;

$R^{12}$ is selected from hydrogen, halogen, —C≡CH, —CN, heteroaryl and heteroaryl substituted with C1-C3 alkyl;

$R^{13}$ is selected from hydrogen, C1-C3 alkyl, C1-C3 haloalkyl, C3-C6 cycloalkyl and C3-C6 cycloalkyl substituted with halogen, C1-C3 alkyl, —C(═O)$CH_3$ and —NHC(═O)$CH_3$;

$V^1$ is absent or selected from —NH—, —$CH_2$NH—, —O—, —$CH_2$O—, —C(═O)O—, —(C═O)—, —C(═O)NH— and —NH(C═O)—;

$V^2$ is absent or selected from —NH— and —O—;

W is selected from C3-C6 cycloalkyl, aryl, heteroaryl and heterocyclyl; and $V^3$ and $V^4$ are, at each occurrence, either absent or independently selected from —NH—, —$CH_2$NH—, —$NHCH_2$—, —O—, —$CH_2$O—, —C(═O)O—, —O(C═O)—, —C(═O)NH— and —NH(C═O)—; or wherein the E3 ubiquitin ligase binding group binds to cereblon (CRBN) and is selected from any structure of Group D;

Group D (d-1)

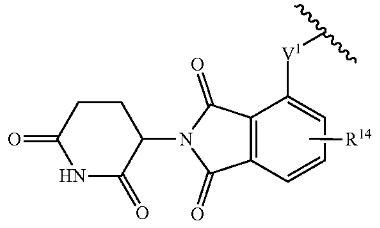

(d-2)

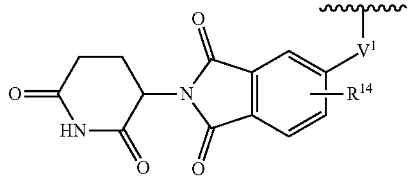

(d-3)

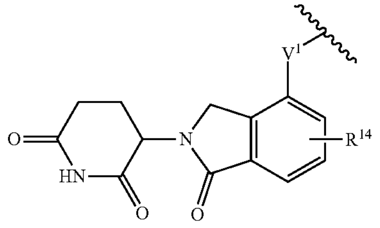

(d-4)

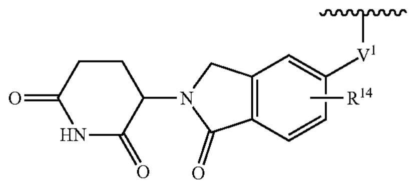

wherein $V^1$ is absent or selected from —NH—, —$CH_2$NH—, —O—, —$CH_2$O—, —C(═O)O—, —O(C═O)—, —C(═O)NH— and —NH(C═O)—; and $R^{14}$ is selected from hydrogen, halogen, and C1-C3 alkyl; or wherein the E3 ubiquitin ligase binding group binds to an inhibitor of apoptosis protein (IAP) and is selected from, any structure of Group E;

Group E (e-1)

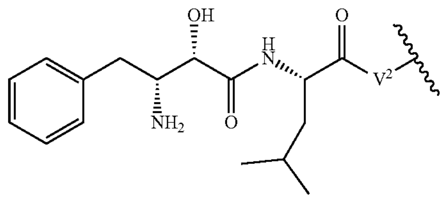

-continued (e-2)

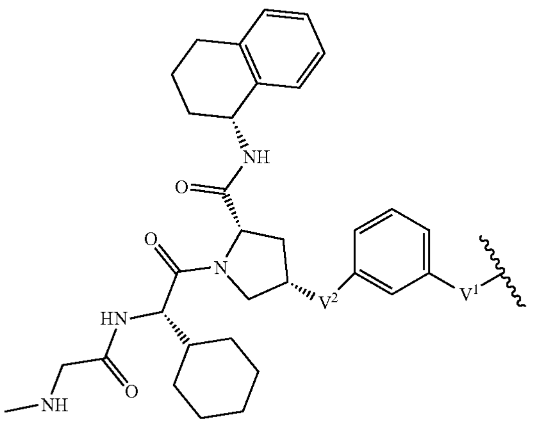

(e-3)

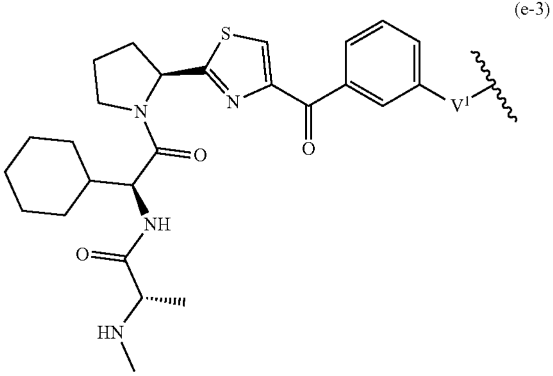

(e-4)

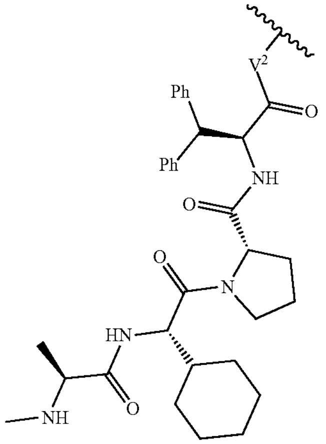

wherein $V^1$ is absent or selected from —NH—, —$CH_2$NH—, —O—, —$CH_2$O—, —C(═O)O—, —O(C═O)—, —C(═O)NH— and —NH(C═O)—; and wherein $V^2$ is absent or selected from —NH— and —O—;

or an enantiomer, stereoisomeric form, mixture of enantiomers, diastereomer, mixture of diastereomers, racemate of such compound or a pharmaceutically acceptable salt thereof.

2. The compound of claim 1, wherein $P^1$ is either absent or is —NH—;

or an enantiomer, stereoisomeric form, mixture of enantiomers, diastereomer, mixture of diastereomers, racemate of such compound or a pharmaceutically acceptable salt thereof.

3. The compound according to claim 1, wherein X is N;

or an enantiomer, stereoisomeric form, mixture of enantiomers, diastereomer, mixture of diastereomers, racemate of such compound or a pharmaceutically acceptable salt thereof.

4. The compound according to claim 1, wherein Y is selected from piperidinyl, piperidinyl substituted with one or two of —$R^9$, piperidinylene, piperidinylene substituted with one or two of —$R^9$, piperazinyl, piperazinyl substituted with one or two of —$R^9$, piperazinylene, and piperazinylene substituted with one or two of —$R^9$; and wherein $R^9$ is selected from the group consisting of halogen, —$NR^7R^8$, —$OR^7$, C1-C3 alkyl and C1-C3 haloalkyl;

or an enantiomer, stereoisomeric form, mixture of enantiomers, diastereomer, mixture of diastereomers, racemate of such compound or a pharmaceutically acceptable salt thereof.

5. The compound according to claim 1, wherein $R^1$ is, independently at each occurrence, selected from hydrogen and C1-C3 alkyl; or an enantiomer, stereoisomeric form, mixture of enantiomers, diastereomer, mixture of diastereomers, racemate of such compound or a pharmaceutically acceptable salt thereof.

6. The compound according to claim 1, wherein $R^7$ and $R^8$ are, at each occurrence, independently selected from hydrogen and C1-C3 alkyl; or an enantiomer, stereoisomeric form, mixture of enantiomers, diastereomer, mixture of diastereomers, racemate of such compound or a pharmaceutically acceptable salt thereof.

7. The compound according to claim 1, wherein $R^9$ is, independently at each occurrence, selected from the group consisting of —$NH_2$, —OH and C1-C3 alkyl; or an enantiomer, stereoisomeric form, mixture of enantiomers, diastereomer, mixture of diastereomers, racemate of such compound or a pharmaceutically acceptable salt thereof.

8. The compound according to claim 1, wherein $Q^1$ is absent, $L^1$ is a linker, $Z^1$ is the E3 ubiquitin ligase binding group, $L^2$ is absent, and $Z^2$ is absent;

or an enantiomer, stereoisomeric form, mixture of enantiomers, diastereomer, mixture of diastereomers, racemate of such compound or a pharmaceutically acceptable salt thereof.

9. The compound according to claim 1, wherein $Q^1$ is selected from any structure of (a-1) to (a-5), as defined in claim 1, $L^1$ is a linker, $Z^1$ is the E3 ubiquitin ligase binding group, $L^2$ is absent, and $Z^2$ is absent; or $Q^1$ is selected from any structure of (a-6) to (a-18), as defined in claim 1, $L^1$ and $Z^1$ are absent, $L^2$ is a linker and $Z^2$ is the E3 ubiquitin ligase binding group;

or an enantiomer, stereoisomeric form, mixture of enantiomers, diastereomer, mixture of diastereomers, racemate of such compound or a pharmaceutically acceptable salt thereof.

10. The compound according to claim 1, wherein $L^2$ is a linker, $Z^2$ is the E3 ubiquitin ligase binding group, $Q^1$ is absent or hydrogen, $L^1$ is absent and $Z^1$ is absent;

or an enantiomer, stereoisomeric form, mixture of enantiomers, diastereomer, mixture of diastereomers, racemate of such compound or a pharmaceutically acceptable salt thereof.

11. The compound according to claim 1, wherein $L^1$ or $L^2$ is an unsubstituted or substituted C1-C20 hydrocarbon chain, optionally wherein one or more carbon chain atoms of the hydrocarbon chain are independently replaced with —C(═O)—, —O—, —$NR^{10}$—, —S— and/or a heterocyclic group;

wherein $R^{10}$ is selected from hydrogen and C1-C3 alkyl;

or an enantiomer, stereoisomeric form, mixture of enantiomers, diastereomer, mixture of diastereomers, racemate of such compound or a pharmaceutically acceptable salt thereof.

12. The compound according to claim 1, wherein $L^1$ or $L^2$ is independently selected from any structure of Group B;

Group B (b-1)

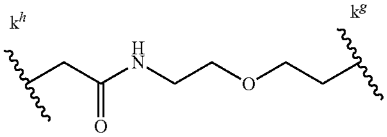

(b-2)

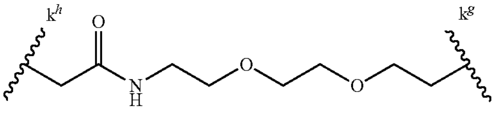

(b-3)

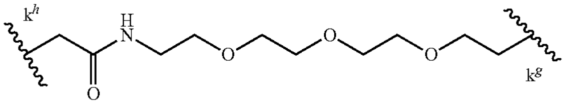

(b-4)

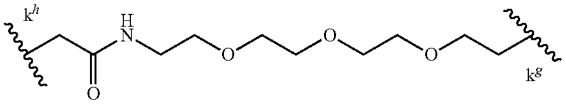

(b-5)

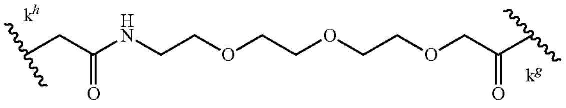

(b-6)

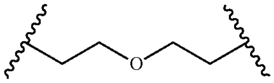

(b-7)

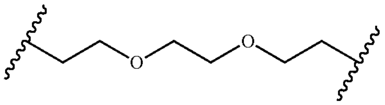

(b-8)

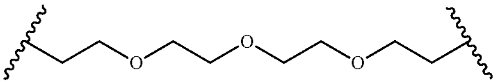

(b-9)

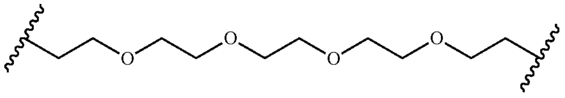

(b-10)

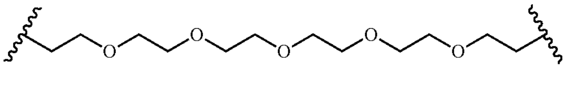

-continued (b-11)

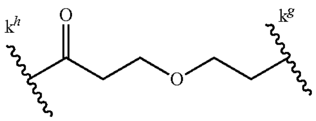

(b-12)

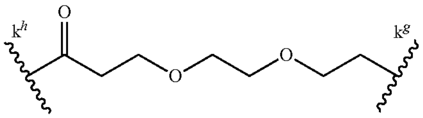

(b-13)

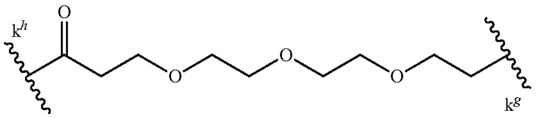

(b-14)

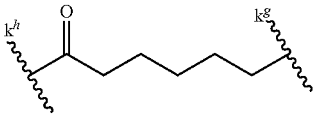

(b-15)

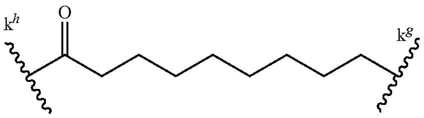

(b-16)

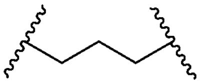

(b-17)

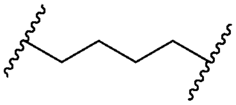

(b-18)

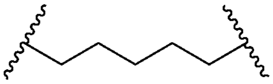

(b-19)

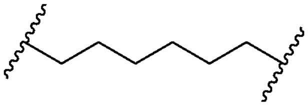

(b-20)

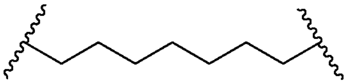

(b-21)

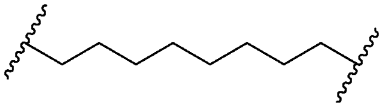

(b-22)

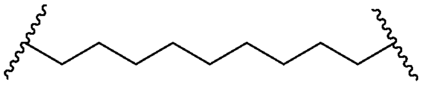

(b-23)

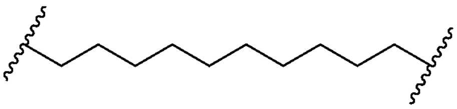

-continued
(b-24)
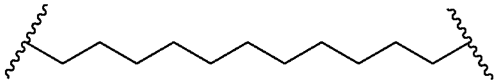
(b-25)
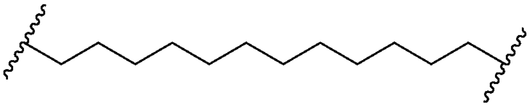
(b-26)
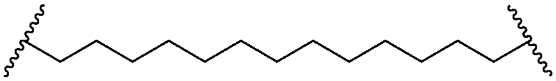
(b-27)
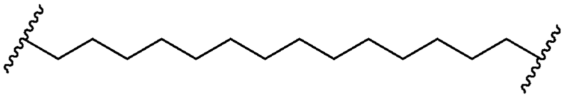
(b-28)
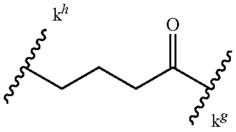
(b-29)
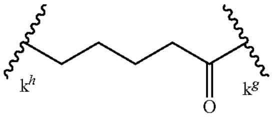
(b-30)
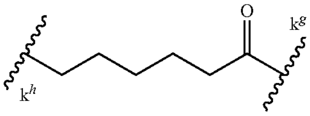
(b-31)
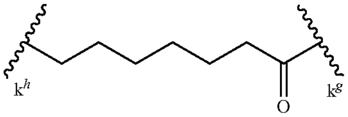
(b-32)
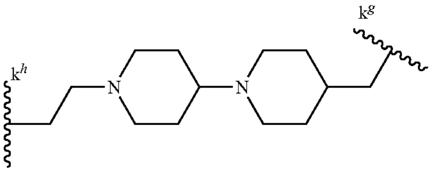
(b-33)
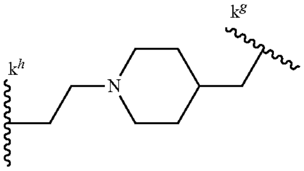
(b-34)
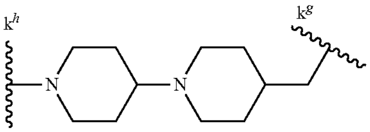
-continued
(b-35)
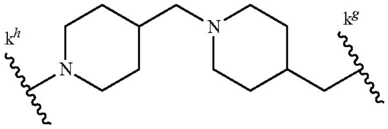
(b-36)
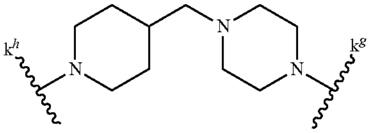
(b-37)
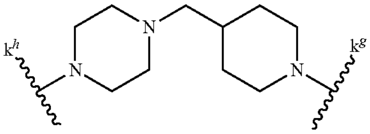
(b-38)
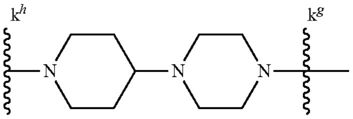
(b-39)
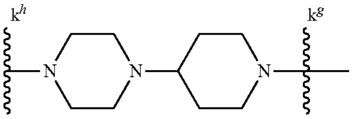
(b-40)
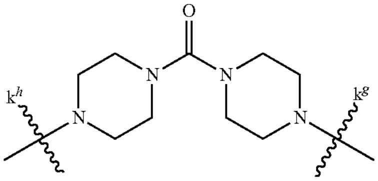
(b-41)
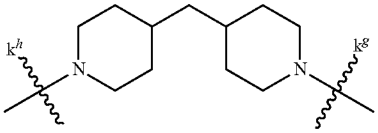
(b-42)
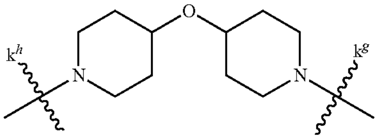
(b-43)
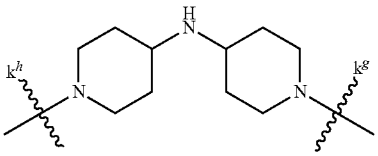
(b-44)
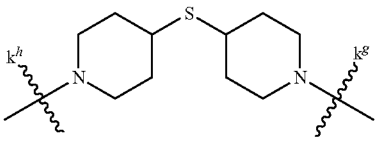

wherein $k^g$ indicates the point of attachment to $Q^1$ or Y; If $Q^1$ is absent, then $k^g$ indicates the point of attachment to $P^1$ or Y; and wherein if $Q^1$ and $P^1$ is absent, then $k^g$ indicates the point of attachment to an aromatic ring or Y; and wherein $k^h$ indicates the point of attachment to $Z^1$ or $Z^2$; or an enantiomer, stereoisomeric form, mixture of enantiomers, diastereomer, mixture of diastereomers racemate of such compound or a pharmaceutically acceptable salt thereof.

13. The compound according to claim 1, wherein said compound has one of the structures 1-36, as defined in the following table:

| Cpd. No. | Structure |
|---|---|
| 1 | 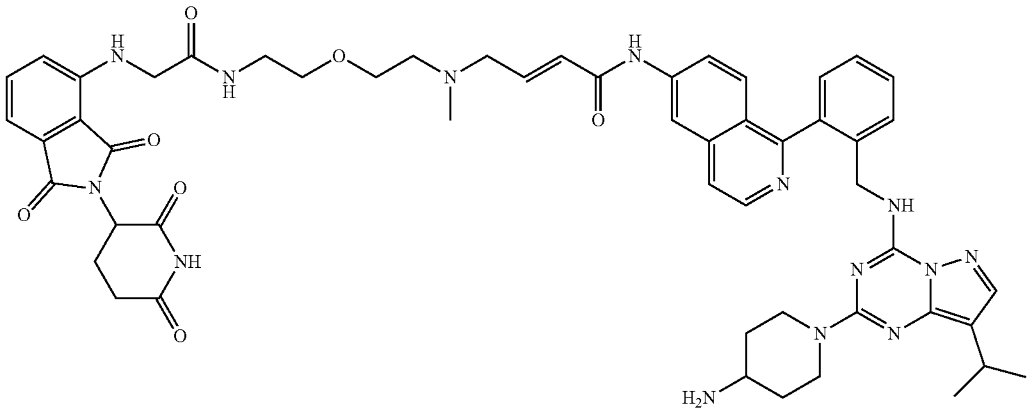 [SMILES: CC(C)c1cnn2c(NCc3ccccc3-c3nccc4cc(NC(=O)/C=C/CN(C)CCOCCNC(=O)CNc5cccc6c5C(=O)N(C5CCC(=O)NC5=O)C6=O)ccc34)nc(N3CCC(N)CC3)nc12] |
| 2 | 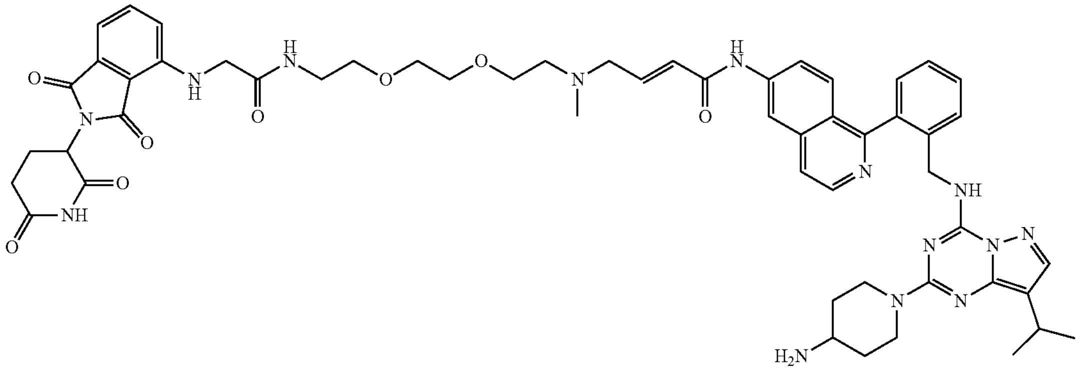 [SMILES: CC(C)c1cnn2c(NCc3ccccc3-c3nccc4cc(NC(=O)/C=C/CN(C)CCOCCOCCNC(=O)CNc5cccc6c5C(=O)N(C5CCC(=O)NC5=O)C6=O)ccc34)nc(N3CCC(N)CC3)nc12] |
| 3 | 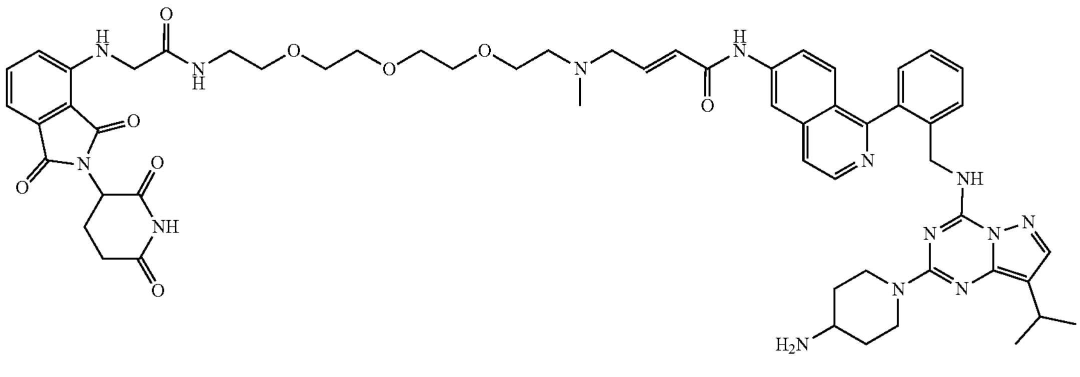 [SMILES: CC(C)c1cnn2c(NCc3ccccc3-c3nccc4cc(NC(=O)/C=C/CN(C)CCOCCOCCOCCNC(=O)CNc5cccc6c5C(=O)N(C5CCC(=O)NC5=O)C6=O)ccc34)nc(N3CCC(N)CC3)nc12] |

-continued
| Cpd. No. | Structure |
|---|---|
| 4 | 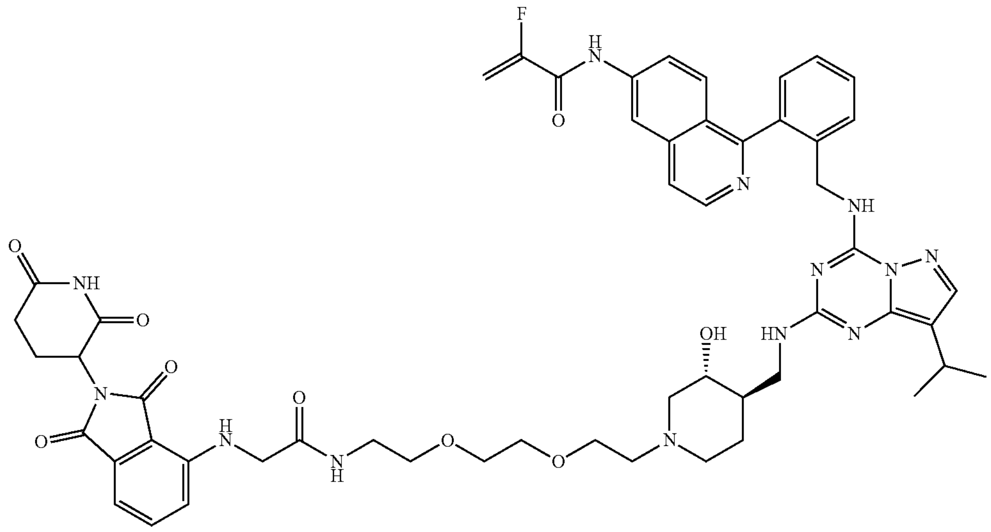 [SMILES: C=C(F)C(=O)Nc1ccc2c(-c3ccccc3CNc3nc(NC[C@H]4CCN(CCOCCOCCNC(=O)CNc5cccc6c5C(=O)N(C5CCC(=O)NC5=O)C6=O)C[C@@H]4O)nc4c(C(C)C)cnn34)nccc2c1] |
| 5 | 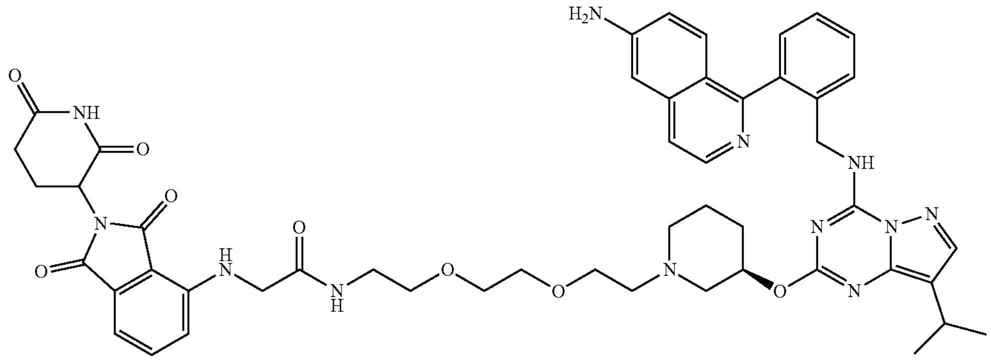 [SMILES: CC(C)c1cnn2c(NCc3ccccc3-c3nccc4cc(N)ccc34)nc(O[C@@H]3CCCN(CCOCCOCCNC(=O)CNc4cccc5c4C(=O)N(C4CCC(=O)NC4=O)C5=O)C3)nc12] |
| 6 | 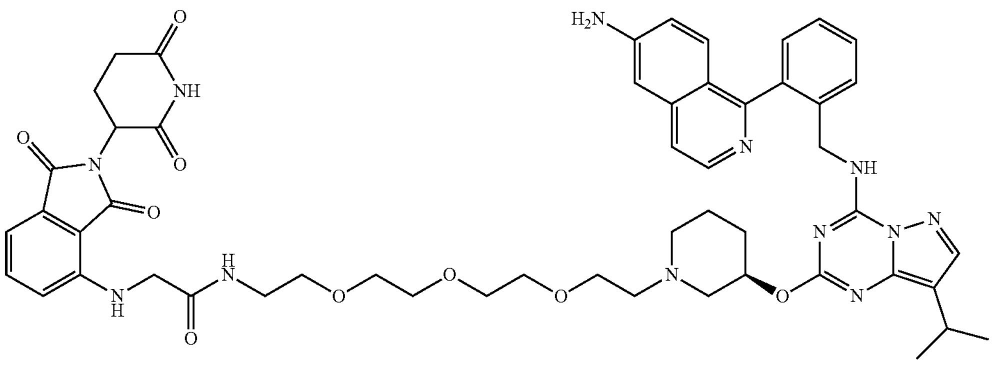 [SMILES: CC(C)c1cnn2c(NCc3ccccc3-c3nccc4cc(N)ccc34)nc(O[C@@H]3CCCN(CCOCCOCCOCCNC(=O)CNc4cccc5c4C(=O)N(C4CCC(=O)NC4=O)C5=O)C3)nc12] |

-continued
| Cpd. No. | Structure |
|---|---|
| 7 | 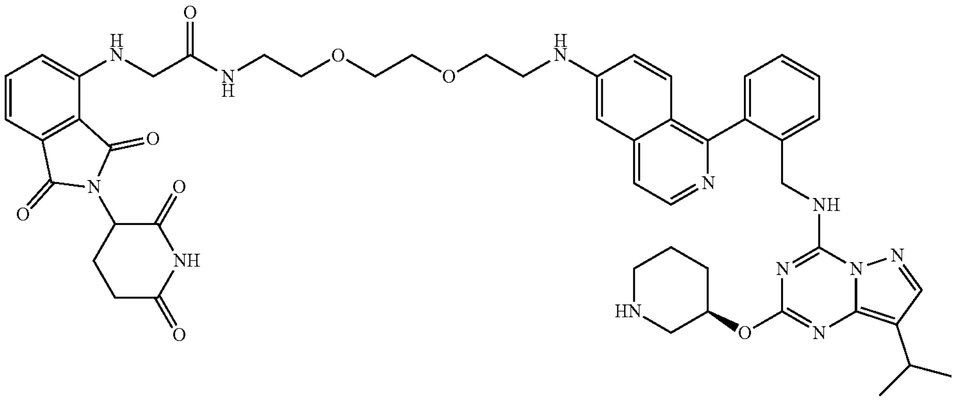 [SMILES: CC(C)c1cnn2c(NCc3ccccc3-c3nccc4cc(NCCOCCOCCNC(=O)CNc5cccc6c5C(=O)N(C5CCC(=O)NC5=O)C6=O)ccc34)nc(O[C@@H]3CCCNC3)nc12] |
| 8 | 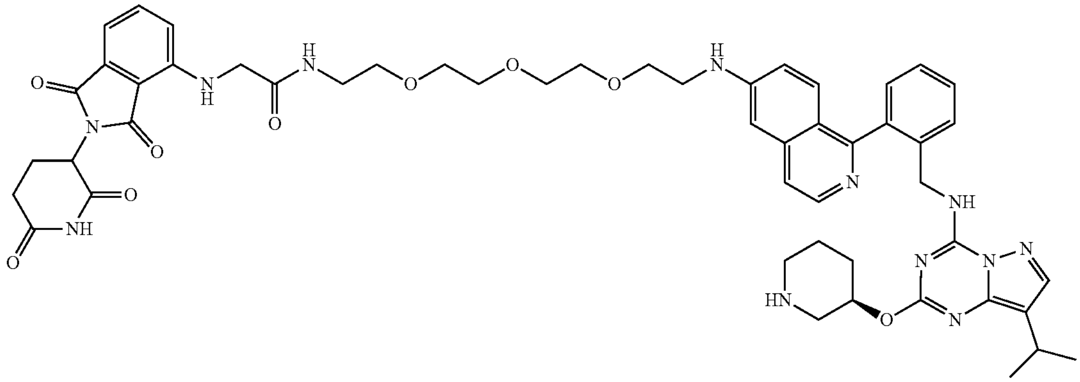 |
| 9 | 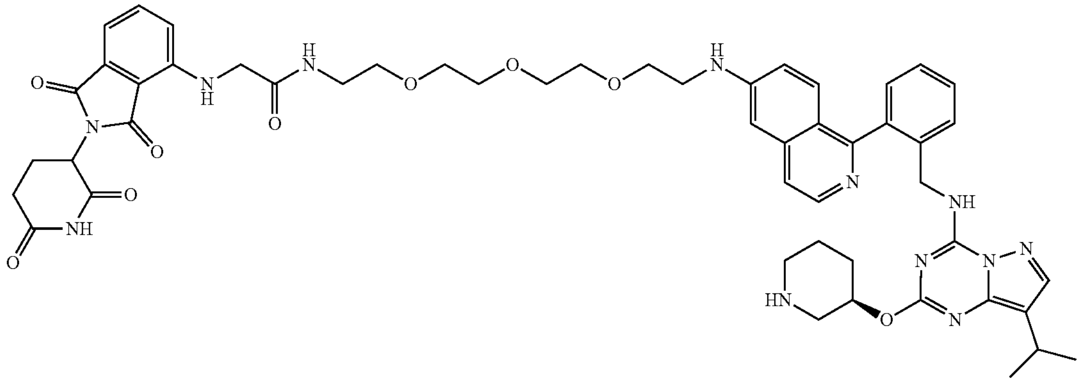 |
| 10 | 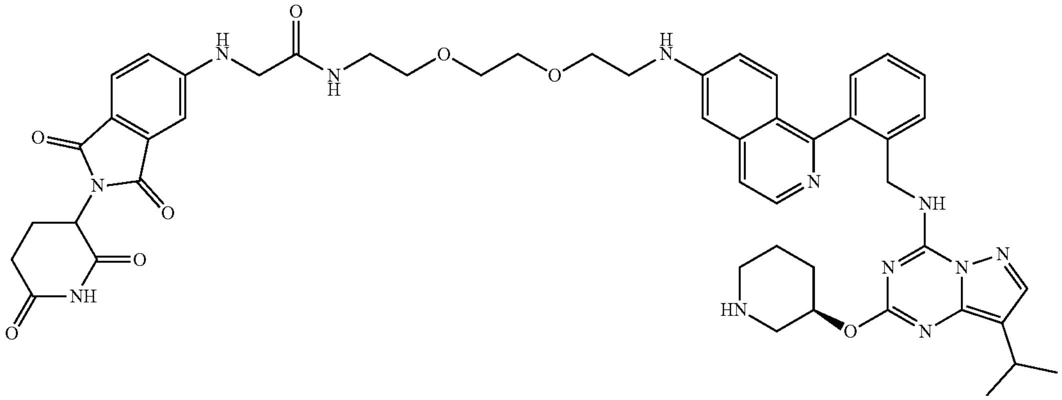 [SMILES: CC(C)c1cnn2c(NCc3ccccc3-c3nccc4cc(NCCOCCOCCNC(=O)CNc5ccc6c(c5)C(=O)N(C5CCC(=O)NC5=O)C6=O)ccc34)nc(O[C@@H]3CCCNC3)nc12] |

-continued
| Cpd. No. | Structure |
|---|---|
| 11 | 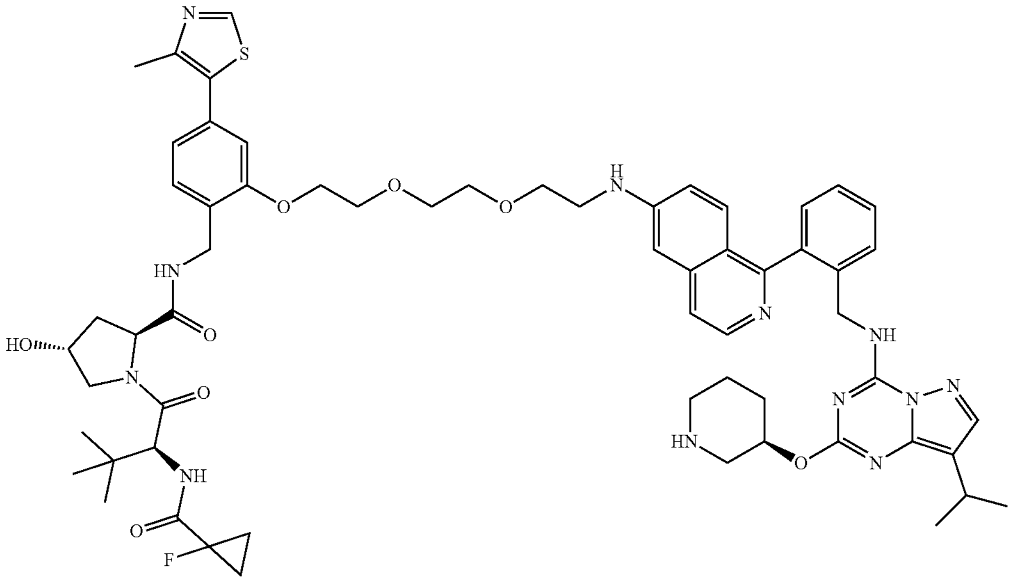 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCNc2ccc3c(-c4ccccc4CNc4nc(O[C@@H]5CCCNC5)nc5c(C(C)C)cnn45)nccc3c2)c1] |
| 12 | 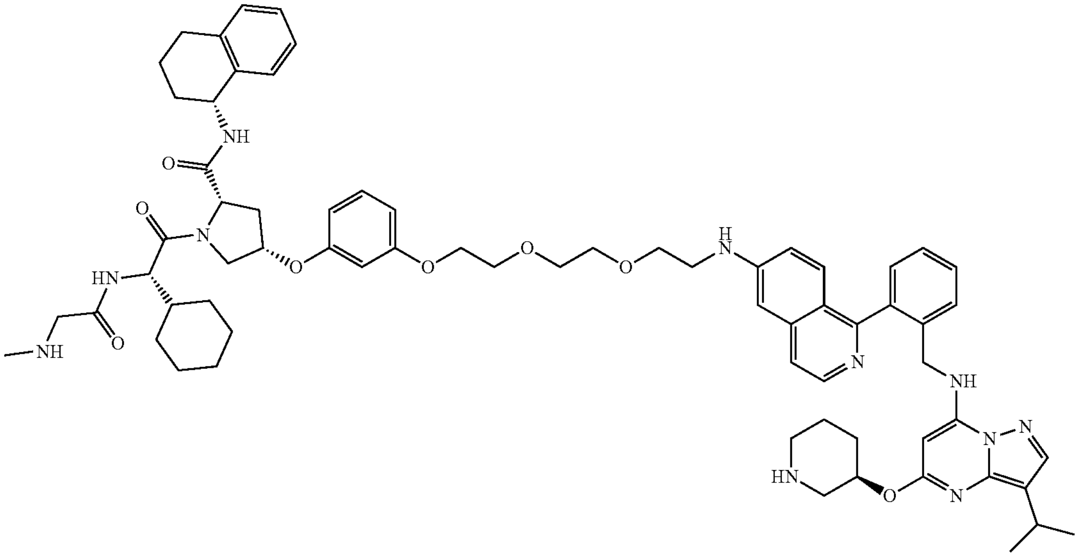 [SMILES: CNCC(=O)N[C@H](C(=O)N1C[C@@H](Oc2cccc(OCCOCCOCCNc3ccc4c(-c5ccccc5CNc5cc(O[C@@H]6CCCNC6)nc6c(C(C)C)cnn56)nccc4c3)c2)C[C@H]1C(=O)N[C@@H]1CCCc2ccccc21)C1CCCCC1] |
| 13 | 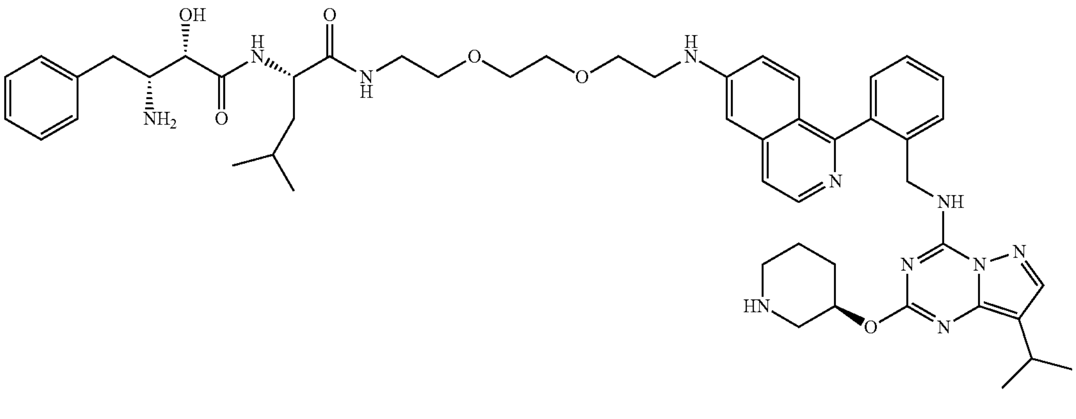 [SMILES: CC(C)C[C@H](NC(=O)[C@@H](O)[C@H](N)Cc1ccccc1)C(=O)NCCOCCOCCNc1ccc2c(-c3ccccc3CNc3nc(O[C@@H]4CCCNC4)nc4c(C(C)C)cnn34)nccc2c1] |

-continued
| Cpd. No. | Structure |
|---|---|
| 14 | 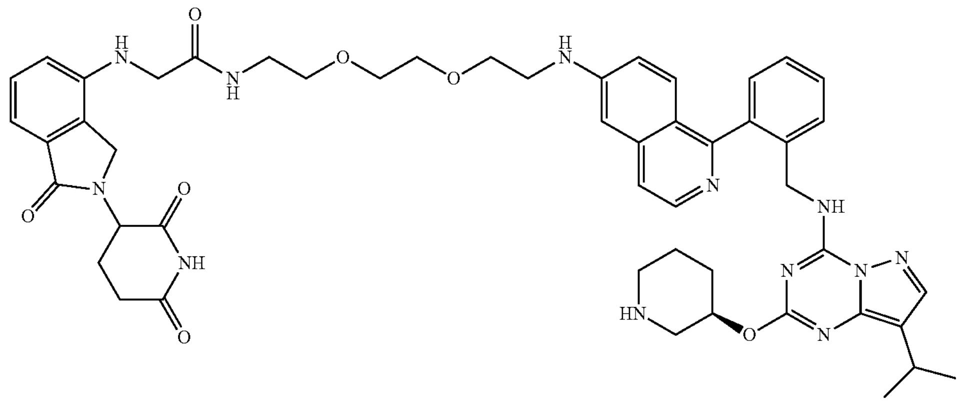 [SMILES: CC(C)c1cnn2c(NCc3ccccc3-c3nccc4cc(NCCOCCOCCNC(=O)CNc5cccc6c5CN(C5CCC(=O)NC5=O)C6=O)ccc34)nc(O[C@@H]3CCCNC3)nc12] |
| 15 | 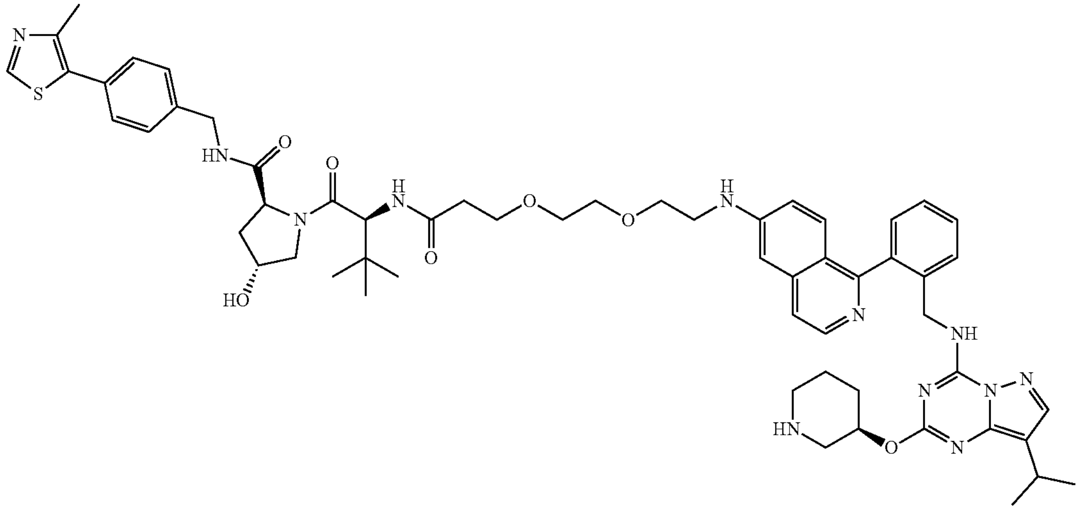 [SMILES: Cc1ncsc1-c1ccc(CNC(=O)[C@@H]2C[C@@H](O)CN2C(=O)[C@@H](NC(=O)CCOCCOCCNc2ccc3c(-c4ccccc4CNc4nc(O[C@@H]5CCCNC5)nc5c(C(C)C)cnn45)nccc3c2)C(C)(C)C)cc1] |
| 16 | 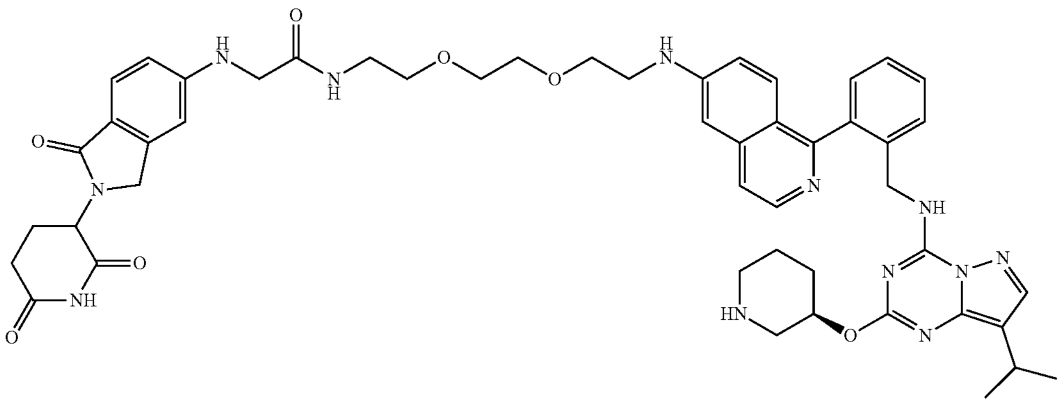 [SMILES: CC(C)c1cnn2c(NCc3ccccc3-c3nccc4cc(NCCOCCOCCNC(=O)CNc5ccc6c(c5)CN(C5CCC(=O)NC5=O)C6=O)ccc34)nc(O[C@@H]3CCCNC3)nc12] |

-continued
| Cpd. No. | Structure |
|---|---|
| 17 | 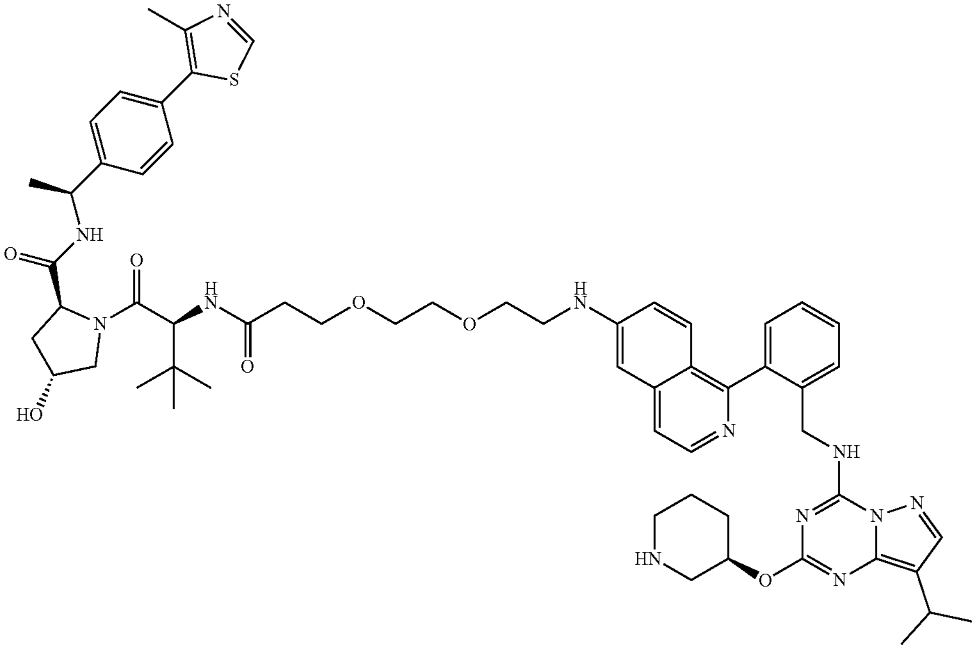 [SMILES: Cc1ncsc1-c1ccc([C@H](C)NC(=O)[C@@H]2C[C@@H](O)CN2C(=O)[C@@H](NC(=O)CCOCCOCCNc2ccc3c(-c4ccccc4CNc4nc(O[C@@H]5CCCNC5)nc5c(C(C)C)cnn45)nccc3c2)C(C)(C)C)cc1] |
| 18 | 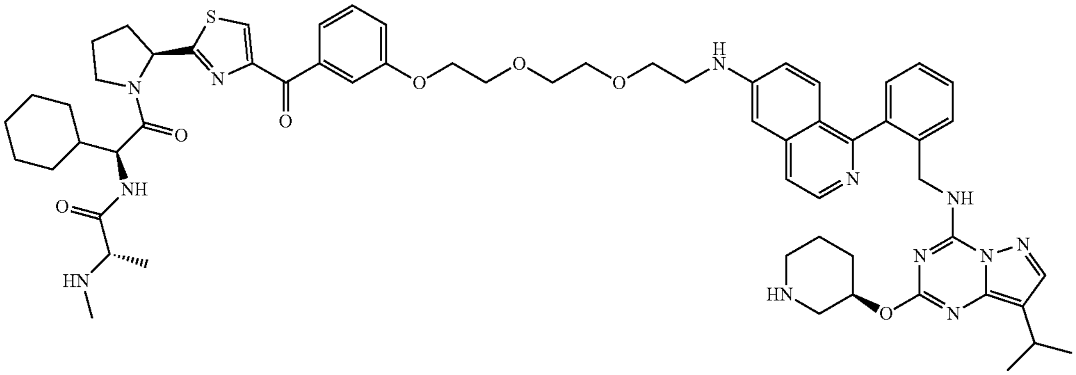 [SMILES: CN[C@@H](C)C(=O)N[C@H](C(=O)N1CCC[C@H]1c1nc(C(=O)c2cccc(OCCOCCOCCNc3ccc4c(-c5ccccc5CNc5nc(O[C@@H]6CCCNC6)nc6c(C(C)C)cnn56)nccc4c3)c2)cs1)C1CCCCC1] |
| 19 | 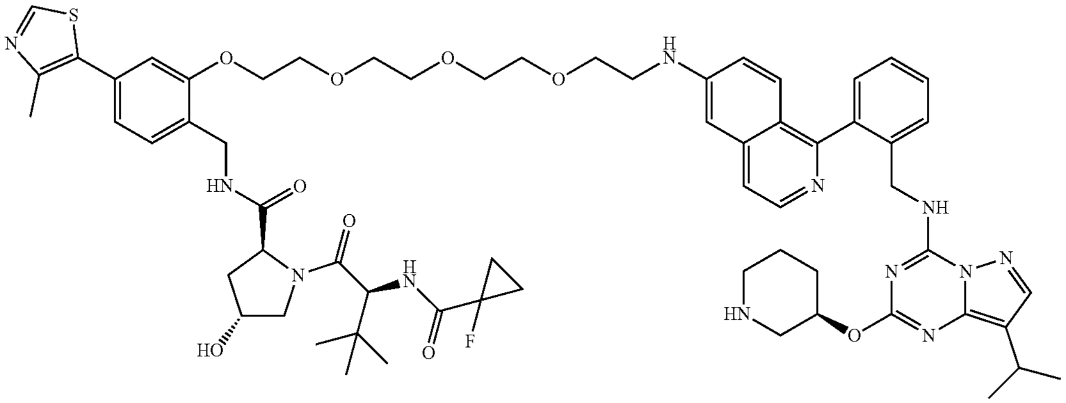 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCNc2ccc3c(-c4ccccc4CNc4nc(O[C@@H]5CCCNC5)nc5c(C(C)C)cnn45)nccc3c2)c1] |

-continued
| Cpd. No. | Structure |
|---|---|
| 20 | 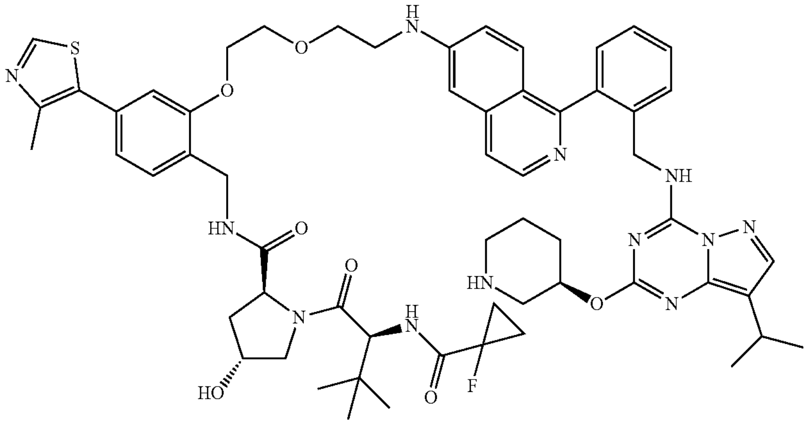 |
| 21 | 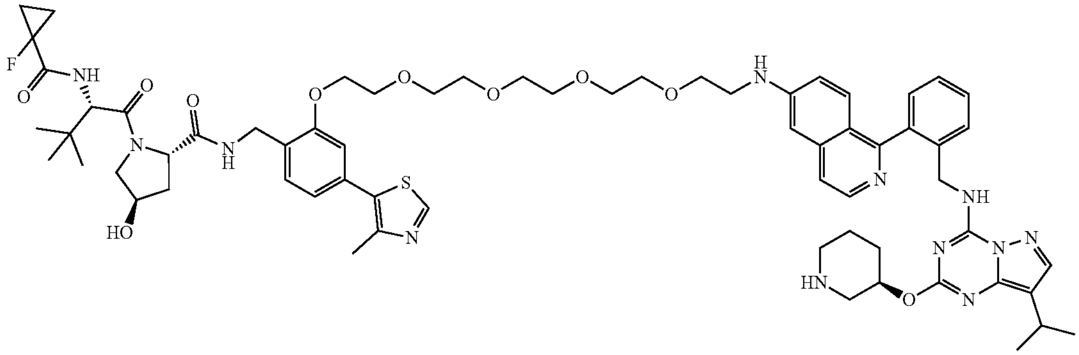 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCNc2ccc3c(-c4ccccc4CNc4nc(O[C@@H]5CCCNC5)nc5c(C(C)C)cnn45)nccc3c2)c1] |
| 22 | 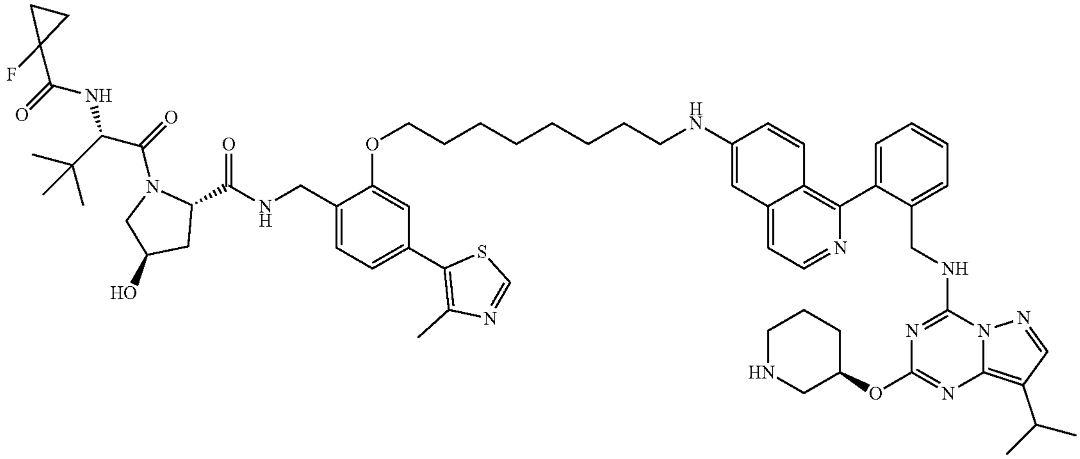 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCCNc2ccc3c(-c4ccccc4CNc4nc(O[C@@H]5CCCNC5)nc5c(C(C)C)cnn45)nccc3c2)c1] |

-continued
| Cpd. No. | Structure |
| --- | --- |
| 23 | 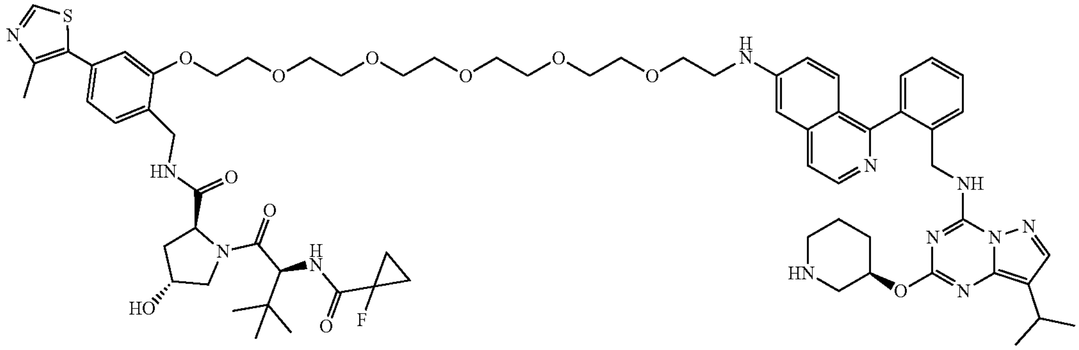 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCOCCNc2ccc3c(-c4ccccc4CNc4nc(O[C@@H]5CCCNC5)nc5c(C(C)C)cnn45)nccc3c2)c1] |
| 24 | 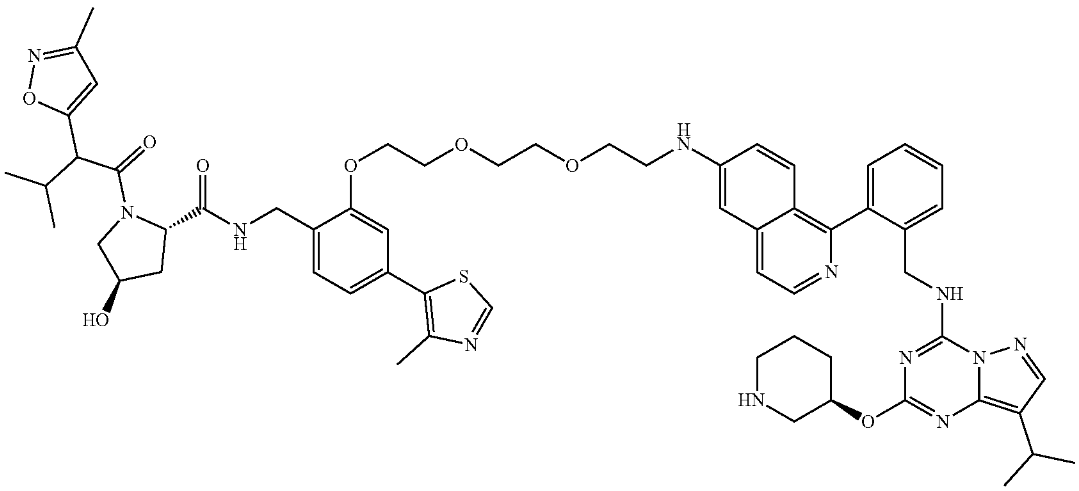 [SMILES: Cc1cc(C(C(=O)N2C[C@H](O)C[C@H]2C(=O)NCc2ccc(-c3scnc3C)cc2OCCOCCOCCNc2ccc3c(-c4ccccc4CNc4nc(O[C@@H]5CCCNC5)nc5c(C(C)C)cnn45)nccc3c2)C(C)C)on1] |
| 25 | 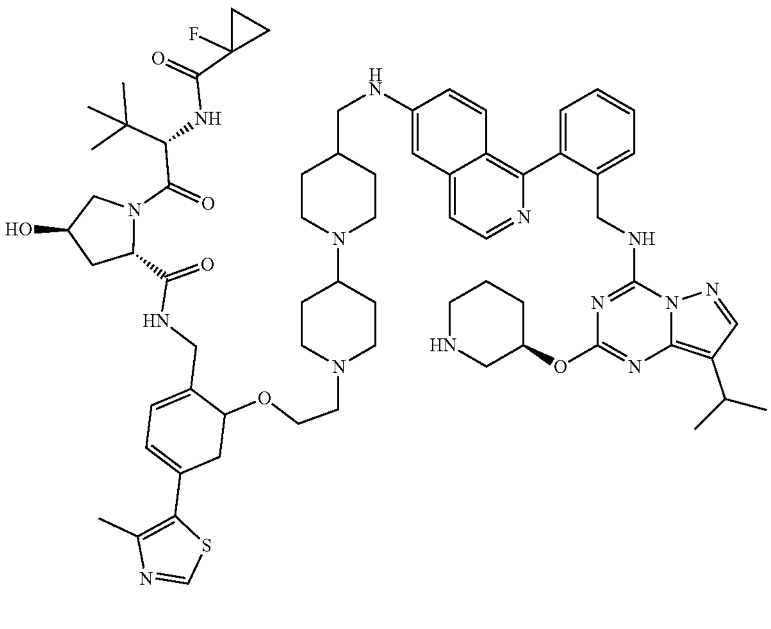 |

-continued
| Cpd. No. | Structure |
| --- | --- |
| 26 | 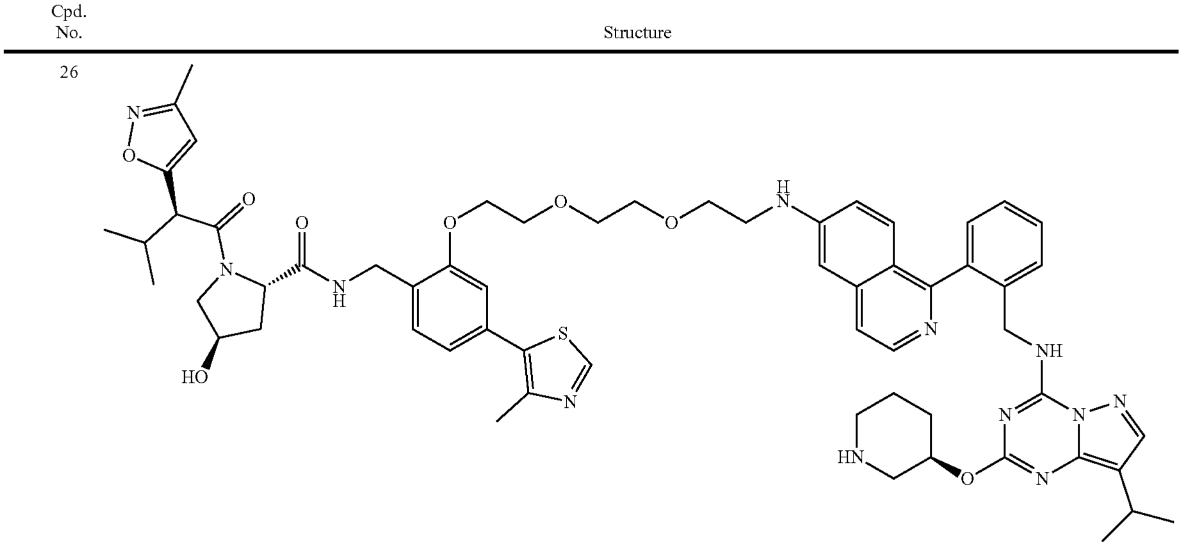 |
| 27 | 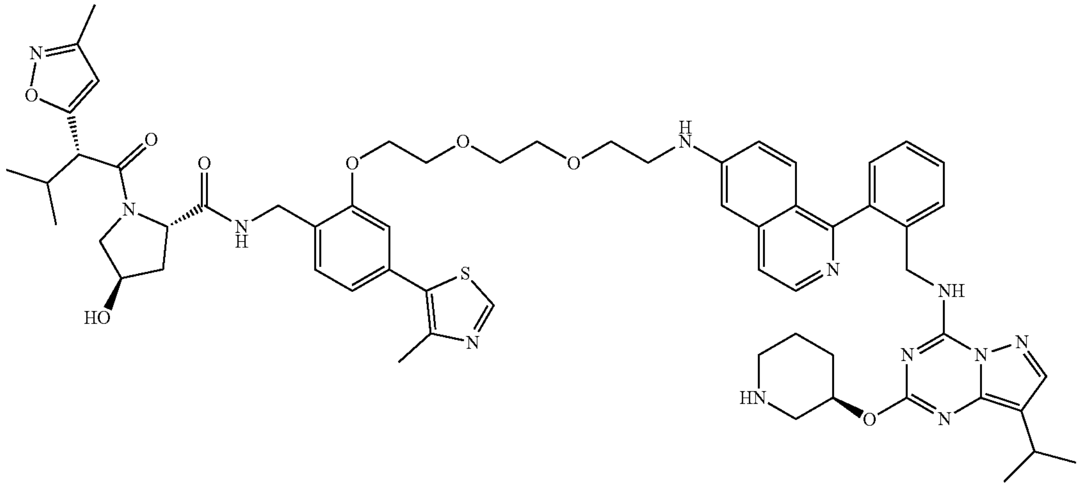 [SMILES: Cc1cc([C@H](C(=O)N2C[C@H](O)C[C@H]2C(=O)NCc2ccc(-c3scnc3C)cc2OCCOCCOCCNc2ccc3c(-c4ccccc4CNc4nc(O[C@@H]5CCCNC5)nc5c(C(C)C)cnn45)nccc3c2)C(C)C)on1] |
| 28 | 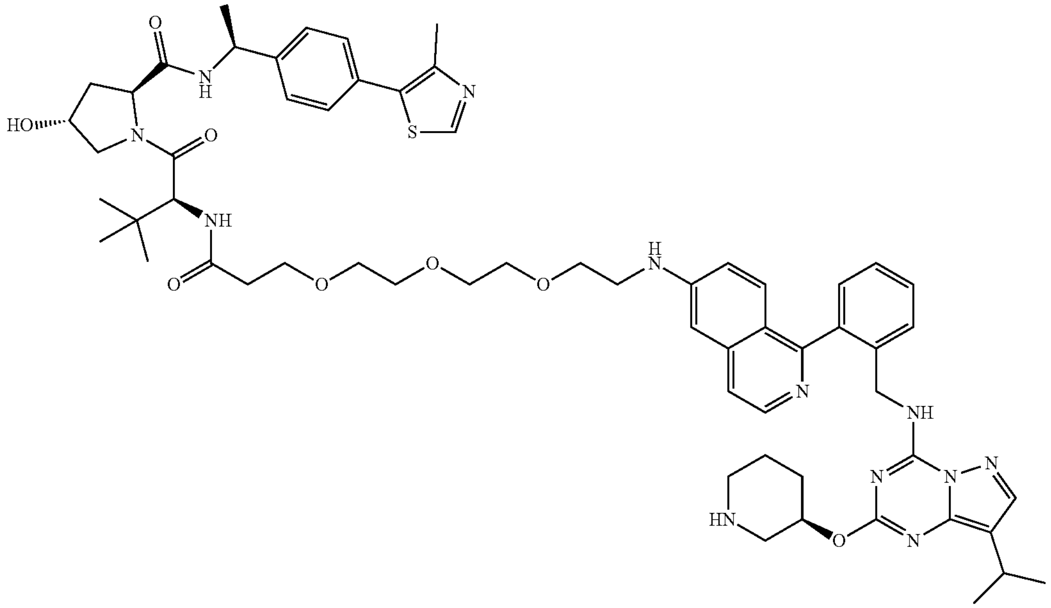 [SMILES: Cc1ncsc1-c1ccc([C@H](C)NC(=O)[C@@H]2C[C@@H](O)CN2C(=O)[C@@H](NC(=O)CCOCCOCCOCCNc2ccc3c(-c4ccccc4CNc4nc(O[C@@H]5CCCNC5)nc5c(C(C)C)cnn45)nccc3c2)C(C)(C)C)cc1] |

-continued
| Cpd. No. | Structure |
| --- | --- |
| 29 | 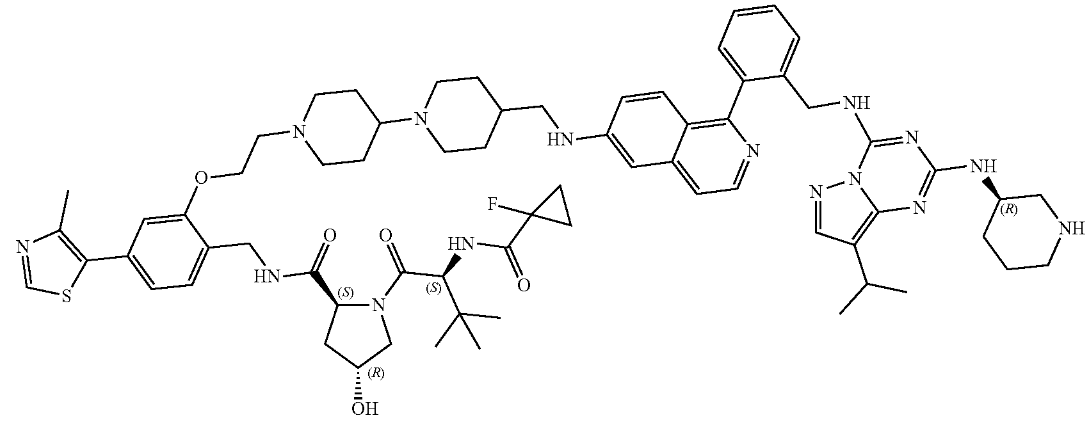 |
| 30 | 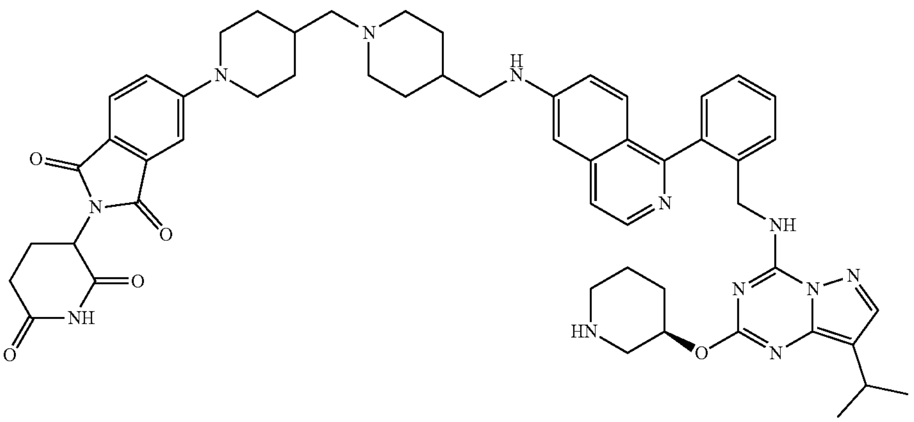 [SMILES: CC(C)c1cnn2c(NCc3ccccc3-c3nccc4cc(NCC5CCN(CC6CCN(c7ccc8c(c7)C(=O)N(C7CCC(=O)NC7=O)C8=O)CC6)CC5)ccc34)nc(O[C@@H]3CCCNC3)nc12] |
| 31 | 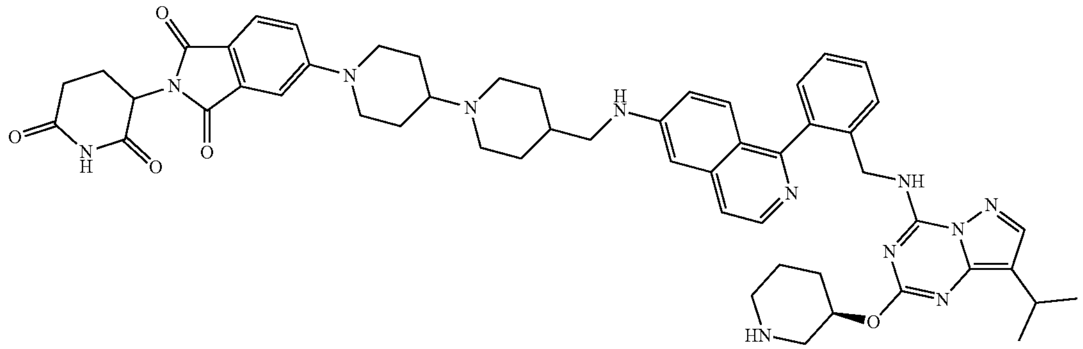 [SMILES: CC(C)c1cnn2c(NCc3ccccc3-c3nccc4cc(NCC5CCN(C6CCN(c7ccc8c(c7)C(=O)N(C7CCC(=O)NC7=O)C8=O)CC6)CC5)ccc34)nc(O[C@@H]3CCCNC3)nc12] |
| 32 | 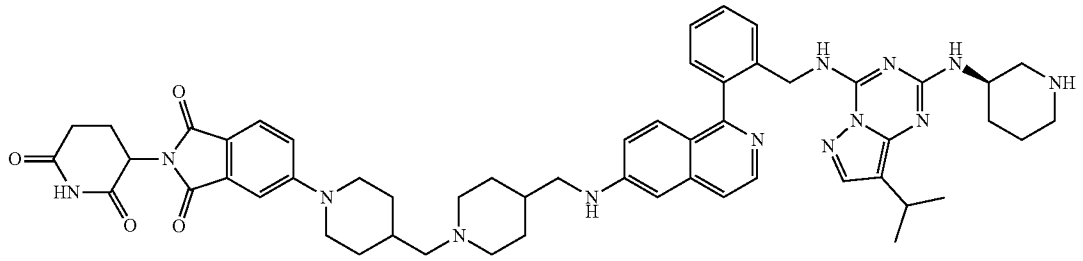 [SMILES: CC(C)c1cnn2c(NCc3ccccc3-c3nccc4cc(NCC5CCN(CC6CCN(c7ccc8c(c7)C(=O)N(C7CCC(=O)NC7=O)C8=O)CC6)CC5)ccc34)nc(N[C@@H]3CCCNC3)nc12] |

-continued
| Cpd. No. | Structure |
| --- | --- |
| 33 | 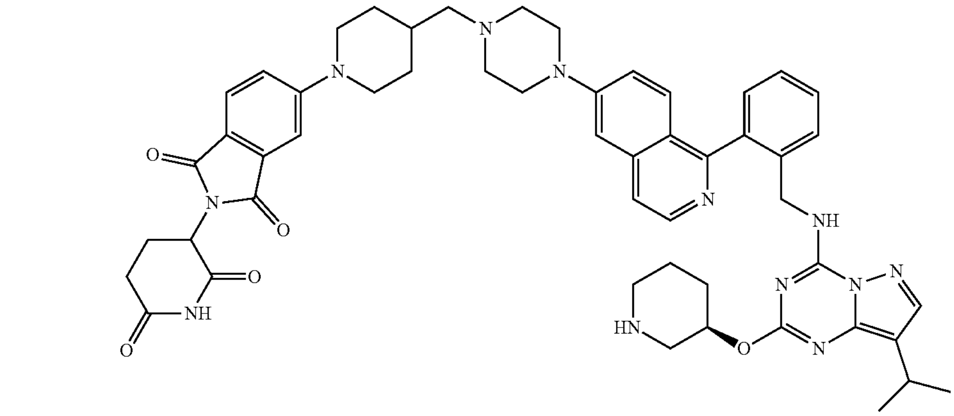 [SMILES: CC(C)c1cnn2c(NCc3ccccc3-c3nccc4cc(N5CCN(CC6CCN(c7ccc8c(c7)C(=O)N(C7CCC(=O)NC7=O)C8=O)CC6)CC5)ccc34)nc(O[C@@H]3CCCNC3)nc12] |
| 34 | 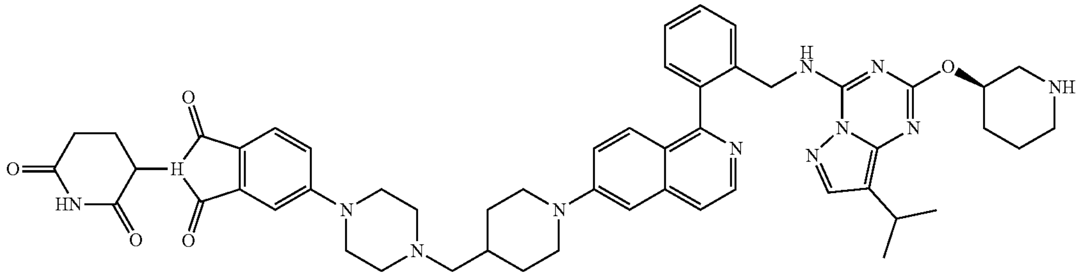 |
| 35 | 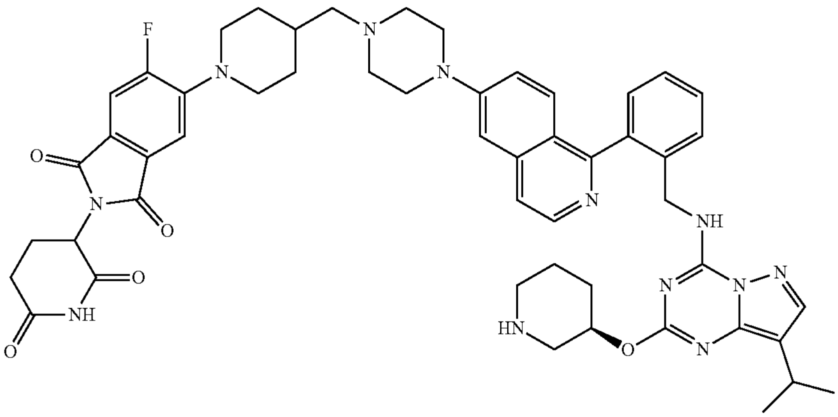 [SMILES: CC(C)c1cnn2c(NCc3ccccc3-c3nccc4cc(N5CCN(CC6CCN(c7cc8c(cc7F)C(=O)N(C7CCC(=O)NC7=O)C8=O)CC6)CC5)ccc34)nc(O[C@@H]3CCCNC3)nc12] |
| 36 | 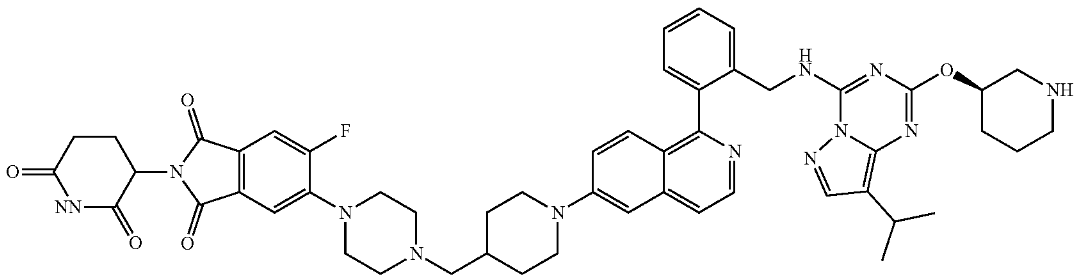 |

or an enantiomer, stereoisomeric form, mixture of enantiomers, diasteromers, mixture of diastereomers racemate of such compound or a pharmaceutically acceptable salt thereof.

14. A pharmaceutical composition comprising a compound according to claim 1, as an active ingredient, together with at least one pharmaceutically acceptable carrier, excipient and/or diluent.

15. A method of treatment of a disease which is associated with inhibition of apoptosis, abnormal transcriptional activity and/or cell cycle arrest by aberrant activity and/or overexpression of one or several cyclin-dependent kinases (CDKs), wherein the disease is selected from proliferative diseases, wherein said method comprises administering a compound according to claim 1 to a subject in need of such treatment; wherein the proliferative disease is a cancer selected from the group consisting of carcinoma, melanoma, leukemia, intestine cancer, ovarian cancer, bladder cancer, pancreatic cancer, gastric cancer, stomach cancer, breast cancer, and prostate cancer.

16. The method according to claim 15, wherein the proliferative disease is a cancer selected from the group consisting of: adenocarcinoma, choroidal melanoma, acute leukemia, ampullary carcinoma, anal carcinoma, basal cell carcinoma, pancreatic cancer, bladder cancer, bronchial carcinoma, estrogen dependent and independent breast cancer, Carcinoma unknown primary tumor (CUP-syndrome), small intestine cancer, endometrial carcinoma, gastric cancer, gall bladder carcinomas, hairy cell leukemia, colorectal carcinoma, colon carcinoma, leukemia, stomach cancer, malignant melanoma, breast carcinoma, melanoma, renal cell carcinomas, esophageal carcinoma, osteolytic carcinomas and osteoplastic carcinomas, ovarian carcinoma, pancreatic carcinoma, prostate cancer, rectal carcinoma, thyroid carcinoma, tube carcinoma, urothelial carcinoma, cervical carcinoma, invasive ductal carcinoma, invasive lobular carcinoma, ductal carcinoma in situ, lobular carcinoma in situ, small-cell lung carcinoma, non-small-cell lung carcinoma, anal gland adenocarcinomas, intraocular melanoma, hepatocellular carcinoma, cholangiocarcinoma, mixed hepatocellular cholangiocarcinoma, squamous cell carcinoma, oral melanoma.

* * * * *